US009937158B2

(12) United States Patent
Tian et al.

(10) Patent No.: US 9,937,158 B2
(45) Date of Patent: Apr. 10, 2018

(54) BENZOHETEROCYCLIC COMPOUNDS AND USE THEREOF

(71) Applicant: Shanghai Kechow Pharma Inc., Shanghai (CN)

(72) Inventors: Hongqi Tian, Shanghai (CN); Conghui Ji, Shanghai (CN); Chunlei Liu, Shanghai (CN); Li Kong, Shanghai (CN); Ying Cheng, Shanghai (CN); Gongchao Huang, Shanghai (CN)

(73) Assignee: SHANGHAI KECHOW PHARMA, INC., Shanghai (CN)

( * ) Notice: Subject to any disclaimer, the term of this patent is extended or adjusted under 35 U.S.C. 154(b) by 0 days.

(21) Appl. No.: 15/050,045

(22) Filed: Feb. 22, 2016

(65) Prior Publication Data

US 2016/0235721 A1 Aug. 18, 2016

Related U.S. Application Data

(62) Division of application No. 14/372,731, filed as application No. PCT/CN2013/000037 on Jan. 16, 2013, now Pat. No. 9,290,468.

(30) Foreign Application Priority Data

Jan. 17, 2012 (CN) .......................... 2012 1 0014021
Jun. 8, 2012 (CN) .......................... 2012 1 0189086
Jun. 8, 2012 (CN) .......................... 2012 1 0189087
Jun. 8, 2012 (CN) .......................... 2012 1 0190520

(51) Int. Cl.

*A61K 31/423* (2006.01)
*A61K 31/428* (2006.01)
*A61K 31/433* (2006.01)
*C07D 277/62* (2006.01)
*C07D 263/56* (2006.01)
*C07D 277/64* (2006.01)
*C07D 285/14* (2006.01)

(52) U.S. Cl.

CPC .......... *A61K 31/433* (2013.01); *A61K 31/423* (2013.01); *A61K 31/428* (2013.01); *C07D 263/56* (2013.01); *C07D 277/62* (2013.01); *C07D 277/64* (2013.01); *C07D 285/14* (2013.01)

(58) Field of Classification Search

CPC ... A61K 31/423; A61K 31/428; A61K 31/433
See application file for complete search history.

(56) References Cited

U.S. PATENT DOCUMENTS 6,469,004 B1 10/2002 Barrett et al.
7,425,637 B2 9/2008 Wallace et al.
7,504,406 B2 3/2009 Bourrie et al.
7,759,518 B2 7/2010 Maderna et al.
7,820,664 B2 10/2010 Vernier et al.
8,063,049 B2 11/2011 Koh et al.
8,101,799 B2 1/2012 Maderna et al.
2004/0116710 A1 6/2004 Wallace et al.
2008/0293785 A1 11/2008 Connolly et al.
2010/0093668 A1 4/2010 Babin et al.
2013/0245008 A1 9/2013 Pellet

FOREIGN PATENT DOCUMENTS

CN 101213196 A 7/2008
CN 101605783 A 12/2009
CN 101678014 A 3/2010
WO WO-98/43960 A1 10/1998
WO WO-99/01421 A1 1/1999
WO WO-99/01426 A1 1/1999
WO WO-00/41003 A1 7/2000
(Continued)

OTHER PUBLICATIONS

Golub et al., Science, vol. 286, Oct. 15, 1999, pp. 531-537.*
CAS Registry No. 1349647-57-9. Entry Date: Dec. 6, 2011.
CAS Registry No. 1348459-26-6. Entry Date: Dec. 4, 2011.
CAS Registry No. 1348015-49-5. Entry Date: Dec. 4, 2011.
CAS Registry No. 1347874-63-8. Entry Date: Dec. 4, 2011.
CAS Registry No. 1347429-11-1. Entry Date: Dec. 2, 2011.
CAS Registry No. 1347361-56-1. Entry Date: Dec. 2, 2011.
CAS Registry No. 1026793-90-7, indexed in the Registry file on STN CAS Online on Jun. 9, 2008.
Extended European Search Report dated Jun. 25, 2015, for EP Application No. 13 738 359.2, filed on Jan. 16, 2013, five pages.
(Continued)

*Primary Examiner* — Laura L Stockton
(74) *Attorney, Agent, or Firm* — Morrison & Foerster LLP

(57) ABSTRACT

Disclosed are compound of formula (I) and pharmaceutically accepted salts and prodrugs thereof, wherein each of $R^1$, $R^2$, $R^3$, $R^4$, $R^5$, $R^6$, $X^1$, and $X^2$ is as defined in the description. These compounds are protein kinases inhibitors, especially the inhibitors of Mek, which are useful in the treatment of cancers and inflammation of mammals. Disclosed are the treatment methods of cancers and inflammation of mammals as well as pharmaceutical expositions comprising the compounds described herein. The preparation of benzoheterocyclic compounds are disclosed. Disclosed are the preparation of potential drug candidates, such as benzooxazol, benzothiazol, benzothiadiazol and the like.

(I)

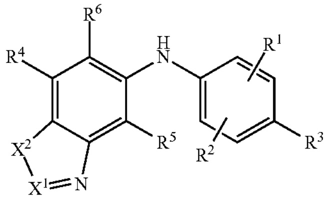

27 Claims, 2 Drawing Sheets

(56) References Cited

FOREIGN PATENT DOCUMENTS

| | | | |
|---|---|---|---|
| WO | WO-00/41505 | A2 | 7/2000 |
| WO | WO-00/41505 | A3 | 7/2000 |
| WO | WO-00/41994 | A1 | 7/2000 |
| WO | WO-00/42002 | A1 | 7/2000 |
| WO | WO-00/42022 | A1 | 7/2000 |
| WO | WO-00/42029 | A1 | 7/2000 |
| WO | WO-00/68201 | A1 | 11/2000 |
| WO | WO-01/05390 | A2 | 1/2001 |
| WO | WO-01/05390 | A3 | 1/2001 |
| WO | WO-01/68619 | A1 | 9/2001 |
| WO | WO-02/06213 | A2 | 1/2002 |
| WO | WO-02/06213 | A3 | 1/2002 |
| WO | WO-03/077855 | A2 | 9/2003 |
| WO | WO-03/077855 | A3 | 9/2003 |
| WO | WO-03/077914 | A1 | 9/2003 |
| WO | WO-2004/056789 | A1 | 7/2004 |
| WO | WO-2005/000818 | A1 | 1/2005 |
| WO | WO-2005/007616 | A1 | 1/2005 |
| WO | WO-2005/009975 | A2 | 2/2005 |
| WO | WO-2005/009975 | A3 | 2/2005 |
| WO | WO-2005/023251 | A1 | 3/2005 |
| WO | WO-2005/023759 | A2 | 3/2005 |
| WO | WO-2005/023759 | A3 | 3/2005 |
| WO | WO-2005/051302 | A2 | 3/2005 |
| WO | WO-2005/046665 | A1 | 5/2005 |
| WO | WO-2005/051300 | A2 | 6/2005 |
| WO | WO-2005/051300 | A3 | 6/2005 |
| WO | WO-2005/051301 | A2 | 6/2005 |
| WO | WO-2005/051301 | A3 | 6/2005 |
| WO | WO-2005/051302 | A3 | 6/2005 |
| WO | WO-2005/051906 | A2 | 6/2005 |
| WO | WO-2005/051906 | A3 | 6/2005 |
| WO | WO-2006/134469 | A1 | 12/2006 |
| WO | WO-2007/014011 | A2 | 2/2007 |
| WO | WO-2007/014011 | A3 | 2/2007 |
| WO | WO-2007/044084 | A2 | 4/2007 |
| WO | WO-2007/044084 | A3 | 4/2007 |
| WO | WO-2007/044515 | A1 | 4/2007 |
| WO | WO-2007/071951 | A1 | 6/2007 |
| WO | WO-2007/121154 | A2 | 10/2007 |
| WO | WO-2007/121154 | A3 | 10/2007 |
| WO | WO-2007/121269 | A2 | 10/2007 |
| WO | WO-2007/121269 | A3 | 10/2007 |
| WO | WO-2007/121481 | A2 | 10/2007 |
| WO | WO-2007/121481 | A3 | 10/2007 |
| WO | WO-2008/021389 | A2 | 2/2008 |
| WO | WO-2008/021389 | A3 | 2/2008 |
| WO | WO-2008/076415 | A1 | 6/2008 |
| WO | WO-2008/078086 | A1 | 7/2008 |
| WO | WO-2008/089459 | A1 | 7/2008 |
| WO | WO-2008/120004 | A1 | 10/2008 |
| WO | WO-2008/124085 | A2 | 10/2008 |
| WO | WO-2008/124085 | A3 | 10/2008 |
| WO | WO-2008/125820 | A1 | 10/2008 |
| WO | WO-2008/137027 | A2 | 11/2008 |
| WO | WO-2008/137027 | A3 | 11/2008 |
| WO | WO-2008/144767 | A1 | 11/2008 |
| WO | WO-2009/013426 | A2 | 1/2009 |
| WO | WO-2009/013426 | A3 | 1/2009 |
| WO | WO-2009/018238 | A1 | 2/2009 |
| WO | WO-2009/074827 | A2 | 6/2009 |
| WO | WO-2009/074827 | A3 | 6/2009 |
| WO | WO-2009/093008 | A1 | 7/2009 |
| WO | WO-2009/093009 | A1 | 7/2009 |
| WO | WO-2009/093013 | A1 | 7/2009 |
| WO | WO-2009/153554 | A1 | 12/2009 |
| WO | WO-2011/070030 | A1 | 6/2011 |
| WO | WO-2012/059041 | A1 | 5/2012 |
| WO | WO-2012/145728 | A1 | 10/2012 |

OTHER PUBLICATIONS

International Search Report dated Apr. 25, 2013, for PCT Patent Application No. PCT/CN2013/000037, filed on Jan. 16, 2013, seven pages.

Written Opinion of the International Searching Authority dated Apr. 25, 2013, for PCT Patent Application No. PCT/CN2013/000037, filed on Jan. 16, 2013, six pages.

Yeh, T.C. et al. (Mar. 1, 2007). "Biological Characterization of ARRY-142886 (AZD6244), a Potent, Highly Selective Mitogen-Activated Protein Kinase Kinase 1/2 Inhibitor," *Clin. Cancer Res.* 13(5):1576-1583.

* cited by examiner

BENZOHETEROCYCLIC COMPOUNDS AND USE THEREOF

CROSS-REFERENCE TO RELATED APPLICATIONS

This application is a divisional application of U.S. patent application Ser. No. 14/372,731, filed Jul. 16, 2014, which is a National Phase application under 35 U.S.C. § 371 of International Application No. PCT/CN2013/000037, filed Jan. 16, 2013, and claims the benefit of priority to People's Republic of China Patent Application No. 201210014021.X filed Jan. 17, 2012, People's Republic of China Patent Application No. 201210189086.8 filed Jun. 8, 2012, People's Republic of China Patent Application No. 201210190520.4 filed Jun. 8, 2012, and People's Republic of China Patent Application No. 201210189087.2 filed Jun. 8, 2012, the disclosures of each of which are hereby incorporated herein by reference in their entireties.

FIELD OF THE INVENTION

The present invention relates to benzoheterocyclic compounds such as benzothiadiazole, benzoxazole and benzothiazole derivatives, which are inhibitors of protein kinases such as MEK. The compounds may be useful in the treatment of conditions or disorders where the MEK cascade is implicated such as cancer and inflammatory diseases.

BACKGROUND OF THE INVENTION

Cell signaling through growth factor receptors and protein kinases is an important regulator of cell growth, proliferation and differentiation. In normal cell growth, factors (i.e. PDGF or EGF and others), through receptor activation (i.e. ErbB2, EGFR, PDGFR), activate MAP (Mitogen-activating protein) kinase pathways. One of the most important and most well understood MAP kinase pathways involved in normal and uncontrolled cell growth is the Ras/Raf/Mek/Erk kinase pathway. In proliferative diseases, genetic mutations and/or overexpression of the growth factor receptors, downstream signaling proteins, or protein kinases involved in the kinase pathway lead to uncontrolled cell proliferation and, eventually, tumor formation. For example, some cancers contain mutations which results in the activation of this pathway due to continuous production of growth factors. The statistics show that mutated, oncogenic forms of Ras are found in 50% of colon and >90% pancreatic cancers. Recently, bRaf mutations have been identified in more than 60% of malignant melanoma. Studies of primary tumor samples and cell lines have also shown constitutive or overactivation of the Ras/Raf/Mek/Erk pathway in cancers of pancreas, colon, lung, ovary and kidney.

As constitutive or overactivation of MAP kinase cascade plays a pivotal role in cell proliferation and differentiation, inhibition of this pathway is believed to be beneficial in hyperproliferative diseases. Mek is a key player in this pathway as it is downstream of Ras and Raf, Additionally, it is an attractive therapeutic target because the only known substrates for Mek phosphorylation are the MAP kinases, Erk 1 and 2. Hence, inhibition of MEK would block Ras/Raf/Mek/Erk pathway and result in cell growth inhibition, especially the cell growth due to the overactivation of Ras or Raf Meanwhile Mek is also related to inflammatory disease and symptoms, including acute and chronic inflammation.

Inhibitors of Mek have shown some effects in clinical experiments of nude mice. Recently, some Mek inhibitors have been applied at clinical experiments of people. Therefore, Mek is a potential new target and more and more Mek inhibitors are developed and reported, for example, WO 98/43960; WO 99/01421; WO 99/01426; WO 00/41505; WO 00/42002; WO 00/41003; WO 00/41994; WO 00/42022; WO 00/42029; WO 00/68201; WO 01/68619; WO 02/06213; WO 03/077914; WO 03/077855; WO 03/077914; WO 05/023251; WO 05/023759; WO 05/051300; WO 05/051301; WO 05/051302; WO 05/051906; WO 05/000818; WO 05/007616; WO 05/009975; WO 05/046665; WO 06/134469; WO 07/044084; WO 07/014011; WO 07/121269; WO 07/121481; WO 07/071951; WO 07/044515; WO 08/021389; WO 08/076415; WO 08/089459; WO 08/078086; WO 08/120004; WO 08/124085; WO 08/125820; WO 09/018238; WO 09/074827; WO 09/013426; WO 09/093008; WO 09/093009; WO 09/093013; WO 09/153554 and so on.

However, many known MEK inhibitors suffer from weak inhibitory activity, intolerable toxicity or lack of desirable pharmaceutical properties. Thus, there remains a need for potent inhibitors of MEK with appropriate pharmaceutical properties for clinical applications.

BRIEF SUMMARY OF THE INVENTION

In one aspect, provided is a compound of the formula (I):

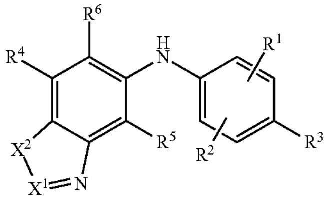

(I)

or a salt, solvate or prodrug thereof, wherein:

$X^1$ is $CR^{11}$ or N;

$X^2$ is O, S or carbonyl;

$R^1$, $R^2$, $R^4$ and $R^5$ are independently hydrogen, halo, nitro, azido, hydroxy, $C_1$-$C_{10}$ alkoxy, halo-substituted $C_1$-$C_{10}$ alkoxy, acyloxy, $C_1$-$C_{10}$ alkylthio, halo-substituted $C_1$-$C_{10}$ alkylthio, amino, carboxy, $C_1$-$C_{10}$ alkyl, $C_2$-$C_{10}$ alkenyl, $C_2$-$C_{10}$ alkynyl or $C_3$-$C_{10}$ cycloalkyl;

$R^3$ is hydrogen, halo, cyano, nitro, azido, hydroxy, $C_1$-$C_{10}$ alkoxy, halo-substituted $C_1$-$C_{10}$ alkoxy, acyloxy, mercapto, $C_1$-$C_{10}$ alkylthio, halo-substituted $C_1$-$C_{10}$ alkylthio, $-SO_2R^a$, $-SO_2N(R^c)R^d$, $-N(R^c)R^d$, $-C(O)OR^b$, $C_1$-$C_{10}$ alkyl, $C_2$-$C_{10}$ alkenyl, $C_2$-$C_{10}$ alkynyl or $C_3$-$C_{10}$ cycloalkyl;

$R^a$ is $C_1$-$C_{10}$ alkyl or $C_6$-$C_{14}$ aryl;

each $R^b$, $R^c$ and $R^d$ is independently hydrogen or $C_1$-$C_{10}$ alkyl;

$R^6$ is $-C(O)OR^7$, $-C(O)NR^7R^8$, $-C(O)N(R^8)OR^7$, $-C(O)R^9$ or $-NHSO_2R^{10}$;

each $R^7$ and $R^8$ is independently hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkyl $C_1$-$C_{10}$ alkyl or $C_1$-$C_{10}$ alkyl $C_3$-$C_{10}$ cycloalkyl;

$R^9$ is $C_1$-$C_{10}$ alkyl, $C_3$-$C_{10}$ cycloalkyl or $C_6$-$C_{14}$ aryl;

$R^{10}$ is $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkyl $C_1$-$C_{10}$ alkyl or $C_1$-$C_{10}$ alkyl $C_3$-$C_{10}$ cycloalkyl; and $R^{11}$ is hydrogen, $C_1$-$C_{10}$ alkyl, $C_2$-$C_{10}$ alkenyl, $C_2$-$C_{10}$ alkynyl, $C_3$-$C_{10}$ cycloalkyl or $C_3$-$C_{10}$ cycloalkyl $C_1$-$C_{10}$ alkyl;

wherein each $C_1$-$C_{10}$ alkyl, $C_2$-$C_{10}$ alkenyl, $C_2$-$C_{10}$ alkynyl or $C_3$-$C_{10}$ cycloalkyl moiety may be unsubstituted or substituted with one or more groups independently selected from the group consisting of hydroxy, oxo, halo, cyano, nitro, trifluoromethyl, azido, amino, carboxy and mercapto;

provided that if $X^1$ is CH, $X^2$ is O or S, $R^1$ is methyl or chloro, $R^2$ is hydrogen and $R^3$ is iodo, then $R^6$ is —$NHSO_2R^{10}$ or —$C(O)N(R^8)OR^7$ where $R^7$ is $C_1$-$C_{10}$ alkyl substituted with at least one hydroxy group.

In some embodiments, provided is a compound of the formula (J):

(J)

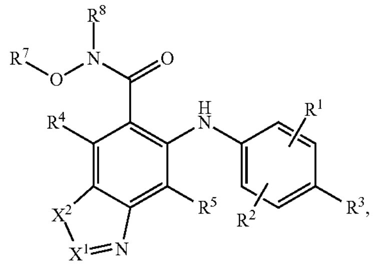

or a salt, solvate or prodrug thereof, wherein $X^1$, $X^2$, $R^1$, $R^2$, $R^3$, $R^4$, $R^5$, $R^7$ and $R^8$ are as defined for the formula (I).

In another aspect, provided is any one of the MEK inhibitor compounds described herein present in a substantially pure form.

Also provided are pharmaceutical compositions and/or formulations comprising any one of the compounds described herein and a carrier (e.g., a pharmaceutically acceptable carrier). In some embodiments, the formulation is suitable for administration to an individual. In some embodiments, the formulation comprises an effective amount of any one of the compounds described herein and a carrier (e.g., a pharmaceutically acceptable carrier). In another aspect, provided are pharmaceutical formulations comprising a MEK inhibitor compound described herein or a MEK inhibitor compound described herein in combination with a pharmaceutically acceptable carrier.

In another aspect, provided are methods for the treatment and/or prevention of a disease, condition, or disorder where the MEK pathway cascade is implicated, such as a disease, condition, or disorder mediated by MEK, comprising administering to an individual in need thereof a therapeutically effective amount of a compound described herein, such as a compound of the formula (I), (J), (K), (A-I) or any variations thereof. In some embodiments, the disease or condition is cancer, chronic inflammatory disease, a skin disease, diabetes, an eye disease, vasculogenesis, angiogenesis or chronic pain. In some embodiments, the disease or condition is rheumatoid arthritis or inflammatory bowel disease. In some embodiments, the disease or condition is a cancer such as colon cancer, colorectal cancer, lung cancer, pancreatic cancer, breast cancer, ovarian cancer, prostate cancer or skin cancer.

Also provided is use of compounds detailed herein, such as a compound of the formula (I), (J), (K), (A-I) or any variations thereof, in the manufacture of a medicament for the treatment or prevention of a disease or condition which can be ameliorated by inhibition of MEK in an individual, such as a mammal (e.g., human), in need thereof.

Kits comprising a compound as described herein and instructions for use are also provided. In one aspect, provided are kits for the treatment or prevention in an individual of a disease or condition mediated by MEK, comprising any one of the compounds detailed herein or a pharmaceutically acceptable salt, solvate, or prodrug thereof; and packaging. In some embodiments, the kit comprises a formulation of any one of the compounds described herein and packaging.

Further provided are methods and processes of making compounds described herein, or a salt (including a pharmaceutically acceptable salt), solvate or prodrug thereof.

DETAILED DESCRIPTION OF THE INVENTION

Definitions

Figure 1:
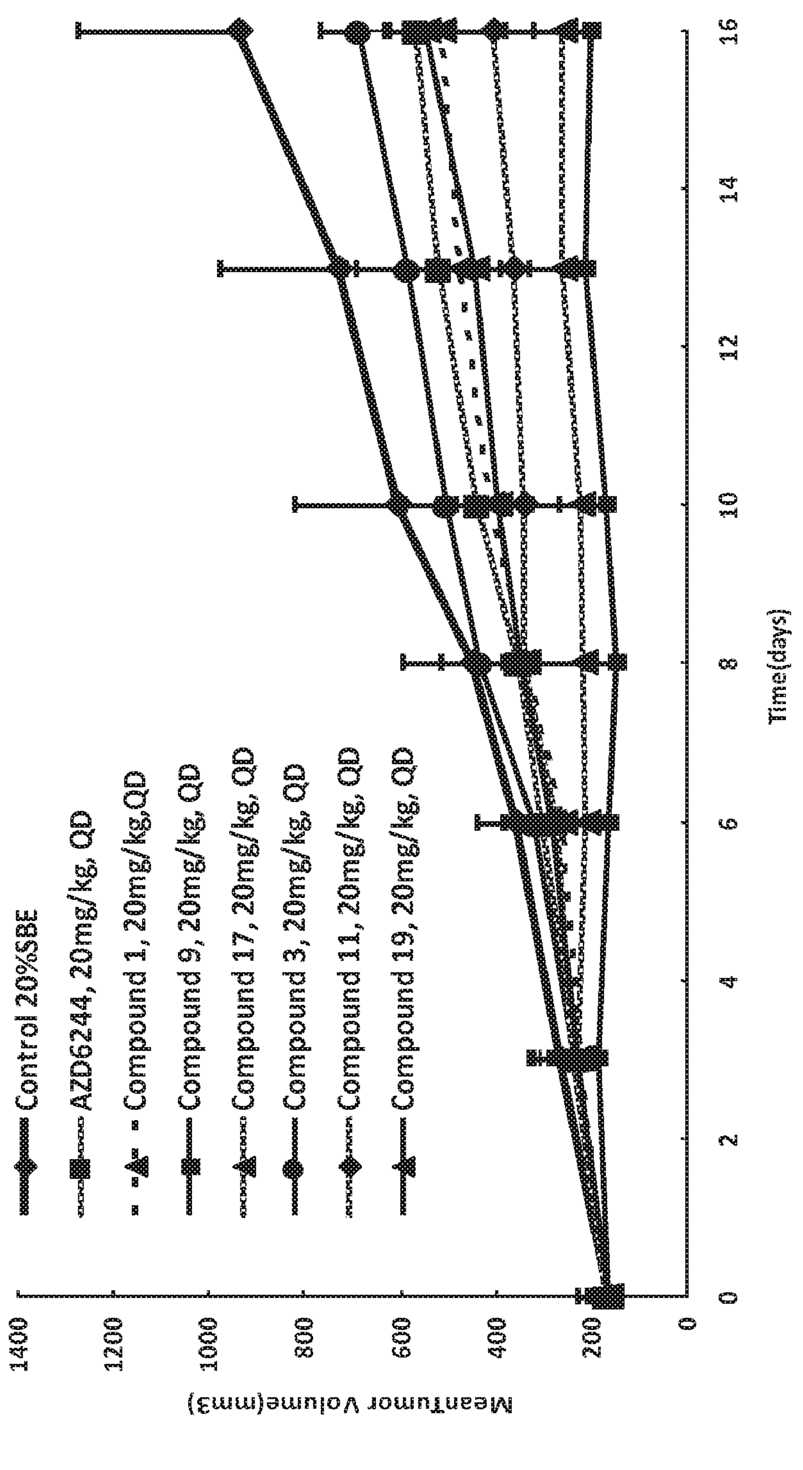
FIG. 1 shows the anti-tumor effect of Compounds 1, 3, 9, 11, 17 and 19 in a mouse xenograft model of human colon HT-29 cells.

For use herein, unless clearly indicated otherwise, use of the terms "a", "an" and the like refers to one or more.

Reference to "about" a valise or parameter herein includes (and describes) embodiments that are directed to that value or parameter per se. For example, description referring to "about X" includes description of "X".

The term "halo" or "halogen", by itself or as part of another substituent, refers to and includes fluoro, chloro, bromo and iodo.

The term "alkyl", by itself or as part of another substituent, refers to and includes saturated linear (i.e. unbranched) or branched hydrocarbon radicals, having the number of carbon atoms designated (i.e., $C_1$-$C_{10}$ means one to ten carbons). Particular alkyl groups are those having 1 to 10 carbon atoms (a "$C_1$-$C_{10}$ alkyl"). More particular alkyl groups are those having 1 to 6 carbon atoms (a "$C_1$-$C_6$ alkyl"), 1 to 4 carbon atoms (a "$C_1$-$C_4$ alkyl"), 1 to 3 carbon atoms (a "$C_1$-$C_3$ alkyl") or 1 to 2 carbon atoms (a "$C_1$-$C_2$ alkyl"). Examples of "$C_1$-$C_{10}$ alkyl" include, but are not limited to, methyl, ethyl, n-propyl, isopropyl, n-butyl, isobutyl, sec-butyl, tert-butyl, n-pentyl, n-hexyl, n-heptyl, n-octyl, n-nonyl, n-decyl and the like.

The term "alkenyl", by itself or as part of another substituent, refers to and includes unsaturated linear (i.e. unbranched) or branched hydrocarbon radicals containing at least one carbon-carbon double bond, having the number of carbon atoms designated (i.e., $C_2$-$C_{10}$ means two to ten carbons). Particular alkenyl groups are those having 2 to 10 carbon atoms (a "$C_2$-$C_{10}$ alkenyl"). More particular alkenyl groups are those having 2 to 8 carbon atoms (a "$C_2$-$C_8$ alkenyl") or 2 to 6 carbon atoms (a "$C_2$-$C_6$ alkenyl"). Examples of "$C_2$-$C_{10}$ alkenyl" include, but are not limited to, ethenyl, 1-propenyl, 2-propenyl, 1-methylethenyl, but-1-en-1-yl, but-2-en-1-yl, but-3-en-1-yl, 1-methyl-1-propenyl, 2-methyl-1-propenyl, 1-methyl-2-propenyl, 2-methyl-2-propenyl, pent-1-en-1-yl, pent-2-en-1-yl, pent-3-en-1-yl, pent-4-en-1-yl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, hex-1-en-1-yl, hex-2-en-1-yl, hex-3-en-1-yl, hex-4-en-1-yl, hex-5-en-1-yl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, l-ethyl-2-butenyl, l-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, l-ethyl-2-methyl-1-propenyl, l-ethyl-2-methyl-2-propenyl, and the like.

The term "alkynyl", by itself or as part of another substituent, refers to and includes unsaturated linear (i.e. unbranched) or branched hydrocarbon radicals containing at least one carbon-carbon triple bond, having the number of carbon atoms designated (i.e., $C_2$-$C_{10}$ means two to ten carbons). Particular alkynyl groups are those having 2 to 10 carbon atoms (a "$C_2$-$C_{10}$ alkynyl"). More particular alkenyl groups are those having 2 to 8 carbon atoms (a "$C_2$-$C_8$ alkynyl") or 2 to 6 carbon atoms (a "$C_2$-$C_6$ alkynyl"). Examples of "$C_2$-$C_{10}$ alkynyl" include, but are not limited to, ethynyl, 1-propynyl, 2-propynyl, but-1-yn-1-yl, but-2-yn-1-yl, but-3-yn-1-yl, 1-methyl-2-propynyl, pent-1-yn-1-yl, pent-2-yn-1-yl, pent-3-yn-1-yl, pent-4-yn-1-yl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, hex-1-yn-1-yl, hex-2-yn-1-yl, hex-3-yn-1-yl, hex-4-yn-1-yl, hex-5-yn-1-yl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl, and the like.

The term "cycloalkyl", by itself or as part of another substituent, refers to and includes saturated monocyclic hydrocarbon radicals, having the number of carbon atoms designated (i.e., $C_3$-$C_{10}$ means three to ten carbons). Particular cycloalkyl groups are those having 3 to 10 carbon atoms (a "$C_3$-$C_{10}$ cycloalkyl"). More particular cycloalkyl groups are those having 3 to 8 carbon atoms (a "$C_3$-$C_8$ cycloalkyl"), 3 to 6 carbon atoms (a "$C_3$-$C_6$ cycloalkyl") or 3 to 4 carbon atoms (a "$C_3$-$C_4$ cycloalkyl"). Examples of "$C_3$-$C_{10}$ cycloalkyl" include, but are not limited to, cyclopropyl, cyclopentyl, cyclohexyl, and the like.

The term "aryl", by itself or as part of another substituent, refers to and includes monocyclic or polycyclic aromatic hydrocarbon radicals, having the number of annular carbon atoms designated (i.e., $C_6$-$C_{14}$ means six to fourteen carbons). Particular aryl groups are those having 6 to 14 annular carbon atoms (a "$C_6$-$C_{14}$ aryl"). Examples of "$C_6$-$C_{14}$ aryl" include, but are not limited to, phenyl, naphthyl, anthracenyl, and the like. In some embodiments, an aryl may contain a single ring (e.g., phenyl). In some embodiments, an aryl may contain multiple rings (e.g., biphenyl). In some embodiments, an aryl may contain multiple condensed rings where at least one of the condensed rings is aromatic (e.g., 1,2,3,4-tetrahydronaphthyl and naphthyl).

The term "$C_3$-$C_{10}$ cycloalkyl $C_1$-$C_{10}$ alkyl" as used herein refers to a $C_1$-$C_{10}$ alkyl moiety which is substituted with a $C_3$-$C_{10}$ cycloalkyl moiety. Examples of "$C_3$-$C_{10}$ cycloalkyl $C_1$-$C_{10}$ alkyl" include, but are not limited to, cyclopropylmethyl and the like.

The term "$C_6$-$C_{14}$ aryl $C_1$-$C_{10}$ alkyl" as used herein refers to a $C_1$-$C_{10}$ alkyl moiety which is substituted with a $C_6$-$C_{14}$ aryl moiety. Examples of "$C_6$-$C_{14}$ aryl $C_1$-$C_{10}$ alkyl" include, but are not limited to, benzyl, phenylethyl, and the like.

The term "heterocyclyl" or "heterocycle" as used herein refers to monocyclic or bicyclic radicals which, may be fully saturated, partially saturated, or fully unsaturated or aromatic, having the number of annular carbon atoms designated (i.e., $C_3$-$C_{10}$ means three to ten annular carbon atoms) and containing at least one or more of the same or different heteroatoms selected from N, S or O, provided that at least one annular carbon atom is present and two annular oxygen atoms, if present, do not occupy directly neighboring positions. A "heterocyclyl" or "heterocycle" may be a 3 to 15-membered saturated or partially unsaturated ring containing 1 to 4 heteroatoms selected from O, S and N, where the ring may be monocyclic, bicyclic or tricyclic, contain at least one annular carbon atom and 1 to 3 nitrogen atoms, and/or 1 oxygen or sulfur atom or 1 or 2 oxygen and/or sulfur atoms; provided that when more than one annular oxygen atoms are present, they do not occupy directly neighboring positions. Examples of "heterocyclyl" or "heterocycle" include, but are not limited to, 2-oxiranyl, 2-aziridinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolinyl, 4-isoxazolinyl, 5-isoxazolinyl, 3-isothiazolinyl, 4-isothiazolinyl, 5-isothiazolinyl, 3-pyrazolinyl, 4-pyrazolinyl, 5-pyrazolinyl, 2-oxazolinyl, 4-oxazolinyl, 5-oxazolinyl, 2-thiazolinyl, 4-thiazolinyl, 5-thiazolinyl, 2-imidazolinyl, 4-imidazolinyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-thiadiazol-2-yl, 1,3,4-oxadiazol-2-yl, 1,3,4-triazol-2-yl, 2,3-dihydrofuran-2-yl, 2,3-dihydrofuran-3-yl, 2,4-dihydrofuran-2-yl, 2,4-dihydrofuran-3-yl, 2,3-dihydrothiophen-2-yl, 2,3-dihydrothiophen-3-yl, 2,4-dihydrothiophen-2-yl, 2,4-dihydrothiophen-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazolin-1-yl, 2,3-dihydropyrazolin-2-yl, 2,3-dihydropyrazolin-3-yl, 2,3-dihydropyrazolin-4-yl, 2,3-dihydropyrazolin-5-yl, 3,4-dihydropyrazoline-1-yl, 3,4-dihydropyrazolin-3-yl, 3,4-dihydropyrazolin-4-yl, 3,4-dihydropyrazolin-5-yl, 4,5-dihydropyrazolin-1-yl, 4,5-dihydropyrazolin-3-yl, 4,5-dihydropyrazolin-4-yl, 4,5-dihydropyrazolin-5-yl, 2,3-dihydrooxazolin-2-yl, 2,3-dihydrooxazolin-3-yl, 2,3-dihydrooxazolin-4-yl, 2,3-dihydrooxazolin-5-yl, 3,4-dihydrooxazolin-2-yl, 3,4-dihydrooxazolin-3-yl, 3,4-dihydrooxazolin-4-yl, 3,4-dihydrooxazolin-5-yl, 4,5-dihydrooxazolin-2-yl, 4,5-dihydrooxazolin-3-yl, 4,5-dihydrooxazolin-4-yl, piperidin-2-yl, piperidine-3-yl, piperidine-4-yl, 1,3-dioxane-5-yl, tetrahydropyran-2-yl, tetrahydropyran-4-yl, tetrahydrothiophen-2-yl, hexahydrodiazin-3-yl, hexahydrodiazin-4-yl, hexahydropyrimidin-2-yl, hexahydropyrimidin-4-yl, hexahydropyrimidin-5-yl, piperazin-2-yl, 1,3,5-triazinan-2-yl, 1,2,4-triazinan-3-yl, and the like.

The term "heteroaryl" as used herein refers to aromatic heterocyclyl or heterocycle as defined herein. Examples of "heteroaryl" include, but are not limited to, 2-furanyl, 3-furanyl, thiophen-2-yl, thiophen-3-yl, 1H-pyrrol-2-yl, 1H-pyrrol-3-yl, isoxazol-3-yl, isoxazol-4-yl, isoxazol-5-yl, isothiazol-3-yl, isothiazol-4-yl, isothiazol-5-yl, 1H-pyrazol-3-yl, 1H-pyrazol-4-yl, 1H-pyrazol-5-yl, oxazol-2-yl, oxazol-4-yl, oxazol-5-yl, thiazol-2-yl, thiazol-4-yl, thiazol-5-yl, 1H-imidazol-2-yl, 1H-imidazol-4-yl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-thiadiazol-2-yl, 1,3,4-oxadiazol-2-yl, 1,3,4-triazol-2-yl, 1H-pyrrol-1-yl, 1H-pyrazol-1-yl, 1,2,4-triazol-1-yl, imidazol-1-yl, 1,2,3-triazol-1-yl, 1,3,4-triazol-1-yl, pyridin-2-yl, pyridin-3-yl, pyridin-4-yl, diazin-2-yl, pyrimidin-2-yl, pyrimidin-4-yl, pyrimidin-5-yl, pyrazin-2-yl, 1,3,5-triazin-2-yl, 1,2,4-triazin-3-yl, 1,2,4,5-tetrazin-3-yl, indol-1-yl, indol-2-yl, indol-3-yl, indol-4-yl, indol-5-yl, indol-6-yl, indol-7-yl, benzo[d]imidazol-1-yl, benzo[d]imidazol-2-yl, benzo[d]imidazol-4-yl, benzo[d]imidazol-5-yl, indazol-1-yl, indazol-2-yl, indazol-3-yl, indazol-4-yl, indazol-5-yl, indazol-6-yl, indazol-7-yl, benzofuran-2-yl, benzofuran-3-yl, benzofuran-4-yl, benzofuran-5-yl, benzofuran-6-yl, benzofuran-7-yl, benzo[b]thiophen-2-yl, benzo[b]thiophen-3-yl, benzo[b]thiophen-4-yl, benzo[b]thiophen-5-yl, benzo[b]thiophen-6-yl, benzo[b]thiophen-7-yl, benzo[d]thiazol-2-yl, benzo[d]thiazol-4-yl, benzo[d]thiazol-5-yl, benzo[d]thiazol-6-yl, benzo[d]thiazol-7-yl, benzo[d]oxazol-2-yl, benzo[d]oxazol-4-yl, benzo[d]oxazol-5-yl, benzo[d]oxazol-6-yl, benzo[d]oxazol-7-yl, quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl, isoquinolin-8-yl, and the like.

The term "heterocyclyl $C_1$-$C_{10}$ alkyl" as used herein refers to a $C_1$-$C_{10}$ alkyl moiety which is substituted with a heterocyclyl moiety. Examples of "heterocyclyl $C_1$-$C_{10}$ alkyl" include, but are not limited to, tetrahydrofuranylmethyl and the like.

The term "heteroaryl $C_1$-$C_{10}$ alkyl" as used herein refers to a $C_1$-$C_{10}$ alkyl moiety which is substituted with a heteroaryl moiety. Examples of "heteroaryl $C_1$-$C_{10}$ alkyl" include, but are not limited to, oxazolylmethyl, pyridylethyl, and the like.

The term "solvate" refers to an aggregate formed by a solute molecule (such a compound of the invention) or ion with one or more solvent molecules via intermolecular forces such as Coulomb force, Van der Waals force, charge-dipole interactions and hydrogen bonding. When the solvent is water, the solvate is referred to as "hydrate."

Unless clearly indicated otherwise, "an individual" as used herein intends a mammal, including but not limited to a human. The invention may find use in both human medicine and in the veterinary context.

The term "administration" and variants thereof (e.g., "administering") in reference to a compound of the invention means introducing the compound or a prodrug of the compound into the system of the animal in need of treatment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treatment" refers to the treatment of a mammal afflicted with a pathological condition and refers to an effect that alleviates the condition, e.g., by killing the cancerous cells, but also to an effect that results in the inhibition of the progress of the condition, and includes a reduction in the rate of progress, a halt in the rate of progress, amelioration of the condition, and cure of the condition.

The term "prevention" includes providing prophylaxis with respect to occurrence or recurrence of a disease in an individual. An individual may be predisposed to, susceptible to the disease, or at risk of developing the disease, but has not yet been diagnosed with the disease.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Unless indicated otherwise, the term "pharmaceutically acceptable salt" as used herein, refers to salts which are suitable for use in contact with the tissues of a subject (e.g., human) without excessive adverse effect. In some embodiments, pharmaceutically acceptable salts include salts of a compound of the invention having an acidic group (for example, but not limited to, potassium salts, sodium, salts, magnesium salts, calcium salt, and the like) or a basic group (for example, but not limited to, sulfate, hydrochloride, phosphate, nitrate, carbonate, and the like).

Compounds

Compounds according to the invention are detailed herein, including in the Brief Summary of the Invention and the appended claims. The invention embraces all compounds detailed herein, including any synthetic intermediates and uses thereof. The invention includes the use of all of the compounds described herein, including any and all stereoisomers, including geometric isomers (cis/trans), salts and solvates of the compounds described herein, as well as methods of making such compounds.

In one aspect, provided is a compound of the formula (I):

(I)

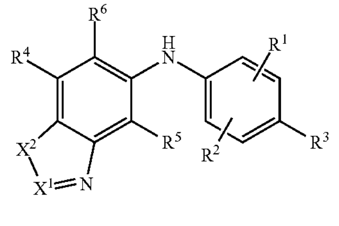

or a salt, prodrug or solvate thereof, wherein:

$X^1$ is $CR^{11}$ or N;

$X^2$ is O, S or carbonyl;

$R^1$, $R^2$, $R^4$ and $R^5$ are independently hydrogen, halo, nitro, azido, hydroxy, $C_1$-$C_{10}$ alkoxy, halo-substituted $C_1$-$C_{10}$ alkoxy, acyloxy, $C_1$-$C_{10}$ alkylthio, halo-substituted $C_1$-$C_{10}$ alkylthio, amino, carboxy, $C_1$-$C_{10}$ alkyl, $C_2$-$C_{10}$ alkenyl, $C_2$-$C_{10}$ alkynyl or $C_3$-$C_{10}$ cycloalkyl;

$R^3$ is hydrogen, halo, cyano, nitro, azido, hydroxy, $C_1$-$C_{10}$ alkoxy, halo-substituted $C_1$-$C_{10}$ alkoxy, acyloxy, mercapto, $C_1$-$C_{10}$ alkylthio, halo-substituted $C_1$-$C_{10}$ alkylthio, $—SO_2R^a$, $—SO_2N(R^c)R^d$, $—N(R^c)R^d$, $—C(O)OR^b$, $C_1$-$C_{10}$ alkyl, $C_2$-$C_{10}$ alkenyl, $C_2$-$C_{10}$ alkynyl or $C_3$-$C_{10}$ cycloalkyl;

$R^a$ is $C_1$-$C_{10}$ alkyl or $C_6$-$C_{14}$ aryl;

each $R^b$, $R^c$ and $R^d$ is independently hydrogen or $C_3$-$C_{10}$ alkyl;

$R^6$ is $—C(O)OR^7$, $—C(O)NR^7R^8$, $—C(O)N(R^8)OR^7$, $—C(O)R^9$ or $—NHSO_2R^{10}$;

each $R^7$ and $R^8$ is independently hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkyl $C_1$-$C_{10}$ alkyl or $C_1$-$C_{10}$ alkyl $C_3$-$C_{10}$ cycloalkyl;

$R^9$ is $C_1$-$C_{10}$ alkyl, $C_3$-$C_{10}$ cycloalkyl or $C_6$-$C_{14}$ aryl;

$R^{10}$ is $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkyl $C_1$-$C_{10}$ alkyl or $C_1$-$C_{10}$ alkyl $C_3$-$C_{10}$ cycloalkyl; and $R^{11}$ is hydrogen, $C_1$-$C_{10}$ alkyl, $C_2$-$C_{10}$ alkenyl, $C_2$-$C_{10}$ alkynyl, $C_3$-$C_{10}$ cycloalkyl or $C_3$-$C_{10}$ cycloalkyl $C_1$-$C_{10}$ alkyl;

wherein each $C_1$-$C_{10}$ alkyl, $C_2$-$C_{10}$ alkenyl, $C_2$-$C_{10}$ alkynyl or $C_3$-$C_{10}$ cycloalkyl moiety may be unsubstituted or substituted with one or more groups independently selected from the group consisting of hydroxy, oxo, halo, cyano, nitro, trifluoromethyl, azido, amino, carboxy and mercapto.

In some embodiments, the compound is of the formula (I), or a salt, prodrug or solvate thereof, provided that if $X^1$ is CH, $X^2$ is O or S, $R^1$ is methyl or chloro, $R^2$ is hydrogen and $R^3$ is iodo, then $R^6$ is —$NHSO_2R^{10}$ or —$C(O)N(R^8)OR^7$ where $R^7$ is $C_1$-$C_{10}$ alkyl substituted with at least one hydroxy group.

In another aspect, provided is a compound is of the formula (I):

(I)

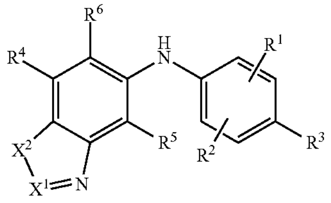

or a salt, prodrug or solvate thereof, wherein:

$X^1$ is $CR^{11}$ or N;

$X^2$ is O, S or carbonyl;

$R^1$, $R^2$, $R^4$ and $R^5$ are independently hydrogen, halo, nitro, azido, hydroxy, $C_1$-$C_{10}$ alkoxy, halo-substituted $C_1$-$C_{10}$ alkoxy, acyloxy, $C_1$-$C_{10}$ alkylthio, halo-substituted $C_1$-$C_{10}$ alkylthio, amino, carboxy, $C_1$-$C_{10}$ alkyl, $C_2$-$C_{10}$ alkenyl, $C_2$-$C_{10}$ alkynyl or $C_3$-$C_{10}$ cycloalkyl;

$R^3$ is hydrogen, halo, cyano, nitro, azido, hydroxy, $C_1$-$C_{10}$ alkoxy, halo-substituted $C_1$-$C_{10}$ alkoxy, acyloxy, mercapto, $C_1$-$C_{10}$ alkylthio, halo-substituted $C_1$-$C_{10}$ alkylthio, —$SO_2R^a$, —$SO_2N(R^c)R^d$, —$N(R^c)R^d$, —$C(O)OR^b$, $C_1$-$C_{10}$ alkyl, $C_2$-$C_{10}$ alkenyl, $C_2$-$C_{10}$ alkynyl or $C_3$-$C_{10}$ cycloalkyl;

$R^a$ is $C_1$-$C_{10}$ alkyl or $C_6$-$C_{14}$ aryl;

each $R^b$, $R^c$ and $R^d$ is independently hydrogen or $C_1$-$C_{10}$ alkyl;

$R^6$ is —$C(O)OR^7$, —$C(O)NR^7R^8$, —$C(O)N(R^8)OR^7$, —$C(O)R^9$ or —$NHSO_2R^{10}$;

each $R^7$ and $R^8$ is independently hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkyl $C_1$-$C_{10}$ alkyl or $C_1$-$C_{10}$ alkyl $C_3$-$C_{10}$ cycloalkyl;

$R^9$ is $C_1$-$C_{10}$ alkyl, $C_3$-$C_{10}$ cycloalkyl or $C_6$-$C_{14}$ aryl;

$R^{10}$ is $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkyl $C_1$-$C_{10}$ alkyl or $C_1$-$C_{10}$ alkyl $C_3$-$C_{10}$ cycloalkyl; and $R^{11}$ is hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkyl $C_1$-$C_{10}$ alkyl, halo, $C_1$-$C_{10}$ alkoxy or $C_1$-$C_{10}$ alkylthio;

wherein each $C_1$-$C_{10}$ alkyl, $C_2$-$C_{10}$ alkenyl, $C_2$-$C_{10}$ alkynyl or $C_3$-$C_{10}$ cycloalkyl moiety may be unsubstituted or substituted with one or more groups independently selected from the group consisting of hydroxy, oxo, halo, cyano, nitro, trifluoromethyl, azido, amino, carboxy and mercapto;

provided that if $X^1$ is CH, $X^2$ is O or S, $R^1$ is methyl or chloro, $R^2$ is hydrogen and $R^3$ is iodo, then $R^6$ is —$NHSO_2R^{10}$ or —$C(O)N(R^8)OR^7$ where $R^7$ is $C_1$-$C_{10}$ alkyl substituted with at least one hydroxy group.

In some embodiments, the compound is of the formula (I), or a salt, prodrug or solvate thereof, wherein $X^1$ is N or $CR^{11}$. In some embodiments, $X^1$ is N. In some embodiments, $X^1$ is $CR^{11}$ where $R^{11}$ is hydrogen, $C_1$-$C_{10}$ alkyl, $C_2$-$C_{10}$ alkenyl, $C_2$-$C_{10}$ alkynyl, $C_3$-$C_{10}$ cycloalkyl or $C_3$-$C_{10}$ cycloalkyl $C_1$-$C_{10}$ alkyl. In some of these embodiments, $R^{11}$ is hydrogen. In some of these embodiments, $R^{11}$ is $C_1$-$C_{10}$ alkyl, $C_3$-$C_{10}$ cycloalkyl or $C_3$-$C_{10}$ cycloalkyl $C_1$-$C_{10}$ alkyl. In some other embodiments, $R^{11}$ is halo, $C_1$-$C_{10}$ alkoxy or $C_1$-$C_{10}$ alkylthio.

In some embodiments, the compound is of the formula (I), or a salt, prodrug or solvate thereof, wherein $X^2$ is O, S or carbonyl. In some embodiments, $X^2$ is S. In some embodiments, $X^2$ is O. In some embodiments, $X^2$ is carbonyl.

It is intended and understood that each and every variations of $X^2$ described for the formula (I) may be combined with each and every variations of $X^1$ described for the formula (I) as if each and every combinations are individually described. For example, in some embodiments, $X^1$ is N and is S. In some embodiments, $X^1$ is N and $X^2$ is O or carbonyl. In some embodiments, $X^1$ is $CR^{11}$ and $X^2$ is O or S. In one variation, $X^1$ is $CR^{11}$ and $X^2$ is O. In another variation, $X^1$ is $CR^{11}$ and $X^2$ is S. In some embodiments. $X^1$ is CH and $X^2$ is O or S. In one variation, $X^1$ is CH and $X^2$ is O. In another variation, $X^1$ is CH and $X^2$ is S.

In some embodiments, the compound is of the formula (I), or a salt, prodrug or solvate thereof, wherein $R^1$ is hydrogen, halo, nitro, azido, hydroxy, $C_1$-$C_{10}$ alkoxy, halo-substituted $C_1$-$C_{10}$ alkoxy, acyloxy, $C_1$-$C_{10}$ alkylthio, halo-substituted $C_1$-$C_{10}$ alkylthio, amino, carboxy, $C_1$-$C_{10}$ alkyl, $C_2$-$C_{10}$ alkenyl, $C_2$-$C_{10}$ alkynyl or $C_3$-$C_{10}$ cycloalkyl. In some embodiments, $R^1$ is halo (e.g., fluoro or chloro). In some embodiments, $R^1$ is nitro, azido, hydroxy, amino or carboxy. In some embodiments, $R^1$ is $C_1$-$C_{10}$ alkoxy, halo-substituted $C_1$-$C_{10}$ alkoxy, acyloxy $C_1$-$C_{10}$ alkylthio or halo-substituted $C_1$-$C_{10}$ alkylthio. In some embodiments, $R^1$ is unsubstituted or substituted $C_1$-$C_{10}$ alkyl, unsubstituted or substituted $C_2$-$C_{10}$ alkenyl, unsubstituted or substituted $C_2$-$C_{10}$ alkynyl or unsubstituted or substituted $C_3$-$C_{10}$ cycloalkyl. In some embodiments, $R^1$ is unsubstituted $C_1$-$C_{10}$ alkyl (e.g., methyl).

In some embodiments, $R^1$ is hydrogen, halo or $C_1$-$C_6$ alkyl. In some embodiments, $R^1$ is hydrogen, halo or $C_1$-$C_4$ alkyl. In some embodiments, $R^1$ is hydrogen, fluoro, chloro, bromo or $C_1$-$C_2$ alkyl. In some embodiments, $R^1$ is hydrogen, fluoro, chloro or methyl.

In some embodiments, the compound is of the formula (I), or a salt, prodrug or solvate thereof, wherein $R^2$ is hydrogen, halo, nitro, azido, hydroxy, $C_1$-$C_{10}$ alkoxy, halo-substituted $C_1$-$C_{10}$ alkoxy, acyloxy, $C_1$-$C_{10}$ alkylthio, halo-substituted $C_1$-$C_{10}$ alkylthio, amino, carboxy, $C_1$-$C_{10}$ alkyl, $C_2$-$C_{10}$ alkenyl, $C_2$-$C_{10}$ alkynyl or $C_3$-$C_{10}$ cycloalkyl. In some embodiments, $R^2$ is hydrogen. In some embodiments, $R^2$ is halo, nitro, azido, hydroxy, $C_1$-$C_{10}$ alkoxy, halo-substituted $C_1$-$C_{10}$ alkoxy, acyloxy, $C_1$-$C_{10}$ alkylthio, halo-substituted $C_1$-$C_{10}$ alkylthio, amino or carboxy. In some embodiments, $R^2$ is $C_1$-$C_{10}$ alkyl, $C_2$-$C_{10}$ alkenyl, $C_2$-$C_{10}$ alkynyl or $C_3$-$C_{10}$ cycloalkyl.

In some embodiments, $R^2$ is hydrogen, halo or $C_1$-$C_6$ alkyl. In some embodiments, $R^2$ is hydrogen, halo or $C_1$-$C_4$ alkyl. In some embodiments, R is hydrogen, fluoro, chloro, bromo or $C_1$-$C_2$ alkyl. In some embodiments, $R^2$ is hydrogen, fluoro, chloro or methyl.

In some embodiments, the compound is of the formula (I), or a salt, prodrug or solvate thereof, wherein $R^3$ is hydrogen, halo, cyano, nitro, azido, hydroxy, $C_1$-$C_{10}$ alkoxy, halo-substituted $C_1$-$C_{10}$ alkoxy, acyloxy, mercapto, $C_1$-$C_{10}$ alkylthio, halo-substituted $C_1$-$C_{10}$ alkylthio, —$SO_2R^a$, —$SO_2N(R^c)R^d$, —$N(R^c)R^d$, —$C(O)OR^b$, $C_1$-$C_{10}$ alkyl, $C_2$-$C_{10}$ alkenyl, $C_2$-$C_{10}$ alkynyl or $C_3$-$C_{10}$ cycloalkyl. In some embodiments, $R^3$ is halo or cyano. In some embodiments, $R^3$ is halo (e.g., iodo or bromo). In some embodiments, $R^3$ is nitro, azido, hydroxy or mercapto, —$SO_2R^a$, —$SO_2N(R^c)R^d$, —$N(R^c)R^d$ or —$C(O)OR^b$. In some of these embodiments, $R^3$ is —$SO_2R^a$ where $R^a$ is $C_1$-$C_{10}$ alkyl or $C_6$-$C_{14}$ aryl. In one variation, $R^a$ is unsubstituted or substituted $C_1$-$C_{10}$ alkyl (e.g., methyl). In some of these embodiments, $R^3$ is —$SO_2N(R^c)R^d$ where $R^c$ and $R^d$ are independently hydrogen or $C_1$-$C_{10}$ alkyl. In one variation, $R^3$ is —$SO_2N(R^c)R^d$ where each $R^c$ and $R^d$ is independently unsubstituted or substituted $C_1$-$C_{10}$ alkyl. In some of these embodiments, $R^3$ is —$N(R^c)R^a$ where $R^c$ and $R^d$ are independently hydrogen or $C_1$-$C_{10}$ alkyl. In one variation, $R^3$ is —$N(R^c)R^d$ where each $R^c$ and $R^d$ is independently hydrogen or methyl. In one particular variation, $R^3$ is $NMe_2$. In some of these embodiments, $R^3$ is —$C(O)OR^b$ where $R^b$ is hydrogen or $C_1$-$C_{10}$ alkyl. In one variation, $R^3$ is —$C(O)OR^b$ where $R^b$ is hydrogen (i.e., $R^3$ is carboxy). In another variation, $R^3$ is —$C(O)OR^b$ where $R^b$ is unsubstituted or substituted $C_1$-$C_{10}$ alkyl (e.g., methyl or ethyl). In some embodiments, $R^3$ is $C_1$-$C_{10}$ alkoxy, halo-substituted $C_1$-$C_{10}$ alkoxy (e.g., trifluoromethoxy), acyloxy, $C_1$-$C_{10}$ alkylthio (e.g., methylthio), or halo-substituted $C_1$-$C_{10}$ alkylthio. In some embodiments, $R^3$ is $C_1$-$C_{10}$ alkyl, $C_2$-$C_{10}$ alkenyl, $C_2$-$C_{10}$ alkynyl or $C_3$-$C_{10}$ cycloalkyl. In some embodiments, $R^3$ is unsubstituted or substituted $C_1$-$C_{10}$ alkyl, such as halo-substituted $C_1$-$C_{10}$ alkyl (e.g., trifluoromethyl).

In some embodiments, $R^3$ is hydrogen, halo, $C_1$-$C_6$ alkoxy, $C_1$-$C_6$ alkyl, halo-substituted $C_1$-$C_6$ alkyl, $C_1$-$C_6$ alkylthio, halo-substituted $C_1$-$C_6$ alkoxy or halo-substituted $C_1$-$C_6$ alkylthio. In some embodiments, $R^3$ is fluoro, chloro, bromo, iodo, $C_1$-$C_4$ alkyl, halo-substituted $C_3$-$C_4$ alkyl, $C_1$-$C_4$ alkoxy, $C_3$-$C_4$ alkylthio, halo-substituted $C_1$-$C_4$ alkoxy or halo-substituted $C_1$-$C_4$ alkylthio. In some embodiments, $R^3$ is bromo, iodo, $C_1$-$C_2$ alkylthio, halo-substituted $C_1$-$C_2$ alkylthio, $C_1$-$C_2$ alkoxy, halo-substituted $C_1$-$C_2$ alkoxy, $C_1$-$C_2$ alkyl or halo-substituted $C_1$-$C_2$ alkyl. In some embodiments, $R^3$ is bromo, iodo, methyl, methoxy, methylthio, trifluoromethyl, trifluoromethoxy or trifluoromethylthio.

In some embodiments, the compound is of the formula (I), or a salt, prodrug or solvate thereof, wherein $R^4$ is hydrogen, halo, nitro, azido, hydroxy, $C_1$-$C_{10}$ alkoxy, halo-substituted $C_1$-$C_{10}$ alkoxy, acyloxy, $C_1$-$C_{10}$ alkylthio, halo-substituted $C_1$-$C_{10}$ alkylthio, amino, carboxy, $C_1$-$C_{10}$ alkyl, $C_2$-$C_{10}$ alkenyl, $C_2$-$C_{10}$ alkynyl or $C_3$-$C_{10}$ cycloalkyl. In some embodiments, $R^4$ is hydrogen. In some embodiments, $R^4$ is halo, nitro, azido, hydroxy, amino or carboxy. In some embodiments, $R^4$ is $C_1$-$C_{10}$ alkoxy, halo-substituted $C_1$-$C_{10}$ alkoxy, acyloxy, $C_1$-$C_{10}$ alkylthio or halo-substituted $C_1$-$C_{10}$ alkylthio. In some embodiments, $R^4$ is $C_1$-$C_{10}$ alkyl, $C_2$-$C_{10}$ alkenyl, $C_2$-$C_{10}$ alkynyl or $C_3$-$C_{10}$ cycloalkyl.

In some embodiments, $R^4$ is hydrogen, halo or $C_1$-$C_6$ alkyl. In some embodiments, $R^4$ is hydrogen or $C_1$-$C_4$ alkyl. In some embodiments, $R^4$ is hydrogen or $C_1$-$C_2$ alkyl. In some embodiments, $R^4$ is hydrogen.

In some embodiments, the compound is of the formula (I), or a salt, prodrug or solvate thereof, wherein $R^5$ is hydrogen, halo, nitro, azido, hydroxy, $C_1$-$C_{10}$ alkoxy, halo-substituted $C_1$-$C_{10}$ alkoxy, acyloxy. $C_1$-$C_{10}$ alkylthio, halo-substituted $C_1$-$C_{10}$ alkylthio, amino, carboxy, $C_1$-$C_{10}$ alkyl, $C_2$-$C_{10}$ alkenyl, $C_2$-$C_{10}$ alkynyl or $C_3$-$C_{10}$ cycloalkyl. In some embodiments, $R^5$ is hydrogen or halo or unsubstituted or substituted $C_1$-$C_{10}$ alkyl. In some embodiments, $R^5$ is hydrogen. In some embodiments, $R^5$ is fluoro. In some embodiments, $R^5$ is $C_1$-$C_{10}$ alkyl (e.g., methyl). In some embodiments, $R^5$ is halo, nitro, azido, hydroxy, amino or carboxy. In some embodiments, $R^5$ is $C_1$-$C_{10}$ alkoxy, halo-substituted $C_1$-$C_{10}$ alkoxy, acyloxy, $C_1$-$C_{10}$ alkylthio or halo-substituted $C_1$-$C_{10}$ alkylthio. In some embodiments, $R^5$ is $C_1$-$C_{10}$ alkyl, $C_2$-$C_{10}$ alkenyl, $C_2$-$C_{10}$ alkynyl or $C_3$-$C_{10}$ cycloalkyl.

In some embodiments, $R^3$ is hydrogen, halo or $C_1$-$C_6$ alkyl. In some embodiments, $R^5$ is hydrogen, halo or $C_1$-$C_4$ alkyl. In some embodiments, $R^5$ is hydrogen, fluoro, chloro, bromo or $C_1$-$C_2$ alkyl. In some embodiments, $R^5$ is hydrogen, fluoro, chloro or methyl.

It is intended and understood that each and every variations of $R^1$, $R^2$, $R^3$, $R^4$ or $R^5$ described for the formula (I) may be combined with each and every variations of another one or more of $R^1$, $R^2$, $R^3$, $R^4$ and $R^5$ and/or each and every variations of $X^1$ and $X^2$ described for the formula (I) as if each and every combinations are individually described. For example, in some embodiments, provided is a compound of the formula (I), or a salt, prodrug or solvate thereof, where $X^1$ is N, $X^2$ is S, $R^1$ is halo (e.g., fluoro or chloro), $R^2$ is hydrogen, $R^3$ is halo (e.g., iodo or bromo), $R^4$ is hydrogen and $R^3$ is fluoro. In some of these embodiments, $X^1$ is N, $X^2$ is S, $R^1$ is fluoro. $R^2$ is hydrogen, $R^3$ is iodo, $R^4$ is hydrogen and $R^5$ is fluoro. In some of these embodiments. $X^1$ is N, $X^2$ is S, $R^1$ is chloro. $R^2$ is hydrogen, $R^3$ is bromo, $R^4$ is hydrogen and $R^5$ is fluoro. In some embodiments, $X^1$ is $CR^{11}$ where $R^{11}$ is hydrogen, $X^2$ is S, $R^1$ is halo (e.g., fluoro or chloro), $R^2$ is hydrogen, $R^3$ is halo (e.g., iodo or bromo), $R^4$ is hydrogen and $R^5$ is fluoro. In some of these embodiments. $X^1$ is CH, $X^2$ is S, $R^1$ is fluoro, $R^2$ is hydrogen, $R^3$ is iodo, $R^4$ is hydrogen and $R^5$ is fluoro. In some of these embodiments, $X^1$ is CH, $X^2$ is S, $R^1$ is chloro, $R^2$ is hydrogen, $R^3$ is bromo, $R^4$ is hydrogen and $R^5$ is fluoro. In some embodiments, $X^1$ is $CR^{11}$ where $R^{11}$ is hydrogen, $X^2$ is O, $R^1$ is halo (e.g., fluoro or chloro), $R^2$ is hydrogen, $R^3$ is halo (e.g., iodo or bromo), $R^4$ is hydrogen and $R^3$ is fluoro. In some of these embodiments, $X^1$ is CH, $X^2$ is O, $R^1$ is fluoro, $R^2$ is hydrogen, $R^3$ is iodo, $R^4$ is hydrogen and $R^5$ is fluoro. In some of these embodiments, $X^1$ is CH, $X^2$ is O, $R^1$ is chloro, $R^2$ is hydrogen, $R^3$ is bromo, $R^4$ is hydrogen and $R^5$ is fluoro.

In some embodiments, the compound is of the formula (I), or a salt, prodrug or solvate thereof, wherein $R^6$ is —$C(O)OR^7$, —$C(O)NR^7R^8$, —$C(O)N(R^8)OR^7$, —$C(O)R^9$ or —$NHSO_2R^{10}$. In some embodiments. $R^6$ is —$C(O)OR^7$. In some embodiments, $R^6$ is —$C(O)NR^7R^8$. In some embodiments, $R^6$ is —$C(O)N(R^8)OR^7$ where each $R^7$ and $R^8$ is independently hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkyl $C_1$-$C_{10}$ alkyl or $C_1$-$C_{10}$ alkyl $C_3$-$C_{10}$ cycloalkyl. In some of these embodiments, $R^7$ is hydrogen, unsubstituted or substituted $C_1$-$C_{10}$ alkyl or unsubstituted or substituted $C_3$-$C_{10}$ cycloalkyl. In some embodiments, $R^7$ is $C_3$-$C_{10}$ cycloalkyl $C_1$-$C_{10}$ alkyl (e.g., cyclopropyl methyl). In some of these embodiments, $R^7$ is substituted $C_1$-$C_{10}$ alkyl, such as $C_1$-$C_{10}$ alkyl substituted with at least one hydroxy group. In some of these embodiments, $R^7$ is $C_1$-$C_{10}$ alkyl substituted with at least 1 to 3 hydroxy groups. In some of these embodiments, $R^7$ is $C_1$-$C_6$ alkyl substituted with at least 1 to 3 hydroxy groups. In some of these embodiments, $R^7$ is $C_1$-$C_4$ alkyl substituted with 1 or 2 hydroxy groups (e.g., 2-hydroxyethyl, 3-hydroxy-2-methylpropyl, 2,3-dihydroxypropyl and 1,3-dihydroxy-2-propyl). In some of these embodiments, $R^7$ is selected from the group consisting of 2-hydroxyethyl, 3-hydroxy-2-methylpropyl, 2,3-dihydroxypropyl and 1,3-dihydroxy-2-propyl. In some of these embodiments, $R^7$ is selected from the group consisting of 2-hydroxyethyl, (R)-3-hydroxy-2-methylpropyl, (S)-3-hydroxy-2-methylpropyl, (R)-2,3-dihydroxypropyl, (S)-2,3-dihydroxypropyl and 1,3-dihydroxy-2-propyl. In some of these embodiments, $R^7$ is unsubstituted or substituted $C_2$-$C_{10}$ alkenyl or unsubstituted or substituted $C_2$-$C_{10}$ alkynyl. In some of these embodiments, $R^7$ is hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkyl $C_1$-$C_{10}$ alkyl or $C_1$-$C_{10}$ alkyl $C_3$-$C_{10}$ cycloalkyl. In some of these embodiments, $R^8$ is hydrogen or unsubstituted or substituted $C_1$-$C_{10}$ alkyl. In some of these embodiments, $R^8$ is $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkyl $C_1$-$C_{10}$ alkyl or $C_1$-$C_{10}$ alkyl $C_3$-$C_{10}$ cycloalkyl. In some embodiments, $R^6$ is —C(O)$R^9$ where $R^9$ is unsubstituted or substituted $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkyl $C_1$-$C_{10}$ alkyl or $C_1$-$C_{10}$ alkyl $C_3$-$C_{10}$ cycloalkyl. In some embodiments, $R^6$ is —$NHSO_2R^{10}$ where $R^{10}$ is $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkyl $C_1$-$C_{10}$ alkyl or $C_1$-$C_{10}$ alkyl $C_3$-$C_{10}$ cycloalkyl. In some of these embodiments, $R^{10}$ is unsubstituted or substituted $C_1$-$C_{10}$ alkyl or optionally substituted $C_3$-$C_{10}$ cycloalkyl. In some of these embodiments, $R^{10}$ is $C_1$-$C_{10}$ alkyl or $C_3$-$C_{10}$ cycloalkyl (e.g., cyclopropyl). In some of these embodiments, $R^{10}$ is unsubstituted or substituted $C_1$-$C_{10}$ alkyl $C_3$-$C_{10}$ cycloalkyl, such as $C_1$-$C_{10}$ alkyl $C_3$-$C_{10}$ cycloalkyl substituted with at least one hydroxy group. In some of these embodiments, $R^{10}$ is $C_1$-$C_{10}$ alkyl $C_3$-$C_{10}$ cycloalkyl substituted with 1 or 2 hydroxy groups (e.g., 1-(2,3-dihydroxypropyl)cyclopropyl). In some of these embodiments, $R^{10}$ is (R)-1-(2,3-dihydroxypropyl)cyclopropyl) or (S)-1-(2,3-dihydroxypropyl)cyclopropyl). In some of these embodiments, $R^{10}$ is $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkyl $C_1$-$C_{10}$ alkyl or $C_1$-$C_{10}$ alkyl $C_3$-$C_{10}$ cycloalkyl.

In some embodiments, $R^6$ is —C(O)N($R^8$)$OR^7$, —C(O)$NR^7R^8$ or —$NHSO_2R^{10}$; each $R^7$ and $R^8$ is independently hydrogen, $C_1$-$C_6$ alkyl, $C_3$-$C_6$ cycloalkyl, $C_3$-$C_6$ cycloalkyl $C_1$-$C_6$ alkyl or $C_1$-$C_6$ alkyl $C_3$-$C_6$ cycloalkyl; and $R^{10}$ is $C_1$-$C_6$ alkyl, $C_3$-$C_6$ cycloalkyl, $C_3$-$C_6$ cycloalkyl $C_1$-$C_6$ alkyl or $C_1$-$C_6$ alkyl $C_3$-$C_6$ cycloalkyl; where each of the $C_1$-$C_6$ alkyl, $C_3$-$C_6$, cycloalkyl, $C_3$-$C_6$ cycloalkyl $C_1$-$C_6$ alkyl and $C_1$-$C_6$ alkyl $C_3$-$C_6$ cycloalkyl groups may be unsubstituted or substituted with one or more groups selected from the group consisting of hydroxy and mercapto. In some embodiments, $R^6$ is —C(O)N($R^8$)$OR^7$, —C(O)$NR^7R^8$ or —$NHSO_2R^{10}$; each $R^7$ and $R^{10}$ is independently $C_1$-$C_4$ alkyl, $C_3$-$C_4$ cycloalkyl, $C_3$-$C_4$ cycloalkyl $C_1$-$C_4$ alkyl or $C_1$-$C_4$ alkyl $C_3$-$C_4$ cycloalkyl, where each of the $C_1$-$C_4$ alkyl, $C_3$-$C_4$ cycloalkyl, $C_3$-$C_4$ cycloalkyl $C_1$-$C_4$ alkyl or $C_1$-$C_4$ alkyl $C_3$-$C_4$ cycloalkyl groups may be unsubstituted or substituted with 1 to 6 hydroxy groups; and $R^8$ is hydrogen or $C_1$-$C_4$ alkyl. In some embodiments, $R^6$ is —C(O)N($R^8$)$OR^7$ or —$NHSO_2R^{10}$ each $R^7$ and $R^{10}$ is independently $C_1$-$C_3$ alkyl, $C_3$-$C_4$ cycloalkyl, $C_3$-$C_4$ cycloalkyl $C_1$-$C_3$ alkyl or $C_1$-$C_3$ alkyl $C_3$-$C_4$ cycloalkyl, where each of the $C_1$-$C_3$ alkyl, $C_3$-$C_4$ cycloalkyl, $C_3$-$C_4$ cycloalkyl $C_1$-$C_3$ alkyl or $C_1$-$C_3$ alkyl $C_3$-$C_4$ cycloalkyl groups may be unsubstituted or substituted with 1 to 3 hydroxy groups; and $R^8$ is hydrogen. In some embodiments, $R^6$ is —C(O)NH$OR^7$ or —$NHSO_2R^{10}$ where each $R^7$ and $R^{10}$ is independently selected from the group consisting of 2-hydroxyethyl, 2,3-dihydroxypropyl, 1,3-dihydroxy-2-propyl, 3-hydroxy-2-methylpropyl, cyclopropyl and 1-(2,3-dihydroxypropyl)cyclopropyl.

It is intended and understood that each and every variations of $R^6$ described for the formula (I) may be combined with each and every variations of $X^1$, $X^2$, $R^1$, $R^2$, $R^3$, $R^4$ and/or $R^5$ described for the formula (I) as if each and every combinations are individually described. For example, in some embodiments, provided is a compound of the formula (I), or a salt, prodrug or solvate thereof, where $X^1$ is N or $CR^{11}$ where $R^{11}$ is H, $X^2$ is O or S, $R^1$ is halo (e.g., fluoro or chloro), $R^2$ is hydrogen, $R^3$ is halo (e.g., iodo or bromo), $R^4$ is hydrogen, $R^5$ is fluoro and $R^6$ is —C(O)N($R^8$)$OR^7$ where $R^7$ is $C_1$-$C_{10}$ alkyl substituted with at least 1 to 3 hydroxy groups and $R^8$ is hydrogen. In some of these embodiments, $X^1$ is N, $X^2$ is S, $R^1$ is halo (e.g., fluoro or chloro), $R^2$ is hydrogen, $R^3$ is halo (e.g., iodo or bromo), $R^4$ is hydrogen, $R^5$ is fluoro and $R^6$ is —C(O)NH$OR^7$ where $R^7$ is $C_1$-$C_4$ alkyl substituted with 1 or 2 hydroxy groups (e.g., 2-hydroxyethyl, 3-hydroxy-2-methylpropyl, 2,3-dihydroxypropyl and 1,3-dihydroxy-2-propyl). In some of these embodiments, $X^1$ is N, $X^2$ is S, $R^1$ is fluoro, $R^2$ is hydrogen, $R^3$ is iodo, $R^4$ is hydrogen, $R^5$ is fluoro and $R^6$ is —C(O)$NHOCH_2CH_2OH$. In some of these embodiments, $X^1$ is N, $X^2$ is S, $R^1$ is chloro, $R^2$ is hydrogen, $R^3$ is bromo, $R^4$ is hydrogen, $R^5$ is fluoro and $R^6$ is —C(O)$NHOCH_2CH_2OH$. In some embodiments, $X^1$ is $CR^{11}$ where $R^{11}$ is hydrogen, $X^2$ is O or S, $R^1$ is halo (e.g., fluoro or chloro), $R^2$ is hydrogen, $R^3$ is halo (e.g., iodo or bromo), $R^4$ is hydrogen, $R^5$ is fluoro and $R^6$ is —C(O)NH$OR^7$ where $R^7$ is $C_1$-$C_4$ alkyl substituted with 1 or 2, hydroxy groups (e.g., 2-hydroxyethyl, 3-hydroxy-2-methylpropyl, 2,3-dihydroxypropyl and 1,3-dihydroxy-2-propyl). In some of these embodiments, $X^1$ is CH, $X^2$ is S, $R^1$ is fluoro, $R^2$ is hydrogen, $R^3$ is iodo, $R^4$ is hydrogen, $R^5$ is fluoro, and $R^6$ is —C(O)$NHOCH_2CH_2OH$. In some of these embodiments, $X^1$ is CH, $X^2$ is S, $R^1$ is chloro, $R^2$ is hydrogen, $R^3$ is bromo, $R^4$ is hydrogen and $R^5$ is fluoro. In some of these embodiments, $X^1$ is CH, $X^2$ is O, $R^1$ is fluoro, $R^2$ is hydrogen, $R^3$ is iodo, $R^4$ is hydrogen, $R^5$ is fluoro, and $R^6$ is —C(O)$NHOCH_2CH_2OH$. In some of these embodiments, $X^1$ is CH, $X^2$ is O, $R^1$ is chloro, $R^2$ is hydrogen, $R^3$ is bromo, $R^4$ is hydrogen, $R^5$ is fluoro, and $R^6$ is —C(O)$NHOCH_2CH_2OH$.

Also provided is a compound of the formula (I-1):

(I-1)

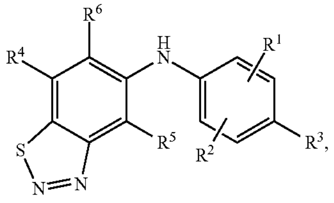

or a salt, prodrug or solvate thereof, wherein:

$R^1$, $R^2$, $R^4$ and $R^5$ are independently hydrogen, halo, nitro, azido, hydroxy, $C_1$-$C_{10}$ alkyl, $C_1$-$C_{10}$ alkoxy, halo-substituted $C_1$-$C_{10}$ alkoxy, $C_1$-$C_{10}$ alkylthio, halo-substituted $C_1$-$C_{10}$ alkylthio, carboxy, —OC(O)H, amino, $C_2$-$C_{10}$ alkenyl, $C_2$-$C_{10}$ alkynyl or $C_3$-$C_{10}$ cycloalkyl;

$R^3$ is hydrogen, halo, cyano, nitro, azido, hydroxy, $C_1$-$C_{10}$ alkoxy, halo-substituted $C_1$-$C_{10}$ alkoxy, mercapto, $C_1$-$C_{10}$ alkylthio, halo-substituted $C_1$-$C_{10}$ alkylthio, carboxy, —OC(O)H, amino, $C_1$-$C_{10}$ alkyl, $C_2$-$C_{10}$ alkenyl, $C_2$-$C_{10}$ alkynyl or $C_3$-$C_{10}$ cycloalkyl;

$R^6$ is —C(O)OR$^7$, —C(O)NR$^7$R$^8$, —C(O)N(R$^8$)OR$^7$, —C(O)($C_3$-$C_{10}$ cycloalkyl), —C(O)($C_1$-$C_{10}$ alkyl), —C(O)($C_6$-$C_{14}$ aryl), or —NHSO$_2$R$^7$;

each $R^7$ and $R^8$ is independently hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkyl $C_1$-$C_{10}$ alkyl or $C_1$-$C_{10}$ alkyl $C_3$-$C_{10}$ cycloalkyl;

wherein each $C_1$-$C_{10}$ alkyl, $C_2$-$C_{10}$ alkenyl, $C_2$-$C_{10}$ alkynyl or $C_3$-$C_{10}$ cycloalkyl moiety may be unsubstituted or substituted with one or more groups independently selected from the group consisting of hydroxy, oxo, halo, cyano, nitro, trifluoromethyl, azido, amino, carboxy and mercapto.

In some embodiments, the compound of the formula (I-1) is a compound of the formula (I-1-a), (I-1-b), (I-1-c) or (I-1-d):

(I-1-a)

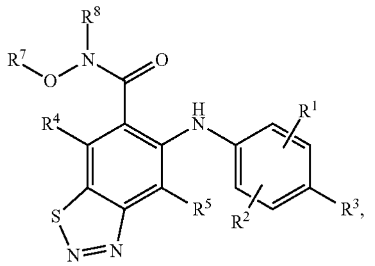

(I-1-b)

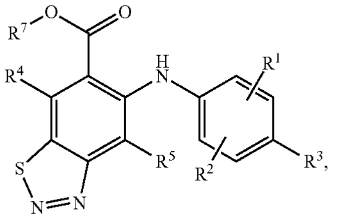

(I-1-c)

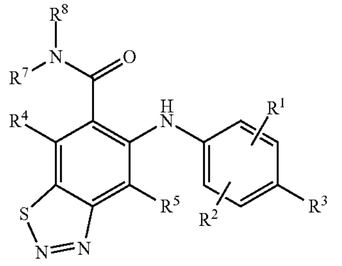

or (I-1-d)

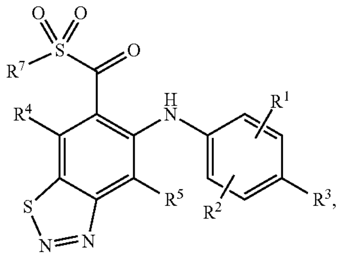

or a salt, prodrug or solvate thereof, wherein $R^1$, $R^2$, $R^3$, $R^4$, $R^5$, $R^6$, $R^7$ and $R^8$ are as defined for the formula (I-1).

In some embodiments, the compound is of the formula (I-1), (I-1-a), (I-1-b), (I-1-c) or (I-1-d), or a salt, prodrug or solvate thereof, wherein $R^1$, $R^2$, $R^3$, $R^4$, $R^5$, $R^6$, $R^7$ and $R^8$, where applicable, are as defined for the formula (I) or any applicable variations thereof.

In some embodiments, the compound of the formula (I-1) is a compound of the formula (I-1-e):

(I-1-e)

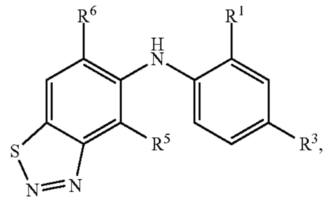

or a salt, prodrug or solvate thereof, wherein $R^1$, $R^3$, $R^5$ and $R^6$ are as defined for the formula (I), (I-1), or any applicable variations thereof. In some particular embodiments of the compound of the formula (I-1-e), or a salt, prodrug or solvate thereof, wherein $R^6$ is selected from the group consisting of:

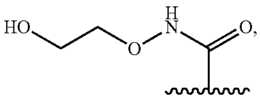

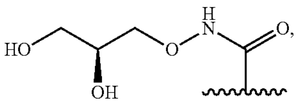

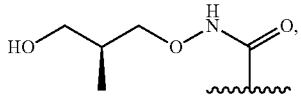

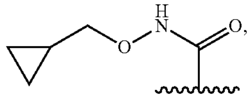

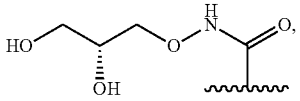

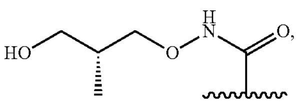

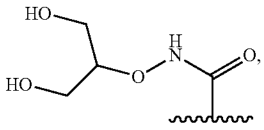

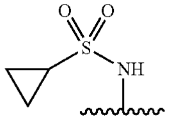

and

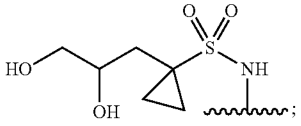

and $R^1$, $R^3$ and $R^5$ are as described in Table 1.

TABLE 1

| $R^1$ | $R^3$ | $R^5$ | $R^1$ | $R^3$ | $R^5$ | $R^1$ | $R^3$ | $R^5$ |
|---|---|---|---|---|---|---|---|---|
| F | Br | F | F | Br | Me | F | Br | H |
| F | I | F | F | I | Me | F | I | H |
| F | SMe | F | F | SMe | Me | F | SMe | H |
| F | $OCF_3$ | F | F | $OCF_3$ | Me | F | $OCF_3$ | H |
| F | $CF_3$ | F | F | $CF_3$ | Me | F | $CF_3$ | H |
| Cl | Br | F | Cl | Br | Me | Cl | Br | H |
| Cl | I | F | Cl | I | Me | Cl | I | H |
| Cl | SMe | F | Cl | SMe | Me | Cl | SMe | H |
| Cl | $OCF_3$ | F | Cl | $OCF_3$ | Me | Cl | $OCF_3$ | H |
| Cl | $CF_3$ | F | Cl | $CF_3$ | Me | Cl | $CF_3$ | H |
| Me | Br | F | Me | Br | Me | Me | Br | H |
| Me | I | F | Me | I | Me | Me | I | H |
| Me | SMe | F | Me | SMe | Me | Me | SMe | H |
| Me | $OCF_3$ | F | Me | $OCF_3$ | Me | Me | $OCF_3$ | H |
| Me | $CF_3$ | F | Me | $CF_3$ | Me | Me | $CF_3$ | H |

Also provided is a compound of the formula (I-2):

(I-2)

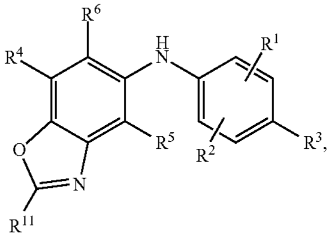

or a salt, prodrug or solvate thereof, wherein:

$R^1$, $R^2$, $R^4$ and $R^5$ are independently hydrogen, halo, nitro, azido, hydroxy, $C_1$-$C_{10}$ alkyl, $C_1$-$C_{10}$ alkoxy, halo-substituted $C_1$-$C_{10}$ alkoxy, $C_1$-$C_{10}$ alkylthio, halo-substituted $C_1$-$C_{10}$ alkylthio, carboxy, —OC(O)H, amino, $C_2$-$C_{10}$ alkenyl, $C_2$-$C_{10}$ alkynyl or $C_3$-$C_{10}$ cycloalkyl;

$R^3$ is hydrogen, halo, cyano, nitro, azido, hydroxy, $C_1$-$C_{10}$ alkoxy, halo-substituted $C_1$-$C_{10}$ alkoxy, mercapto, $C_1$-$C_{10}$ alkylthio, halo-substituted $C_1$-$C_{10}$ alkylthio, carboxy, —OC(O)H, amino, $C_1$-$C_{10}$ alkyl, $C_2$-$C_{10}$ alkenyl, $C_2$-$C_{10}$ alkynyl or $C_3$-$C_{10}$ cycloalkyl;

$R^6$ is —C(O)OR$^7$, —C(O)NR$^7$R$^8$, —C(O)N(R$^8$)OR$^7$, —C(O)($C_3$-$C_{10}$ cycloalkyl), —C(O)($C_1$-$C_{10}$ alkyl), —C(O)($C_6$-$C_{14}$ aryl), or —NHSO$_2$R$^7$;

each $R^7$ and $R^8$ is independently hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkyl $C_1$-$C_{10}$ alkyl or $C_1$-$C_{10}$ alkyl $C_3$-$C_{10}$ cycloalkyl;

$R^{11}$ is hydrogen, $C_1$-$C_{10}$ alkyl, $C_2$-$C_{10}$ alkenyl, $C_2$-$C_{10}$ alkynyl, $C_3$-$C_{10}$ cycloalkyl or $C_3$-$C_{10}$ cycloalkyl $C_1$-$C_{10}$ alkyl;

wherein each $C_1$-$C_{10}$ alkyl, $C_2$-$C_{10}$ alkenyl, $C_2$-$C_{10}$ alkynyl or $C_3$-$C_{10}$ cycloalkyl moiety may be unsubstituted or substituted with one or more groups independently selected from the group consisting of hydroxy, oxo, halo, cyano, nitro, trifluoromethyl, azido, amino, carboxy and mercapto.

In some embodiments, the compound is of the formula (I-2) wherein $R^1$, $R^2$, $R^3$, $R^4$, $R^5$, $R^6$ and $R^{11}$ are as defined for the formula (I-2) provided that if $R^1$ is methyl or chloro, $R^2$ is hydrogen and $R^3$ is iodo, then $R^6$ is —NHSO$_2$R$^7$ where $R^7$ is as defined for the formula (I-2), or —C(O)N(R$^8$)OR$^7$ where $R^7$ is $C_1$-$C_{10}$ alkyl substituted with at least one hydroxy group.

In some embodiments, the compound of the formula (I-2) is a compound of the formula (I-2-a), (I-2-b), (I-2-c) or (I-2-d):

(I-2-a)

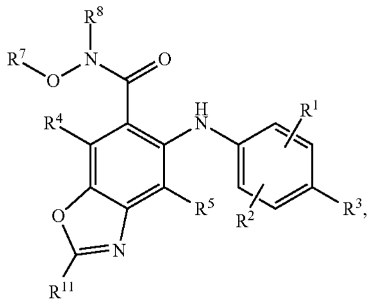

-continued (I-2-b)

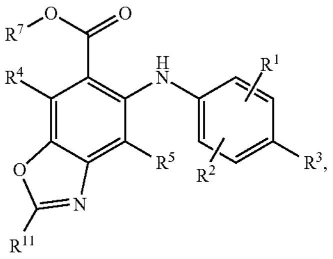

(I-2-c)

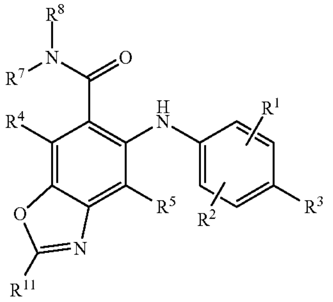

or (I-2-d)

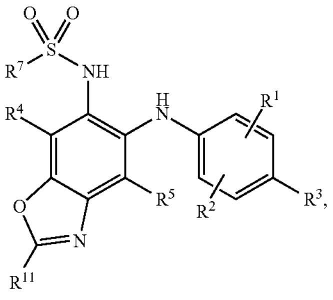

or a salt, prodrug or solvate thereof, wherein $R^1$, $R^2$, $R^3$, $R^4$, $R^5$, $R^6$, $R^7$, $R^8$ and $R^{11}$ are as defined for the formula (I-2).

In some embodiments, the compound is of the formula (I-2), (I-2-a), (I-2b), (I-2-c) or (I-2-d), or a salt, prodrug or solvate thereof, wherein $R^1$, $R^2$, $R^3$, $R^4$, $R^5$, $R^6$, $R^7$, $R^8$ and $R^{11}$, where applicable, are as defined for the formula (I) or any applicable variations thereof.

In some embodiments, the compound of the formula (I-2) is a compound of the formula (I-2-e):

(I-2-e)

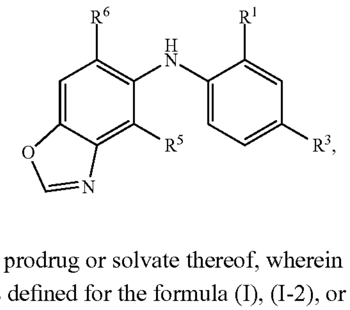

or a salt, prodrug or solvate thereof, wherein $R^1$, $R^3$, $R^5$ and $R^6$ are as defined for the formula (I), (I-2), or any applicable variations thereof. In some particular embodiments of the compound of the formula (I-2-e), or a salt, prodrug or solvate thereof, wherein $R^6$ is selected from the group consisting of:

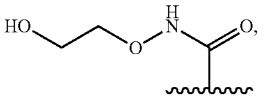
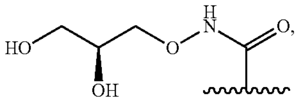
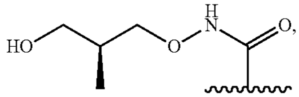
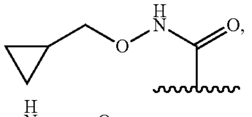
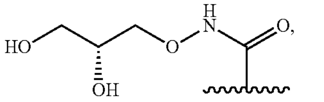
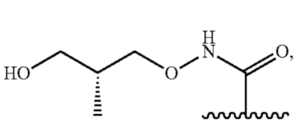
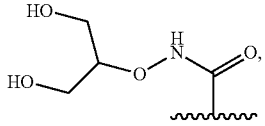
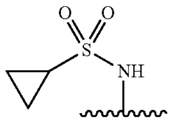
and
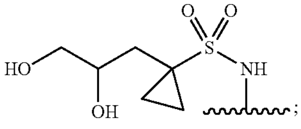
;

and $R^1$, $R^3$ and $R^5$ are as specified in Table 2.

TABLE 2

| $R^1$ | $R^3$ | $R^5$ | $R^1$ | $R^3$ | $R^5$ | $R^1$ | $R^3$ | $R^5$ |
|---|---|---|---|---|---|---|---|---|
| F | Br | F | F | Br | Me | F | Br | H |
| F | I | F | F | I | Me | F | I | H |
| F | SMe | F | F | SMe | Me | F | SMe | H |
| F | $OCF_3$ | F | F | $OCF_3$ | Me | F | $OCF_3$ | H |
| F | $CF_3$ | F | F | $CF_3$ | Me | F | $CF_3$ | H |
| Cl | Br | F | Cl | Br | Me | Cl | Br | H |
| Cl | SMe | F | Cl | I | Me | Cl | I | H |
| Cl | $OCF_3$ | F | Cl | SMe | Me | Cl | SMe | H |
| Cl | $CF_3$ | F | Cl | $OCF_3$ | Me | Cl | $OCF_3$ | H |
| Me | Br | F | Cl | $CF_3$ | Me | Cl | $CF_3$ | H |
| Me | SMe | F | Me | Br | Me | Me | Br | H |
| Me | $OCF_3$ | F | Me | I | Me | Me | I | H |
| Me | $CF_3$ | F | Me | SMe | Me | Me | SMe | H |
| Me | $OCF_3$ | H | Me | $OCF_3$ | Me | | | |
| Me | $CF_3$ | H | Me | $CF_3$ | Me | | | |

Also provided is a compound of the formula (I-3):

(I-3)

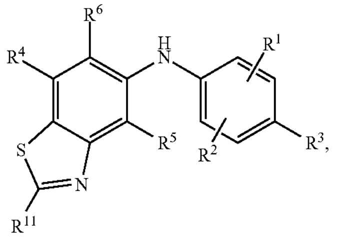

or a salt, prodrug or solvate thereof, wherein:

$R^1$, $R^2$, $R^4$ and $R^5$ are independently hydrogen, halo, nitro, azido, hydroxy, $C_1$-$C_{10}$ alkyl, $C_1$-$C_{10}$ alkoxy, halo-substituted $C_1$-$C_{10}$ alkoxy, $C_1$-$C_{10}$ alkylthio, halo-substituted $C_1$-$C_{10}$ alkylthio, carboxy, —OC(O)H, amino, $C_2$-$C_{10}$ alkenyl, $C_2$-$C_{10}$ alkynyl or $C_3$-$C_{10}$ cycloalkyl;

$R^3$ is hydrogen, halo, cyano, nitro, azido, hydroxy, $C_1$-$C_{10}$ alkoxy, halo-substituted $C_1$-$C_{10}$ alkoxy, mercapto, $C_1$-$C_{10}$ alkylthio, halo-substituted $C_1$-$C_{10}$ alkylthio, carboxy, —OC(O)H, amino, $C_1$-$C_{10}$ alkyl, $C_2$-$C_{10}$ alkenyl, $C_2$-$C_{10}$ alkynyl or $C_3$-$C_{10}$ cycloalkyl;

$R^6$ is —C(O)OR$^7$, —C(O)NR$^7$R$^8$, —C(O)N(R$^8$)OR$^7$, —C(O)($C_3$-$C_{10}$ cycloalkyl), —C(O)($C_1$-$C_{10}$ alkyl), —C(O)($C_6$-$C_{14}$ aryl), or —NHSO$_2$R$^7$;

each $R^7$ and $R^8$ is independently hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkyl $C_1$-$C_{10}$ alkyl or $C_1$-$C_{10}$ alkyl $C_3$-$C_{10}$ cycloalkyl;

$R^{11}$ is hydrogen, $C_1$-$C_{10}$ alkyl, $C_2$-$C_{10}$ alkenyl, $C_2$-$C_{10}$ alkynyl, $C_3$-$C_{10}$ cycloalkyl or $C_3$-$C_{10}$ cycloalkyl $C_1$-$C_{10}$ alkyl;

wherein each $C_1$-$C_{10}$ alkyl, $C_2$-$C_{10}$ alkenyl, $C_2$-$C_{10}$ alkynyl or $C_3$-$C_{10}$ cycloalkyl moiety may be unsubstituted or substituted with one or more groups independently selected from the group consisting of hydroxy, oxo, halo, cyano, nitro, trifluoromethyl, azido, amino, carboxy and mercapto.

In some embodiments, the compound is of the formula (I-3) wherein $R^1$, $R^2$, $R^3$, $R^4$, $R^5$, $R^6$ and $R^{11}$ are as defined for the formula (I-3) provided that if $R^1$ is methyl or chloro, $R^2$ is hydrogen and $R^3$ is iodo, then $R^6$ is —NHSO$_2$R$^7$ where $R^7$ is as defined for the formula (I-3), or —C(O)N(R$^8$)OR$^7$ where $R^7$ is $C_1$-$C_{10}$ alkyl substituted with at least one hydroxy group.

In some embodiments, the compound of the formula (I-3) is a compound of the formula (I-3-a), (I-3-b), (I-3-c) or (I-3-d):

(I-3-a)

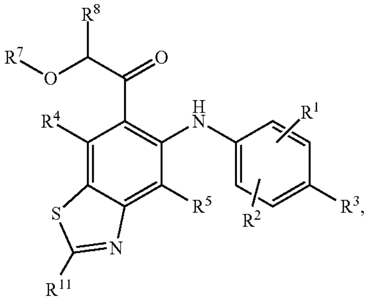

(I-3-b)

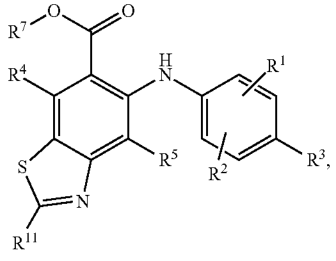

(I-3-c)

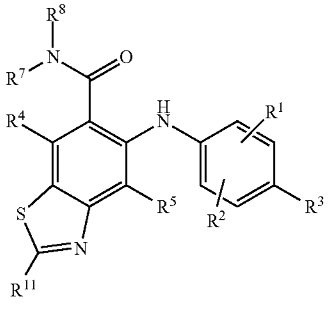

or

-continued (I-3-d)

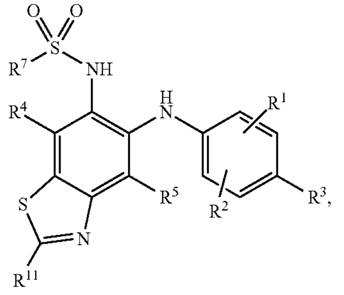

or a salt, prodrug or solvate thereof, wherein $R^1$, $R^2$, $R^3$, $R^4$, $R^5$, $R^6$, $R^7$, $R^8$ and $R^{11}$ are as defined for the formula (I-3).

In some embodiments, the compound is of the formula (I-3), (I-3-a), (I-3-b), (I-3-c) or (I-3-d), or a salt, prodrug or solvate thereof, wherein $R^1$, $R^2$, $R^3$, $R^4$, $R^5$, $R^6$, $R^7$, $R^8$ and $R^{11}$, where applicable, are as defined for the formula (I) or any applicable variations thereof.

In some embodiments, the compound of the formula (I-3) is a compound of the formula (I-3-e):

(I-3-e)

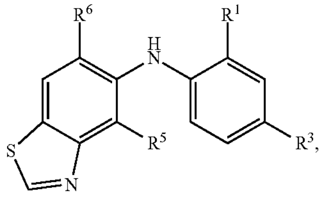

or a salt, prodrug or solvate thereof, wherein $R^1$, $R^3$, $R^5$ and $R^6$ are as defined for the formula (I), (I-3), or any applicable variations thereof. In some particular embodiments of the compound of the formula (I-3-e), or a salt, prodrug or solvate thereof, wherein $R^6$ is selected from the group consisting of:

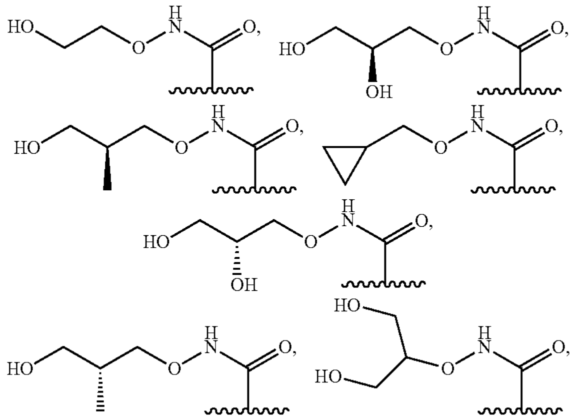

and

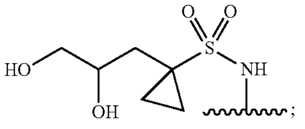

;

and $R^1$, $R^3$ and $R^5$ are as specified in Table 2.

In one embodiment, provided is a compound of the formula (J):

(J)

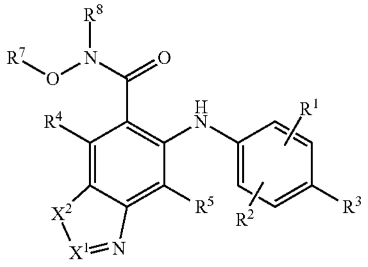

or a salt, prodrug or solvate thereof, where $X^1$, $X^2$, $R^1$, $R^2$, $R^3$, $R^4$, $R^5$, $R^7$ and $R^8$ are as described for the formula (I), or any variations thereof. It is intended and understood that each and every variations of $X^1$, $X^2$, $R^1$, $R^2$, $R^3$, $R^4$, $R^5$, $R^7$ and $R^8$, and each and every combinations thereof described herein for the formula (I) apply to the formula (J) as if each and every variations and combinations are individually described. For example, in some embodiments, provided is a compound of the formula (J), or a salt, prodrug or solvate thereof, where $X^1$ is N or $CR^{11}$ where $R^{11}$ is H, $X^2$ is O or S, $R^1$ is halo (e.g., fluoro or chloro), $R^2$ is hydrogen, $R^3$ is halo (e.g., iodo or bromo), $R^4$ is hydrogen, $R^5$ is fluoro, $R^7$ is $C_1$-$C_{10}$ alkyl substituted with at least 1 to 3 hydroxy groups and $R^8$ is hydrogen.

In one embodiment, the compound of the formula (J) is of the formula (J-1):

(J-1)

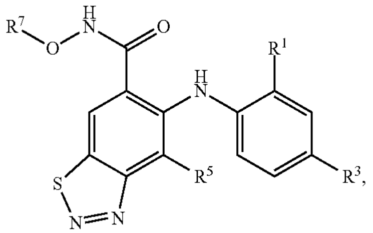

or a salt, prodrug or solvate thereof, wherein $R^1$, $R^3$, $R^5$ and $R^7$ are as defined for the formula (J) or formula (I) or any variations thereof. In some of these embodiments, $R^1$ is halo or unsubstituted or substituted $C_1$-$C_{10}$ alkyl; $R^3$ is halo, unsubstituted or substituted $C_1$-$C_{10}$ alkyl, $C_1$-$C_{10}$ alkoxy, halo-substituted $C_1$-$C_{10}$ alkoxy, $C_1$-$C_{10}$ alkylthio, halo-substituted $C_1$-$C_{10}$ alkylthio, —$SO_2R^a$, —$SO_2N(R^c)R^d$, —$N(R^c)R^d$ or —$C(O)OR^b$; $R^5$ is hydrogen, halo or unsubstituted or substituted $C_1$-$C_{10}$ alkyl; and $R^7$ is hydrogen, unsubstituted or substituted $C_1$-$C_{10}$ alkyl, unsubstituted or substituted $C_3$-$C_{10}$ cycloalkyl, or unsubstituted or substituted $C_3$-$C_{10}$ cycloalkyl $C_1$-$C_{10}$ alkyl.

In some embodiments, provided is a compound of the formula (J-1), or a salt, prodrug or solvate thereof, wherein $R^1$ is halo (e.g., fluoro or chloro) or $C_1$-$C_{10}$ alkyl (e.g., methyl). In some of these embodiments, $R^3$ is halo (e.g., iodo or bromo), substituted $C_1$-$C_{10}$ alkyl (e.g., trifluoromethyl), halo-substituted $C_1$-$C_{10}$ alkoxy (e.g., trifluoromethoxy), $C_1$-$C_{10}$ alkylthio (e.g., methylthio), —$SO_2R^a$, —$SO_2N(R^c)R^d$, —$N(R^c)R^d$ or —$C(O)OR^b$. In some of these embodiments, $R^3$ is —$SO_2R^a$ where $R^a$ is unsubstituted or substituted $C_1$-$C_{10}$ alkyl (e.g., $SO_2Me$). In some of these embodiments, $R^3$ is —$N(R^c)R^d$ where $R^c$ and $R^d$ are independently hydrogen or $C_1$-$C_{10}$ alkyl (e.g., $NMe_2$). In some of these embodiments, $R^3$ is —C(O)OR$^b$ where $R^b$ is unsubstituted or substituted $C_1$-$C_{10}$ alkyl (e.g., $CO_2Me$). In some of these embodiments, $R^5$ is hydrogen, halo (e.g., fluoro) or $C_1$-$C_{10}$ alkyl (e.g., methyl). In some of these embodiments, $R^7$ is $C_1$-$C_{10}$ alkyl substituted with at least one hydroxy group. In some of these embodiments, $R^7$ is $C_1$-$C_{10}$ alkyl substituted with at least 1 to 3 hydroxy groups. In some of these embodiments, $R^7$ is $C_1$-$C_6$ alkyl substituted with at least 1 to 3 hydroxy groups. In some of these embodiments, $R^7$ is $C_1$-$C_4$ alkyl substituted with 1 or 2 hydroxy groups (e.g., 2-hydroxyethyl, 3-hydroxy-2-methylpropyl, 2,3-dihydroxypropyl and 1,3-dihydroxy-2-propyl). In some of these embodiments, $R^7$ is unsubstituted or substituted $C_3$-$C_{10}$ cycloalkyl $C_1$-$C_{10}$ alkyl. In some of these embodiments, $R^7$ is unsubstituted or substituted $C_3$-$C_6$ cycloalkyl $C_1$-$C_6$ alkyl. In some of these embodiments, $R^7$ is unsubstituted or substituted $C_3$-$C_4$ cycloalkyl $C_1$-$C_3$ alkyl (e.g., cyclopropylmethyl). In some particular embodiments, the compound is of the formula (J-1), or a salt, prodrug or solvate thereof, wherein $R^1$ is fluoro or chloro, $R^3$ is iodo or bromo, $R^5$ is fluoro, and $R^7$ is selected from the group consisting of cyclopropylmethyl, 2-hydroxyethyl, 3-hydroxy-2-methylpropyl, 2,3-dihydroxypropyl and 1,3-dihydroxy-2-propyl. In some of these embodiments, $R^7$ is selected from the group consisting of 2-hydroxyethyl, 3-hydroxy-2-methylpropyl, 2,3-dihydroxypropyl and 1,3-dihydroxy-2-propyl. In some of these embodiments, $R^7$ is selected from the group consisting of 2-hydroxyethyl, (R)-3-hydroxy-2-methylpropyl, (S)-3-hydroxy-2-methylpropyl, (R)-2,3-dihydroxypropyl, (S)-2,3-dihydroxypropyl and 1,3-dihydroxy-2-propyl.

In one embodiment, the compound of the formula (J) is of the formula (J-2):

(J-2)

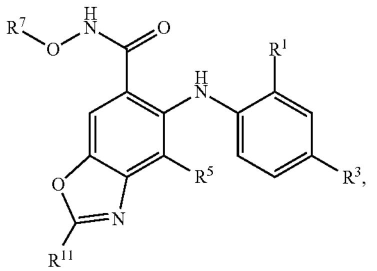

or a salt, prodrug or solvate thereof, wherein $R^1$, $R^3$, $R^5$, $R^7$ and $R^{11}$ are as defined for the formula (J), (I) or any variations thereof.

In one embodiment, the compound of the formula (J) is of the formula (J-3):

(J-3)

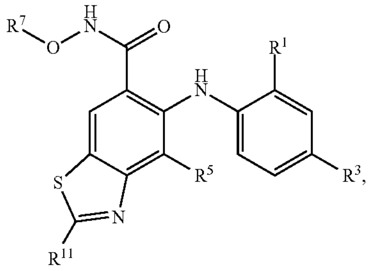

or a salt, prodrug or solvate thereof, wherein $R^1$, $R^3$, $R^5$, $R^7$ and $R^{11}$ are as defined for the formula (J), (I) or any variations thereof.

In some embodiments, provided is a compound of the formula (J-2) or (J-3), or a salt, prodrug or solvate thereof, wherein $R^1$ is halo or unsubstituted or substituted $C_1$-$C_{10}$ alkyl; $R^3$ is halo, unsubstituted or substituted $C_1$-$C_{10}$ alkyl, $C_1$-$C_{10}$ alkoxy, halo-substituted $C_1$-$C_{10}$ alkoxy, acyloxy, $C_1$-$C_{10}$ alkylthio, halo-substituted $C_1$-$C_{10}$ alkylthio, —SO$_2$R$^a$, —SO$_2$N(R$^c$)R$^d$, —N(R$^c$)R$^d$ or —C(O)OR$^b$; $R^5$ is hydrogen, halo or unsubstituted or substituted $C_1$-$C_{10}$ alkyl; $R^7$ is $C_1$-$C_{10}$ alkyl substituted with at least one hydroxy group; and $R^{11}$ is hydrogen.

In some embodiments, provided is a compound of the formula (J-2) or (J-3), or a salt, prodrug or solvate thereof, wherein $R^1$ is halo (e.g., fluoro or chloro) or $C_1$-$C_{10}$ alkyl (e.g., methyl). In some of these embodiments, $R^3$ is halo (e.g., iodo or bromo), substituted $C_1$-$C_{10}$ alkyl (e.g., trifluoromethyl), halo-substituted $C_1$-$C_{10}$ alkoxy(e.g., trifluoromethoxy), $C_1$-$C_{10}$ alkylthio(e.g., methylthio), —SO$_2$R$^a$, —SO$_2$N(R$^c$)R$^d$, —N(R$^c$)R$^d$ or —C(O)OR$^b$. In some of these embodiments, $R^3$ is —SO$_2$R$^a$ where $R^a$ is unsubstituted or substituted $C_1$-$C_{10}$ alkyl (e.g., $SO_2Me$). In some of these embodiments, $R^3$ is —N(R$^c$)R$^d$ where $R^c$ and $R^d$ are independently hydrogen or $C_1$-$C_{10}$ alkyl (e.g., $NMe_2$). In some of these embodiments, $R^3$ is —C(O)OR$^b$ where $R^b$ is unsubstituted or substituted $C_1$-$C_{10}$ alkyl (e.g., $CO_2Me$). In some of these embodiments, $R^5$ is hydrogen, halo (e.g., fluoro) or $C_1$-$C_{10}$ alkyl (e.g., methyl). In some of these embodiments, $R^5$ is $C_1$-$C_{10}$ alkyl substituted with at least 1 to 3 hydroxy groups. In some of these embodiments, $R^7$ is $C_1$-$C_6$ alkyl substituted with at least 1 to 3 hydroxy groups. In some of these embodiments, $R^7$ is $C_1$-$C_4$ alkyl substituted with 1 or 2 hydroxy groups (e.g., 2-hydroxyethyl, 3-hydroxy-2-methylpropyl, 2,3-dihydroxypropyl and 1,3-dihydroxy-2-propyl). In some particular embodiments, the compound is of the formula (J-2) or (J-3), or a salt, prodrug or solvate thereof, wherein $R^1$ is fluoro or chloro, $R^3$ is iodo or bromo, $R^5$ is fluoro, and $R^7$ is selected from the group consisting of 2-hydroxy ethyl, 3-hydroxy-2-methylpropyl, 2,3-dihydroxypropyl and 1,3-dihydroxy-2-propyl.

In one embodiment, the compound of the formula (J) is of the formula (J-4):

(J-4)

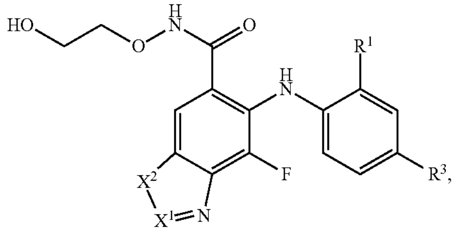

or a salt, prodrug or solvate thereof, wherein $X^1$, $X^2$, $R^1$ and $R^3$ are as defined for the formula (J) or (I), or any variations thereof. In one variation, $X^1$ is N and $X^2$ is S. In another variation, $X^1$ is CH and $X^2$ is O. In yet another variation, $X^1$ is CH and $X^2$ is S. In some of these variations, $R^1$ is fluoro and $R^3$ is iodo. In some of these variations, $R^1$ is chloro and $R^3$ is bromo.

In another embodiment, the compound is of the formula (K):

(K)

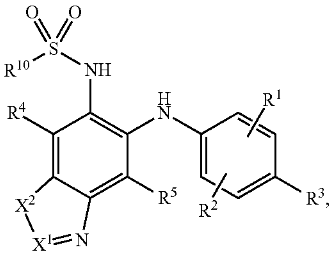

or a salt, prodrug or solvate thereof, where $X^1$, $X^2$, $R^1$, $R^2$, $R^3$, $R^4$, $R^5$ and $R^{10}$ are as described for the formula (I), or any variations thereof. It is intended and understood that each and every variations of $X^1$, $X^2$, $R^1$, $R^2$, $R^3$, $R^4$, $R^5$ and $R^{10}$, and each and every combinations thereof described herein for the formula (I) apply to the formula (K) as if each and every variations and combinations are individually described. For example, in some embodiments, provided is a compound of the formula (K), or a salt, prodrug or solvate thereof, where $X^1$ is N or $CR^{11}$ where $R^{11}$ is H, $X^2$ is O or S, $R^1$ is halo (e.g., fluoro or chloro), $R^2$ is hydrogen, $R^3$ is halo (e.g., iodo or bromo), $R^4$ is hydrogen, $R^5$ is fluoro, and $R^{10}$ is $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkyl $C_1$-$C_{10}$ alkyl or $C_1$-$C_{10}$ alkyl $C_3$-$C_{10}$ cycloalkyl. In one variation, $X^1$ is N and $X^2$ is S. In another variation, $X^2$ is S and $X^1$ is $CR^{11}$ where $R^{11}$ is hydrogen, $C_1$-$C_{10}$ alkyl, $C_2$-$C_{10}$ alkenyl, $C_2$-$C_{10}$ alkynyl, $C_3$-$C_{10}$ cycloalkyl or $C_3$-$C_{10}$ cycloalkyl $C_1$-$C_{10}$ alkyl. In another variation, $X^2$ is O and $X^1$ is $CR^{11}$ where R is hydrogen, $C_1$-$C_{10}$ alkyl, $C_2$-$C_{10}$ alkenyl, $C_2$-$C_{10}$ alkynyl, $C_3$-$C_{10}$ cycloalkyl or $C_3$-$C_{10}$ cycloalkyl $C_1$-$C_{10}$ alkyl.

In one embodiment, the compound of the formula (K) is of the formula (K-1):

(K-1)

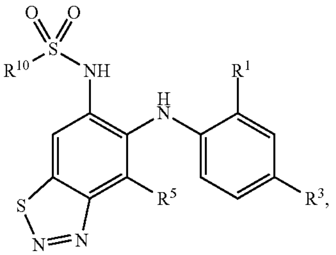

or a salt, prodrug or solvate thereof, wherein $R^1$, $R^3$, $R^5$ and $R^{10}$ are as defined for the formula (K), (I) or any variations thereof.

In one embodiment, the compound of the formula (K) is of the formula (K-2):

(K-2)

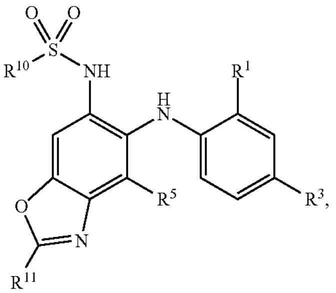

or a salt, prodrug or solvate thereof, wherein $R^1$, $R^3$, $R^5$, $R^{10}$ and $R^{11}$ are as defined for the formula (K), (I) or any variations thereof.

In one embodiment, the compound of the formula (K) is of the formula (K-3):

(K-3)

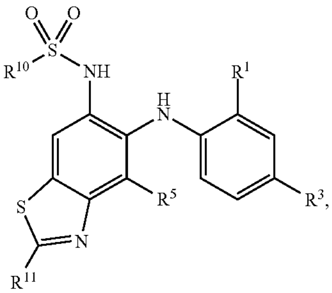

or a salt, prodrug or solvate thereof, wherein $R^1$, $R^3$, $R^5$, $R^{10}$ and $R^{11}$ are as defined for the formula (K), (1) or any variations thereof.

In some embodiments, provided is a compound of the formula (K-1), (K-2) or (K-3), or a salt, prodrug or solvate thereof, wherein $R^1$ is halo or unsubstituted or substituted $C_1$-$C_{10}$ alkyl; $R^3$ is halo, unsubstituted or substituted $C_1$-$C_{10}$ alkyl, $C_1$-$C_{10}$ alkoxy, halo-substituted $C_1$-$C_{10}$ alkoxy, acyloxy, $C_1$-$C_{10}$ alkylthio, halo-substituted $C_1$-$C_{10}$ alkylthio, $—SO_2R^a$, $—SO_2N(R^c)R^d$, $—N(R^c)R^d$ or $—C(O)OR^b$; $R^5$ is hydrogen, halo or unsubstituted or substituted $C_1$-$C_{10}$ alkyl; $R^{10}$ is unsubstituted or substituted $C_1$-$C_{10}$ alkyl, unsubstituted or substituted $C_3$-$C_{10}$ cycloalkyl or unsubstituted or substituted $C_1$-$C_{10}$ alkyl $C_3$-$C_{10}$ cycloalkyl; and $R^{11}$ is hydrogen where present. In some of these embodiments, $R^1$ is halo (e.g., fluoro or chloro). In some of these embodiments, $R^3$ is halo (e.g., iodo or bromo). In some of these embodiments, $R^3$ is $—SO_2R^a$ where $R^a$ is unsubstituted or substituted $C_1$-$C_{10}$ alkyl (e.g., $SO_2Me$). In some of these embodiments, $R^3$ is $—N(R^c)R^d$ where $R^c$ and $R^d$ are independently hydrogen or $C_1$-$C_{10}$ alkyl (e.g., $NMe_2$). In some of these embodiments, $R^3$ is $—C(O)OR^b$ where $R^b$ is unsubstituted or substituted $C_1$-$C_{10}$ alkyl (e.g., $CO_2Me$). In some of these embodiments, $R^3$ is $SO_2Me$ or $CO)_2Me$. In some of these embodiments, $R^5$ is hydrogen, halo (e.g., fluoro) or $C_1$-$C_{10}$ alkyl (e.g., methyl). In one particular embodiment, $R^5$ is fluoro. In some of these embodiments, $R^{10}$ is $C_1$-$C_{10}$ alkyl, $C_3$-$C_{10}$ cycloalkyl, or $C_1$-$C_{10}$ alkyl $C_3$-$C_{10}$ cycloalkyl substituted with at least one hydroxy group. In some of these embodiments, $R^{10}$ is $C_1$-$C_{10}$ alkyl $C_3$-$C_{10}$ cycloalkyl substituted with 1 or 2 hydroxy groups (e.g., 1-(2,3-dihydroxypropyl)cyclopropyl).

In some embodiments, provided is a compound of the formula (K-1), (K-2) or (K-3), or a salt, prodrug or solvate thereof, wherein $R^1$ is fluoro or chloro, $R^3$ is iodo or bromo, $R^5$ is fluoro, $R^{10}$ is selected from the group consisting of cyclopropyl and 1-(2,3-dihydroxypropyl)cyclopropyl, and $R^{11}$ is hydrogen where present. In some of these embodiments, $R^1$ is fluoro $R^3$ is iodo, $R^5$ is fluoro, $R^{10}$ is 1-(2,3-dihydroxypropyl)cyclopropyl and $R^{11}$ is absent for a compound of the formula (K-1) or is hydrogen for a compound of the formula (K-2) or (K-3).

Representative examples of compounds detailed herein, including intermediates and final compounds according to the invention are depicted in the Tables and Examples herein. It is understood that in one aspect, any of the compounds may be used in the methods detailed herein, including, where applicable, intermediate compounds that may be isolated and administered to an individual.

Representative compounds of the invention are shown in Table 3. In some embodiments, the invention provides a compound of Table 3, in its free base form or as pharmaceutically acceptable salts, or a stereoisomer thereof

TABLE 3

| Exemplary compounds | | |
|---|---|---|
| Compound No. | Structure | Compound Name |
| 1 | 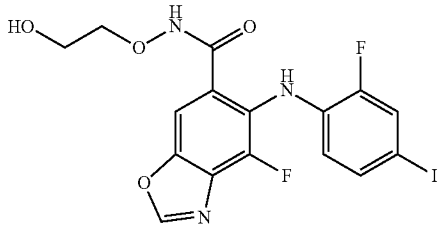 | 4-fluoro-5-((2-fluoro-4-iodophenyl)amino)-N(2-hydroxyethoxy)benzo[d]oxazole-6-carboxamide |
| 2 | 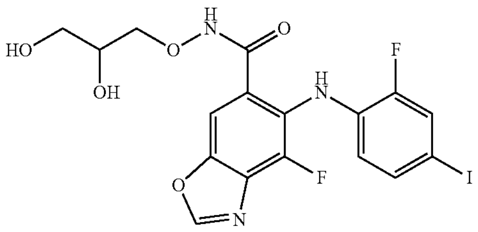 [SMILES: O=C(NOCC(O)CO)c1cc2ocnc2c(F)c1Nc1ccc(I)cc1F] | N-(2,3-dihydroxypropoxy)-4-fluoro-5-((2-fluoro-4-iodophenyl)amino)benzo[d]oxazole-6-carboxamide |
| 3 | 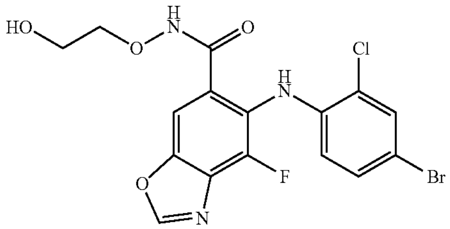 [SMILES: O=C(NOCCO)c1cc2ocnc2c(F)c1Nc1ccc(Br)cc1Cl] | 5-((4-bromo-2-chlorophenyl)amino)-4-fluoro-N-(2-hydroxyethoxy)benzo[d]oxazole-6-carboxamide |
| 4 | 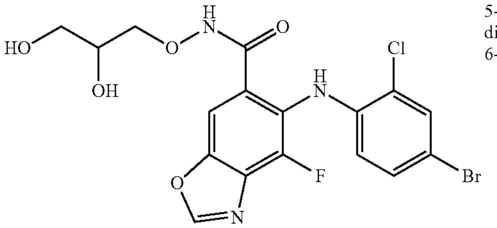 | 5-((4-bromo-2-chlorophenyl)amino)-N(2,3-dihydroxypropoxy)-4-fluorobenzo[d]oxazole-6-carboxamide |
| 5 | 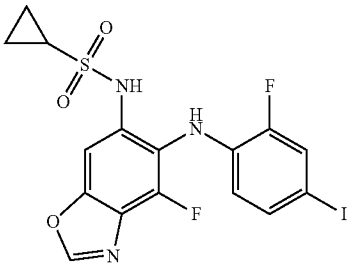 [SMILES: O=S(=O)(Nc1cc2ocnc2c(F)c1Nc1ccc(I)cc1F)C1CC1] | N-(4-fluoro-5-((2-fluoro-4-iodophenyl)amino)benzo[d]oxazol-6-yl)cyclopropanesulfonamide |

TABLE 3-continued

| Exemplary compounds | | |
|---|---|---|
| Compound No. | Structure | Compound Name |
| 6 | 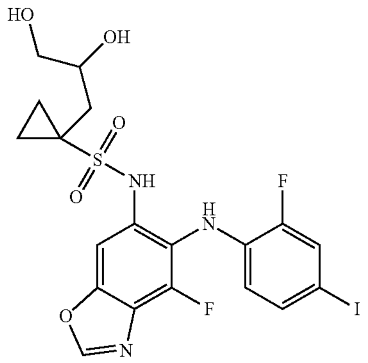 [SMILES: O=S(=O)(Nc1cc2ocnc2c(F)c1Nc1ccc(I)cc1F)C1(CC(O)CO)CC1] | N-(4-fluoro-5-((2-fluoro-4-iodophenyl)amino)benzo[d]oxazol-6-yl)-1-(2,3-dihydroxypropyl)cyclopropane-1-sulfonamide |
| 7 | 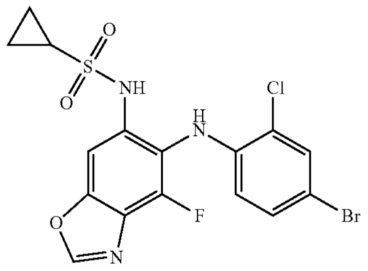 [SMILES: O=S(=O)(Nc1cc2ocnc2c(F)c1Nc1ccc(Br)cc1Cl)C1CC1] | N-(5-((4-bromo-2-chlorophenyl)amino)-4-fluorobenzo[d]oxazol-6-yl)cyclopropanesulfonamide |
| 8 | 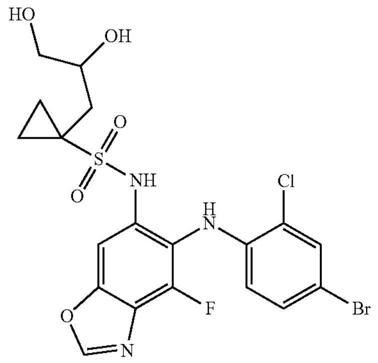 [SMILES: O=S(=O)(Nc1cc2ocnc2c(F)c1Nc1ccc(Br)cc1Cl)C1(CC(O)CO)CC1] | N-(5-((4-bromo-2-chlorophenyl)amino)-4-fluorobenzo[d]oxazol-6-yl)-1-(2,3-dihydroxypropyl)cyclopropane-1-sulfonamide |
| 9 | 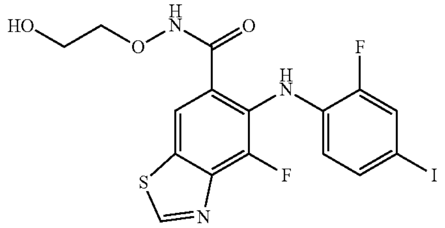 [SMILES: O=C(NOCCO)c1cc2scnc2c(F)c1Nc1ccc(I)cc1F] | 4-fluoro-5-((2-fluoro-4-iodophenyl)amino)-N-(2-hydroxyethoxy)benzo[d]thiazole-6-carboxamide |
| 10 | 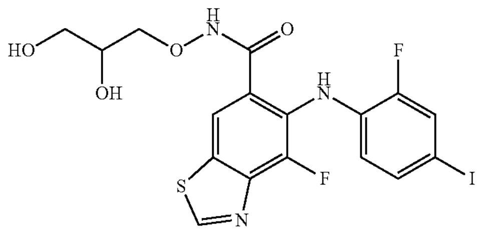 [SMILES: O=C(NOCC(O)CO)c1cc2scnc2c(F)c1Nc1ccc(I)cc1F] | N-(2,3-dihydroxypropoxy)-4-fluoro-5-((2-fluoro-4-iodophenyl)amino)benzo[d]thiazole-6-carboxamide |

TABLE 3-continued

| Exemplary compounds | | |
|---|---|---|
| Compound No. | Structure | Compound Name |
| 11 | 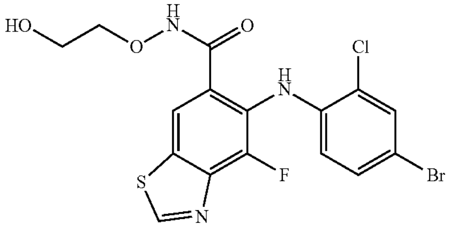 [SMILES: O=C(NOCCO)c1cc2scnc2c(F)c1Nc1ccc(Br)cc1Cl] | 5-((4-bromo-2-chlorophenyl)amino)-4-fluoro-N-(2-hydroxyethoxy)benzo[d]thiazole-6-carboxamide |
| 12 | 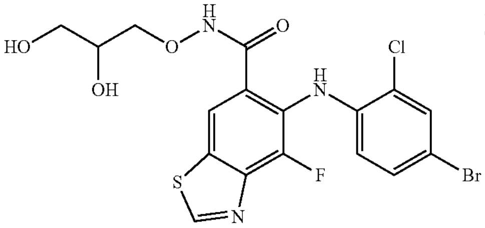 [SMILES: O=C(NOCC(O)CO)c1cc2scnc2c(F)c1Nc1ccc(Br)cc1Cl] | 5-((4-bromo-2-chlorophenyl)amino)-N-(2,3-dihydroxypropoxy)-4-fluorobenzo[d]thiazole-6-carboxamide |
| 13 | 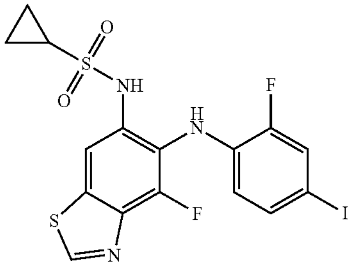 [SMILES: O=S(=O)(Nc1cc2scnc2c(F)c1Nc1ccc(I)cc1F)C1CC1] | N-(4-fluoro-5-((2-fluoro-4-iodophenyl)amino)benzo[d]thiazol-6-yl)cyclopropanesulfonamide |
| 14 | 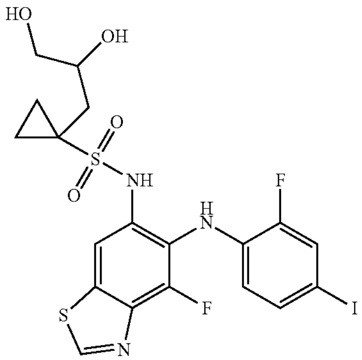 [SMILES: O=S(=O)(Nc1cc2scnc2c(F)c1Nc1ccc(I)cc1F)C1(CC(O)CO)CC1] | 1-(2,3-dihydroxypropyl)-N-(4-fluoro-5-((2-fluoro-4-iodophenyl)amino)benzo[d]thiazol-6-yl)cyclopropane-1-sulfonamide |
| 15 | 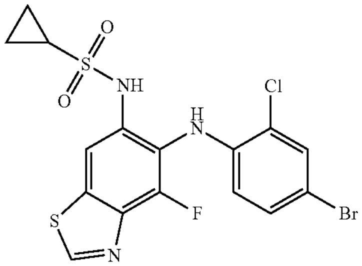 | N-(5-((4-bromo-2-chlorophenyl)amino-4-fluorobenzo[d]thiazol-6-yl)cyclopropanesulfonamide |

TABLE 3-continued

| Exemplary compounds | | |
|---|---|---|
| Compound No. | Structure | Compound Name |
| 16 | 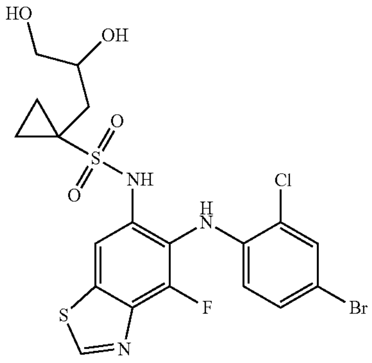 [SMILES: O=S(=O)(Nc1cc2scnc2c(F)c1Nc1ccc(Br)cc1Cl)C1(CC(O)CO)CC1] | N-(5-((4-bromo-2-chlorophenyl)amino)-4-fluorobenzo[d]thiazol-6-yl)-1-(2,3-dihydroxypropyl)cyclopropane-1-sulfonamide |
| 17 | 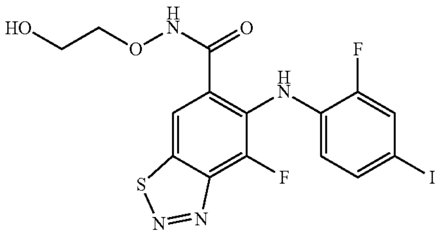 [SMILES: O=C(NOCCO)c1cc2snnc2c(F)c1Nc1ccc(I)cc1F] | 4-fluoro-5-((2-fluoro-4-iodophenyl)amino)-N-(2-hydroxyethoxy)benzo[d][1,2,3]thiadiazole-6-carboxamide |
| 18 | 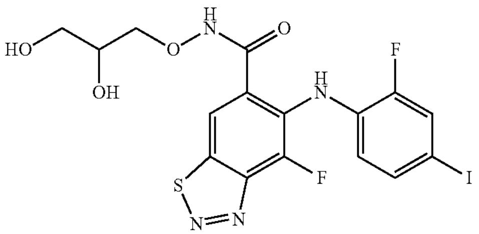 [SMILES: O=C(NOCC(O)CO)c1cc2snnc2c(F)c1Nc1ccc(I)cc1F] | N-(2,3-dihydroxypropoxy)-4-fluoro-5-((2-fluoro-4-iodophenyl)amino)benzo[d][1,2,3]thiadiazole-6-carboxamide |
| 19 | 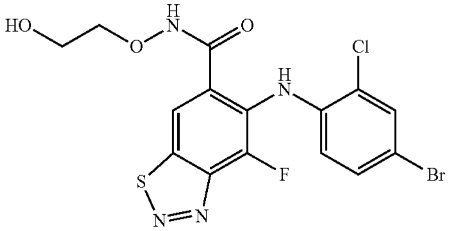 [SMILES: O=C(NOCCO)c1cc2snnc2c(F)c1Nc1ccc(Br)cc1Cl] | 5-((4-bromo-2-chlorophenyl)amino)-4-fluoro-N-(2-hydroxyethoxy)benzo[d][1,2,3]thiadiazole-6-carboxamide |
| 20 | 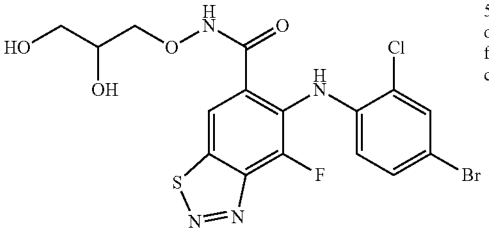 | 5-((4-bromo-2-chlorophenyl)amino)-N-(2,3-dihydroxypropoxy)-4-fluorobenzo[d][1,2,3]thiadiazole-6-carboxamide |

TABLE 3-continued

| Exemplary compounds | | |
|---|---|---|
| Compound No. | Structure | Compound Name |
| 21 | 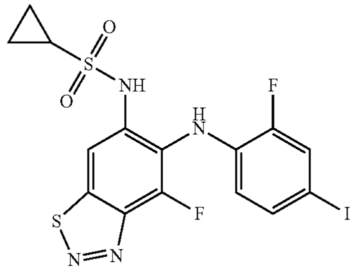 [SMILES: O=S(=O)(Nc1cc2snnc2c(F)c1Nc1ccc(I)cc1F)C1CC1] | N-(4-fluoro-5-((2-fluoro-4-iodophenyl)amino)benzo[d][1,2,3]thiadiazol-6-yl)cyclopropanesulfonamide |
| 22 | 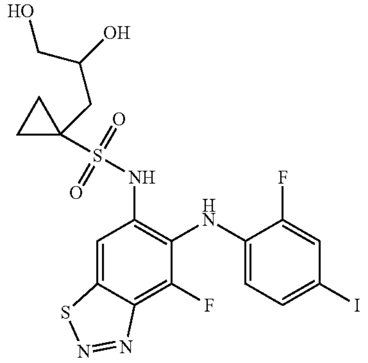 [SMILES: O=S(=O)(Nc1cc2snnc2c(F)c1Nc1ccc(I)cc1F)C1(CC(O)CO)CC1] | 1-(2,3-dihydroxypropyl)-N-(4-fluoro-5-((2-fluoro-4-iodophenyl)amino)benzo[d][1,2,3]thiadiazol-6-yl)cyclopropane-1-sulfonamide |
| 23 | 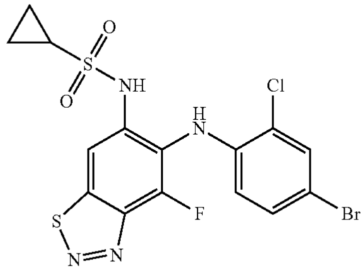 [SMILES: O=S(=O)(Nc1cc2snnc2c(F)c1Nc1ccc(Br)cc1Cl)C1CC1] | N-(5-((4-bromo-2-chlorophenyl)amino)-4-fluorobenzo[d][1,2,3]thiadiazol-6-yl)cyclopropanesulfonamide |
| 24 | 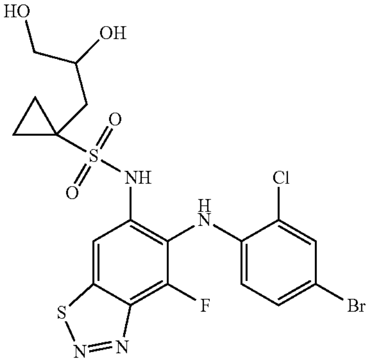 [SMILES: O=S(=O)(Nc1cc2snnc2c(F)c1Nc1ccc(Br)cc1Cl)C1(CC(O)CO)CC1] | N-(5((4-bromo-2-chlorophenyl)amino)-4-fluorobenzo[d][1,2,3]thiadiazol-6-yl)-1-(2,3-dihydroxypropyl)cyclopropane-1-sulfonamide |
| 25 | 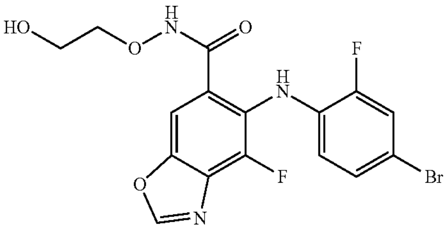 [SMILES: O=C(NOCCO)c1cc2ocnc2c(F)c1Nc1ccc(Br)cc1F] | 4-fluoro-5-((2-fluoro-4-bromophenyl)amino)-N-(2-hydroxyethoxy)benzo[d]oxazole-6-carboxamide |

TABLE 3-continued

| Exemplary compounds | | |
|---|---|---|
| Compound No. | Structure | Compound Name |
| 26 | 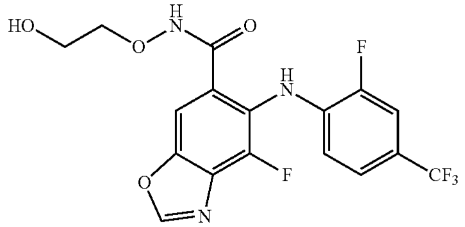 [SMILES: O=C(NOCCO)c1cc2ocnc2c(F)c1Nc1ccc(C(F)(F)F)cc1F] | 4-fluoro-5-((2-fluoro-4-trifluoromethylphenyl)amino)-N-(2-hydroxyethoxy)benzo[d]oxazole-6-carboxamide |
| 27 | 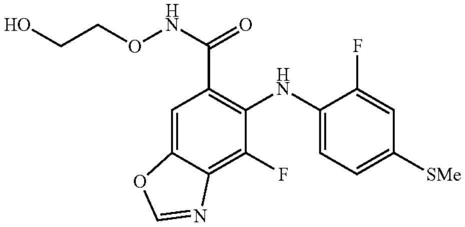 | 4-fluoro-5-((2-fluoro-4-methylthiophenyl)amino)-N-(2-hydroxyethoxy)benzo[d]oxazole-6-carboxamide |
| 28 | 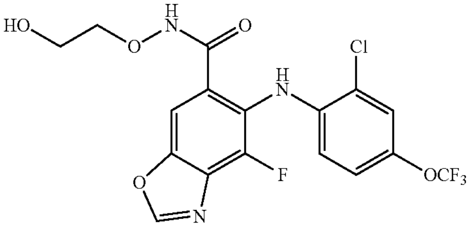 [SMILES: O=C(NOCCO)c1cc2ocnc2c(F)c1Nc1ccc(OC(F)(F)F)cc1Cl] | 5-((4-trifluoromethoxy-2-chlorophenyl)amino)-4-fluoro-N-(2-hydroxyethoxy)benzo[d]oxazole-6-carboxamide |
| 29 | 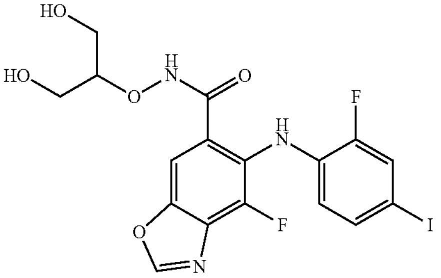 [SMILES: O=C(NOC(CO)CO)c1cc2ocnc2c(F)c1Nc1ccc(I)cc1F] | 5((2-fluoro-4-iodophenyl)amino)-N-(1,3-dihydroxy-isopropoxy)-4-fluorobenzo[d]oxazole-6-carboxamide |
| 30 | 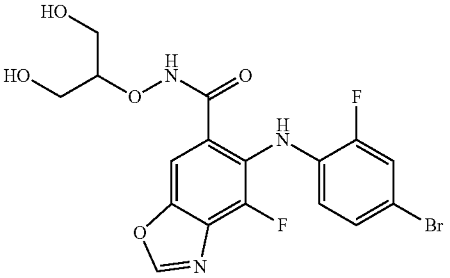 [SMILES: O=C(NOC(CO)CO)c1cc2ocnc2c(F)c1Nc1ccc(Br)cc1F] | 5-((4-bromo-2-fluorophenyl)amino)-N-(1,3-dihydroxy-isopropoxy)-4-fluorobenzo[d]oxazole-6-carboxamide |
| 31 | 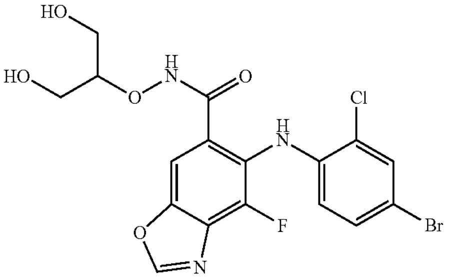 [SMILES: O=C(NOC(CO)CO)c1cc2ocnc2c(F)c1Nc1ccc(Br)cc1Cl] | 5-((4-bromo-2-chlorophenyl)amino)-N-(1,3-dihydroxy-isopropoxy)-4-fluorobenzo[d]oxazole-6-carboxamide |

TABLE 3-continued

| Compound No. | Structure | Compound Name |
|---|---|---|
| 32 | 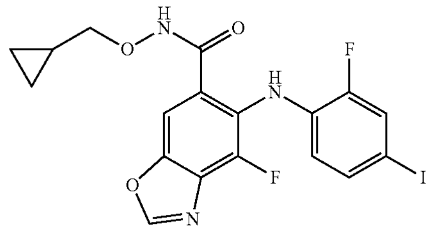 [SMILES: O=C(NOCC1CC1)c1cc2ocnc2c(F)c1Nc1ccc(I)cc1F] | 4-fluoro-5-((2-fluoro-4-iodophenyl)amino)-N-cyclopropylmethyl-benzo[d]oxazole-6-carboxamide |
| 33 | 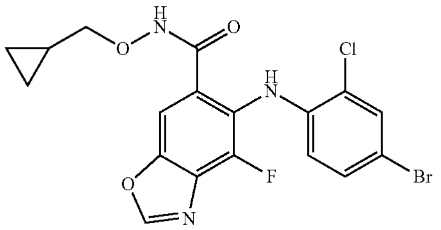 [SMILES: O=C(NOCC1CC1)c1cc2ocnc2c(F)c1Nc1ccc(Br)cc1Cl] | 4-fluoro-5-((4-bromo-2-chlorophenyl)amino)-N-cyclopropylmethyl-benzo[d]oxazole-6-carboxamide |
| 34 | 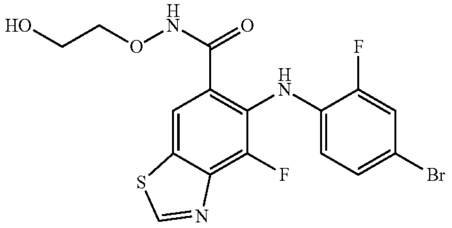 | 4-fluoro-5-((2-fluoro-4-bromophenyl)amino)-N-(2-hydroxyethoxy)benzo[d]thiazol-6-carboxamide |
| 35 | 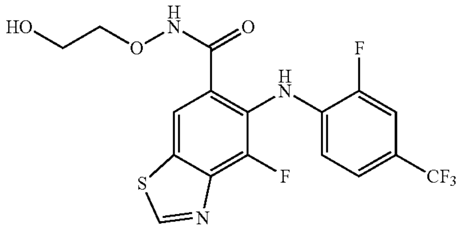 | 4-fluoro-5-((2-fluoro-4-trifluoromethylphenyl)amino)-N-(2-hydroxyethoxy)benzo[d]thiazol-6-carboxamide |
| 36 | 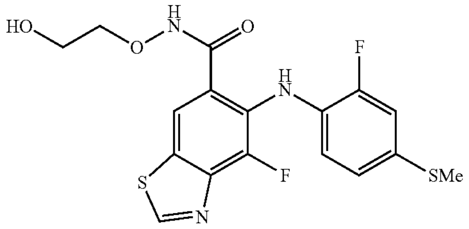 | 4-fluoro-5-((2-fluoro-4-methylthiophenyl)amino)-N-(2-hydroxyethoxy)benzo[d]thiazol-6-carboxamide |
| 37 | 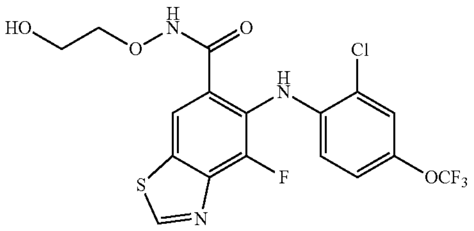 | 5-((4-trifluoromethoxy-2-chlorophenyl)amino)-4-fluoro-N-(2-hydroxyethoxy)benzo[d]thiazol-6-carboxamide |

Exemplary compounds

TABLE 3-continued

| Exemplary compounds | | |
|---|---|---|
| Compound No. | Structure | Compound Name |
| 38 | 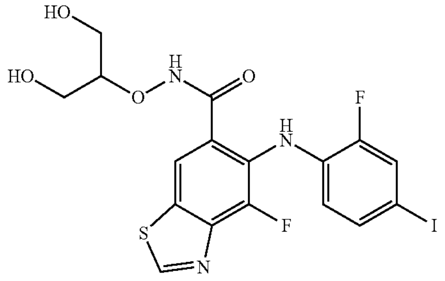 [SMILES: O=C(NOC(CO)CO)c1cc2scnc2c(F)c1Nc1ccc(I)cc1F] | 5-((2-fluoro-4-iodophenyl)amino)-N-(1,3-dihydroxy-isopropoxy)-4-fluorobenzo[d]thiazol-6-carboxamide |
| 39 | 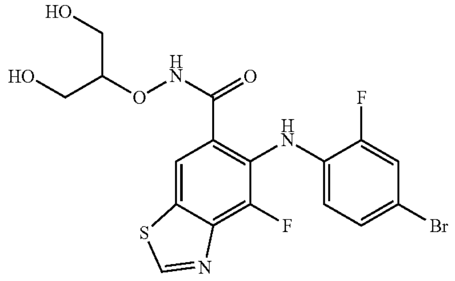 | 5-((4-bromo-2-fluorophenyl)amino)-N-(1,3-dihydroxy-isopropoxy)-4-fluorobenzo[d]thiazol-6-carboxamide |
| 40 | 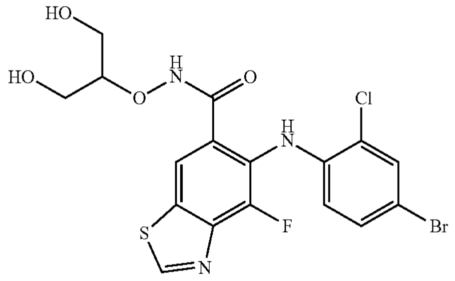 | 5-((4-bromo-2-chlorophenyl)amino-N-(1,3-dihydroxy-isopropoxy)-4-fluorobenzo[d]thiazol-6-carboxamide |
| 41 | 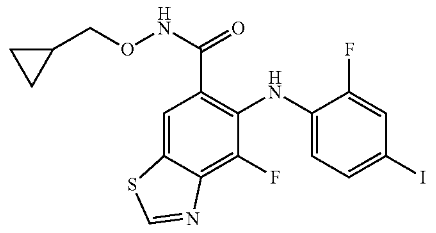 [SMILES: O=C(NOCC1CC1)c1cc2scnc2c(F)c1Nc1ccc(I)cc1F] | 4-fluoro-5-((2-fluoro-4-iodophenyl)amino)-N-cyclopropylmethyl-benzo[d]thiazol-6-carboxamide |
| 42 | 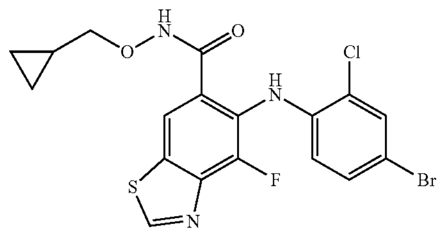 [SMILES: O=C(NOCC1CC1)c1cc2scnc2c(F)c1Nc1ccc(Br)cc1Cl] | 4-fluoro-5-((4-bromo-2-chlorophenyl)amino)-N-cyclopropylmethyl-benzo[d]thiazol-6-carboxamide |

TABLE 3-continued

Exemplary compounds

| Compound No. | Structure | Compound Name |
|---|---|---|
| 43 | 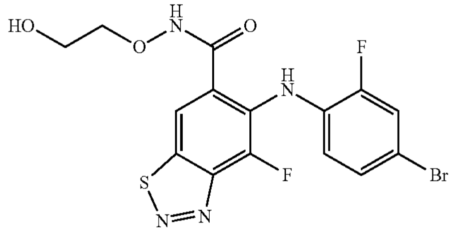 [SMILES: O=C(NOCCO)c1cc2snnc2c(F)c1Nc1ccc(Br)cc1F] | 5-((4-bromo-2-fluorophenyl)amino)-4-fluoro-N-(2-hydroxyethoxy)benzo[d][1,2,3]thiadiazole-6-carboxamide |
| 44 | 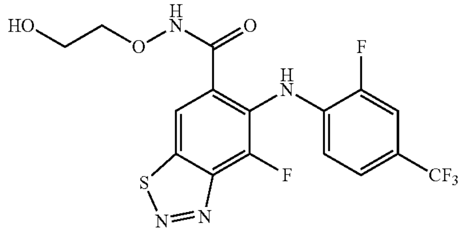 [SMILES: O=C(NOCCO)c1cc2snnc2c(F)c1Nc1ccc(C(F)(F)F)cc1F] | 4-fluoro-5-((2-fluoro-4-trifluoromethylphenyl)amino)-N-(2-hydroxyethoxy)benzo[d][1,2,3]thiadiazol-6-carboxamide |
| 45 | 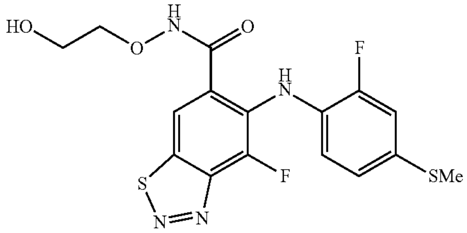 [SMILES: CSc1ccc(Nc2c(C(=O)NOCCO)cc3snnc3c2F)c(F)c1] | 4-fluoro-5-((2-fluoro-4-methylthiophenyl)amino-N-(2-hydroxyethoxy)benzo[d][1,2,3]thiadiazol-6-carboxamide |
| 46 | 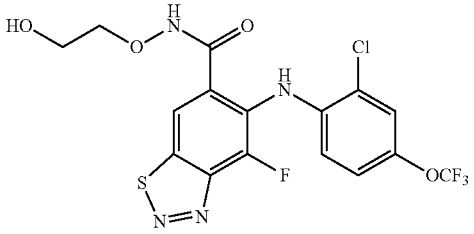 [SMILES: O=C(NOCCO)c1cc2snnc2c(F)c1Nc1ccc(OC(F)(F)F)cc1Cl] | 5-((4-trifluoromethoxy-2-chlorophenyl)amino)-4-fluoro-N-(2-hydroxyethoxy)benzo[d][1,2,3]thiadiazol-6-carboxamide |
| 47 | 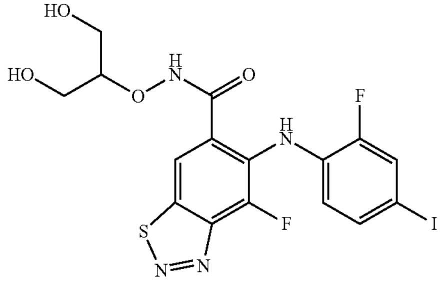 [SMILES: O=C(NOC(CO)CO)c1cc2snnc2c(F)c1Nc1ccc(I)cc1F] | 5-((2-fluoro-4-iodophenyl)amino-N-(1,3-dihydroxy-isopropoxy)-4-fluorobenzo[d][1,2,3]thiadiazol-6-carboxamide |
| 48 | 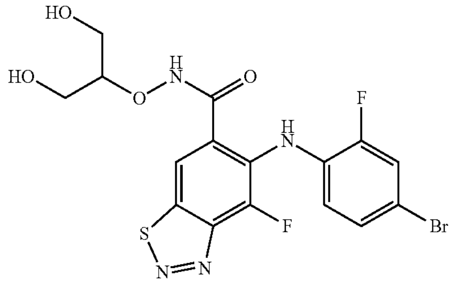 [SMILES: O=C(NOC(CO)CO)c1cc2snnc2c(F)c1Nc1ccc(Br)cc1F] | 5-((4-bromo-2-fluorophenyl)amino)-N-(1,3-dihydroxy-isopropoxy)-4-fluorobenzo[d][1,2,3]thiadiazol-6-carboxamide |

TABLE 3-continued

| Compound No. | Structure | Compound Name |
|---|---|---|
| | Exemplary compounds | |
| 49 | 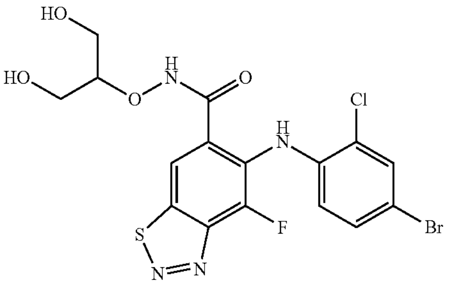 [SMILES: O=C(NOC(CO)CO)c1cc2snnc2c(F)c1Nc1ccc(Br)cc1Cl] | 5-((4-bromo-2-chlorophenyl)amino)-N-(1,3-dihydroxy-isopropoxy)-4-fluorobenzo[d][1,2,3]thiadiazol-6-carboxamide |
| 50 | 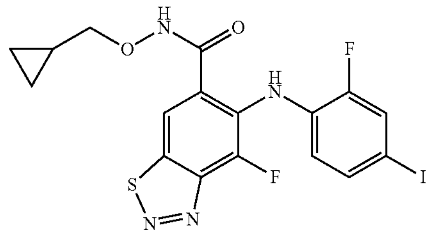 [SMILES: O=C(NOCC1CC1)c1cc2snnc2c(F)c1Nc1ccc(I)cc1F] | 4-fluoro-5-((2-fluoro-4-iodophenyl)amino)-N-cyclopropylmethyl-benzo[d][1,2,3]thiadiazol-6-carboxamide |
| 51 | 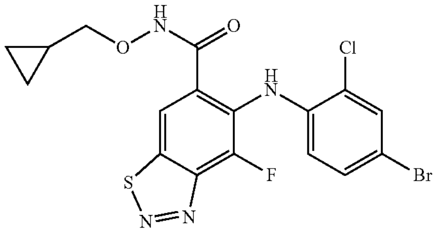 [SMILES: O=C(NOCC1CC1)c1cc2snnc2c(F)c1Nc1ccc(Br)cc1Cl] | 4-fluoro-5-((4-bromo-2-chlorophenyl)amino)-N-cyclopropylmethyl-benzo[d][1,2,3]thiadiazol-6-carboxamide |

Compounds detailed herein may be present as salts even if salts are not depicted and it is understood that the invention embraces all salts and solvates (e.g., hydrate) of the compounds depicted here, as well as the non-salt and non-solvate form of the compound, as is well understood by the skilled artisan. In some embodiments, the salts of the compounds of the invention are pharmaceutically acceptable salts.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The compounds depicted herein may have more than one stereoisomer, and occur as racemates, racemic mixtures where one enantiomer may be enriched, individual diastereomers, and mixtures of stereoisomers. All stereoisomers, including enantiomers and diastereomers are embraced by the present invention. Stereoisomers may be separated by methods known in the art. Compositions comprising compounds detailed herein where stereoisomers may exist may contain one pure stereomer or more than one stereoisomer where the stereoisomers are present in equal amounts or where some of the stereoisomers are enriched relative to the others.

The present invention includes within its scope prodrugs of the compound, such as the compound of the formula (I), (J), (K), (A-I) or any variations thereof. In general, such prodrugs are functional derivatives of the compound, such as functional derivatives of the compound of the formula (T), (J), (K), (A-I) or any variations thereof, which are readily convertible in vivo into the required compound of the formula (I), (J), (K), (A-I) or any variations thereof. Conventional procedures for the selection and preparation of suitable prodrug derivatives are described, for example, in "Prodrugs: Challenges and Rewards", ed. V. J. Stella et al, Springer, 2007. A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxy lie, phosphoric or sulfuric ester, or reduction or oxidation of a susceptible functionality. In some embodiments, a prodrug for a compound containing a hydroxy group may be an ester formed with an appropriate acid, such as lactic acid, citric acid, ascorbic acid, and the like.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. Unless otherwise stated, "substantially pure" intends a composition that contains no more than 30% impurity, wherein the impurity denotes a compound other than the compound comprising the majority of the composition or a salt thereof. In some embodiments, a composition of substantially pure compound or a salt thereof is provided wherein the composition contains no more than about 30%, about 25%, about 20%, about 15%, about 10%, about 5%, about 3% or about 1% impurity.

In one aspect, provided are kits comprising a compound detailed herein, or a salt, prodrug or solvate thereof, and suitable packaging. In one embodiment, a kit further comprises instructions for use. In one aspect, a kit comprises a compound detailed herein, such as a compound of the formula (I), (J), (K), (A-I) or any variations thereof, or a salt, prodrug or solvate thereof, and instructions for use of the compounds in the treatment or prevention of a disease or condition which can be ameliorated by inhibition of MEK in an individual in need thereof.

Articles of manufacture comprising a compound detailed herein, or a salt, prodrug or solvate thereof in a suitable container are provided. The container may be a vial, jar, ampoule and the like.

Synthetic Methods

The compounds of the invention may be prepared by a number of processes as generally described below and more specifically in the Examples hereinafter. In the following process descriptions, the symbols when used in the formulae depicted are to be understood to represent those groups described above in relation to the formulae herein.

Common organic solvents can be used in the following synthesis schemes. Typical solvents include, but not limited to, aliphatic and aromatic hydrocarbon (such as pentane, hexane, heptane, cyclohexane, petroleum ether, petrol, benzine, benzene, toluene, xylene), aliphatic and aromatic halohydrocarbon (such as dichloromethane, 1,2-dichloroethane, chloroform, phenixin, chlorobenzene, o-dichlorobenzene), alcohols (such as methanol, ethanol, propan-1-ol, isopropanol, t-butanol, ethane-1,2-diol), ether (such as diethyl ether, dibutyl ether, glycol dimethyl ether, 2-methoxyethyl ether, tetrahydrofuran, dioxane), ketone (such as acetone, methyl ethyl ketone, methyl isopropyl ketone, methyl isobutyl ketone), ester (such as ethyl acetate, methyl acetate), nitrile (such as acetonitrile, propiononitrile), amide (such as N,N-dimethylformamide, N,N-dimethylacetamide and N-methylpyrrolidin-2-one), DMSO, sulfolane, HMPA, DMPU and so on.

General Synthesis of Compounds of Formula (I)

The compound of the formula (I) where $X^1$ is N, $X^2$ is S, $R^6$ is —C(O)NHOR$^7$, and $R^3$ is halo can be synthesized according to Scheme 1, wherein $R^1$, $R^2$, $R^4$, $R^5$ and $R^7$ are as defined for the formula (J), (I) or any variations thereof; and each $R^{14}$ and $R^{15}$ is independently allyl, benzyl, benzyl substituted with 1 to 3 methoxy groups, $C_1$-$C_5$ alkyl or —SiR$^{16}$R$^{17}$R$^{18}$ where $R^{16}$, $R^{17}$ and $R^{18}$ are independently selected from $C_1$-$C_{10}$ alkyl and $C_6$-$C_{14}$ aryl.

Scheme 1

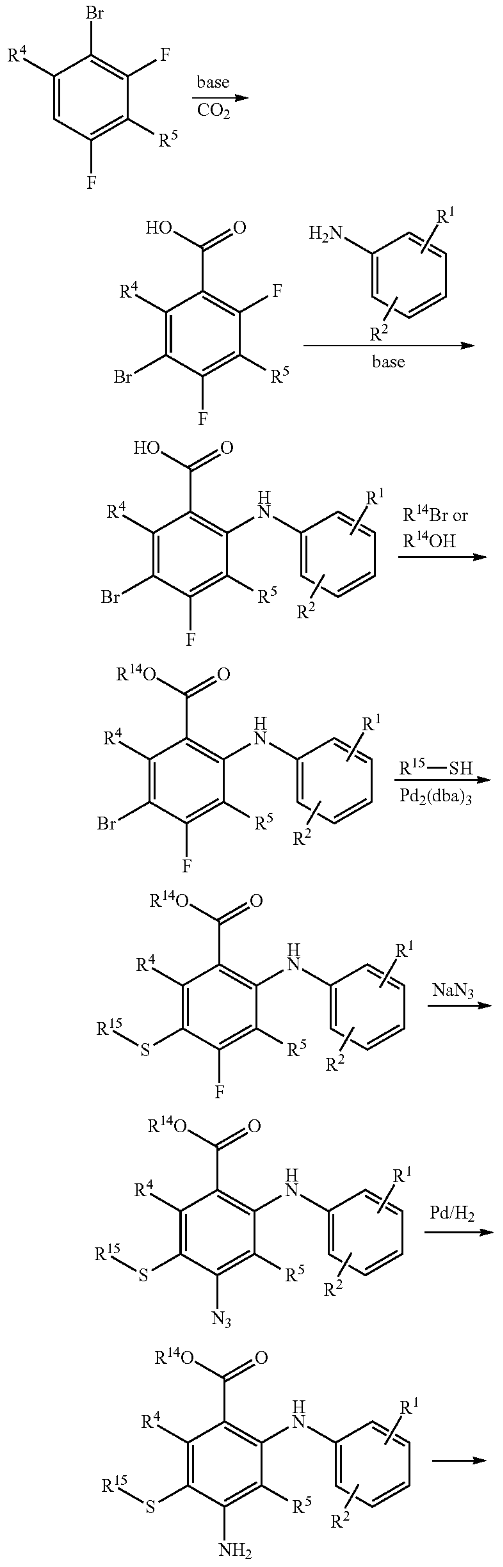

-continued
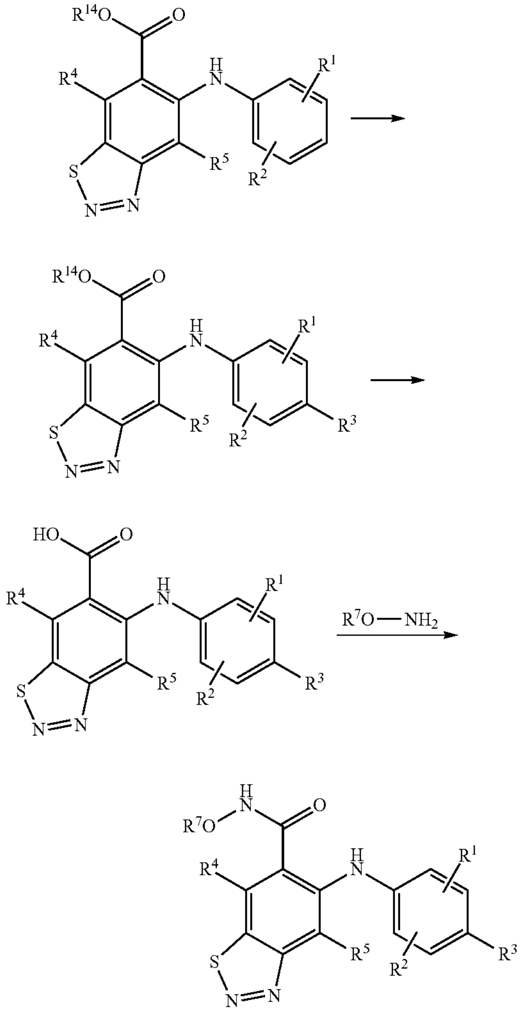
The steps in Scheme 1 are illustrated further by an exemplary synthesis of 4-fluoro-5-((2-fluoro-4-iodophenyl)amino)-N-(2-hydroxy ethoxy)benzo[d][1,2,3]thiadiazole-6-carboxamide, according to the reactions outlined in Scheme 1.1.
Scheme 1.1
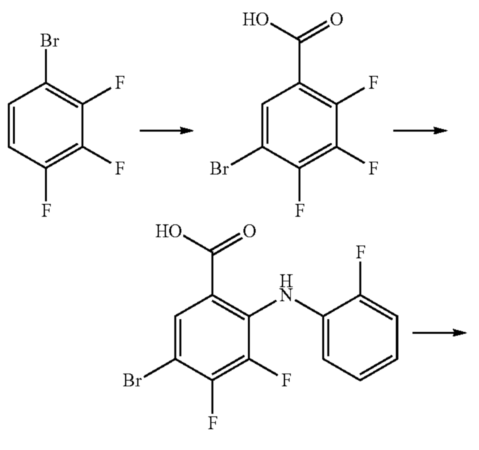
-continued
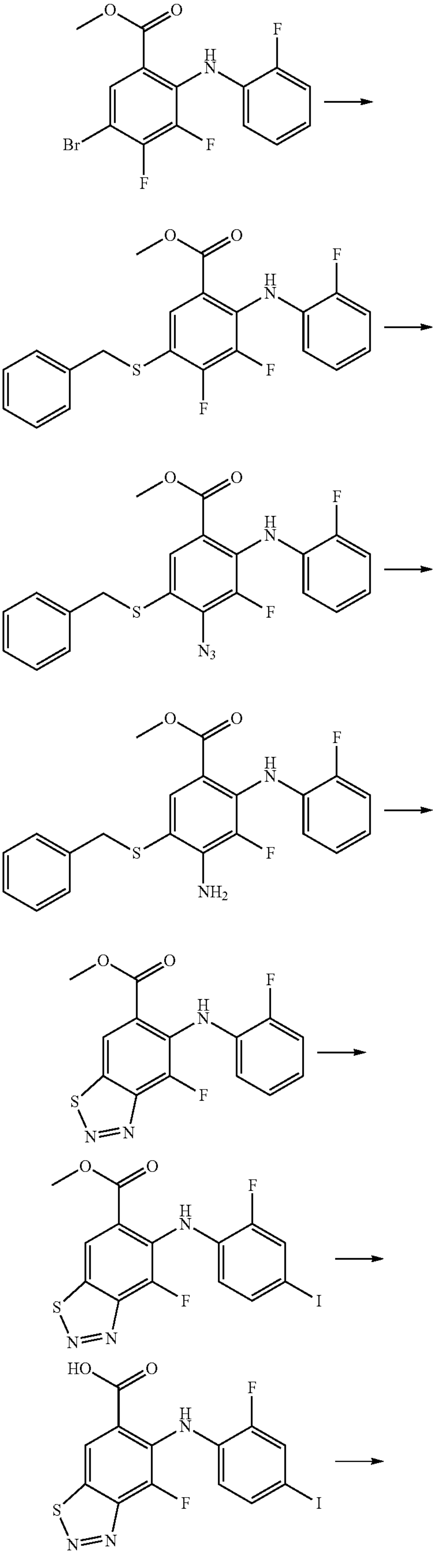

-continued

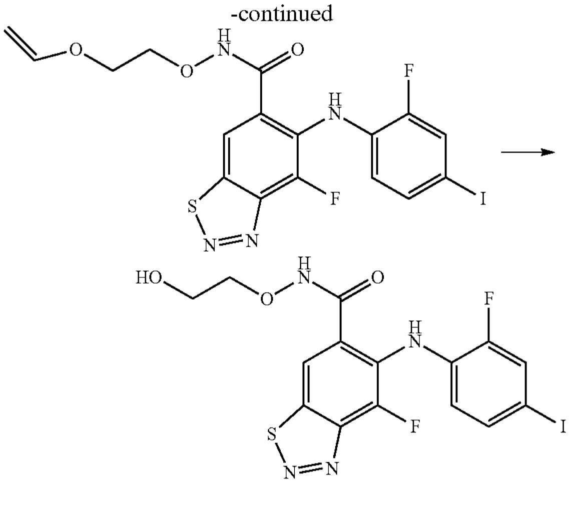

Step 1.1.1

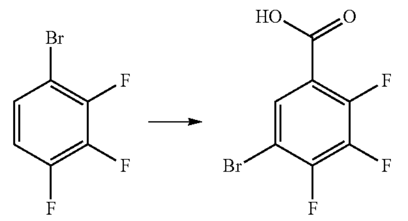 [SMILES: Fc1ccc(Br)c(F)c1F ; O=C(O)c1cc(Br)c(F)c(F)c1F]

To a solution of 2,3,4-trifluorobromobenzene in appropriate solvent is added strong base (such as LDA, nBuLi, LiHDMS) under nitrogen atmosphere. The reaction is generally carried out at low temperature (−50-−80° C., prefer −78° C.). The reaction is kept stirring for some time (0.5-12 h, preferably select 0.5-2 h) and is added dry ice. The resulting mixture is kept stirring for some time (3-12 h, prefer 5-10 h) and 5-bromo-2,3,4-trifluorobenzoic acid is obtained after conventional workup.

Typical solvents are as defined above and prefer anhydrous THF, ethyl ether and dioxane).

Step 1.1.2

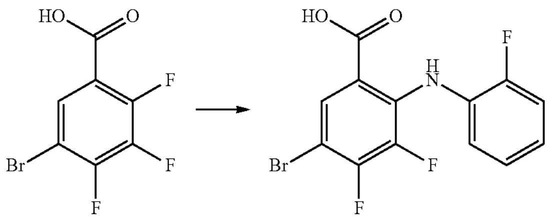 [SMILES: O=C(O)c1cc(Br)c(F)c(F)c1F ; O=C(O)c1cc(Br)c(F)c(F)c1Nc1ccccc1F]

5-Bromo-2,3,4-trifluorobenzoic acid can be reacted with halogenated aniline (such as o-fluoroaniline, o-chloroaniline, o-bromoaniline, o-iodoaniline) under strong basic condition (such as LDA, n-BuLi, LiHDMS) in appropriate solvent. The reaction is generally carried out at low temperature (−50-−80° C., prefer −78° C.) and normally completes within several hours (3-12 h, prefer 5-10 h). 5-Bromo-3,4-difluoro-2-((2-fluorophenyl)amino)benzoic acid is obtained after conventional workup.

Typical solvents are as defined above and prefer anhydrous THF, ethyl ether and dioxane).

Step 1.1.3

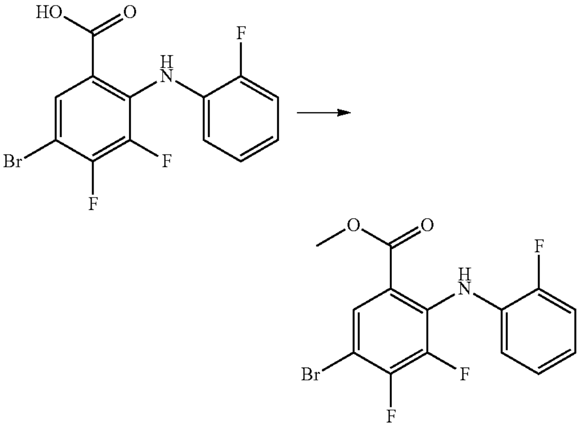

5-Bromo-3,4-difluoro-2-((2-fluorophenyl)amino)benzoic acid can be reacted with MeOH in the presence of $SOCl_2$ in appropriate solvent. The reaction normally completes within several hours (3-12 h, prefer 5-10 h). Methyl 5-bromo-3,4-difluoro-2-((2-fluorophenyl)amino)benzoate is obtained after conventional workup.

Typical solvents are as defined above and prefer methanol and ethanol.

Step 1.1.4

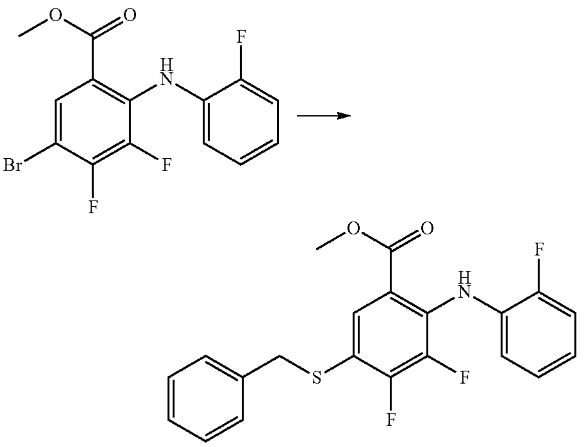

To a solution of methyl 5-bromo-3,4-difluoro-2-((2-fluorophenyl)amino)benzoate in appropriate solvent is added base under nitrogen atmosphere, followed by Pd catalyst, phosphine ligand and phenylmethanethiol. The reaction is generally carried out at high temperature (80-130° C., prefer 90-110° C.) and normally complete within several hours (8-24 h, prefer 12-18 h). Methyl 5-(benzylthio)-3,4-difluoro-2-((2-fluorophenyl)amino)benzoate is obtained after conventional workup.

Typical bases include, but are not limited to, aliphatic and aromatic amine (such as, but not limited to, N-ethyl-N-isopropylpropan-2-amine, triethylamine, diethylamine, DBU, t-butylamine, cyclopropanamine, dibutylamine, diisopropylamine, 1,2-dimethylpropanamine), inorganic base (such as $Na_2CO_3$, $K_2CO_3$, $NaHCO_3$, $KHCO_3$, $^t$BuONa, $^t$BuOK) and prefer N-ethyl-N-isopropylpropan-2-amine.

Typical Pd catalysts include, but are not limited to, tris(dibenzylideneacetone)dipalladium, bis(dibenzylideneacetone) palladium, bis(triphenylphosphine)palladium(II) chloride, palladium diacetate, tetrakis(triphenylphosphine) palladium, bis(triphenylphosphinepalladium)acetate and preferably select tris(dibenzylideneacetone)dipaliadium.

Typical phosphine ligands include, but are not limited to, dimethylbisdiphenylphosphinoxanthene, tri-tert-butylphosphine, tri-p-tolylphosphine, tris(4-chlorophenyl)phosphine, triisopropylphosphine, tris(2,6-dimethoxyphenyl)phosphine, 1,1'-bis (diphenylphosphino)ferrocene and preferably select dimethylbisdiphenylphosphinoxanthene.

Typical solvents are as defined above and prefer dioxane.

Step 1.1.5

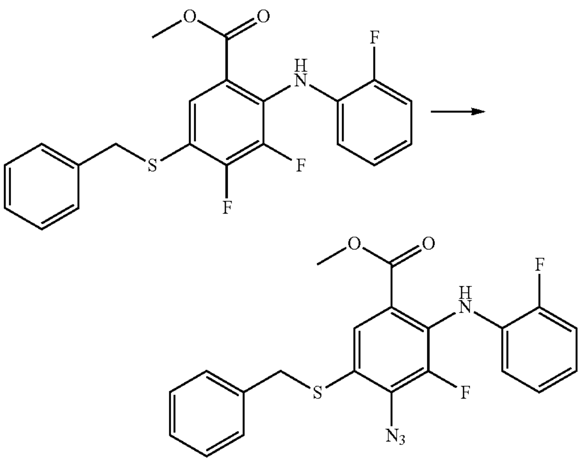

Methyl 5-(benzylthio)-3,4-difluoro-2-((2-fluorophenyl) amino)benzoate can be reacted with azide (such as $NaN_3$, $KN_3$) in appropriate solvent. The reaction is generally carried out at high temperature (60-120° C., prefer 80-100° C.) and normally completes within several hours (1-12 h, prefer 3-10 h). Methyl 4-azido-5-(benzylthio)-3-fluoro-2-((2-fluorophenyl)amino)benzoate is obtained after conventional workup.

Typical solvents are as defined above and prefer N,N-dimethylformamide and N,N dimethylacetamide.

Step 1.1.6

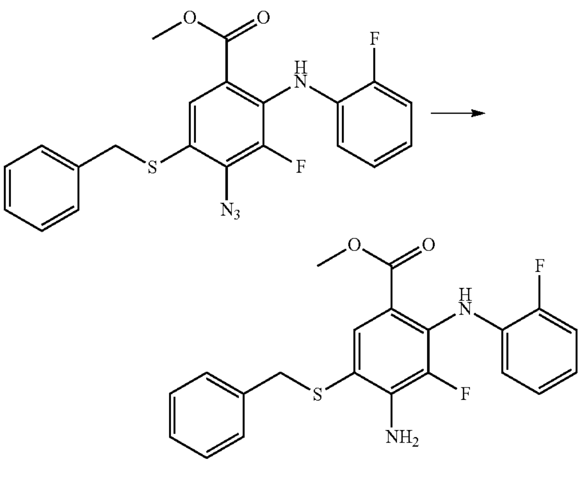

Methyl 4-azido-5-(benzylthio)-3-fluoro-2-((2-fluorophenyl)amino)benzoate can be hydrogenated in the presence of appropriate catalyst (such as Pd/C, Pt, Ni) in appropriate solvent. The reaction normally completes within several hours (1-12 h, prefer 3-10 h). Methyl 4-amino-5-(benzylthio)-3-fluoro-2-((2-fluorophenyl)amino)benzoate is obtained after conventional workup.

Typical solvents are as defined above and prefer methanol, ethanol, propan-1-ol and water.

Step 1.1.7

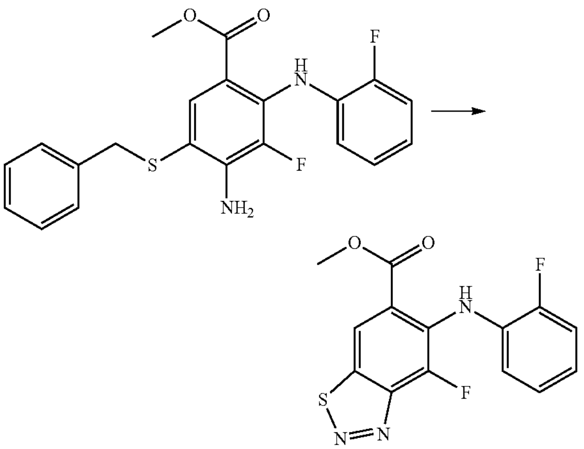

Methyl 4-fluoro-5-((2-fluorophenyl)amino)benzo[d][1,2,3]thiadiazole-6-carboxylate can be readily prepared by cyclization of methyl 4-amino-5-(benzylthio)-3-fluoro-2-((2-fluorophenyl)amino)benzoate in the presence of inorganic acid and alkali nitrite in the appropriate solvent.

Said inorganic acids include, but are not limited to, hydrochloric acid, sulfuric acid, nitric acid and phosphoric acid.

Said alkali nitrite includes, but is not limited to, sodium nitrite, potassium nitrite and cesium nitrite.

Typical solvents are as defined above and prefer organic acid such as, but not limited to acetic acid and formic acid.

Step 1.1.8

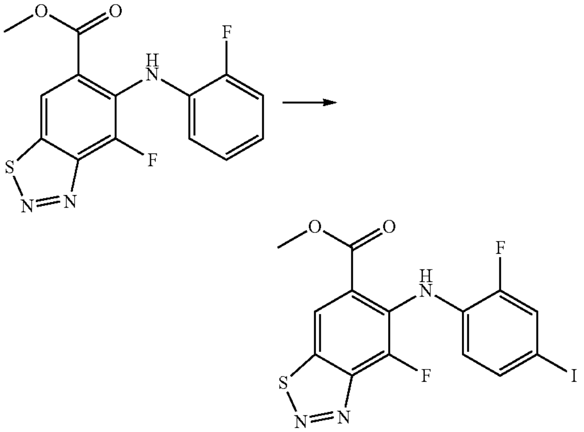

Methyl 4-fluoro-5-((2-fluorophenyl)amino)benzo[d][1,2,3]thiadiazole-6-carboxylate can be reacted with halogenations reagent (such as NIS) in the presence of acid at ambient temperature in appropriate solvent. The reaction normally completes within several hours (1-12 h, prefer 3-10 h). Methyl 4-fluoro-5-((2-fluoro-4-iodophenyl)amino)benzo[d][1,2,3]thiadiazole-6-carboxylate is obtained after conventional workup.

Typical acids include, but are not limited to, trifluoroacetic acid, trifluoromethanesulfonic acid, methanesulfonic acid, formic acid, and acetic acid.

Typical solvents are as defined above and prefer N,N-dimethylformamide and N,N dimethylacetamide.

Step 1.1.9

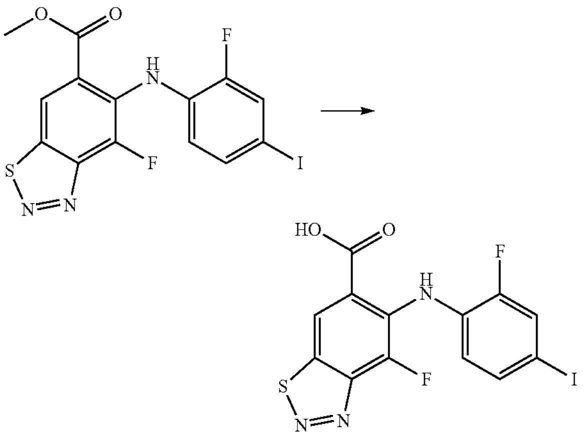

4-Fluoro-5-((2-fluoro-4-iodophenyl)amino)benzo[d][1,2,3]thiadiazole-6-carboxylic acid can be prepared from methyl 4-fluoro-5-((2-fluoro-4-iodophenyl)amino)benzo[d][1,2,3]thiadiazole-6-carboxylate be deprotection in appropriate solvent.

Typical deprotection reagents may be base, Pd/C, Lewis acid or $R_4NF$.

Said base includes, but are not limited to, NaOH, KOH, $Na_2CO_3$, $K_2CO_3$.

Said Lewis acids include, but are not limited to $AlCl_3$, $BF_3$ and $BBr_3$.

Typical solvents are as defined above and prefer dichloromethane, THF, MeOH and DMF.

Step 1.1.10

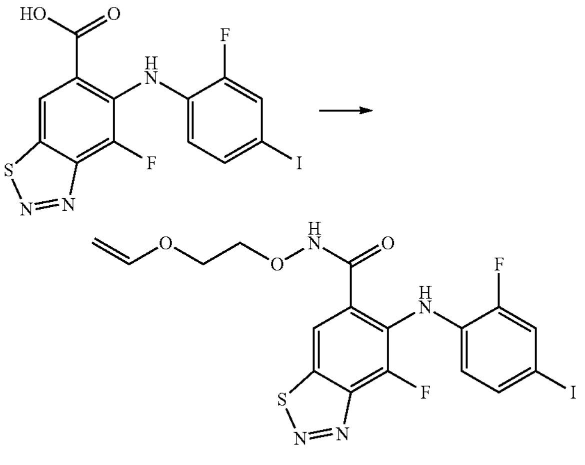

4-Fluoro-5-((2-fluoro-4-iodophenyl)amino)benzo[d][1,2,3]thiadiazole-6-carboxylic acid can be reacted with O-(2-(vinyloxy)ethyl)hydroxyl amine in the presence of coupling reagent in appropriate solvent. The reaction is generally carried out at ambient temperature and normally complete within several hours (1-12 h, prefer 3-10 h). 4-Fluoro-5-((2-fluoro-4-iodophenyl)amino)-N-(2-(vinyloxy)ethoxy)benzo[d][1,2,3]thiadiazole-6-carboxamide is obtained after conventional workup.

Coupling reagents include, but are not limited to, HOBt, EDCI, HATU and TBTU.

Typical solvents are as defined above and prefer dichloromethane, 1,2-dichloroethane and N,N-dimethylformamide.

Step 1.1.11

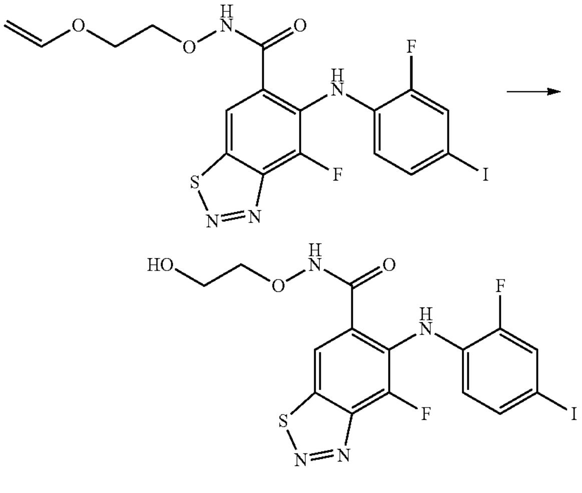

4-Fluoro-5-((2-fluoro-4-iodophenyl)amino)-N-(2-(vinyloxy)ethoxy)benzo[d][1,2,3]thiadiazole-6-carboxamide can be reacted under acidic condition in appropriate solvent. The reaction normally completes within (1-12 h, prefer 3-10 h). 4-Fluoro-5-((2-fluoro-4-iodophenyl)amino)-N-(2-hydroxyethoxy)benzo[d][1,2,3]thiadiazole-6-carboxamide is obtained after conventional workup.

Typical acids include, but are not limited to, hydrochloric acid, sulfuric acid and trifluoroacetic acid.

Typical solvents are as defined above and prefer dichloromethane and 1,2-dichloroethane.

A compound of the formula (I-1-a), i.e., a compound of the formula (I) where $X^1$ is N, $X^2$ is S and $R^6$ is —C(O)N($R^8$)O$R^7$, where $R^3$ is halo may be synthesized according to Scheme X-1, wherein $R^1$, $R^2$, $R^4$, $R^5$, $R^7$ and $R^8$ are as defined for the formula (J), (I) or any variations thereof; each $R^{14}$ and $R^{15}$ is independently benzyl, benzyl substituted with 1 to 3 methoxy groups, $C_1$-$C_5$ alkyl or —Si$R^{16}R^{17}R^{18}$ where $R^{16}$, $R^{17}$ and $R^{18}$ are independently selected from $C_1$-$C_{10}$ alkyl and $C_6$-$C_{14}$ aryl, and X is fluoro, chloro, bromo or iodo.

Scheme X-1

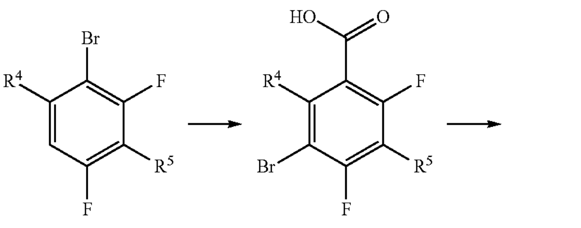

-continued

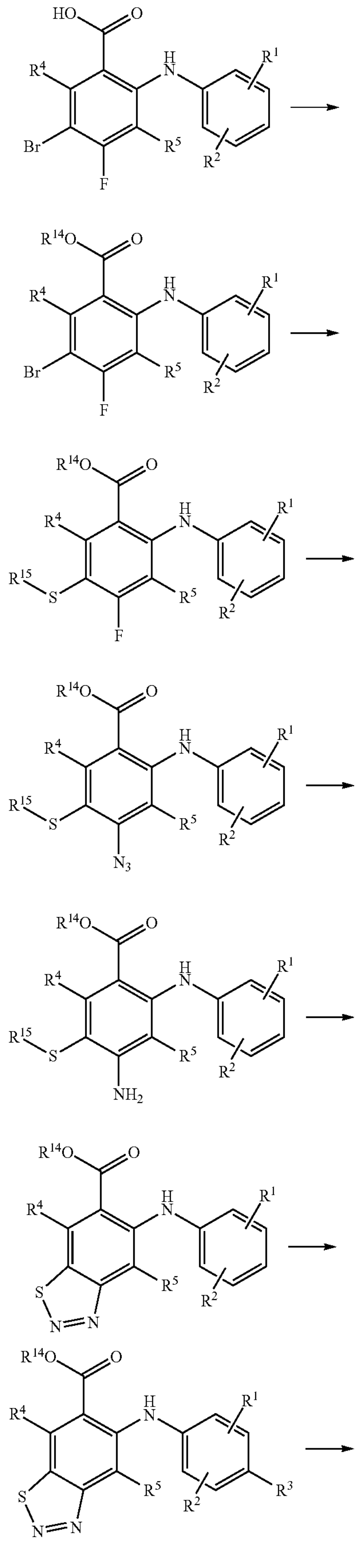

-continued

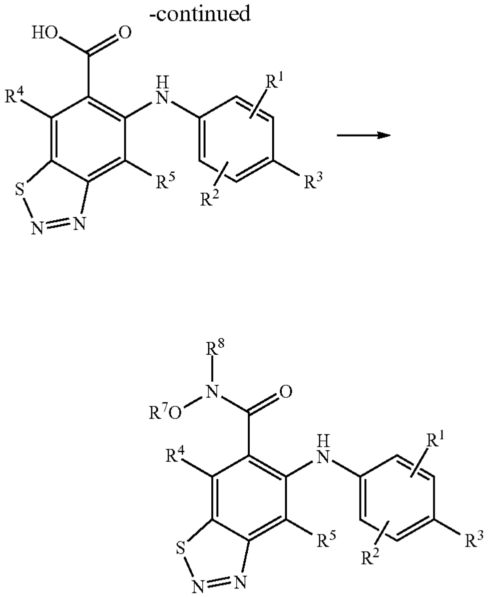

Step 1:

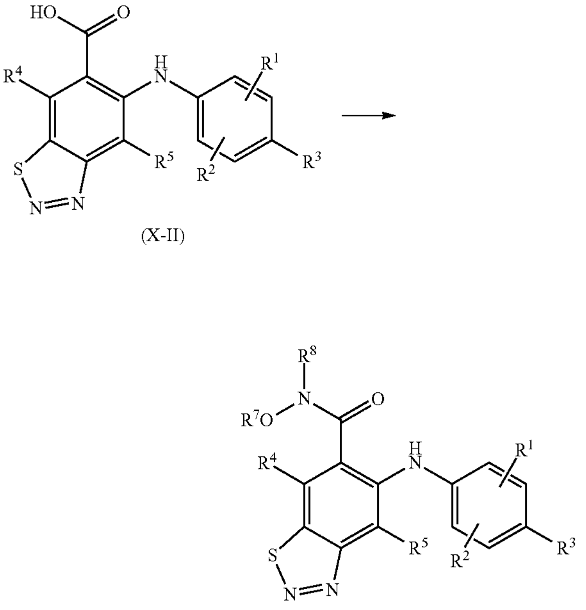

(X-II)

(I-1-a)

The compound of formula (I-1-a) can be prepared from the reaction of the compound of formula (X-II) with hydroxylamine ($R^7OR^8NH$) in the presence of coupling reagents in appropriate solvent.

Typical coupling reagents include, but are not limited to 1-Hydroxy-1H-benzotriazole (HOBt), 3-(ethyliminomethyleneamino)-N,N-dimethylpropan-1-amine(EDCI), O-(7-azabenzotriazol-1-yl)-N,N,N',N'-tetramethyluronium hexafluorophosphate (HATU) and O-Benzotriazol-1-yl-N,N,N',N'-tetramethyluronium tetrafluoroborate (TBTU).

Typical solvents are as defined above and prefer dichloromethane, 1,2-dichloroethane, THF and N,N-dimethylformamide.

Step 2:

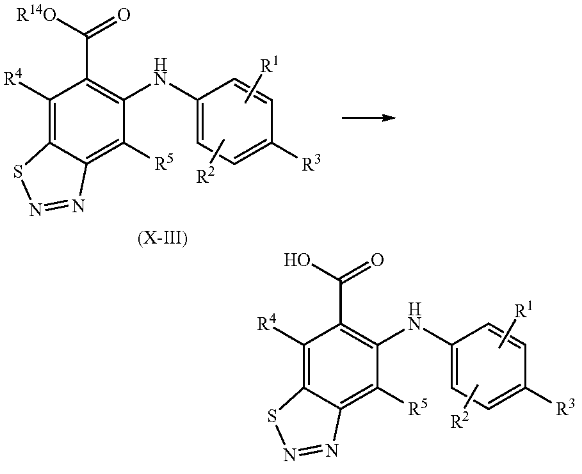

(X-III)

(X-II)

The compound of formula (X-II) can be prepared from deprotection of the compound of formula (X-III) in appropriate solvent.

Typical deprotection reagents may be base, Pd/C, Lewis acid or $R_4NF$ according to different $R^{14}$.

Said base includes, but are not limited to, NaOH, KOH, $Na_2CO_3$, $K_2CO_3$.

Said Lewis acids include, but are not limited to $AlCl_3$, $BF_3$ and $BBr_3$.

Typical solvents are as defined above and prefer dichloromethane, THF, MeOH and DMF.

Step 3:

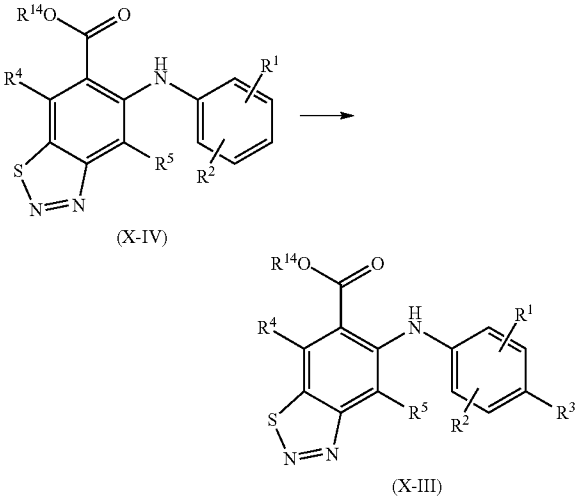

(X-IV)

(X-III)

The compound of formula (X-III) where $R^3$ is halo can be prepared from halogenation of the compound of formula (X-IV) in the presence of halogenation reagents and acid in appropriate solvent.

Typical halogenation reagents include, but are not limited to NCS, NBS, NIS and so on.

Typical acids include, but are not limited to, trifluoroacetic acid, trifluoromethanesulfonic acid, methanesulfonic acid, formic acid, and acetic acid.

Typical solvents are as defined above and prefer $CH_2Cl_2$, $CHCl_3$, N,N-dimethylformamide and N,N-dimethylacetamide.

Step 2.1.4

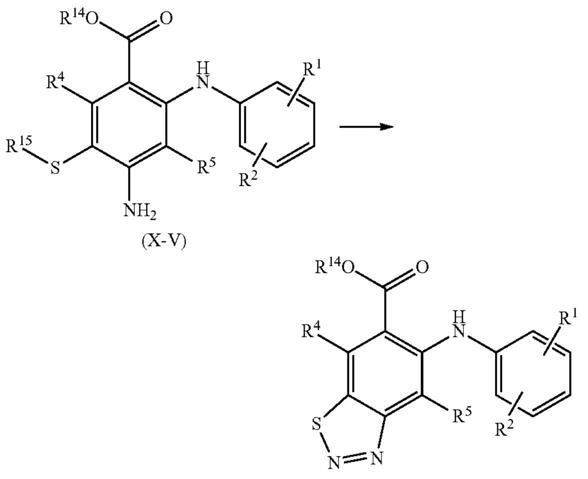

(X-V)

(X-IV)

The compound of formula (X-IV) can be prepared from cyclization of the compound of formula (X-Y) in the presence of diazotization reagents (such as inorganic acid and alkali nitrite) in appropriate solvent.

Typical inorganic acids include, but are not limited to, hydrochloric acid, sulfuric acid, nitric acid and phosphoric acid.

Typical alkali nitrite includes, but is not limited to, sodium nitrite, potassium nitrite and cesium nitrite.

Typical solvents are as defined above and prefer organic acid such as, but not limited to acetic acid and formic acid.

Step 5:

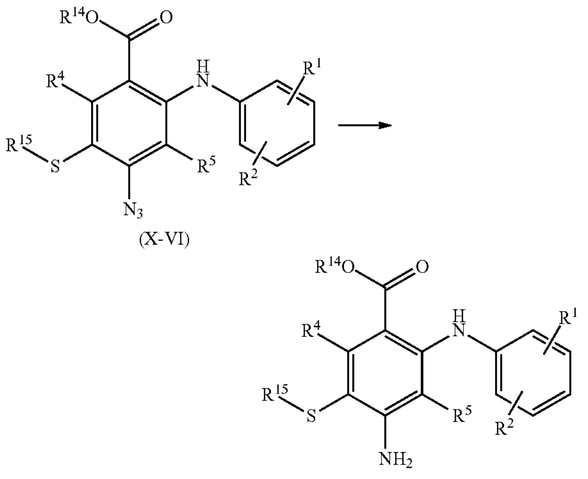

(X-VI)

(X-V)

The compound of formula (X-V) can be prepared from reduction of the compound of formula (X-VI) in the presence of reduction reagents in appropriate solvent.

Typical reduction reagents include, but are not limited to hydrogenation catalyst, $SnCl_2$, $PPh_3$, $NaBH_4$, $BH_3$ and Raney Ni.

Typical solvents are as defined above and prefer methanol, ethanol, ethyl acetate and THF.

Step 6:

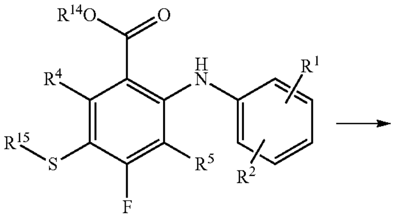

(X-VII)

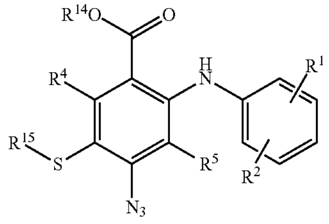

(X-VI)

The compound of formula (X-VI) can be prepared from reaction of the compound of formula (X-VII) with azide in appropriate solvent.

Typical azides prefer alkali azide, such as but not limited to $NaN_3$ and $KN_3$ Typical solvents are as defined above and prefer DMSO, N,N-dimethylformamide and N,N-dimethylacetamide.

Step 7:

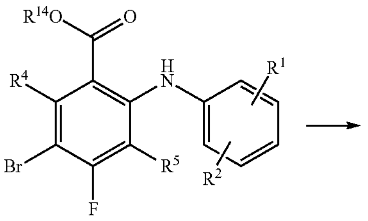

(X-VIII)

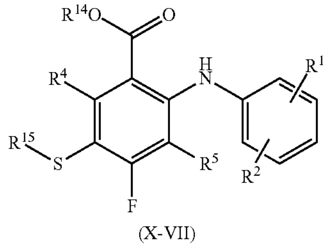

(X-VII)

The compound of formula (X-VII) can be prepared from the reaction of the compound of formula (X-VIII) with mercaptan ($R^{15}SH$) in the presence of base, phosphine ligand and catalyst in appropriate solvent.

Typical bases include, but are not limited to, aliphatic and aromatic amine (such as, but not limited to, N-ethyl-N-isopropylpropan-2 amine, triethylamine, diethylamine, DBU, t-butylamine, cyclopropanamine, dibutylamine, diisopropylamine, 1,2-dimethylpropanamine), inorganic base (such as $Na_2CO_3$, $K_2CO_3$, $NaHCO_3$, $KHCO_3$, $^t$BuONa, $^t$BuOK) and prefer N-ethyl-N-isopropylpropan-2-amine.

Typical catalysts prefer Pd catalysts, such as, but are not limited to, tris(dibenzylideneacetone)dipalladium, bis (dibenzylideneacetone) palladium, bis(triphenylphosphine) palladium(II) chloride, palladium diacetate, tetrakis(triphenylphosphine)palladium, bis(triphenylphosphinepalladium)acetate and preferably select tris(dibenzylideneacetone)dipalladium.

Typical phosphine ligands include, but are not limited to, dimethylbisdiphenylphosphinoxanthene, tri-tert-butylphosphine, tri-p-tolylphosphine, tris(4-chlorophenyl)phosphine, triisopropylphosphine, tris(2,6-dimethoxyphenyl)phosphine, 1,1'-bis (diphenylphosphino)ferrocene and preferably select dimethylbisdiphenyl phosphinoxanthene.

Typical solvents are as defined above and prefer dioxane.

Step 8

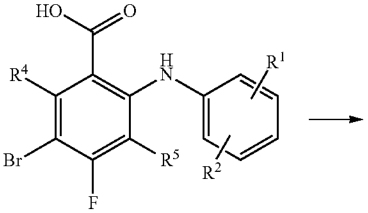

(X-IX)

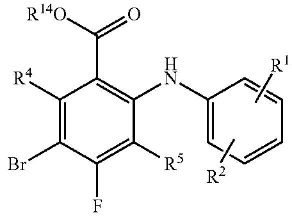

(X-VIII)

The compound of formula (X-VIII) can be prepared from the reaction of the compound of formula (X-IX) with alcohol ($R^{14}OH$) or halide ($R^{14}X$) in the presence of optional catalyst in appropriate solvent.

Typical catalysts are selected according to different substrates and include $SOCl_2$, sulfuric acid, inorganic base (such as $NaHCO_3$, $KHCO_3$, $Na_2CO_3$) and organic base (such as triethylamine and N-ethyl-N-isopropylpropan-2-amine).

Typical solvents are as defined above and prefer methanol, ethanol, THF and DMF.

Step 9:

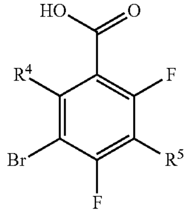

(X-X)

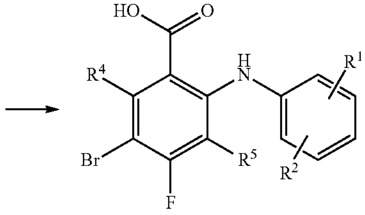

(X-IX)

The compound of formula (X-IX) can be prepared from the reaction of the compound of formula (X-X) with the following compound in the presence of strong base in appropriate solvent.

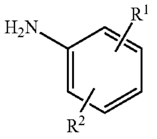

Typical strong base include, but are not limited to IDA, n-BuLi and LiHDMS.

Typical solvents are as defined above and prefer anhydrous THF.

Step 10:

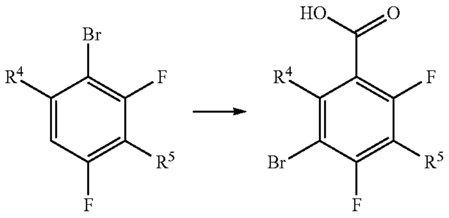

(X-XI) (X-X)

The compound of formula (X-X) can be prepared from the reaction of the compound of formula (X-XI) with $CO_2$ in the presence of strong base in appropriate solvent.

Typical strong base include, but are not limited to LDA, n-BuLi and LiHDMS.

Typical solvents are as defined above and prefer anhydrous THF.

A compound of the formula (I-1-a) where $R^3$ is other than halo may be synthesized according to Scheme X-2, where $R^1$, $R^2$, $R^4$, $R^5$, $R^7$ and $R^8$ are as defined for the formula (J), (I) or any variations thereof; and each $R^{14}$ and $R^{15}$ is independently benzyl, benzyl substituted with 1 to 3 methoxy groups, $C_1$-$C_5$ alkyl or —$SiR^{16}R^{17}R^{18}$ where $R^{16}$, $R^{17}$ and $R^{18}$ are independently selected from $C_1$-$C_{10}$ alkyl and $C_6$-$C_{14}$ aryl.

Scheme X-2

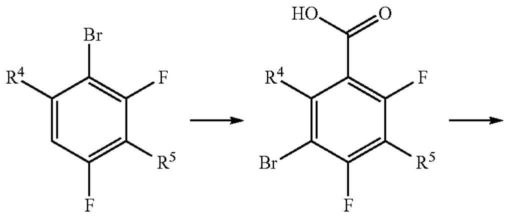

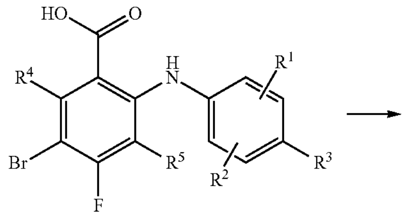

-continued

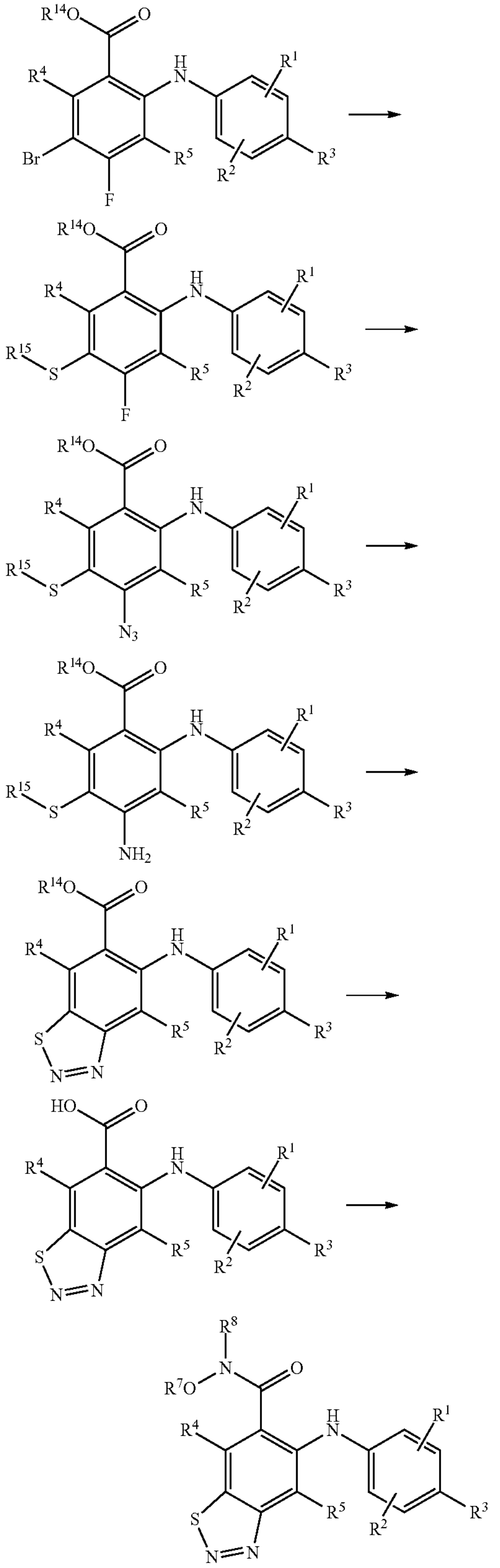

The synthetic scheme (X-2) for formula (I-1-a) compound wherein $R^3$ is other than halo is similar to the Scheme (X-1) for formula (I-1-a) wherein $R^3$ is halo. The difference between the two schemes is that the following aniline is used in the synthetic scheme (X-2) and the corresponding Step 3 is omitted.

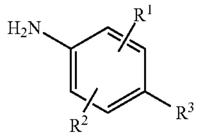

The compound of formula (I-1-b), where $R^1$, $R^2$, $R^3$, $R^4$, $R^5$, $R^7$ and $R^8$ are as defined for the formula (J), (I) or any variations thereof, is prepared according to the method outlined in the following scheme:

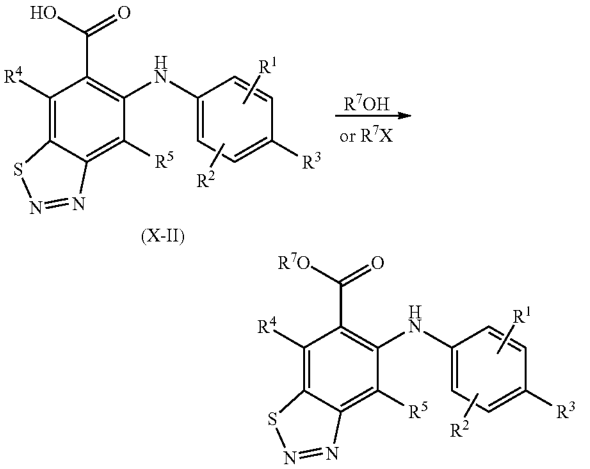

(X-II)

(I-1-b)

The compound of formula (I-1-b) can be prepared from the reaction of the compound of formula (X-II) with alcohol ($R^7OH$) in the presence of coupling reagents or with halide ($R^7X$) in the presence of base in appropriate solvent.

Typical coupling reagents include, but are not limited to 1-Hydroxy-1H-benzotriazole (HOBt), 3-(ethyliminomethyleneamino)-N,N-dimethylpropan-1-amine(EDCI), O-(7-azabenzotriazol-1-yl)-N,N,N',N'-tetramethyluronium hexafluorophosphate (HATU) and O-Benzotriazol-1-yl-N,N,N',N'-tetramethyluronium tetrafluoroborate (TBTU).

Typical solvents are as defined above and prefer dichloromethane, chloroform and THF.

The compound of formula (I-1-c), where $R^1$, $R^2$, $R^3$, $R^4$, $R^5$, $R^7$ and $R^8$ are as defined for the formula (J), (I) or any variations thereof, is prepared according to the method outlined in the following scheme:

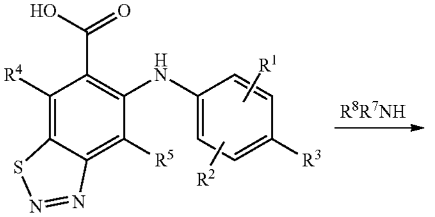

(X-II)

-continued

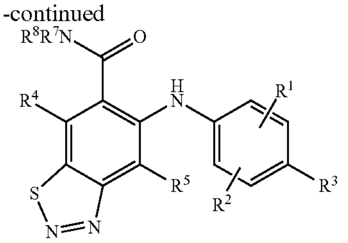

(I-1-c)

The compound of formula (I-1-c) can be prepared from the reaction of the compound of formula (X-II) with amine ($R^8R^7NH$) in the presence of coupling reagents in appropriate solvent.

Typical coupling reagents include, but are not limited to 1-Hydroxy-1H-benzotriazole (HOBt), 3-(ethyliminomethyleneamino)-N,N-dimethylpropan-1-amine(EDCI), O-(7-azabenzotriazol-1-yl)-N,N,N',N'-tetramethyluronium hexafluorophosphate (HATU) and O-Benzotriazol-1-yl-N,N,N',N'-tetramethyluronium tetrafluoroborate (TBTU).

Typical solvents are as defined above and prefer dichloromethane, chloroform and THF.

The compound of formula (I-1-d), where $R^1$, $R^2$, $R^3$, $R^4$, $R^5$, $R^7$ and $R^8$ are as defined for the formula (J), (I) or any variations thereof, is prepared according to the method outlined in the following scheme:

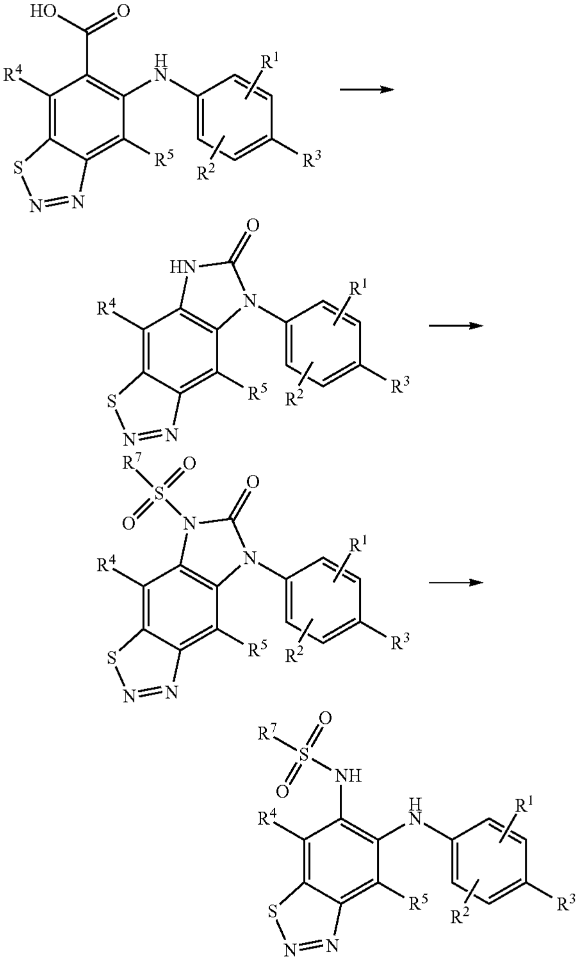

Step 1:

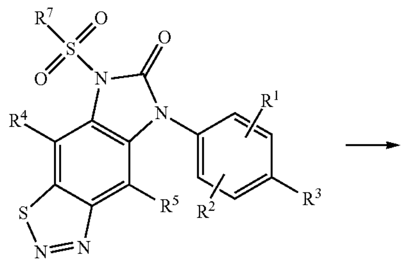

(X-XII)

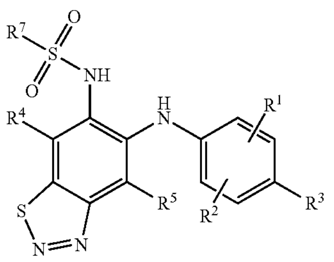

(I-1-d)

The compound of formula (I-1-d) can be prepared from the compound of formula (X-XII) in the presence of base in appropriate solvent.

Typical bases include, but are not limited to, inorganic base (such as $Na_2CO_3$, $K_2CO_3$, $NaHCO_3$, $KHCO_3$, $^{t}$BuONa and $^{t}$BuOK) and organic base (such as diethylamine, triethylamine, pyridine and potassium trimethylsilanolate) and prefer potassium trimethylsilanolate.

Typical solvents are as defined above and prefer THF.

Step 2:

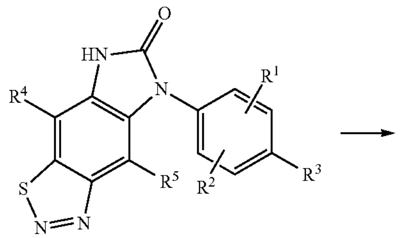

(X-XIII)

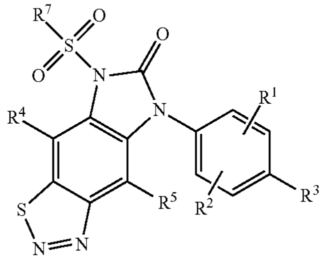

(X-XII)

The compound of formula (XII) can be prepared from the reaction of the compound of formula (XIII) with $R^7SO_2X$ (wherein X is fluoro, chloro, bromo and iodo) in the presence of base and catalyst in appropriate solvent.

Typical bases include, but are not limited to, inorganic base (such as $Na_2CO_3$, $K_2CO_3$, $NaHCO_3$, $KHCO_3$, $^{t}$BuONa and $^{t}$BuOK) and organic base (such as diethylamine, triethylamine and pyridine) and prefer triethylamine.

Typical catalysts include, but are not limited to, 4-dimethylaminopyridine (DMAP).

Typical solvents are as defined above and prefer dichloromethane and chloroform.

Step 3:

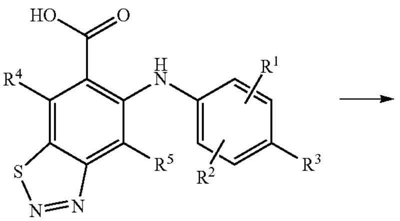

(X-II)

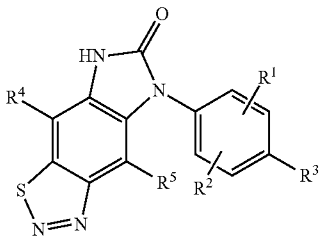

(X-XIII)

The compound of formula (X-XIII) can be prepared from the reaction of the compound of formula (X-II) with azide in the presence of base in appropriate solvent.

Typical bases include, but are not limited to, inorganic base (such as $Na_2CO_3$, $K_2CO_3$, $NaHCO_3$, $KHCO_3$, $^{t}$BuONa and $^{t}$BuOK) and organic base (such as diethylamine, triethylamine and pyridine) and prefer triethylamine.

Typical azides include diphenyl phosphoryl azide (DPPA) and ethyl carbonochloridate/$NaN_3$ and prefer diphenyl phosphoryl azide (DPPA).

Typical solvents are as defined above and prefer t-BuOH.

In some embodiments, each $R^{14}$ and $R^{15}$ is independently benzyl, benzyl substituted with 1-3 methoxy, $C_1$-$C_4$ alkyl or —$SiR^{16}R^{17}R^{18}$, wherein each of $R^{16}$, $R^{17}$ and $R^{18}$ is independently selected from $C_1$-$C_6$ alkyl and $C_6$-$C_{10}$ aryl. In some embodiments, each $R^{14}$ and $R^{15}$ is independently benzyl, benzyl substituted with 1 to 2, methoxy, $C_1$-$C_4$ alkyl, t-$BuMe_2Si$, $Ph_3Si$, $Et_3Si$, n-$Pr_3Si$ or i-$Pr_3Si$. In some embodiments, each $R^{14}$ and $R^{15}$ is independently benzyl, o-methoxybenzyl, m-methoxybenzyl, p-methoxybenzyl or $C_1$-$C_2$ alkyl. In some embodiments, each $R^{14}$ and $R^{15}$ is independently benzyl, p-methoxybenzyl or methyl.

The compound of the formula (I) where $X^1$ is $CR^{11}$, $X^2$ is O, $R^6$ is —C(O)NHOR$^7$, and $R^3$ is halo can be synthesized according to Scheme 2, wherein $R^1$, $R^2$, $R^3$, $R^4$, $R^5$ and $R^{11}$ are as defined for the formula (J), (I) or any variations thereof; $R^{14}$ is hydrogen, allyl or $R^{13}$; and each $R^{12}$ and $R^{13}$ is independently benzyl, benzyl substituted with 1 to 3 methoxy groups, $C_1$-$C_5$ alkyl or —$SiR^{16}R^{17}R^{18}$ where $R^{16}$, $R^{17}$ and $R^{18}$ are independently selected from $C_1$-$C_{10}$ alkyl and $C_6$-$C_{14}$ aryl.

Scheme 2
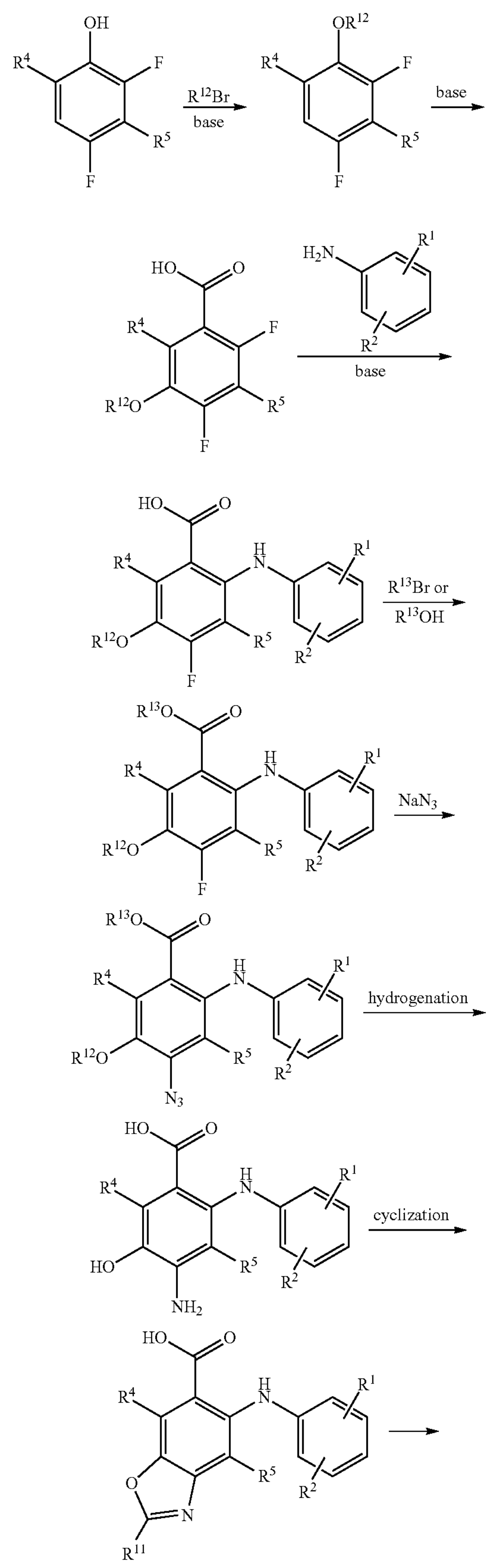
-continued
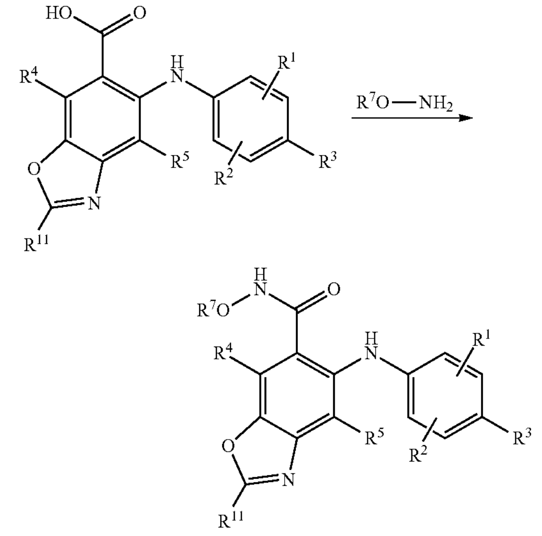
The steps in Scheme 2 are illustrated further by an exemplary synthesis of 4-fluoro-5-((2-fluoro-4-iodophenyl) amino)-N-(2-hydroxy ethoxy)benzo[d]oxazole-6-carboxamide, according to the reactions outlined in Scheme 2.1.
Scheme 2.1
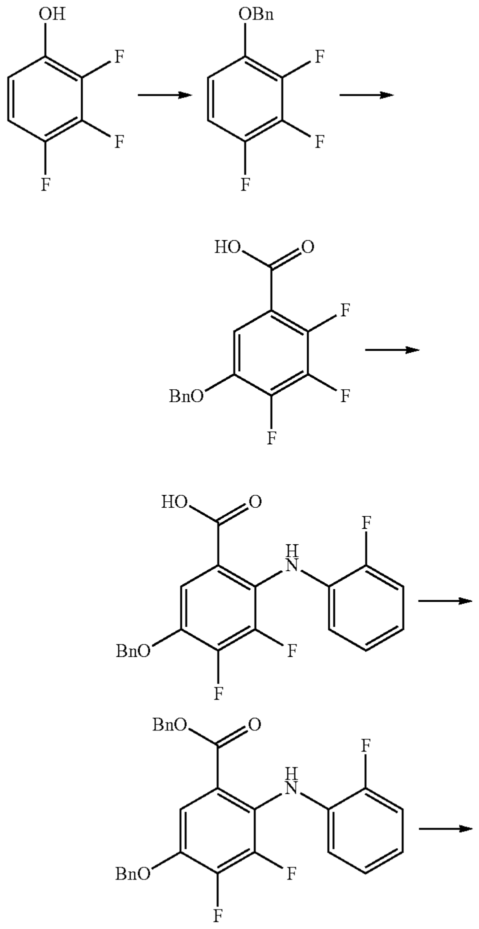

-continued

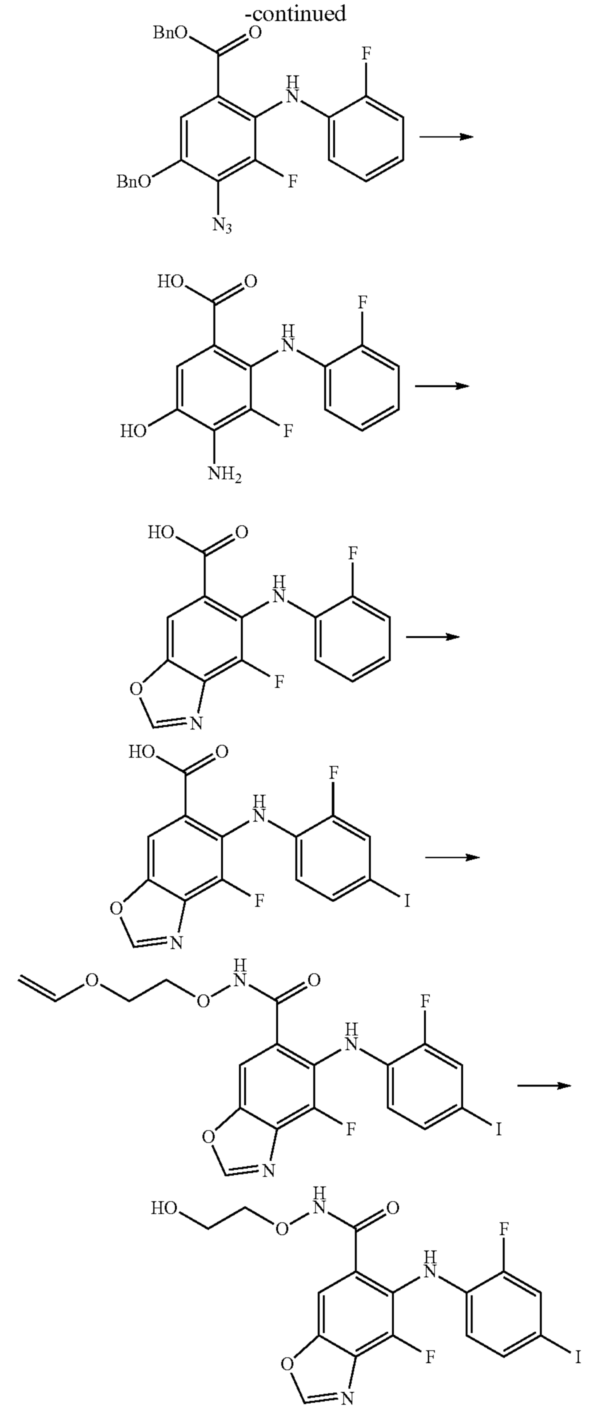

Step 2.1.1

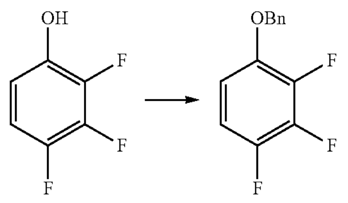 [SMILES: Oc1ccc(F)c(F)c1F ; Fc1ccc(OCc2ccccc2)c(F)c1F]

2,3,4-Trifluorophenol can be protected with hydroxy protection reagent (such as BnBr, BnCl) in the presence of base in appropriate inert solvent. The reaction generally is carried out at ambient temperature and normally completes within several hours (3-12 h, prefer 5-10 h). 1-(Benzyloxy)-2,3,4-trifluorobenzene is obtained after conventional workup.

Typical bases include $Na_2CO_3$, $K_2CO_3$, $NaHCO_3$, $KHCO_3$, t-BuOK and t-BuONa.

Typical solvents are as defined above and prefer acetone and methyl ethyl ketone.

Step 2.1.2

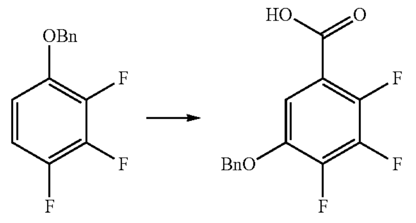 [SMILES: Fc1ccc(OCc2ccccc2)c(F)c1F ; O=C(O)c1cc(OCc2ccccc2)c(F)c(F)c1F]

To a solution of 1-benzyloxy-2,3,4-trifluorobenzene in appropriate inert solvent is added strong base (such as LDA, n-BuLi, LiHDMS) at low temperature (−50° C.-−80° C., prefer −78° C.) under nitrogen atmosphere. The stirring is maintained at this temperature for several hours (0.5-12 h, prefer 0.5-2 h). The mixture is transferred to a bottle with dry ice and the resulting mixture is stirred for some time (such as 3-12 h, prefer 5-10 h). 5-Benzoxy-2,3,4-trifluorobenzoic acid is obtained after conventional workup.

Typical solvents are as defined above and prefer tetrahydrofuran.

Step 2.1.3

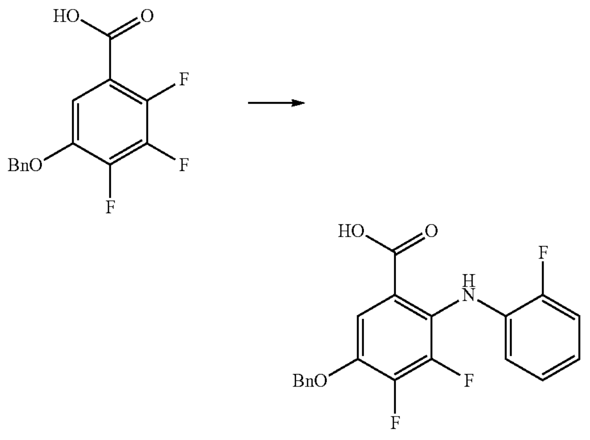

5-Benzoxy-2,3,4-trifluorobenzoic acid can be reacted with halogenated aniline (such as o-fluoroaniline, o-chloroaniline, o-bromoaniline, o-iodoaniline) in the presence of strong base (such as LDA, n-BuLi, LiHDMS). The reaction generally is carried out at low temperature (−50° C.-−80° C., prefer −78° C.) and normally completes within several hours (3-12 h, prefer 5-10 h). 5-(Benzyloxy)-3,4-difluoro-2-((2-fluorophenyl)amino)benzoic acid is obtained after conventional workup.

Step 2.1.4

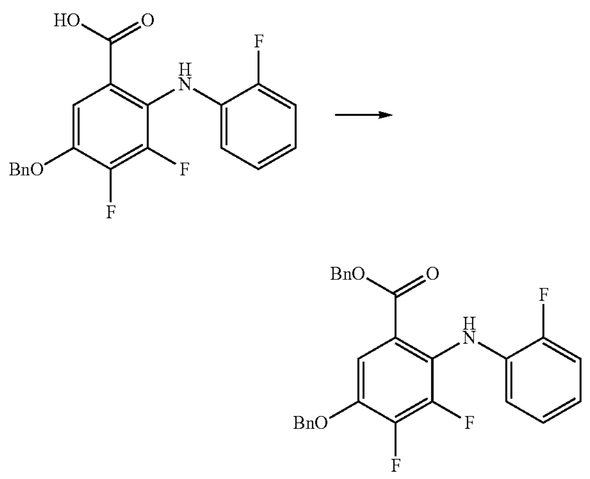

5-(Benzyloxy)-3,4-difluoro-2-((2-fluorophenyl)amino) benzoic acid can be protected by protection reagent of acid or hydroxyl (such as BnBr, BnCl) under basic condition in appropriate inert solvent The reaction normally complete within several hours (3-12 h, prefer 5-10 h). Benzyl 5-(benzyloxy)-3,4-difluoro-2-((2-fluorophenyl)amino)benzoate is obtained after conventional workup.

Typical bases include, but are not limited to, $Na_2CO_3$, $K_2CO_3$, $NaHCO_3$, $KHCO_3$, tBuOK, and tBuONa.

Typical solvents are as defined above and prefer acetone and methyl ethyl ketone.

Step 2.1.5

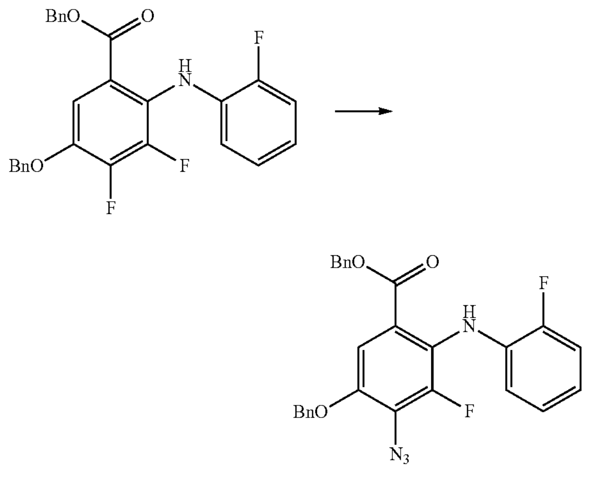

Benzyl 5-(benzyloxy)-3,4-difluoro-2-((2-fluorophenyl) amino)benzoate can be reacted with azide (such as $NaN_3$, $KN_3$) in appropriate solvent. The reaction generally is carried out at high temperature (60-120° C., prefer 80-100° C.) and normally completes within several hours (1-12 h, prefer 3-10 h). The desired product is obtained after conventional workup.

Typical solvents are as defined above and prefer N,N-dimethylformamide and N,N-dimethylacetamide.

Step 2.1.6

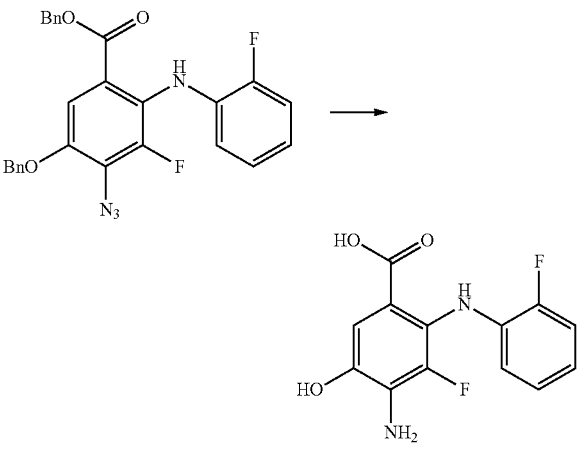

Benzyl 4-azido-5-(benzyloxy)-3-fluoro-2-((2-fluorophenyl)amino)benzoate can be hydrogenated in the presence of appropriate catalyst (such as Pd/C, Pt, Ni). The reaction normally completes within several hours (1-12 h, prefer 3-10 h). 4-Amino-3-fluoro-2-((2-fluorophenyl)amino)-5-hydroxybenzoic acid is obtained after conventional workup.

Typical solvents are as defined above and prefer methanol, ethanol, propan-1-ol and water.

Step 2.1.4

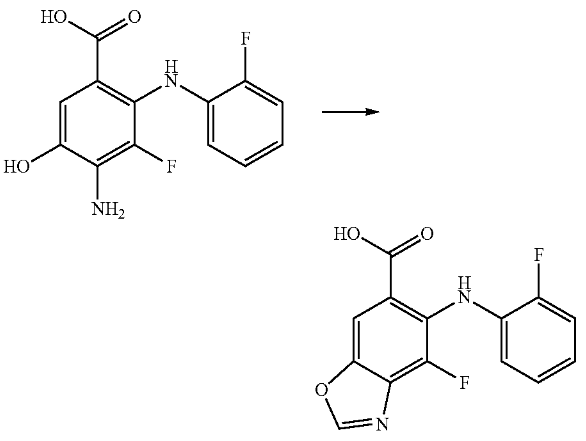

4-Amino-3-fluoro-2-((2-fluorophenyl)amino)-5-hydroxybenzoic acid can be cyclized by trialkoxymethane in the presence of acid in appropriate solvent. The reaction normally completes within several hours (0.2-12 h, prefer 3-10 h). 4-Fluoro-5-((2-fluoro phenyl)amino)benzo[d]oxazole-6-carboxylic acid is obtained after conventional workup.

Said trialkoxymethane includes, but are not limited to, trimethoxymethane and triethoxymethane.

Typical acids include p-toluenesulfonic acid, pyridinium toluene-4-sulphonate, formic acid, acetic acid and sulfuric acid.

Typical solvents are as defined above and prefer methyl acetate, ethyl acetate and trimethoxymethane.

Step 2.1.8

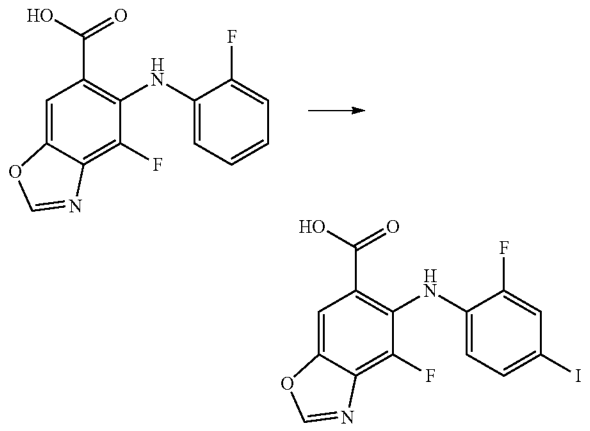

4-Fluoro-5-((2-fluorophenyl)amino)benzo[d]oxazole-6-carboxylic acid can be reacted with halogenations reagent (such as NIS) under acidic condition in appropriate solvent. The reaction generally is carried out at ambient temperature and normally completes within several hours (1-12 h, prefer 3-10 h). 4-Fluoro-5-((2-fluoro-4-iodophenyl)amino)benzo[d]oxazole-6-carboxylic acid is obtained after conventional workup.

Typical acids include, but are not limited to, trifluoroacetic acid, trifluoromethanesulfonic acid, methanesulfonic acid, formic acid and acetic acid.

Typical solvents are as defined above and prefer N,N-dimethylformamide and N,N dimethylacetamide.

Step 2.1.9

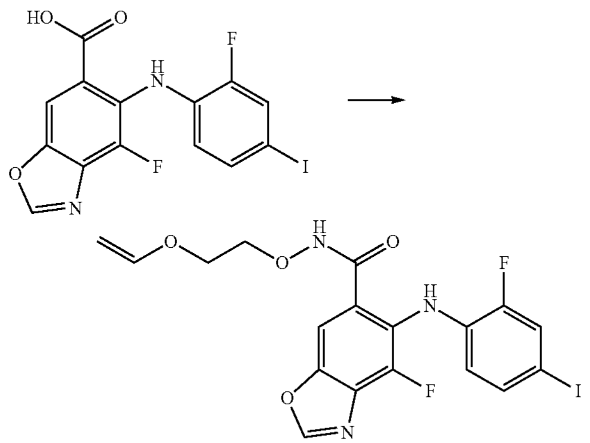

4-Fluoro-5-((2-fluoro-4-iodophenyl)amino)benzo[d]oxazole-6-carboxylic acid can be reacted with O-(2-(vinyloxy)ethyl)hydroxylamine in the presence of coupling reagent in appropriate solvent. The reaction is generally carried out at ambient temperature and normally complete within several hours (1-12 h, prefer 3-10 h). 4-Fluoro-5-((2-fluoro-4-iodophenyl)amino)-N-(2-(vinyloxy)ethoxy)benzo[d]oxazole-6-carboxamide is obtained after conventional workup.

Coupling reagents include, but are not limited to, HOBt, EDCI, HATU and TBTU.

Typical solvents are as defined above and prefer dichloromethane, 1,2-dichloroethane and N,N-dimethylformamide.

Step 2.1.10

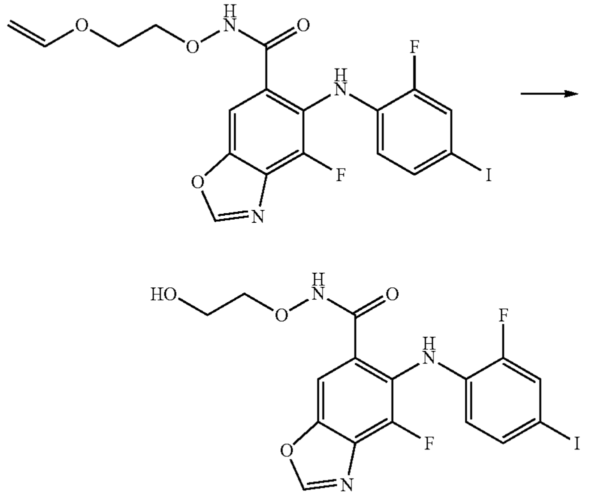

4-Fluoro-5-((2-fluoro-4-iodophenyl)amino)-N-(2-(vinyloxy)ethoxy)benzo[d]oxazole-6-carboxamide can be reacted under acidic condition in appropriate solvent. The reaction normally completes within (1-12 h, prefer 3-10 h). 4-Fluoro-5-((2-fluoro-4-iodophenyl)amino)-N-(2-hydroxyethoxy)benzo[d]oxazole-6-carboxamide is obtained after conventional workup.

Typical acids include, but not limited to, hydrochloric acid, sulfuric acid and trifluoroacetic acid.

Typical solvents are as defined above and prefer dichloromethane and 1,2-dichloroethane.

A compound of the formula (I-2-a), i.e., a compound of the formula (I) where $X^1$ is $CR^{11}$, $X^2$ is O and $R^6$ is —$C(O)N(R^8)OR^7$, where $R^3$ is halo may be synthesized according to Scheme Y-1, wherein $R^1$, $R^2$, $R^4$, $R^5$, $R^7$ and $R^8$ are as defined for the formula (J), (I) or any variations thereof; each $R^{14}$ and $R^{15}$ is independently benzyl, benzyl substituted with 1 to 3 methoxy groups, $C_1$-$C_5$ alkyl or —$SiR^{16}R^{17}R^{18}$ where $R^{16}$, $R^{17}$ and $R^{18}$ are independently selected from $C_1$-$C_{10}$ alkyl and $C_6$-$C_{14}$ aryl, and X is fluoro, chloro, bromo or iodo.

Scheme Y-1

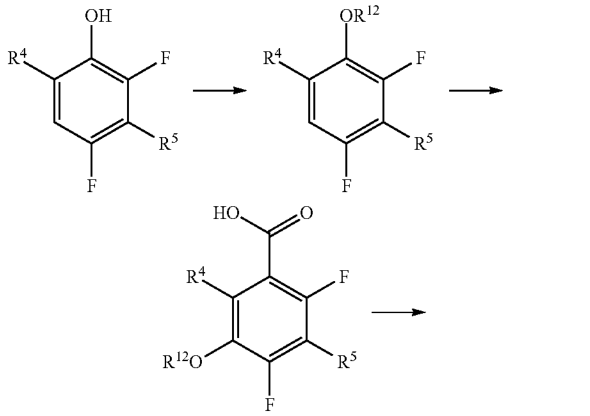

-continued

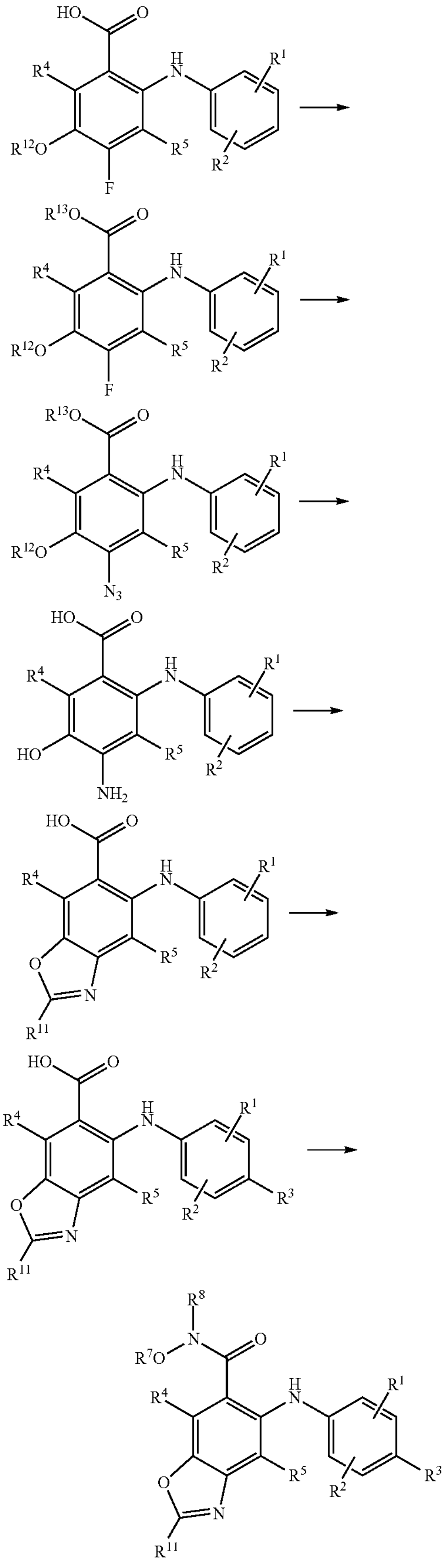

Step 1:

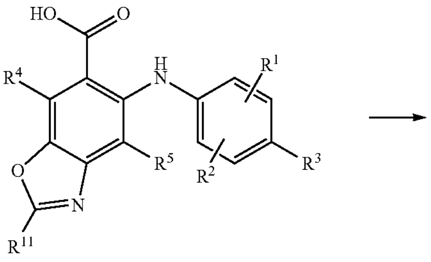

(Y-II)

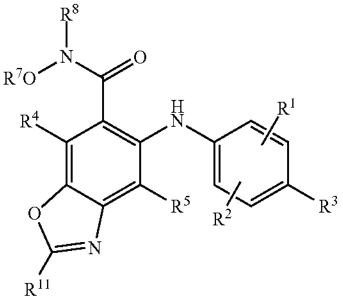

(I-2-a)

The compound of formula (I-2-a) can be prepared from the reaction of the compound of formula (Y-II) with hydroxylamine ($R^7OR^8NH$) in the presence of coupling reagents in appropriate solvent.

Typical coupling reagents include, but are not limited to 1-Hydroxy-1H-benzotriazole (HOBt), 3-(ethyliminomethyleneamino)-N,N-dimethylpropan-1-amine(EDCI), O-(7-azabenzotriazol-1-yl)-N,N,N',N'-tetramethyluronium hexafluorophosphate (HATU) and O-Benzotriazol-1-yl-N,N,N',N'-tetramethyluronium tetrafluoroborate (TBTU).

Typical solvents are as defined above and prefer dichloromethane, 1,2-dichloroethane, THF and N,N-dimethylformamide.

Step 2:

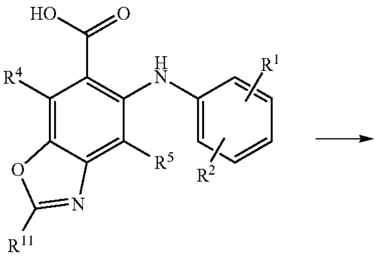

(Y-III)

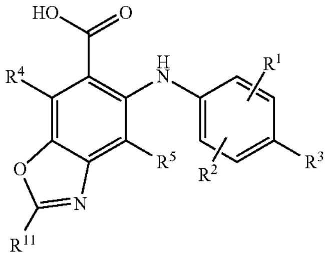

(Y-II)

The compound of formula (Y-II) where $R^3$ is halo can be prepared from halogenation of the compound of formula (Y-III) in the presence of halogenation reagents and acid in appropriate solvent.

Typical halogenation reagents include, but are not limited to NCS, NBS, NIS and so on.

Typical acids include, but are not limited to, trifluoroacetic acid, trifluoromethanesulfonic acid, methanesulfonic acid, formic acid, and acetic acid.

Typical solvents above and prefer $CH_2Cl_2$, $CHCl_3$, N,N-dimethylformamide and N,N-dimethylacetamide.

Step 3;

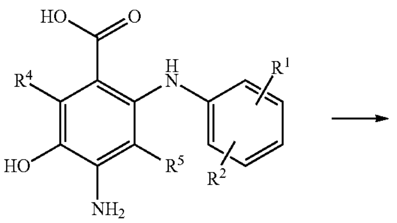

(Y-IV)

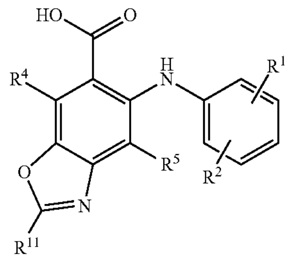

(Y-III)

The compound of formula (Y-III) where $R^{11}$ is hydrogen can be prepared from cyclization of the compound of formula (Y-IV) in the presence of acid and tri($C_1$-$C_6$ alkyl) orthoformate in appropriate solvent.

Typical acids include, but are not limited to p-toluenesulfonic acid, pyridinium toluene-4-sulphonate, methane sulfonic acid and benzenesulfonic acid.

Said tri($C_1$-$C_6$ alkyl) orthoformate includes trimethoxymethane and triethoxymethane.

Typical solvents are as defined above and prefer MeOH, $CH_2Cl_2$, $CHCl_3$, DMSO and N,N-dimethylformamide.

The compound of formula (Y-III) where $R^{11}$ is other than hydrogen can be prepared from the reaction of the compound of formula (Y-IV) with substituted acid ($R^{11}COOH$) in the presence of catalyst in appropriate solvent.

Typical catalyst includes, but is not limited to polyphosphoric acids.

Step 4:

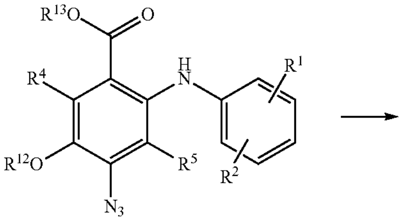

(Y-V)

-continued

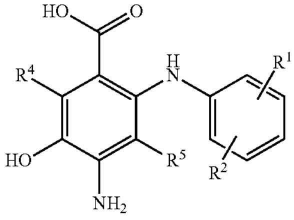

(Y-IV)

The compound of formula (Y-IV) can be prepared from hydrogenation of the compound of formula (Y-V) in the presence of catalyst in appropriate solvent.

Typical hydrogenation catalysts include, but are not limited to Pd/C, Pt and Ni.

Typical solvents are as defined above and prefer methanol, ethanol and THF.

Step 5:

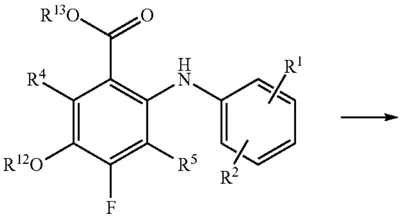

(Y-VI)

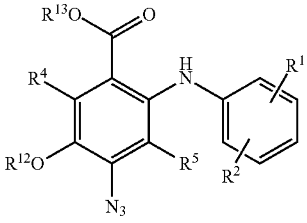

(Y-V)

The compound of formula (Y-V) can be prepared from reaction of the compound of formula (Y-VI) with azide in appropriate solvent.

Typical azides prefer alkali azide, such as but not limited to $NaN_3$ and $KN_3$ Typical solvents are as defined above and prefer DMSO, N,N-dimethylformamide and N,N-dimethylacetamide.

Step 6:

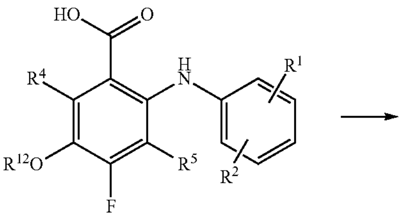

(Y-VII)

-continued

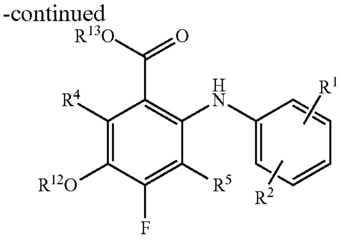

(Y-VI)

The compound of formula (Y-VI) can be prepared from the reaction of the compound of formula (Y-VII) with alcohol ($R^{13}OH$) or halide ($R^{13}X$, X prefers Br) in the presence of acid or base in appropriate solvent.

Where the compound of formula (Y-VII) is reacted with alcohol ($R^{13}OH$), typical acids include, but are not limited to, sulfuric acid, p-toluenesulfonic acid, pyridinium toluene-4-sulphonate and trifluoroacetic acid.

Typical solvents are as defined above and prefer benzyl alcohol, methanol, ethanol, 1-propanol and n-butanol.

Where the compound of formula (Y-VII) is reacted with halide ($R^{13}X$), typical bases include, but are not limited to, $Na_2CO_3$, $K_2CO_3$, $NaHCO_3$, $KHCO_3$, t-BuONa and t-BuOK.

Typical solvents are as defined above and prefer N,N-dimethylformamide, N,N-dimethylacetamide.

Step 7:

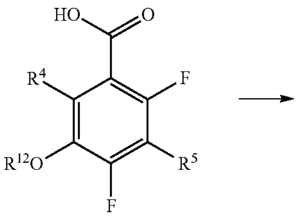

(Y-VIII)

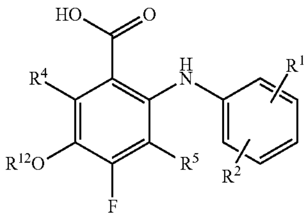

(Y-VII)

The compound of formula (Y-VII) can be prepared from the reaction of the compound of formula (Y-VIII) with the following compound in the presence of strong base in appropriate solvent.

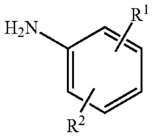

Typical strong base include, but are not limited to LDA, n-BuLi and LiHDMS.

Typical solvents are as defined above and prefer anhydrous THF.

Step 8:

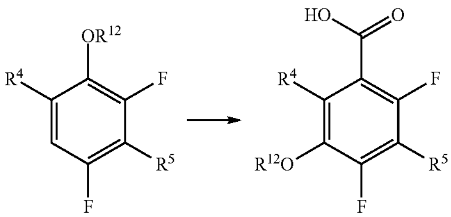

(Y-IX) (Y-VIII)

The compound of formula (Y-VIII) can be prepared from the reaction of the compound of formula (Y-IX) with $CO_2$ in the presence of strong base in appropriate solvent.

Typical strong base include, but are not limited to LDA, n-BuLi and LiHDMS.

Typical solvents are as defined above and prefer anhydrous THF.

Step 9:

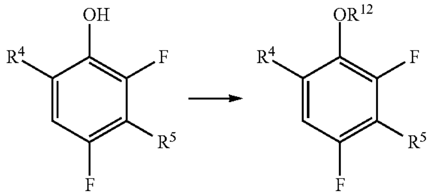

(Y-X) (Y-IX)

The compound of formula (Y-IX) can be prepared from the reaction of the compound of formula (Y-X) with $R^{12}X$ (X prefers bromo) in the presence of base in appropriate solvent.

Typical bases include, but are not limited to, $Na_2CO_3$, $K_2CO_3$, $NaHCO_3$, $KHCO_3$, t-BuONa and t-BuOK.

Typical solvents are as defined above and prefer THF, DMF and acetone.

A compound of the formula (I-2-a), i.e., a compound of the formula (I) where $X^1$ is $CR^{11}$, $X^2$ is O and $R^6$ is —C(O)N($R^8$)$OR^7$, where $R^3$ is other than halo may be synthesized according to Scheme Y-2, wherein $R^1$, $R^2$, $R^3$, $R^4$, $R^5$, $R^7$ and $R^8$ are as defined for the formula (J), (I) or any variations thereof; and each $R^{14}$ and $R^{15}$ is independently benzyl, benzyl substituted with 1 to 3 methoxy groups, $C_1$-$C_5$ alkyl or —$SiR^{16}R^{17}R^{18}$ where $R^{16}$, $R^{17}$ and $R^{18}$ are independently selected from $C_1$-$C_{10}$ alkyl and $C_6$-$C_{14}$ aryl Scheme Y-2

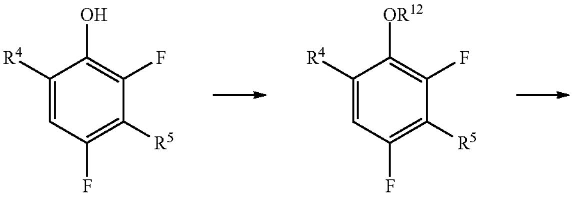

-continued

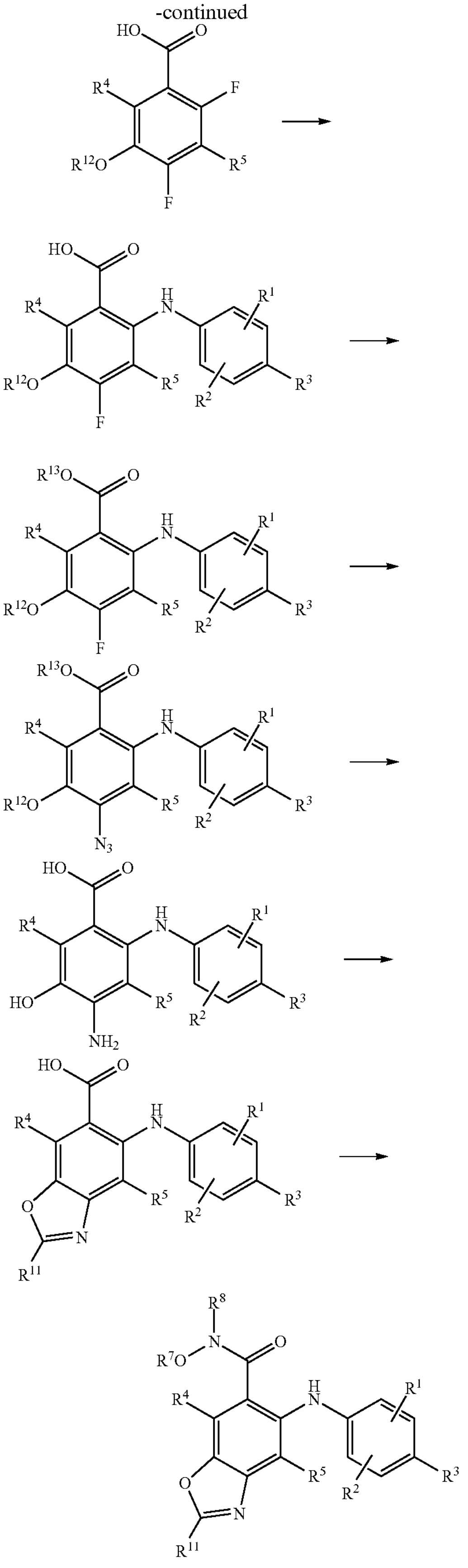

The Synthetic scheme (Y-2) for compound of the formula (I-2-a) wherein $R^3$ is other than halo is similar to the scheme (Y-1) for formula (I-2-a) wherein $R^3$ is halo. The difference between the two schemes is that the following aniline is used in the synthetic scheme (A-2) and the corresponding Step 2 is omitted.

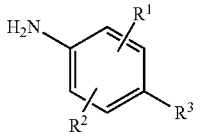

The compound of formula (I-2-b), where $R^1$. $R^2$, $R^3$, $R^4$, $R^5$, $R^7$ and $R^8$ are as defined for the formula (J), (I) or any variations thereof, is prepared according to the method outlined in the following scheme:

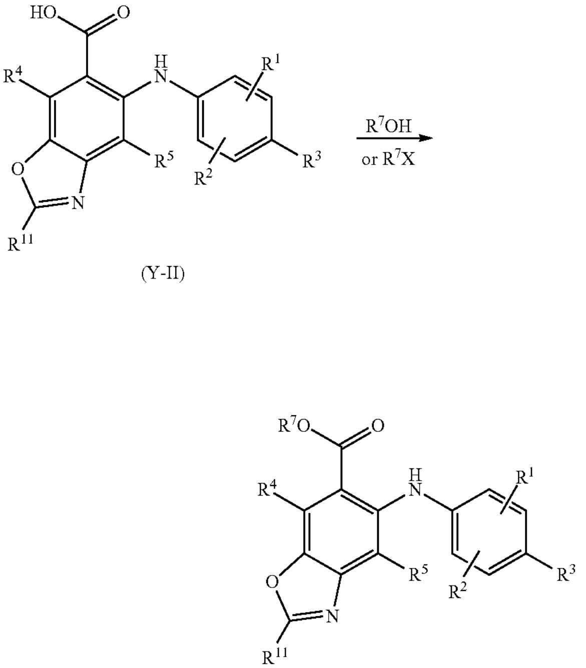

(Y-II)

(I-2-b)

The compound of formula (I-2-b) can be prepared from the reaction of the compound of formula (Y-II) with alcohol ($R^7OH$) in the presence of coupling reagents or with halide ($R^7X$) in the presence of base in appropriate solvent.

Typical coupling reagents include, but are not limited to 1-Hydroxy-1H-benzotriazole (HOBt), 3-(ethyliminomethyl-eneamino)-N,N-dimethylpropan-1-amine(EDCI), O-(7-azabenzotriazol-1-yl)-N,N,N',N'-tetramethyluronium hexafluorophosphate (HATU) and O-Benzotriazol-1 yl-N, N,N',N'-tetramethyluronium tetrafluoroborate (TBTU).

Typical solvents are as defined above and prefer dichloromethane, chloroform and THF.

The compound of formula (I-2-c), where $R^1$, $R^2$, $R^3$, $R^4$, $R^5$, $R^7$ and $R^8$ are as defined for the formula (J), (I) or any variations thereof, is prepared according to the method outlined in the following scheme:

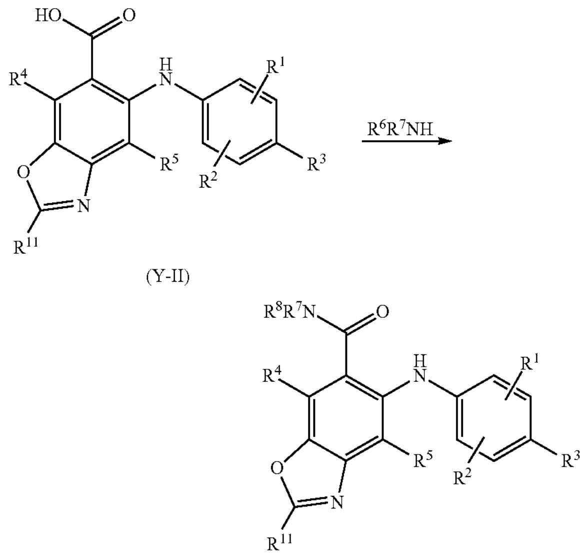

(Y-II)
(I-2-c)

The compound of formula (I-2-c) can be prepared from the reaction of the compound of formula (Y-II) with amine ($R^8R^7NH$) in the presence of coupling reagents in appropriate solvent.

Typical coupling reagents include, but are not limited to 1-Hydroxy-1H-benzotriazole (HOBt), 3-(ethyliminomethyleneamino)-N,N-dimethylpropan-1-amine(EDCI), O-(7-azabenzotriazol-1-yl)-N,N,N',N'-tetramethyluronium hexafluorophosphate (HATU) and O-Benzotriazol-1-yl-N,N,N',N'-tetramethyluronium tetrafluoroborate (TBTU).

Typical solvents are as defined above and prefer dichloromethane, chloroform and THF.

The compound of formula (I-2-d), where $R^1$, $R^2$, $R^3$, $R^4$, $R^5$, $R^7$ and $R^8$ are as defined for the formula (J), (I) or any variations thereof, is prepared according to the method outlined in the following scheme:

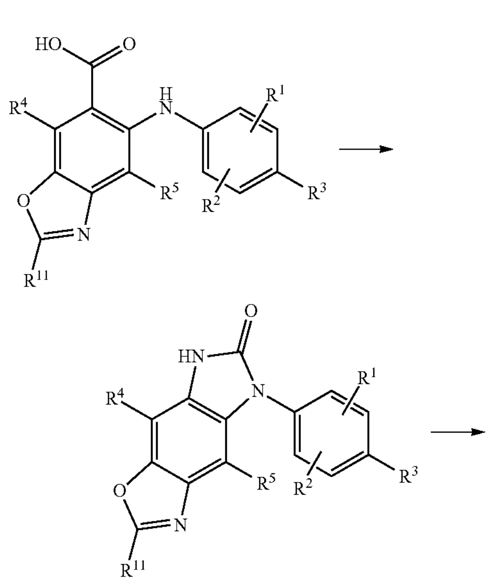

-continued

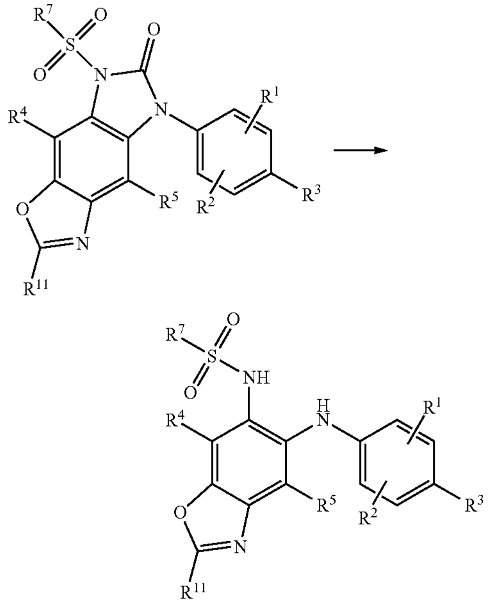

Step 1:

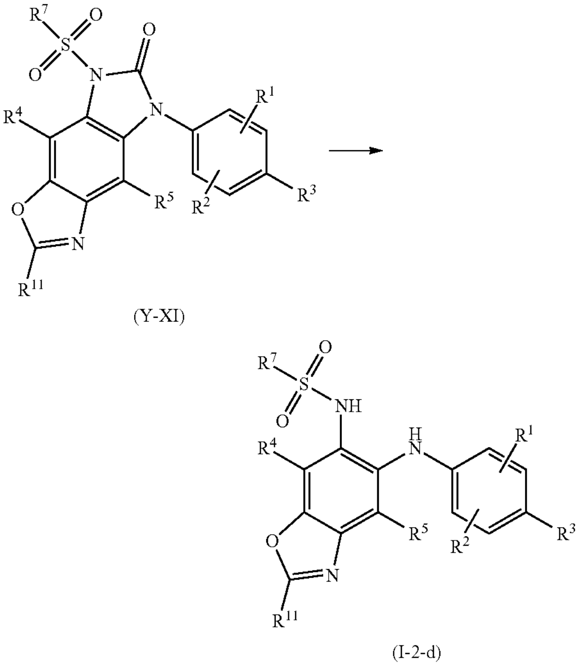
(Y-XI)
(I-2-d)

The compound of formula (I-2-d) can be prepared from the compound of formula (Y-XI) in the presence of base in appropriate solvent.

Typical bases include, but are not limited to, inorganic base (such as $Na_2CO_3$, $K_2CO_3$, $NaHCO_3$, $KHCO_3$, $^t$BuONa and $^t$BuOK) and organic base (such as diethylamine, tri ethyl amine, pyridine and potassium trimethylsilanolate) and prefer potassium trimethylsilanolate.

Typical solvents are as defined above and prefer THF and $CH_2Cl_2$.

Step 2:

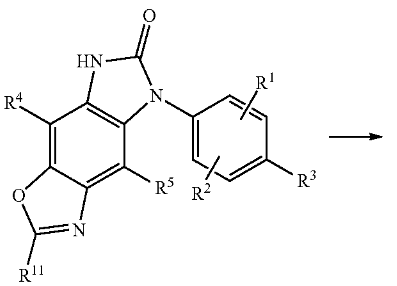

(Y-XII)

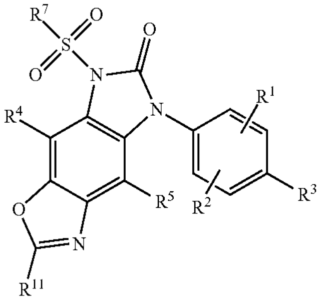

(Y-XI)

The compound of formula (Y-XI) can be prepared from the reaction of the compound of formula (Y-XII) with $R^7SO_2X$ (wherein X is fluoro, chloro, bromo and iodo) in the presence of base and catalyst in appropriate solvent.

Typical bases include, but are not limited to, inorganic base (such as $Na_2CO_3$, $K_2CO_3$, $NaHCO_3$, $KHCO_3$, $^t$BuONa and $^t$BuOK) and organic base (such as diethylamine, triethylamine and pyridine) and prefer triethylamine.

Typical catalysts include, but are not limited to 4-dimethylaminopyridine (DMAP).

Typical solvents are as defined above and prefer dichloromethane and chloroform.

Step 3:

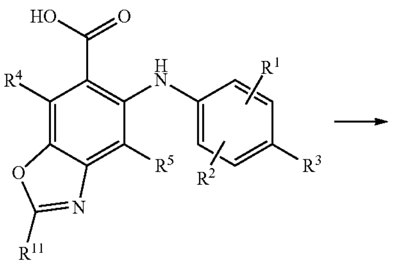

(Y-II)

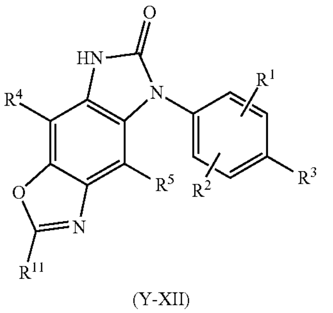

(Y-XII)

The compound of formula (Y-XII) can be prepared from the reaction of the compound of formula (Y-XI) with azide in the presence of base in appropriate solvent.

Typical bases include, but are not limited to, inorganic base (such as $Na_2CO_3$, $K_2CO_3$, $NaHCO_3$, $KHCO_3$, $^t$BuONa and $^t$BuOK) and organic base (such as diethylamine, triethylamine and pyridine) and prefer triethylamine.

Typical azides include diphenyl phosphoryl azide (DPPA) and ethyl carbonochloridate/$NaN_3$ and prefer diphenyl phosphoryl azide (DPPA).

Typical solvents are as defined above and prefer t-BuOH.

In some embodiments, each $R^{14}$ and $R^{15}$ is independently benzyl, benzyl substituted with 1-3 methoxy, $C_1$-$C_4$ alkyl or —$SiR^{16}R^{17}R^{18}$, wherein each of $R^{16}$, $R^{17}$ and $R^{18}$ is independently selected from $C_1$-$C_6$ alkyl and $C_6$-$C_{10}$ aryl. In some embodiments, each $R^{14}$ and $R^{15}$ is independently benzyl, benzyl substituted with 1 to 2 methoxy, $C_1$-$C_4$ alkyl, t-$BuMe_2Si$, $Ph_3Si$, $Et_3Si$, n-$Pr_3Si$ or i-$Pr_3Si$. In some embodiments, each $R^{14}$ and $R^{15}$ is independently benzyl, o-methoxybenzyl, m-methoxybenzyl, p-methoxybenzyl or $C_1$-$C_2$ alkyl. In some embodiments, each $R^{14}$ and $R^{15}$ is independently benzyl, p-methoxybenzyl or methyl.

The compound of the formula (I) where $X^1$ is $CR^{11}$, $X^2$ is S, $R^6$ is —C(O)NHOR$^7$, and $R^3$ is halo can be synthesized according to Scheme 3, wherein $R^1$, $R^2$, $R^4$, $R^5$, $R^7$ and $R^{11}$ are as defined for the formula (J), (I) or any variations thereof; $R^{14}$ is hydrogen, allyl, or $R^{13}$; and each $R^{12}$ and $R^{13}$ is independently benzyl, benzyl substituted with 1 to 3 methoxy groups, $C_1$-$C_5$ alkyl or —$SiR^{16}R^{17}R^{18}$ where $R^{16}$, $R^{17}$ and $R^{18}$ are independently selected from $C_1$-$C_{10}$ alkyl and $C_6$-$C_{14}$ aryl.

Scheme 3

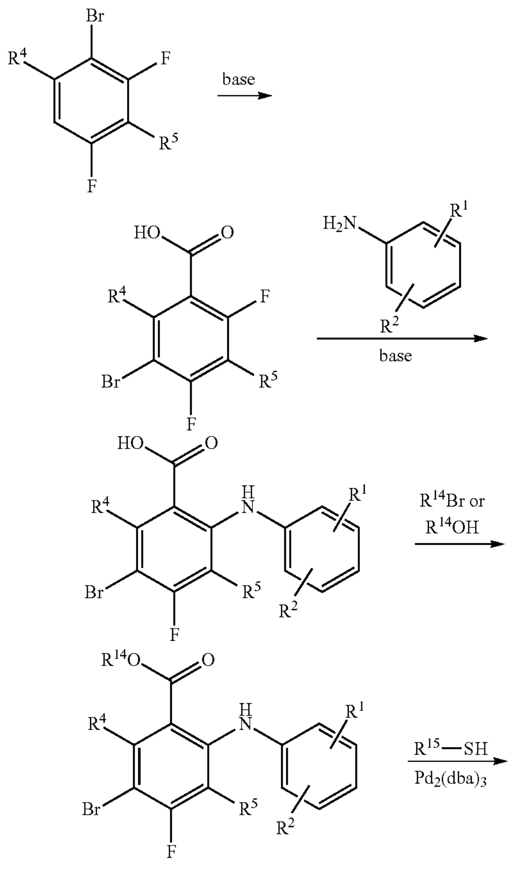

-continued
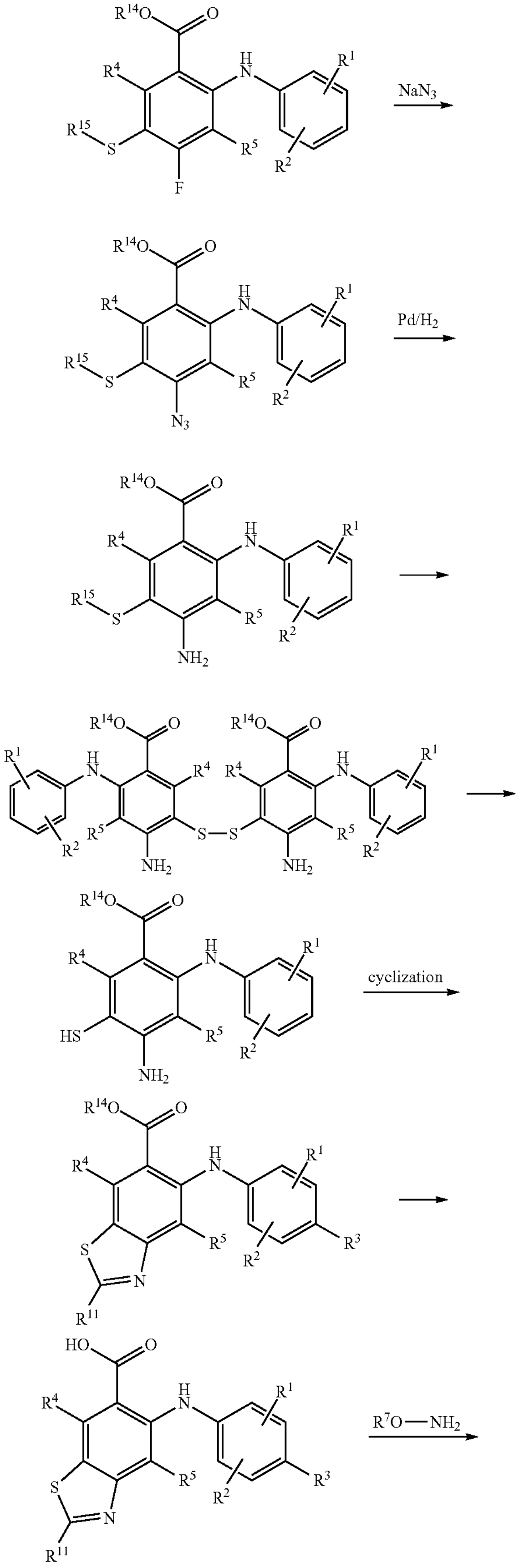
-continued
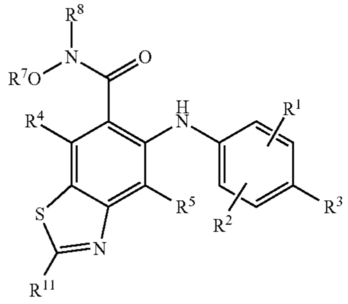
The steps in Scheme 3 are illustrated further by an exemplary synthesis of 4-fluoro-5-((2-fluoro-4-iodophenyl) amino)-N-(2-hydroxy ethoxy)benzo[d]thiazole-6-carboxamide, according to the reactions outlined in Scheme 3.1.
Scheme 3.1
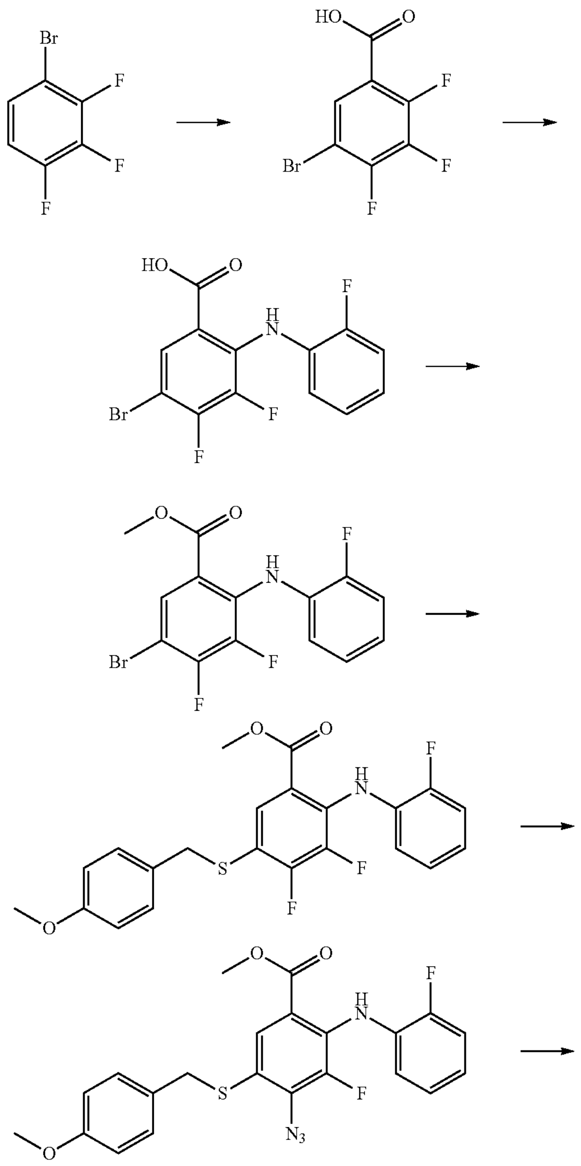

-continued

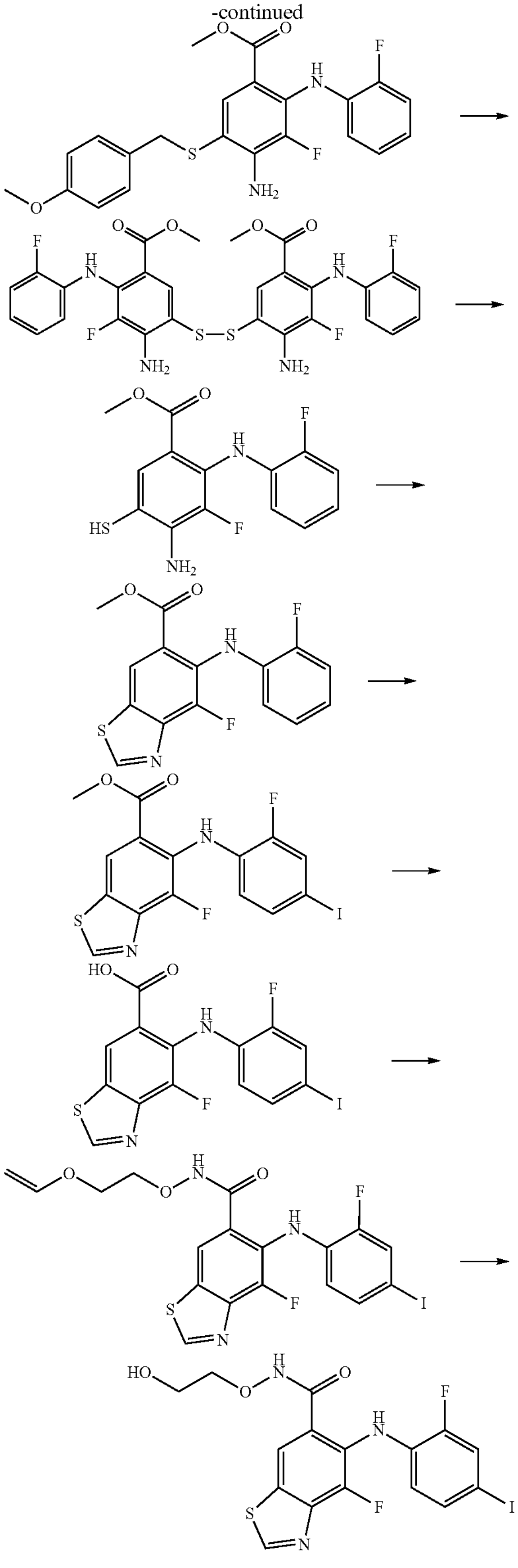

Step 3.1.1

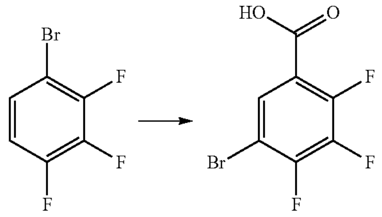 [SMILES: Fc1ccc(Br)c(F)c1F ; O=C(O)c1cc(Br)c(F)c(F)c1F]

To a solution of 2,3,4-trifluorobromobenzene in appropriate solvent is added strong base (such as LDA, nBuLi, LiHDMS) under nitrogen atmosphere. The reaction is generally carried out at low temperature (−50-−80° C., prefer −78° C.). The reaction is kept stirring for some time (0.5-12 h, preferably select 0.5-2 h) and is added dry ice. The resulting mixture is kept stirring for some time (3-12 h, prefer 5-10 h) and 5-bromo-2,3,4-trifluorobenzoic acid is obtained after conventional workup.

Typical solvents are as defined above and prefer anhydrous THF, ethyl ether and dioxane).

Step 3.1.2

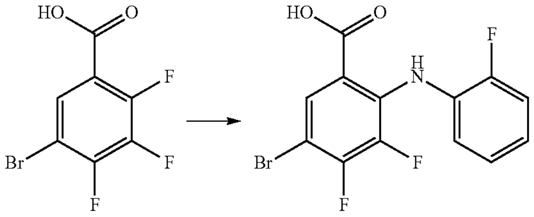 [SMILES: O=C(O)c1cc(Br)c(F)c(F)c1F ; O=C(O)c1cc(Br)c(F)c(F)c1Nc1ccccc1F]

5-Bromo-2,3,4-trifluorobenzoic acid can be reacted with halogenated aniline (such as O-fluoroaniline, o-chloroaniline, o-bromoaniline, o-iodoaniline) under strong basic condition (such as LDA, n-BuLi, LiHDMS) in appropriate solvent. The reaction is generally carried out at low temperature (−50-−80° C., prefer −78° C.) and normally completes within several hours (3-12 h, prefer 5-10 h). 5-Bromo-3,4-difluoro-2-((2-fluorophenyl)amino)benzoic acid is obtained after conventional workup.

Typical solvents are as defined above and prefer anhydrous THF, ethyl ether and dioxane).

Step 3.1.3

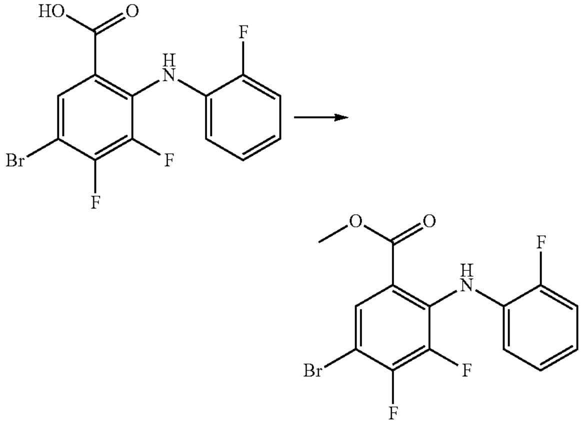

5-Bromo-3,4-difluoro-2-((2-fluorophenyl)amino)benzoic acid can be reacted with MeOH in the presence of $SOCl_2$ in appropriate solvent. The reaction normally completes within several hours (3-12 h, prefer 5-10 h). Methyl 5-bromo-3,4-difluoro-2-((2-fluorophenyl)amino)benzoate is obtained after conventional workup.

Typical solvents are as defined above and prefer methanol and ethanol.

Step 3.1.4

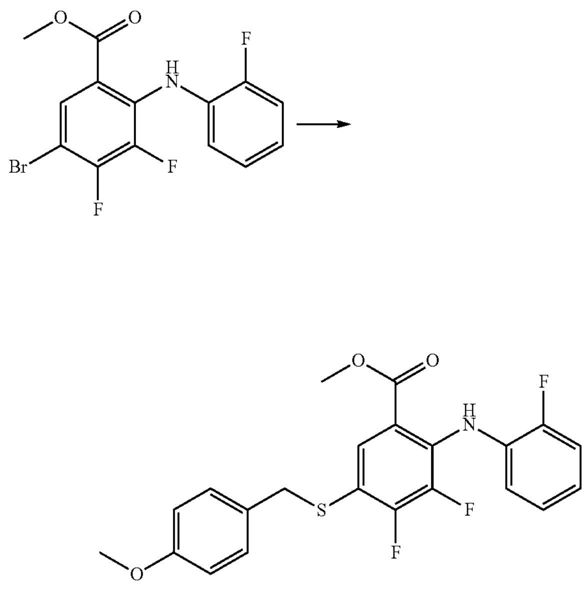

To a solution of methyl 5-bromo-3,4-difluoro-2-((2-fluorophenyl)amino)benzoate in appropriate solvent is added base under nitrogen atmosphere, followed by Pd catalyst, phosphine ligand and (4-methoxyphenyl)methanethiol. The reaction is generally carried out at high temperature (80-130° C., prefer 90-110° C.) and normally complete within several hours (8-24 h, prefer 12-18 h). Methyl 3,4-difluoro-2-((2-fluorophenyl)amino)-5-((4-methoxybenzyl)thio)benzoate is obtained after conventional workup.

Typical bases include, but are not limited to, aliphatic and aromatic amine (such as, but not limited to, N-ethyl-N-isopropylpropan-2-amine, triethylamine, diethylamine, DBU, t-butylamine, cyclopropanamine, dibutylamine, diisopropylamine, 1,2-dimethylpropanamine), inorganic base (such as $Na_2CO_3$, $K_2CO_3$, $NaHCO_3$, $KHCO_3$, $^t$BuONa, $^t$BuOK) and prefer N-ethyl-N-isopropylpropan-2-amine.

Typical Pd catalysts include, but are not limited to, tris(dibenzylideneacetone)dipalladium, bis(dibenzylideneacetone) palladium, bis(triphenylphosphine)palladium(II) chloride, palladium diacetate, tetrakis(triphenylphosphine) palladium, bis(triphenylphosphinepalladium)acetate and preferably select tris(dibenzylideneacetone)dipalladium.

Typical phosphine ligands include, but are not limited to, dimethylbisdiphenylphosphinoxanthene, tri-tert-butylphosphine, tri-p-tolylphosphine, tris(4-chlorophenyl)phosphine, triisopropylphosphine, tris(2,6-dimethoxyphenyl)phosphine, 1,1'-bis (diphenylphosphino)ferrocene and preferably select dimethylbisdiphenyl phosphinoxanthene.

Typical solvents are as defined above and prefer dioxane.

Step 3.1.5

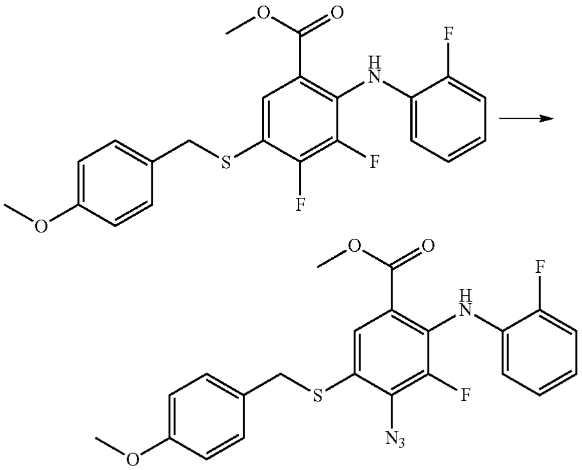

Methyl 3,4-difluoro-2-((2-fluorophenyl)amino)-5-((4-methoxy benzyl)thio)benzoate can be reacted with azide (such as $NaN_3$, $KN_3$) in appropriate solvent. The reaction is generally carried out at high temperature (60-120° C., prefer 80-100° C.) and normally completes within several hours (1-12 h, prefer 3-10 h). Methyl 4-azido-3-fluoro-2-((2-fluorophenyl)amino)-5-((4-methoxybenzyl)thio)benzoate is obtained after conventional workup.

Typical solvents are as defined above and prefer N,N-dimethylformamide and N,N dimethylacetamide.

Step 3.1.6

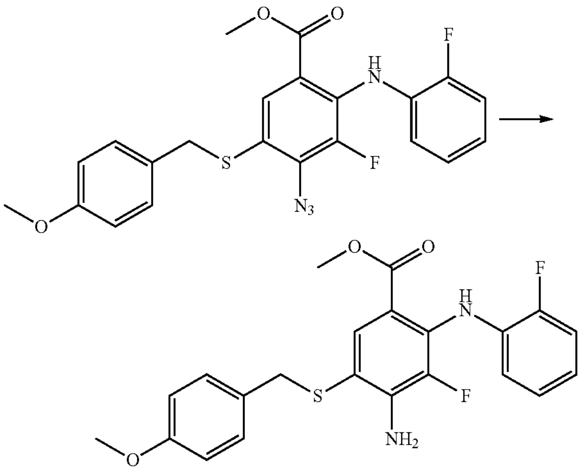

Methyl 4-azido-3-fluoro-2-((2-fluorophenyl)amino)-5-((4-methoxy benzyl)thio)benzoate can be hydrogenated in the presence of appropriate catalyst (such as Pd/C, Pt, Ni) in appropriate solvent. The reaction normally completes within several hours (1-12 h, prefer 3-10 h). Methyl 4-amino-3-fluoro-2-((2-fluorophenyl)amino)-5-((4-methoxybenzyl) thio)benzoate is obtained after conventional workup.

Typical solvents are as defined above and prefer methanol, ethanol, propan-1-ol and water.

Step 3.1.7

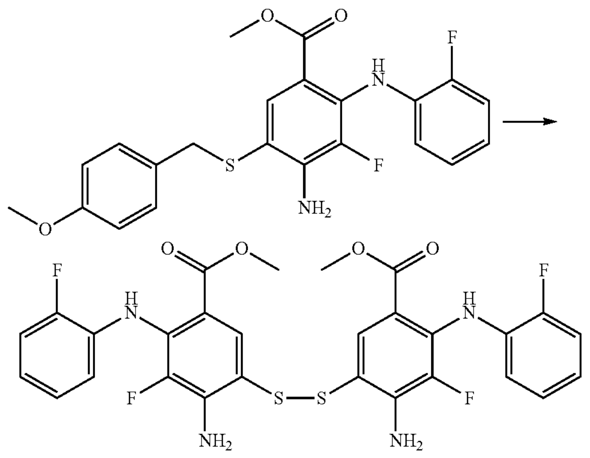

5,5'-Disulfanediylbis(4-amino-3-fluoro-2-((2-fluorophenyl)amino)benzoate) can be prepared from methyl 4-amino-3-fluoro-2-((2-fluoro phenyl)amino)-5-((4-methoxybenzyl) thio)benzoate by deprotection in appropriate solvent. The desired product is obtained after conventional workup.

Typical deprotection reagents may be acid, Pd/C, Lewis acid or $R_4NF$ according to $R^{15}$.

Said acid includes, but are not limited to, $CF_3COOH$.

Said Lewis acid includes, but is not limited to, $BF_3$ and $BBr_3$.

Said deprotection reagents include oxidative reagents such as, but are not limited to, ammonium eerie nitrate and DDQ and prefer DDQ.

Typical solvents are as defined above and prefer dichloromethane, chloroform, MeOH and EtOH.

Step 3.1.8

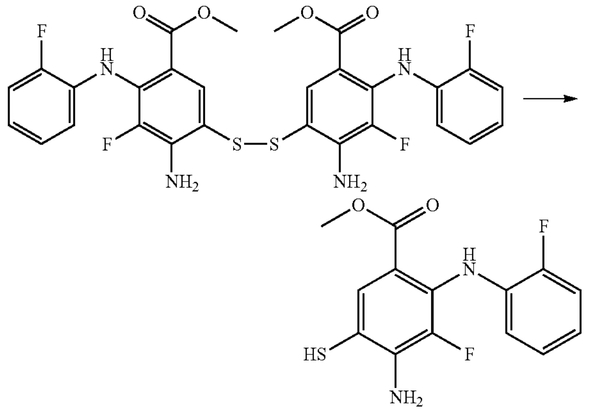

5,5'-Disulfanediylbis(4-amino-3-fluoro-2-((2-fluorophenyl)amino)benzoate) can be reduced in appropriate solvent. Methyl 4-amino-3-fluoro-2-((2-fluorophenyl)amino)-5-mercaptobenzoate is obtained after conventional workup.

Said reductive reagents include $NaBH_4$, $NaCNBH_3$, $NaBH(OAc)_3$, Zn powder and Fe powder.

Typical solvents are as defined above and prefer the mixture or THF and MeOH.

Step 3.1.9

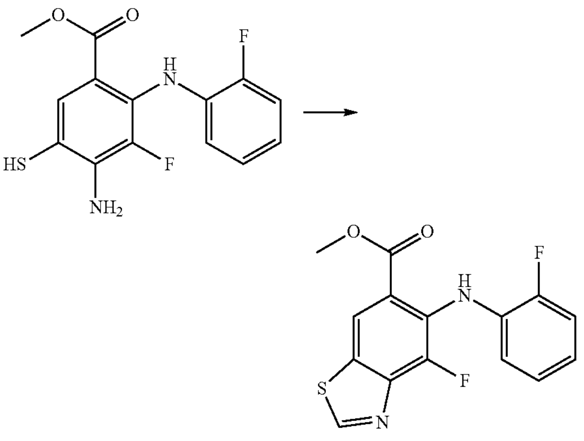

Methyl 4-amino-3-fluoro-2-((2-fluorophenyl)amino)-5-mercapto benzoate can be cyclized in the presence of acid in appropriate solvent. The reaction normally completes within several hours (0.2-12 h, prefer 0.5-10 h). Methyl 4-fluoro-5-((2-fluorophenyl)amino)benzo [d]thiazole-6-carboxylate is obtained after conventional workup.

Typical acids include, but are not limited to p-toluenesulfonic acid, pyridinium toluene-4-sulphonate, formic acid, acetic acid and sulfuric acid.

Typical solvents are as defined above and prefer methyl acetate, ethyl acetate and trimethoxymethane.

Step 3.1.10

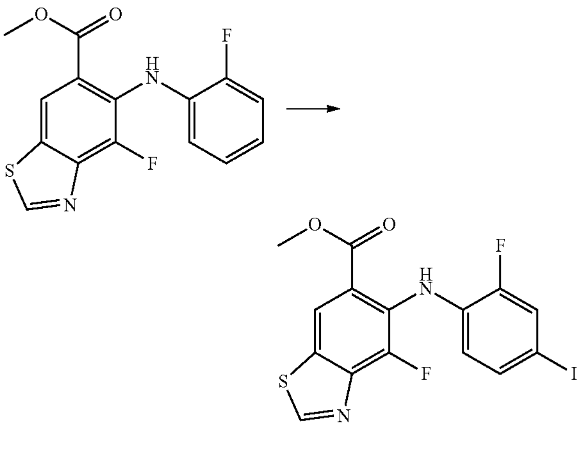

Methyl 4-fluoro-5-((2-fluorophenyl)amino)benzo[d]thiazole-6-carboxylate can be reacted with halogenations reagent (such as NIS) in the presence of acid at ambient temperature in appropriate solvent. The reaction normally completes within several hours (1-12 h, prefer 3-10 h). Methyl 4-fluoro-5-((2-fluoro-4-iodophenyl)amino)benzo[d] thiazole-6-carboxylate is obtained after conventional workup.

Typical acids include, but are not limited to, trifluoroacetic acid, trifluoromethanesulfonic acid, methanesulfonic acid, formic acid, and acetic acid.

Typical solvents are as defined above and prefer N,N-dimethylformamide and N,N-dimethylacetamide.

Step 3.1.11

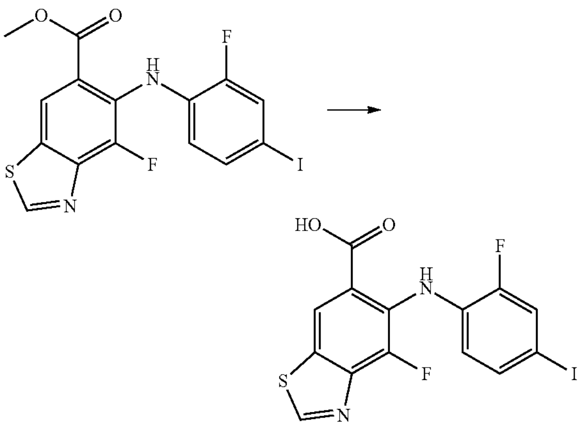

4-Fluoro-5-((2-fluoro-4-iodophenyl)amino)benzo[d]thiazole-6-carboxylic acid can be prepared from methyl 4-fluoro-5-((2-fluoro-4-iodo phenyl)amino)benzo[d]thiazole-6-carboxylate be deprotection in appropriate solvent.

Typical deprotection reagents may be base, Pd/C, Lewis acid or $R_4NF$.

Said base includes, but are not limited to, NaOH, KOH, $Na_2CO_3$ and $K_2CO_3$.

Said Lewis acids include, but are not limited to $AlCl_3$, $BF_3$ and $BBr_3$.

Typical solvents are as defined above and prefer dichloromethane, THF, MeOH and DMF.

Step 3.1.12

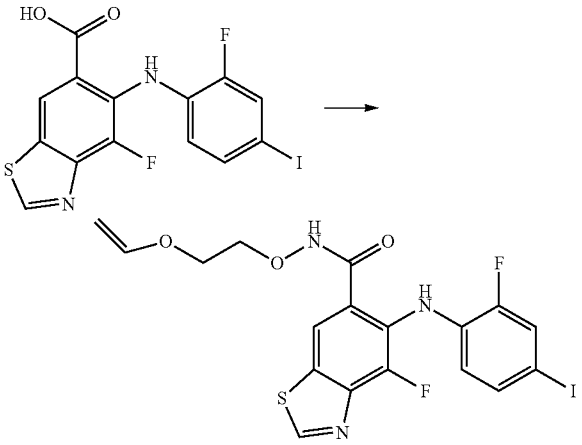

4-Fluoro-5-((2-fluoro-4-iodophenyl)amino)benzo[d]thiazole-6-carboxylic acid can be reacted with O-(2-(vinyloxy)ethyl)hydroxylamine in the presence of coupling reagent in appropriate solvent. The reaction is generally carried out at ambient temperature and normally complete within several hours (1-12 h, prefer 3-10 h). 4-Fluoro-5-((2-fluoro-4-iodophenyl)amino)-N-(2-(vinyloxy)ethoxy)benzo[d]thiazole-6-carboxamide is obtained after conventional workup.

Coupling reagents include, but are not limited to, HOBt, EDCI, HATU and TBTU.

Typical solvents are as defined above and prefer dichloromethane, 1,2-dichloroethane and N,N-dimethylformamide.

Step 3.1.13

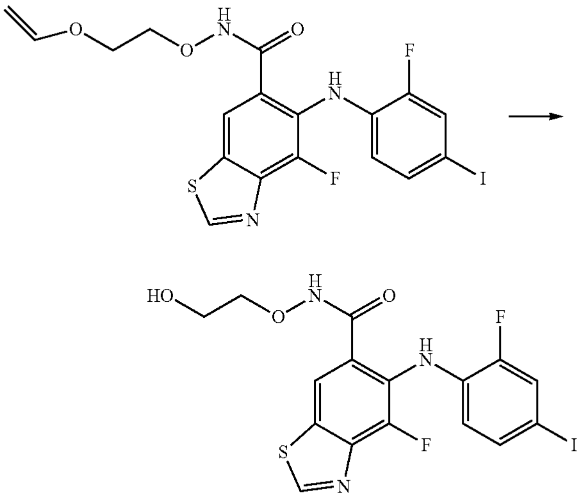

4-Fluoro-5-((2-fluoro-4-iodophenyl)amino)-N-(2-(vinyloxy)ethoxy)benzo[d]thiazole-6-carboxamide can be reacted under acidic condition in appropriate solvent. The reaction normally completes within (1-12 h, prefer 3-10 h). 4-Fluoro-5-((2-fluoro-4-iodophenyl)amino)-N-(2-hydroxyethoxy)benzo[d]thiazole-6-carboxamide is obtained after conventional workup.

Typical acids include, but not limited to, hydrochloric acid, sulfuric acid and trifluoroacetic acid.

Typical solvents are as defined above and prefer dichloromethane and 1,2-dichloroethane.

A compound of the formula (I-3-a), i.e., a compound of the formula (I) where $X^1$ is $CR^{11}$, $X^2$ is S and $R^6$ is —$C(O)N(R^8)OR^7$, where $R^3$ is halo may be synthesized according to Scheme Z-1, wherein $R^1$, $R^2$, $R^4$, $R^5$, $R^7$ and $R^8$ are as defined for the formula (J), (I) or any variations thereof; each $R^{14}$ and $R^{15}$ is independently benzyl, benzyl substituted with 1 to 3 methoxy groups, $C_1$-$C_5$ alkyl or —$SiR^{16}R^{17}R^{18}$ where $R^{16}$, $R^{17}$ and $R^{18}$ are independently selected from $C_1$-$C_{10}$ alkyl and $C_6$-$C_{14}$ aryl, and X is fluoro, chloro, bromo or iodo.

Scheme Z-1

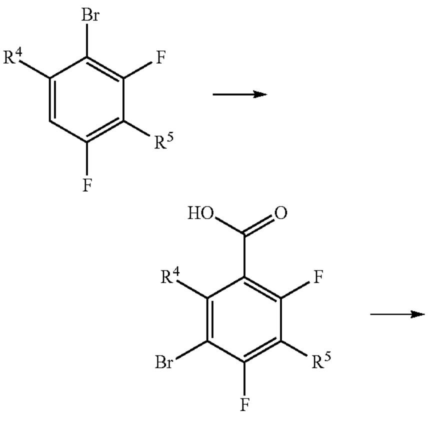

-continued
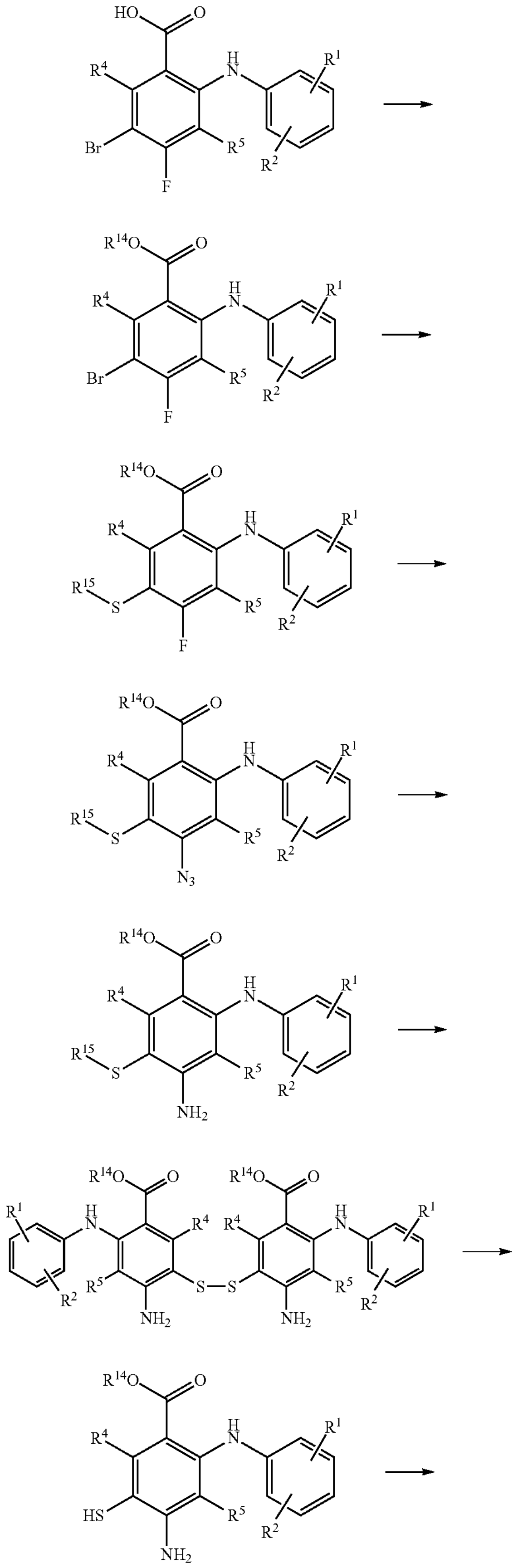
-continued
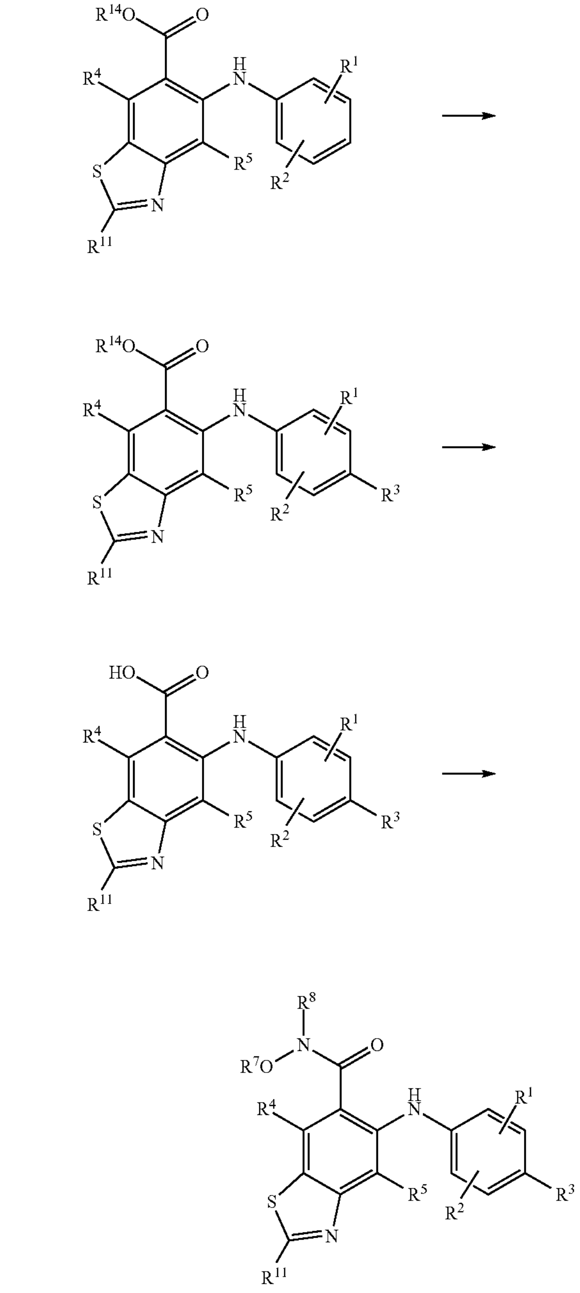
Step 1:
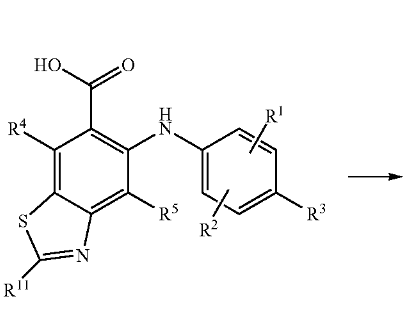
(Z-II)

-continued

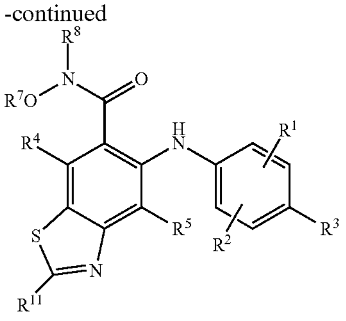

(I-3-a)

The compound of formula (I-3-a) can be prepared from the reaction of the compound of formula (Z-II) with hydroxylamine ($R^7OR^8NH$) in the presence of coupling reagents in appropriate solvent.

Typical coupling reagents include, but are not limited to 1-Hydroxy-1H-benzotriazole (HOBt), 3-(ethyliminomethyleneamino)-N,N-dimethylpropan-1-amine(EDCI), O-(7-azabenzotriazol-1-yl)-N,N,N',N'-tetramethyluronium hexafluorophosphate (HATU) and O-Benzotriazol-1-yl-N,N,N',N'-tetramethyluronium tetrafluoroborate (TBTU).

Typical solvents are as defined above and prefer dichloromethane, 1,2-dichloroethane, THF and N,N-dimethylformamide.

Step 2:

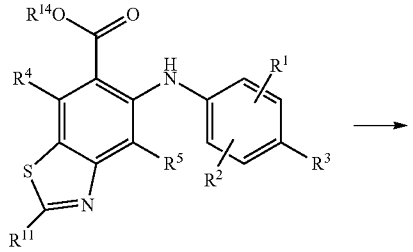

(Z-III)

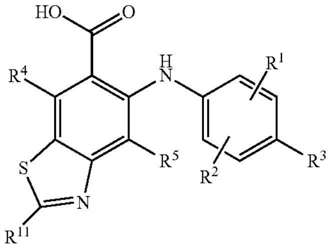

(Z-II)

The compound of formula (Z-II) can be prepared from deprotection of the compound of formula (Z-III) in appropriate solvent.

Typical deprotection reagents may be base, Pd/C, Lewis acid or $R_4NF$ according to different $R^{14}$.

Said base includes, but are not limited to, NaOH, KOH, $Na_2CO_3$, $K_2CO_3$.

Said Lewis acids include, but are not limited to $AlCl_3$, $BF_3$ and $BBr_3$.

Typical solvents are as defined above and prefer dichloromethane, THF, MeOH and DMF.

Step 3:

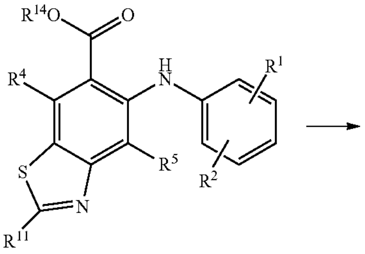

(Z-IV)

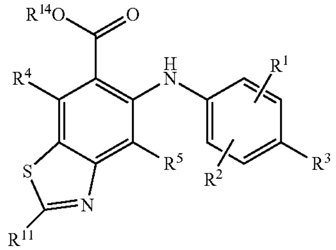

(Z-III)

The compound of formula (Z-III) where $R^3$ is halo can be prepared from halogenation of the compound of formula (Z-IV) in the presence of halogenation reagents and acid in appropriate solvent.

Typical halogenation reagents include, but are not limited to NCS, NBS, NIS and so on.

Typical acids include, but are not limited to, trifluoroacetic acid, trifluoromethanesulfonic acid, methanesulfonic acid, formic acid, and acetic acid.

Typical solvents are as defined above and prefer $CH_2Cl_2$, $CHCl_3$, N,N-dimethylformamide and N,N-dimethylacetamide.

Step 4:

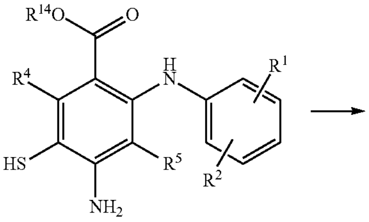

(Z-V)

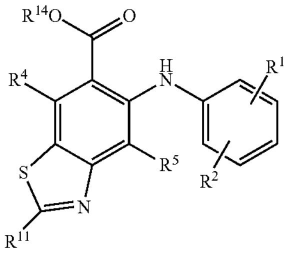

(Z-IV)

The compound of formula (Z-IV) where $R^{11}$ is hydrogen can be prepared from cyclization of the compound of formula (Z-V) in the presence of acid and tri($C_1$-$C_6$ alkyl) orthoformate in appropriate solvent.-

Typical acids include, but are not limited to p-toluenesulfonic acid, pyridinium toluene-4-sulphonate, methane sulfonic acid and benzenesulfonic acid.

Said tri($C_1$-$C_6$ alkyl) orthoformate includes trimethoxymethane and triethoxymethane.

Typical solvents are as defined above and prefer MeOH, $CH_2Cl_2$, $CHCl_3$, DMSO and N,N-dimethylformamide.

The compound of formula (Z-IV) where $R^{11}$ is other than hydrogen can be prepared from the reaction of the compound of formula (Z-V) with substituted acid ($R^{11}COOH$), $R^{11}C(OMe)_3$ or $R^{11}C(OEt)_3$ in the presence of catalyst in appropriate solvent.

Typical catalyst includes, but is not limited to polyphosphoric acids.

Step 5:

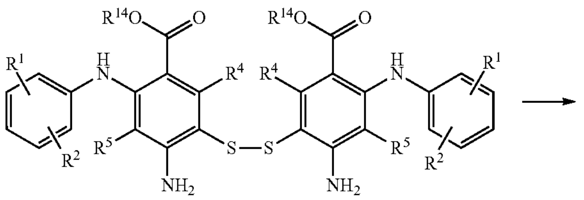

(Z-VI)

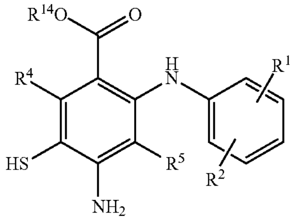

(Z-V)

The compound of formula (Z-V) can be prepared from the compound of formula (Z-VI) in the presence of reduction reagent in appropriate solvent.

Typical reduction reagents include, but are not limited to $NaBH_4$, $NaBH_3CN$, $NaBH(Ac)_3$, Zn powder and Fe powder.

Typical solvents are as defined above and prefer the mixture of THF and MeOH.

Step 6:

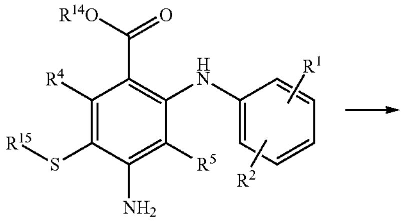

(Z-VII)

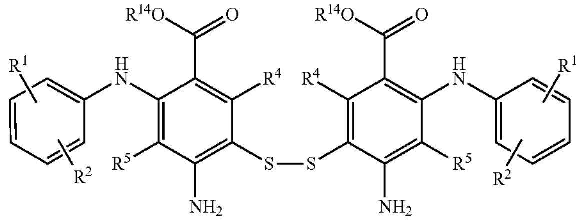

(Z-VI)

The compound of formula (Z-VI) can be prepared from the compound of formula (Z-VII) in the presence of deprotection reagent in appropriate solvent.

Typical deprotection reagents may be acid, Pd/C, Lewis acid or $R_4NF$ according to $R^{15}$.

Said acid includes, but are not limited to, $CF_3COOH$.

Said Lewis acid includes, but is not limited to, $BF_3$ and $BBr_3$.

Said deprotection reagents include oxidative reagents such as, but are not limited to, ammonium eerie nitrate and DDQ and prefer DDQ.

Typical solvents are as reagents above and prefer dichloromethane, chloroform, MeOH and EtOH.

Step 7:

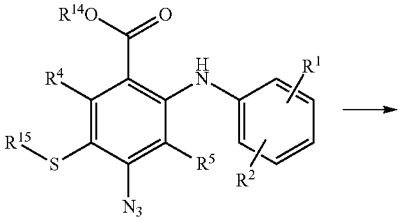

(Z-VIII)

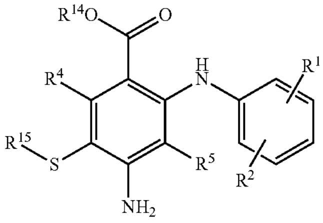

(Z-VII)

The compound of formula (Z-VII) can be prepared from reduction of the compound of formula (Z-VIII) in the presence of reduction reagents in appropriate solvent.

Typical reduction reagents include, but are not limited to hydrogenation catalyst, $SnCl_2$, $PPh_3$, $NaBH_4$, $BH_3$ and Raney Ni.

Typical solvents are as defined above and prefer methanol, ethanol, ethyl acetate and THF.

Step 8:

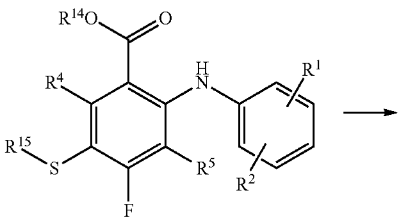

(Z-IX)

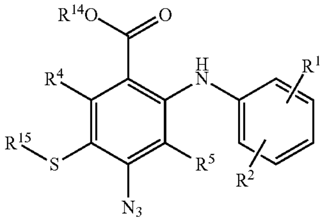

(Z-VIII)

The compound of formula (Z-VIII) can be prepared from reaction of the compound of formula (Z-IX) with azide in appropriate solvent.

Typical azides prefer alkali azide, such as but not limited to $NaN_3$ and $KN_3$ Typical solvents are as defined above and prefer DMSO, N,N-dimethylformamide and N,N-dimethylacetamide.

Step 9:

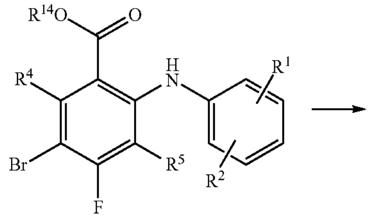

(Z-X)

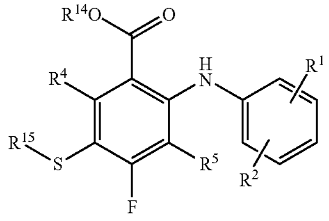

(Z-IX)

The compound of formula (Z-IX) can be prepared from the reaction of the compound of formula (Z-X) with mercaptan ($R^{15}SH$) in the presence of base, phosphine ligand and catalyst in appropriate solvent.

Typical bases include, but are not limited to, aliphatic and aromatic amine (such as, but not limited to, N-ethyl-M-isopropylpropan-2-amine, triethylamine, diethylamine, DBU, t-butylamine, cyclopropanamine, dibutylamine, diisopropylamine, 1,2-dimethylpropanamine), inorganic, base (such as $Na_2CO_3$, $K_2CO_3$, $NaHCO_3$, $KHCO_3$, $^{t}BuONa$, $^{t}BuOK$) and prefer N-ethyl-N-isopropylpropan-2-amine.

Typical catalysts prefer Pd catalysts, such as, but are not limited to, tris(dibenzylideneacetone)dipalladium, bis(dibenzylideneacetone) palladium, bis(triphenylphosphine) palladium(II) chloride, palladium diacetate, tetrakis(triphenylphosphine)palladium, bis(triphenylphosphinepalladium)acetate and preferably select tris(dibenzylideneacetone)dipalladium.

Typical phosphine ligands include, but are not limited to, dimethylbisdiphenylphosphinoxanthene, tri-tert-butylphosphine, tri-p-tolylphosphine, tris(4-chlorophenyl)phosphine, triisopropylphosphine, tris(2,6-dimethoxyphenyl)phosphine, 1,1'-bis (diphenylphosphino)ferrocene and preferably select dimethylbisdiphenyl phosphinoxanthene.

Typical solvents are as defined above and prefer dioxane.

Step 10:

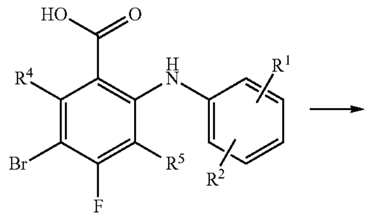

(Z-XI)

-continued

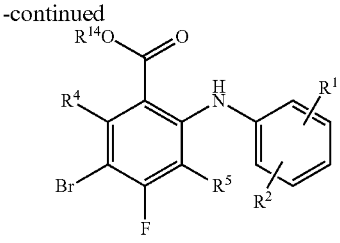

(Z-X)

The compound of formula (Z-X) can be prepared from the reaction of the compound of formula (Z-XI) with alcohol ($R^{14}OH$) or halide ($R^{14}X$) in the presence of optional catalyst in appropriate solvent.

Typical catalysts are selected according to different substrates and include $SOCl_2$, sulfuric acid, inorganic base (such as $NaHCO_3$, $KHCO_3$, $Na_2CO_3$) and organic base (such as triethylamine and N-ethyl-N-isopropylpropan-2-amine).

Typical solvents are as defined above and prefer methanol and ethanol.

Step 11:

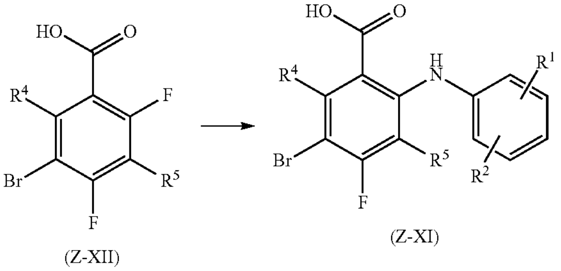

(Z-XII) (Z-XI)

The compound of formula (Z-XI) can be prepared from the reaction of the compound of formula (Z-XII) with the following compound in the presence of strong base in appropriate solvent.

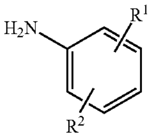

Typical strong base include, but are not limited to LDA, n-BuLi and LiHDMS.

Typical solvents are as defined above and prefer anhydrous THF.

Step 12:

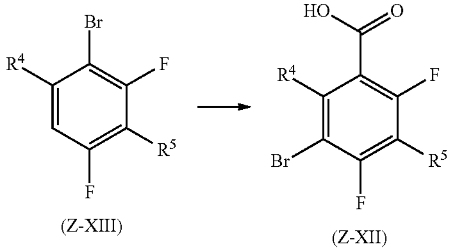

(Z-XIII) (Z-XII)

The compound of formula (Z-XII) can be prepared from the reaction of the compound of formula (Z-XIII) with $CO_2$ in the presence of strong base in appropriate solvent.

Typical strong base include, but are not limited to LDA, n-BuLi and LiHDMS.

Typical solvents are as defined above and prefer anhydrous THF.

A compound of the formula (I-3-a), i.e., a compound of the formula (I) where $X^1$ is $CR^{11}$, $X^2$ is S and $R^6$ is —C(O)N($R^8$)$OR^7$, where $R^3$ is other than halo may be synthesized according to Scheme Z-2, wherein $R^1$, $R^2$, $R^3$, $R^4$, $R^5$, $R^7$ and $R^8$ are as defined for the formula (J), (I) or any variations thereof; and each $R^{14}$ and $R^{15}$ is independently benzyl, benzyl substituted with 1 to 3 methoxy groups, $C_1$-$C_5$ alkyl or —$SiR^{16}R^{17}R^{18}$ where $R^{16}$, $R^{17}$ and $R^{18}$ are independently selected from $C_1$-$C_{10}$ alkyl and $C_6$-$C_{14}$ aryl.

Scheme Z-2

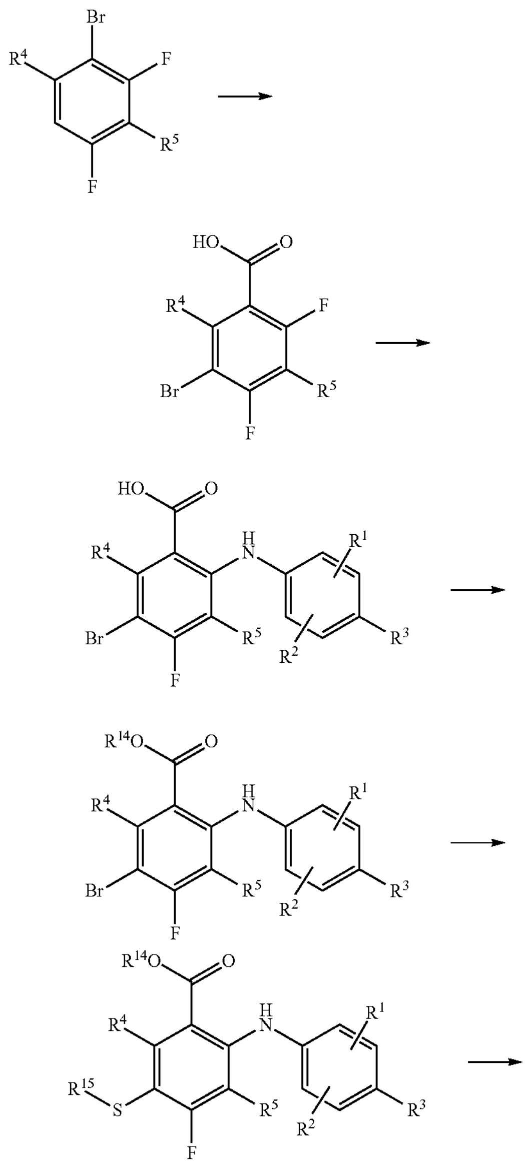

-continued

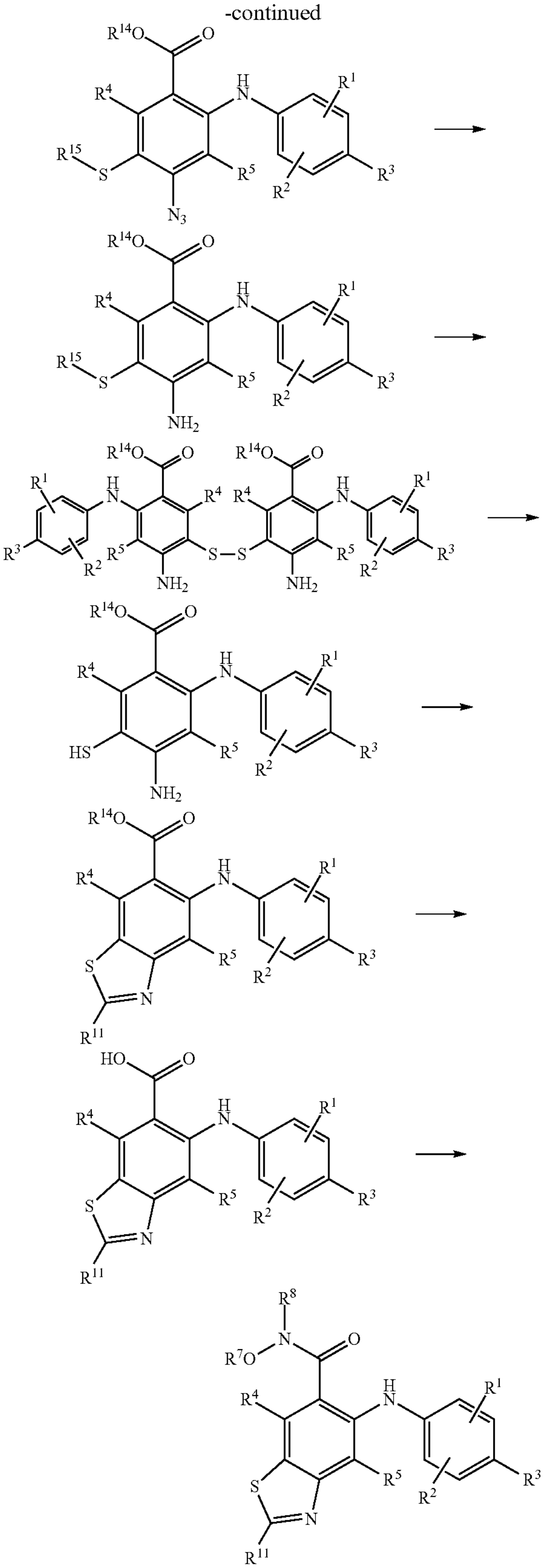

The synthetic scheme (Z-2) of formula (I-3-a) compound wherein $R^3$ is other than halo is similar to the scheme (Z-1) of formula (I-1) wherein $R^3$ is halo. The difference between the two schemes is that the following aniline is used in the synthetic scheme (Z-2) and the corresponding Step 3 is omitted.

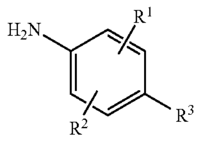

The compound of formula (I-3-b), where $R^1$, $R^2$, $R^3$, $R^4$, $R^5$, $R^7$ and $R^8$ are as defined for the formula (J), (I) or any variations thereof, is prepared according to the method outlined in the following scheme:

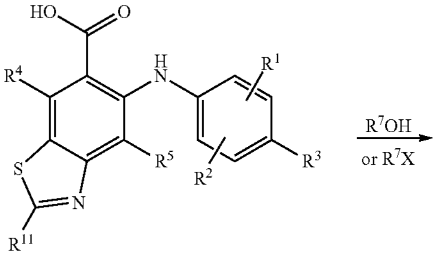

(Z-II)

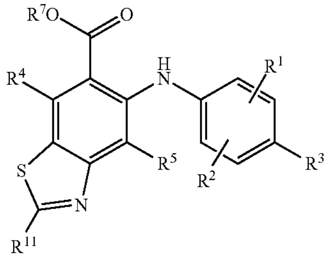

(I-3-b)

The compound of formula (I-3-b) can be prepared from the reaction of the compound of formula (Z-II) with alcohol ($R^7OH$) in the presence of coupling reagents or with halide ($R^7X$) in the presence of base in appropriate solvent.

Typical coupling reagents include, but are not limited to 1-Hydroxy-1H-benzotriazole (HOBt), 3-(ethyliminomethyleneamino)-N,N-dimethylpropan-1-amine(EDCI), O-(7-azabenzotriazol-1-yl)-N,N,N',N'-tetramethyluronium hexafluorophosphate (HATU) and O-Benzotriazol-1-yl-N,N,N',N'-tetramethyluronium tetrafluoroborate (TBTU).

Typical solvents are as defined above and prefer dichloromethane, chloroform, and THF.

The compound of formula (I-3-c), where $R^1$, $R^2$, $R^3$, $R^4$, $R^5$, $R^7$ and $R^8$ are as defined for the formula (J), (I) or any variations thereof, is prepared according to the method outlined in the following scheme:

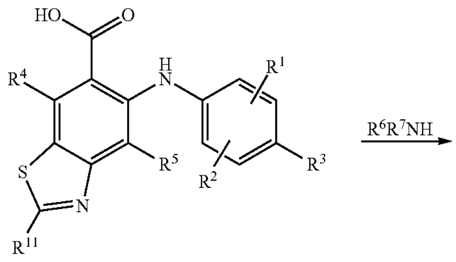

(Z-II)

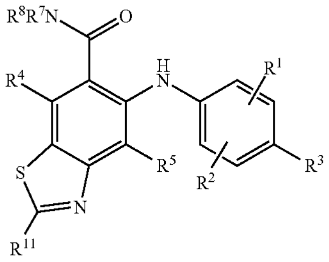

(I-3-c)

The compound of formula (I-3-c) can be prepared from the reaction of the compound of formula (Z-II) with amine ($R^8R^7NH$) in the presence of coupling reagents in appropriate solvent.

Typical coupling reagents include, but are not limited to 1-Hydroxy-1H-benzotriazole (HOBt), 3-(ethyliminomethyleneamino)-N,N-dimethylpropan-1-amine(EDCI), O-(7-azabenzotriazol-1-yl)-N,N,N',N'-tetramethyluronium hexafluorophosphate (HATU) and O-Benzotriazol-1-yl-N,N,N',N'-tetramethyluronium tetrafluoroborate (TBTU).

Typical solvents are as defined above and prefer dichloromethane, chloroform and THF.

The compound of formula (I-3-d), where $R^1$, $R^2$, $R^3$, $R^4$, $R^5$, $R^7$ and $R^8$ are as defined for the formula (J), (I) or any variations thereof, is prepared according to the method outlined in the following scheme:

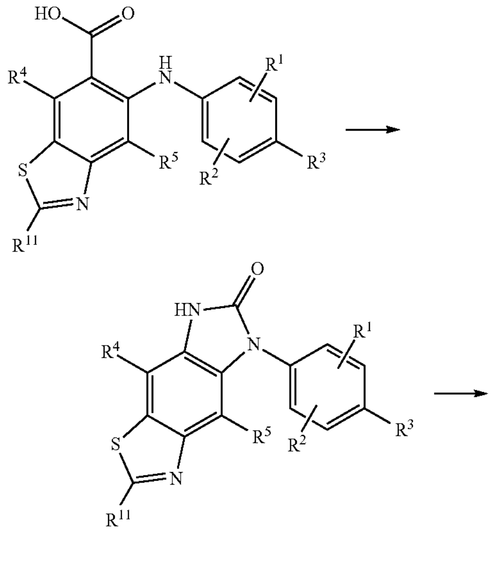

-continued

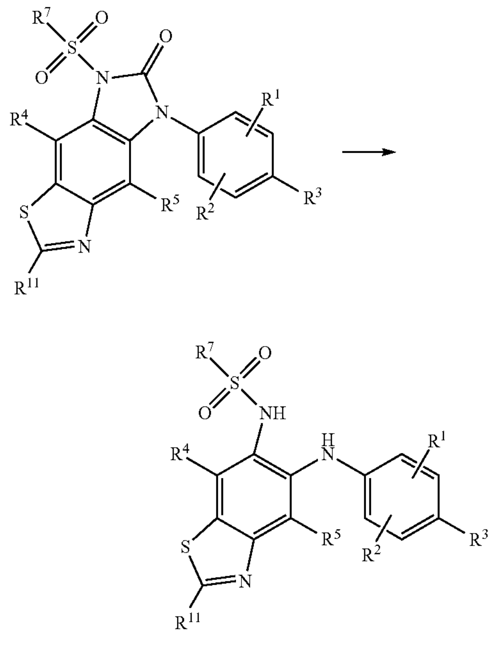

Step 1:

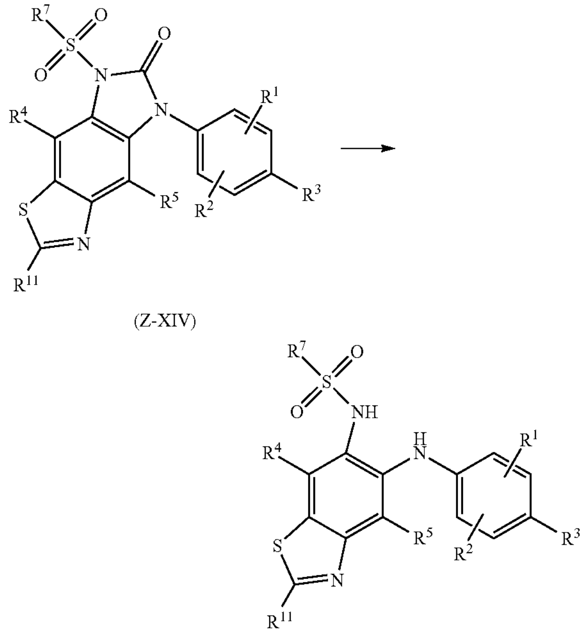

(Z-XIV)

(I-3-d)

The compound of formula (I-3-d) can be prepared from the compound of formula (Z-XIV) in the presence of base in appropriate solvent.

Typical bases include, but are not limited to, inorganic base (such as $Na_2CO_3$, $K_2CO_3$, $NaHCO_3$, $KHCO_3$, $^t$BuONa and $^t$BuOK) and organic base (such as diethylamine, triethylamine, pyridine and potassium trimethylsilanolate) and prefer potassium trimethylsilanolate.

Typical solvents are as defined above and prefer THF.

Step 2:

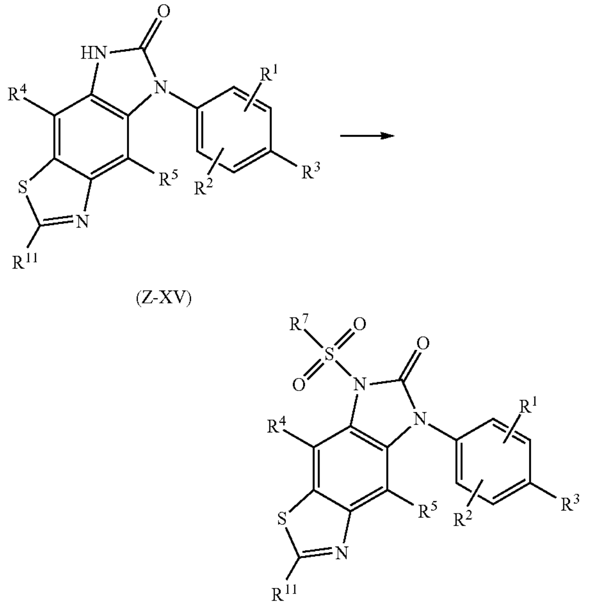

(Z-XV)

(Z-XIV)

The compound of formula (Z-XIV) can be prepared from the reaction of the compound of formula (Z-XV) with $R^7SO_2X$ (wherein X is fluoro, chloro, bromo and iodo) in the presence of base and catalyst in appropriate solvent.

Typical bases include, but are not limited to, inorganic base (such as $Na_2CO_3$, $K_2CO_3$, $NaHCO_3$, $KHCO_3$, $^t$BuONa and $^t$BuOK) and organic base (such as diethylamine, triethylamine and pyridine) and prefer triethylamine.

Typical catalysts include, but are not limited to 4-dimethylaminopyridine (DMAP).

Typical solvents are as defined above and prefer dichloromethane and chloroform.

Step 3:

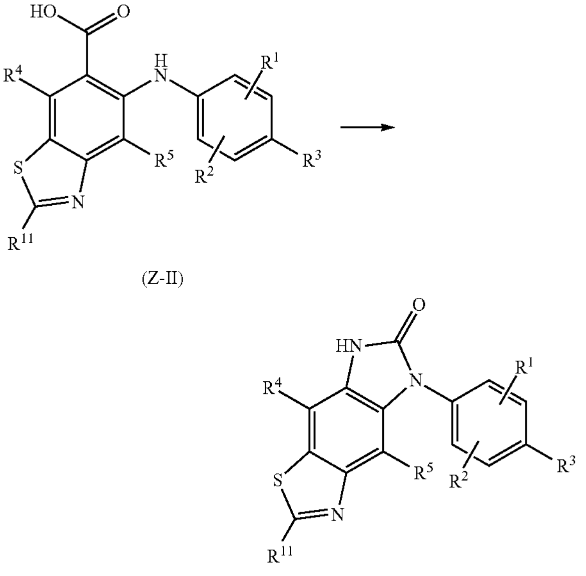

(Z-II)

(Z-XV)

The compound of formula (Z-XV) can be prepared from the reaction of the compound of formula (Z-II) with azide in the presence of base in appropriate solvent.

Typical bases include, but are not limited to, inorganic base (such as $Na_2CO_3$, $K_2CO_3$, $NaHCO_3$, $KHCO_3$, $^t$BuONa and $^t$BuOK) and organic base (such as diethylamine, triethylamine and pyridine) and prefer triethylamine.

Typical azides include diphenyl phosphoryl azide (DPPA) and ethyl carbonochloridate/$NaN_3$ and prefer diphenyl phosphoryl azide (DPPA).

Typical solvents are as defined above and prefer t-BuOH.

In some embodiments, each $R^{14}$ and $R^{15}$ is independently benzyl, benzyl substituted with 1-3 methoxy, $C_1$-$C_4$ alkyl or —$SiR^{16}R^{17}R^{18}$, wherein each of $R^{16}$, $R^{17}$ and $R^{18}$ is independently selected from $C_1$-$C_6$ alkyl and $C_6$-$C_{10}$ aryl. In some embodiments, each $R^{14}$ and $R^{15}$ is independently benzyl, benzyl substituted with 1 to 2 methoxy, $C_1$-$C_4$ alkyl, t-$BuMe_2Si$, $Ph_3Si$, $Et_3Si$, n-$Pr_3Si$ or i-$Pr_3Si$. In some embodiments, each $R^{14}$ and $R^{15}$ is independently benzyl, o-methoxybenzyl, m-methoxybenzyl, p-methoxybenzyl or $C_1$-$C_2$ alkyl. In some embodiments, each $R^{14}$ and $R^{15}$ is independently benzyl, p-methoxybenzyl or methyl.

The compound of the formula (I) where $X^1$ is N, $X^2$ is O, $R^6$ is —C(O)NHOR$^7$, and $R^3$ is halo can be synthesized according to Scheme 4, wherein $R^1$, $R^2$, $R^4$, $R^5$ and $R^7$ are as defined for the formula (J), (I) or any variations thereof; and each $R^{12}$ and $R^{13}$ is independently benzyl, benzyl substituted with 1 to 3 methoxy groups, $C_1$-$C_5$ alkyl or —$SiR^{16}R^{17}R^{18}$ where $R^{16}$, $R^{17}$ and $R^{18}$ are independently selected from $C_1$-$C_{10}$ alkyl and $C_6$-$C_{14}$ aryl.

Scheme 4

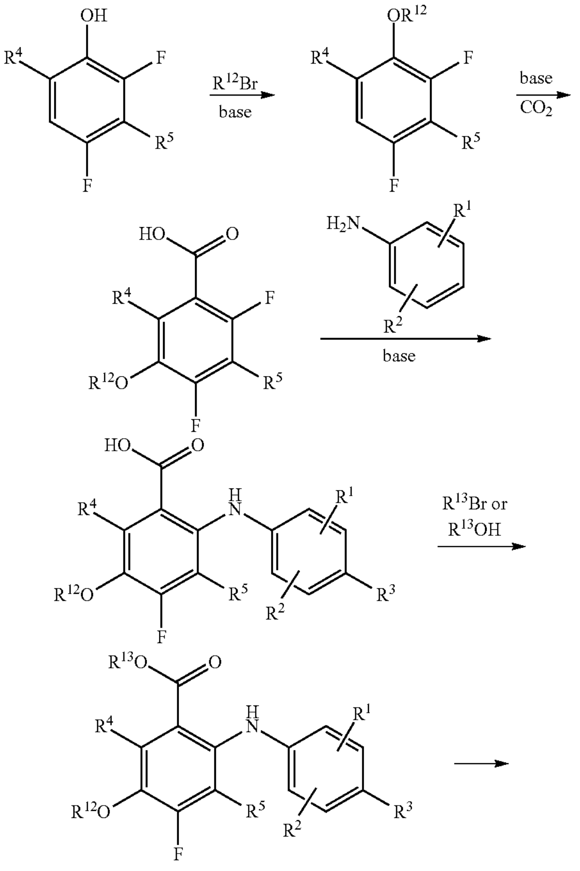

-continued

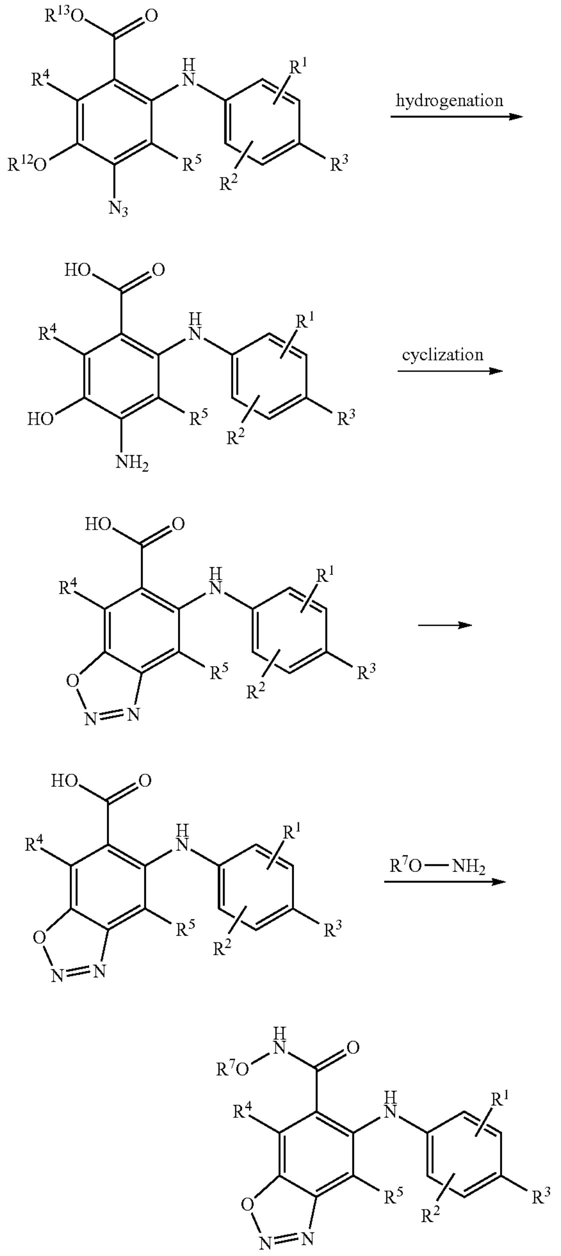

The steps in Scheme 4 are illustrated further by an exemplary synthesis of 4-fluoro-5-((2-fluoro-4-iodophenyl)amino)-N-(2-hydroxy ethoxy)benzo[d][1,2,3]oxadiazole-6-carboxamide, according to the reactions outlined in Scheme 4.1.

Scheme 4.1

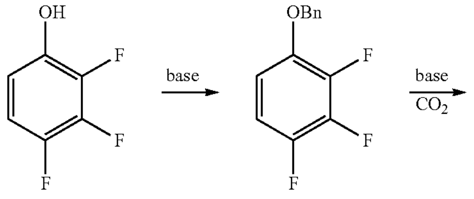

-continued

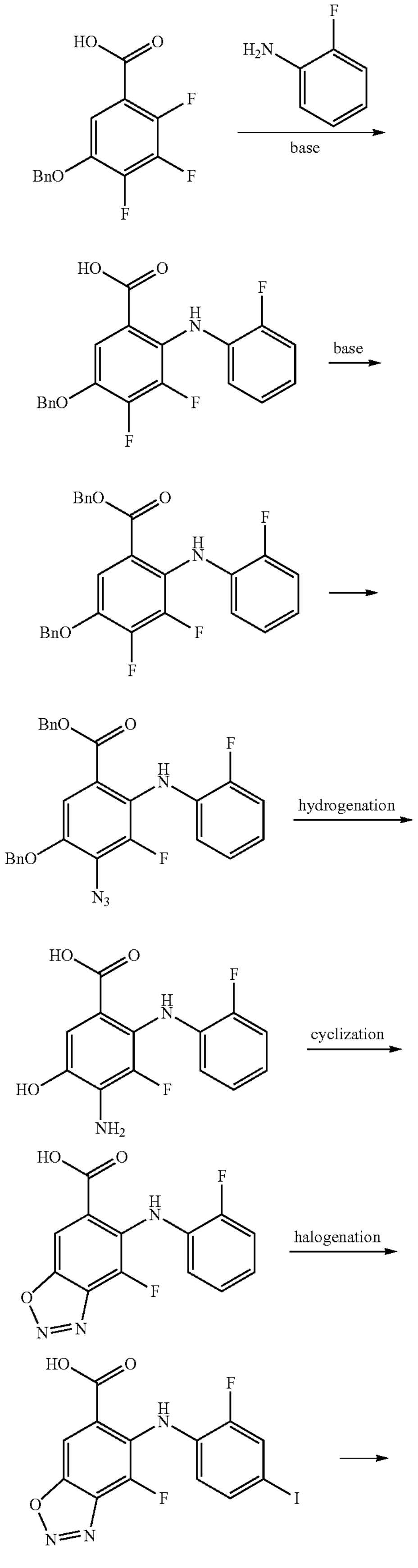

-continued

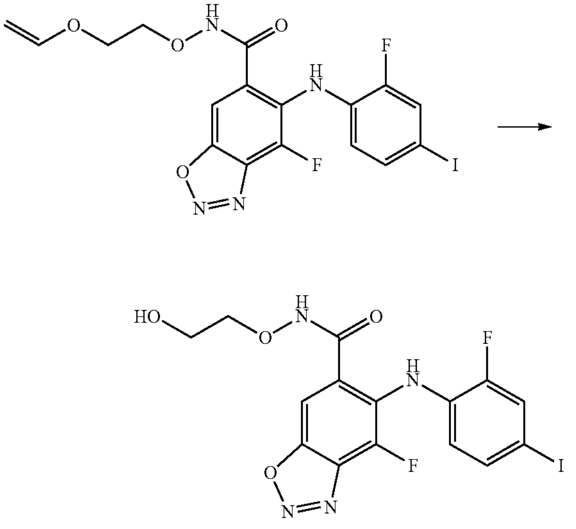

Thus, in one aspect, the invention provides methods and processes for making a compound of the formula (J), or a salt thereof, comprising coupling of a compound of the formula (G), or a salt thereof, with a hydroxylamine derivative of the formula $R^7O-N(R^8)H$ or a salt thereof:

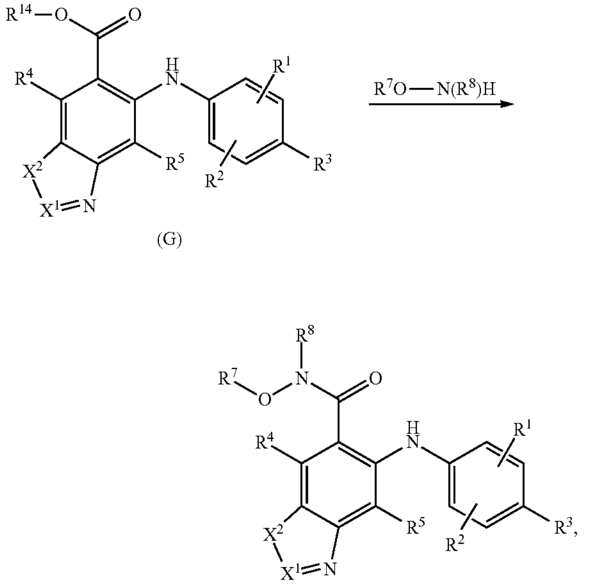

(G)

(J)

wherein $X^1$, $X^2$, $R^1$, $R^2$, $R^3$, $R^4$, $R^5$, $R^7$ and $R^8$ are as defined for the formula (J), (I) or any variations thereof, and $R^{14}$ is hydrogen, benzyl, benzyl substituted with 1 to 3 methoxy groups, $C_1$-$C_5$ alkyl or —$SiR^{16}R^{17}R^{18}$ where $R^{16}$, $R^{17}$ and $R^{18}$ are independently selected from $C_1$-$C_{10}$ alkyl and $C_6$-$C_{14}$ aryl.

In some embodiments, provided is a method of making a compound of the formula (J), or a salt thereof, wherein $X^1$ is N and $X^2$ is S, comprising coupling of a compound of the formula (G-1a), or a salt thereof, with a hydroxylamine derivative of the formula $R^7O—N(R^8)H$ or a salt thereof:

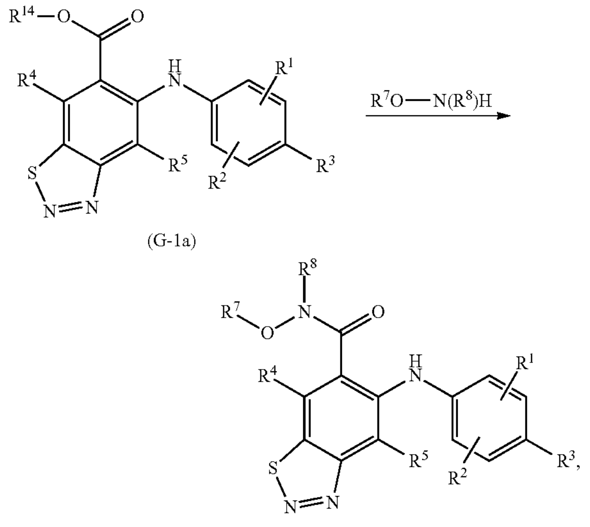

(G-1a)

(J-1a)

wherein $R^1$, $R^2$, $R^3$, $R^4$, $R^5$, $R^7$ and $R^8$ are as defined for the formula (J), (I) or any variations thereof, and $R^{14}$ is hydrogen, benzyl, benzyl substituted with 1 to 3 methoxy groups, $C_1$-$C_5$ alkyl or —$SiR^{16}R^{17}R^{18}$ where $R^{16}$, $R^{17}$ and $R^{18}$ are independently selected from $C_1$-$C_{10}$ alkyl and $C_6$-$C_{14}$ aryl. In some embodiments, the method further comprises converting a compound of the formula (F-1a) or a salt thereof to the compound of the formula (G-1a) or a salt thereof:

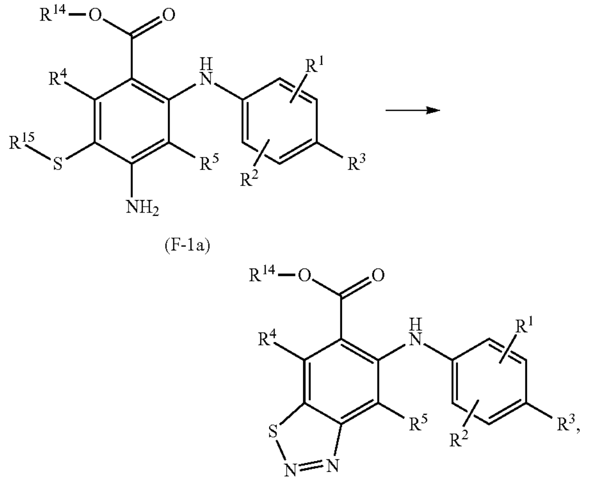

(F-1a)

(G-1a)

wherein $R^{15}$ is allyl, benzyl, benzyl substituted with 1 to 3 methoxy groups, $C_1$-$C_5$ alkyl or —$SiR^{16}R^{17}R^{18}$ where $R^{16}$, $R^{17}$ and $R^{18}$ are independently selected from $C_1$-$C_{10}$ alkyl and $C_6$-$C_{14}$ aryl. In some embodiments, the method further comprises diazotization of the compound of the formula (F-1a) or a salt thereof.

In some embodiments, provided is a method of making a compound of the formula (J), or a salt thereof, wherein, $X^1$ is $CR^{11}$ and $X^2$ is O, comprising coupling of a compound of the formula (G-2a), or a salt thereof, with a hydroxylamine derivative of the formula $R^7O$—$N(R^8)H$ or a salt thereof:

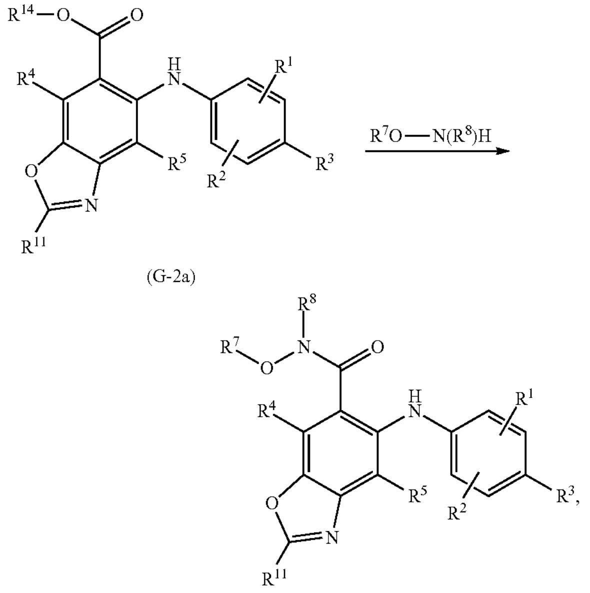

(G-2a)

(J-2a)

wherein $R^1$, $R^2$, $R^3$, $R^4$, $R^5$, $R^7$, $R^8$ and $R^{11}$ are as defined for the formula (J), (I) or any variations thereof, and $R^{14}$ is hydrogen, benzyl, benzyl substituted with 1 to 3 methoxy groups, $C_1$-$C_5$ alkyl or —$SiR^{16}R^{17}R^{18}$ where $R^{16}$, $R^{17}$ and $R^{18}$ are independently selected from $C_1$-$C_{10}$ alkyl and $C_6$-$C_{14}$ aryl. In some embodiments, the method further comprises converting a compound of the formula (F-2a) or a salt thereof to the compound of the formula (G-2a) or a salt thereof:

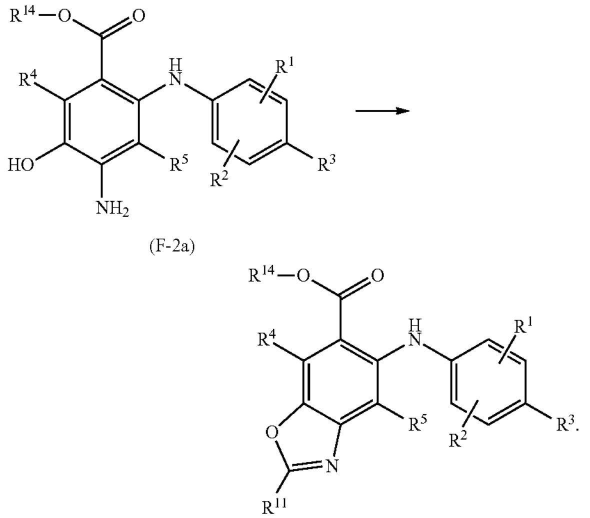

(F-2a)

(G-2a)

In some embodiments of the method where $R^{11}$ is hydrogen, the method comprises contacting an orthoester of formic acid with the compound of the formula (F-2a) or a salt thereof.

In some embodiments, provided is a method of making a compound of the formula (J), or a salt thereof, wherein $X^1$ is $CR^{11}$ and $X^2$ is S, comprising coupling of a compound of the formula (G-3a), or a salt thereof, with a hydroxylamine derivative of the formula $R^7O$—$N(R^8)H$ or a salt thereof:

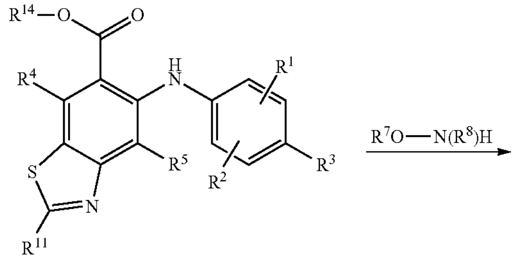

(G-3a)

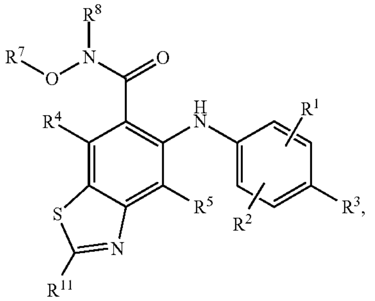

(J-3a)

wherein $R^1$, $R^2$, $R^3$, $R^4$, $R^5$, $R^7$, $R^8$ and $R^{11}$ are as defined for the formula (J), (I) or any variations thereof, and $R^{14}$ is hydrogen, benzyl, benzyl substituted with 1 to 3 methoxy groups, $C_1$-$C_5$ alkyl or —$SiR^{16}R^{17}R^{18}$ where $R^{16}$, $R^{17}$ and $R^{18}$ are independently selected from $C_1$-$C_{10}$ alkyl and $C_6$-$C_{14}$ aryl. In some embodiments, the method further comprises converting a compound of the formula (F-3a) or a salt thereof to the compound of the formula (G-3a) or a salt thereof:

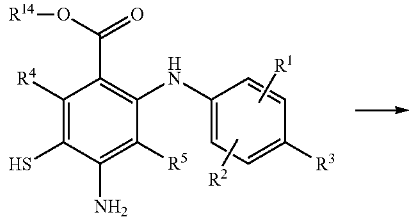

(F-3a)

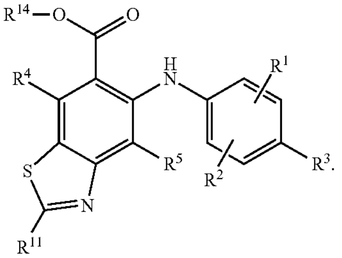

(G-3a)

In some embodiments, the method further comprises converting a compound of the formula (F-1a) or a salt thereof to the compound of the formula (F-3a) or a salt thereof:

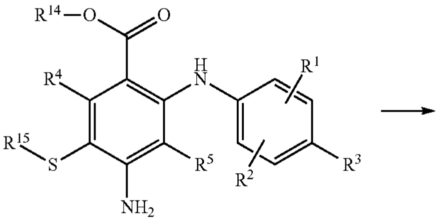

(F-1a)

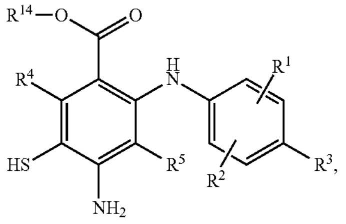

(F-3a)

wherein $R^{15}$ is allyl, benzyl, benzyl substituted with 1 to 3 methoxy groups, $C_1$-$C_5$ alkyl or —$SiR^{16}R^{17}R^{18}$ where $R^{16}$, $R^{17}$ and $R^{18}$ are independently selected from $C_1$-$C_{10}$ alkyl and $C_6$-$C_{14}$ aryl. In one variation of the method, the compound of the formula (F-1a) or a salt thereof is converted to the compound of the formula (F-3a) or a salt thereof via an intermediate of the formula (F-3a') or a salt thereof:

(F-3a')

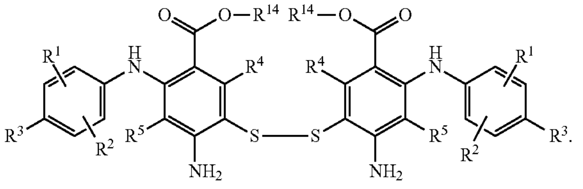

In some of these embodiments of the method where $R^{11}$ is hydrogen, the method comprises reacting an orthoester of formic acid with a compound of the formula (F-3a) or a salt thereof.

In some embodiments, provided is a method of making a compound of the formula (J-1a), or a salt thereof, comprising the steps according to Scheme 1A:

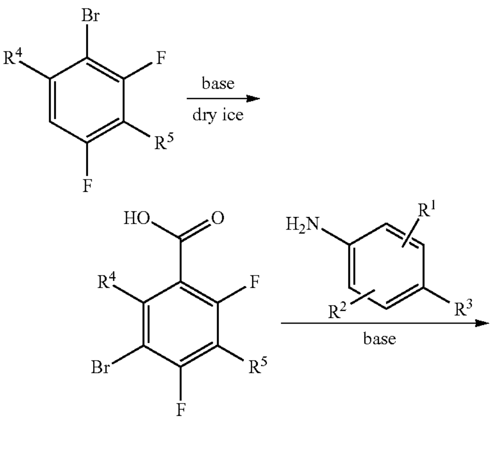

-continued

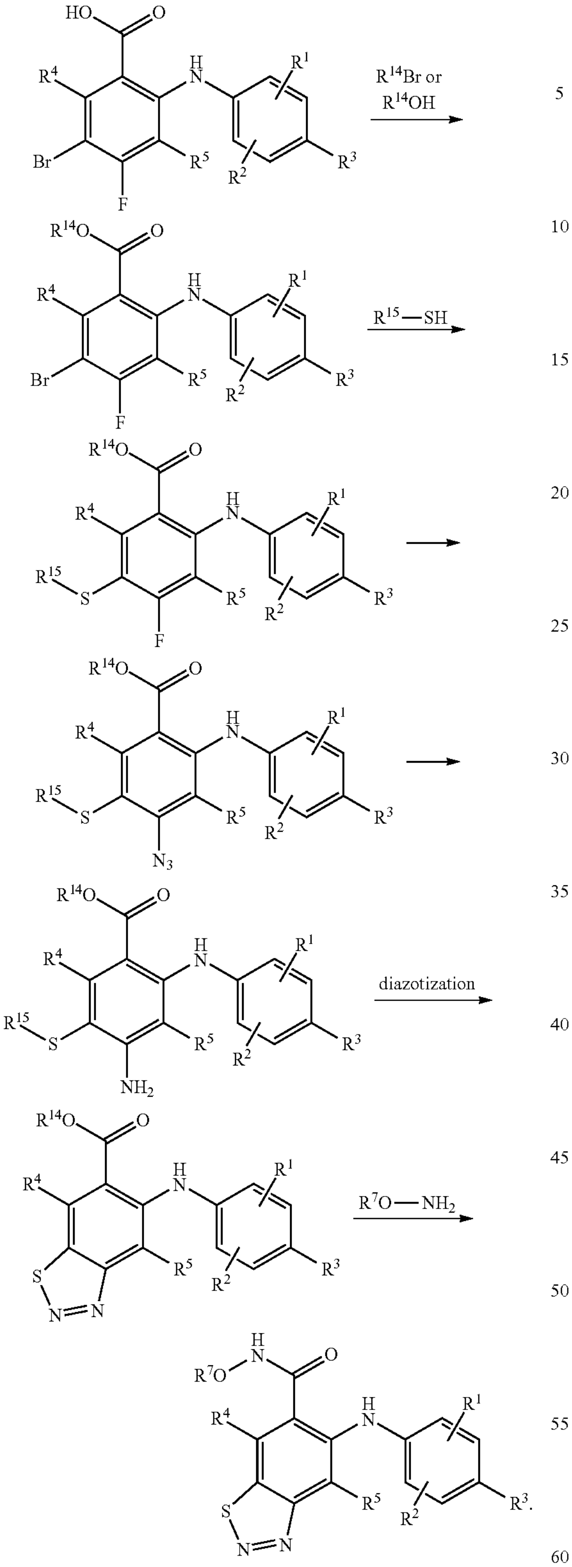

(J-1a)

wherein $R^1$, $R^2$, $R^3$, $R^4$, $R^5$ and $R^7$ are as defined for the formula (J), (I) or any variations thereof, provided that $R^3$ is other than halo; and each $R^{14}$ and $R^{15}$ is independently allyl, benzyl, benzyl substituted with 1 to 3 methoxy groups, $C_1$-$C_5$ alkyl or —$SiR^{16}R^{17}R^{18}$ where $R^{16}$, $R^{17}$ and $R^{18}$ are independently selected from $C_1$-$C_{10}$ alkyl and $C_6$-$C_{14}$ aryl.

In some embodiments, provided is a method of making a compound of the formula (J-1a) where $R^3$ is halo, or a salt thereof, comprising the steps according to Scheme 1B:

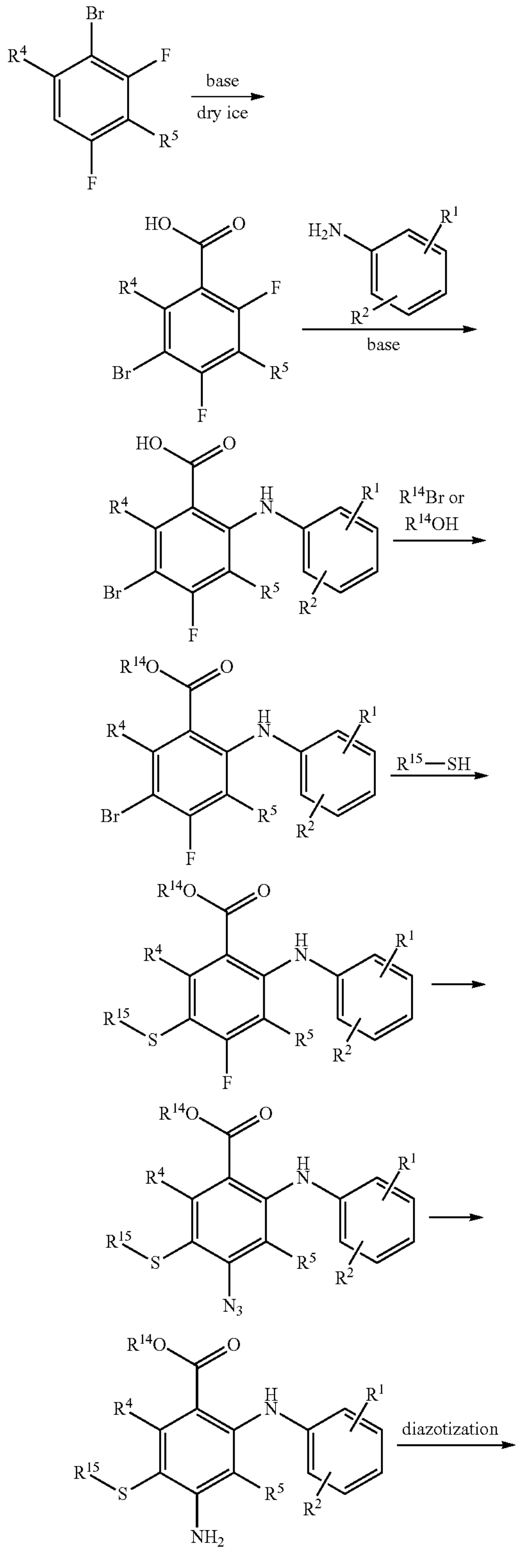

-continued

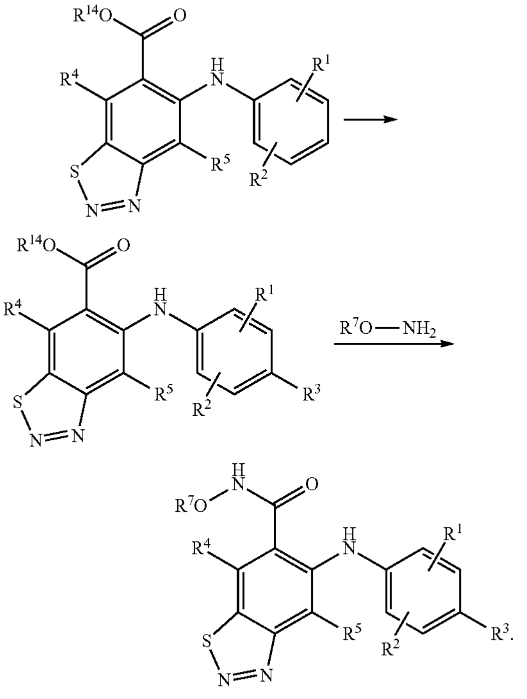

(J-1a)

wherein $R^1$, $R^2$, $R^4$, $R^5$ and $R^7$ are as defined for the formula (J), (I) or any variations thereof, and each $R^{14}$ and $R^{15}$ is independently allyl, benzyl, benzyl substituted with 1 to 3 methoxy groups, $C_1$-$C_5$ alkyl or —$SiR^{16}R^{17}R^{18}$ where $R^{16}$, $R^{17}$ and $R^{18}$ are independently selected from $C_1$-$C_{10}$ alkyl and $C_6$-$C_{14}$ aryl.

In some embodiments, provided is a method of making a compound of the formula (J-2a) or a salt thereof, comprising the steps according to Scheme 2A:

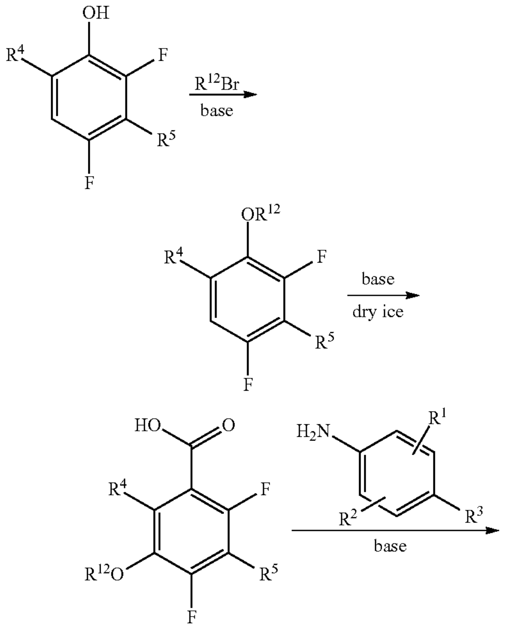

-continued

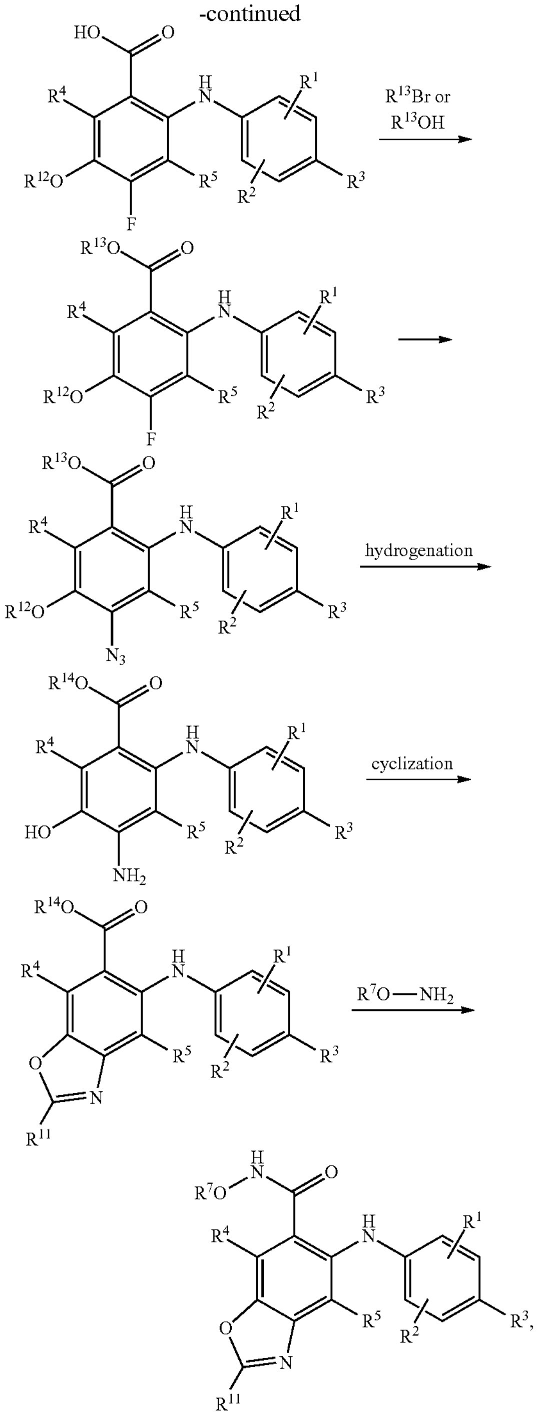

(J-2a)

wherein $R^1$, $R^2$, $R^3$, $R^4$, $R^5$, $R^7$ and $R^8$ are as defined for the formula (J), (I) or any variations thereof, provided that $R^3$ is other than halo; $R^{14}$ is hydrogen, allyl or $R^{13}$; and each $R^{12}$ and $R^{13}$ is independently benzyl, benzyl substituted with 1 to 3 methoxy groups, $C_1$-$C_5$ alkyl or —$SiR^{16}R^{17}R^{18}$ where $R^{16}$, $R^{17}$ and $R^{18}$ are independently selected from $C_1$-$C_{10}$ alkyl and $C_6$-$C_{14}$ aryl.

In some embodiments, provided is a method of making a compound of the formula (J-2a), where $R^3$ is halo, or a salt thereof comprising the steps according to Scheme 2B:

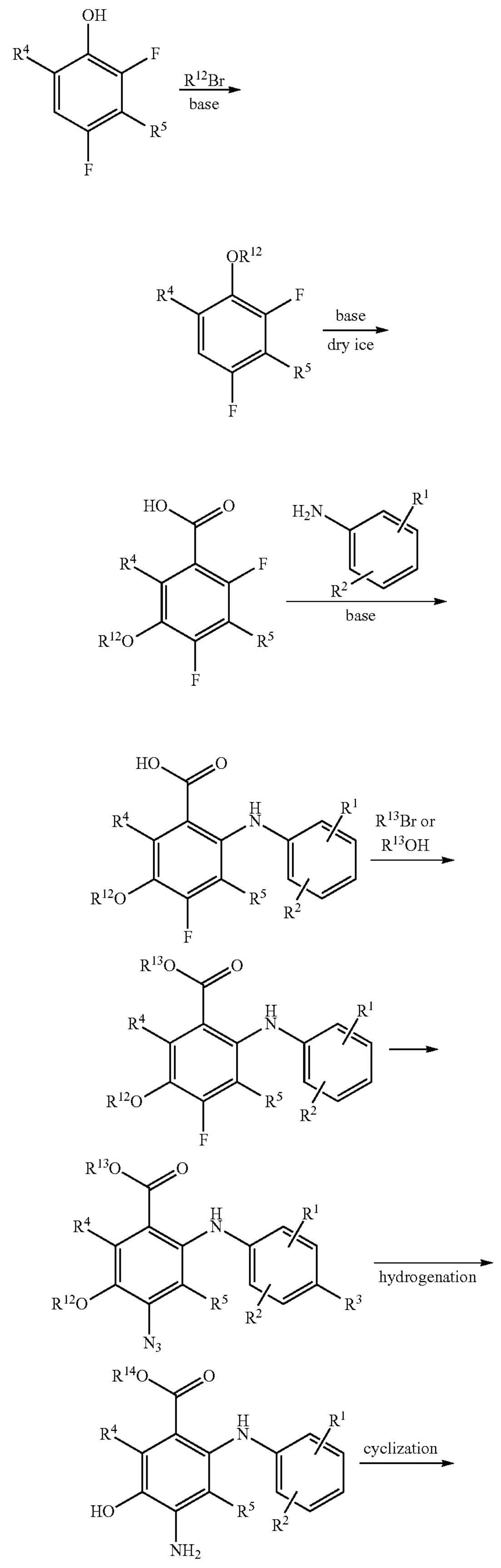

-continued

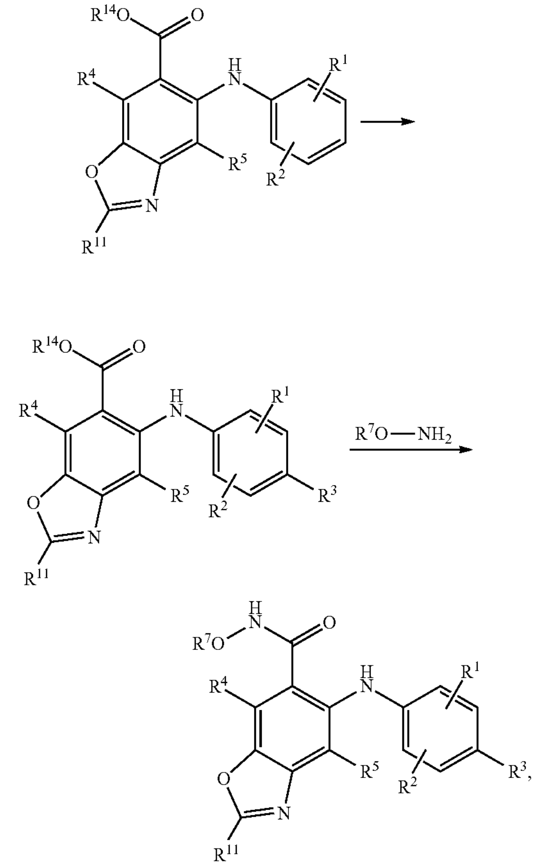

(J-2a)

wherein $R^1$, $R^2$, $R^4$, $R^5$, $R^7$ and $R^{11}$ are as defined for the formula (J), (I) or any variations thereof; $R^{14}$ is hydrogen, allyl or $R^{13}$; and each $R^{12}$ and $R^{13}$ is independently benzyl, benzyl substituted with 1 to 3 methoxy groups, $C_1$-$C_5$ alkyl or —$SiR^{16}R^{17}R^{18}$ where $R^{16}$, $R^{17}$ and $R^{18}$ are independently selected from $C_1$-$C_{10}$ alkyl and $C_6$-$C_{14}$ aryl.

In some embodiments, provided is a method of making a compound of the formula (J-3a) or a salt thereof, comprising the steps according to Scheme 3A:

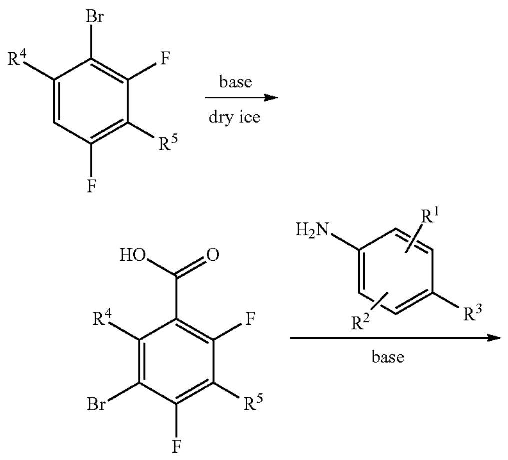

-continued

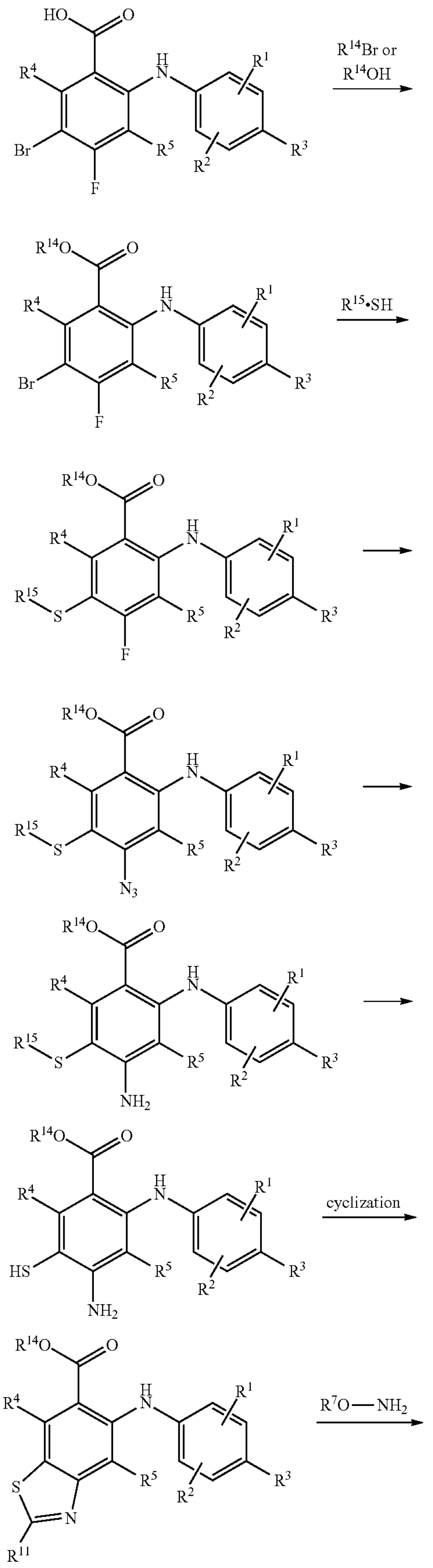

-continued

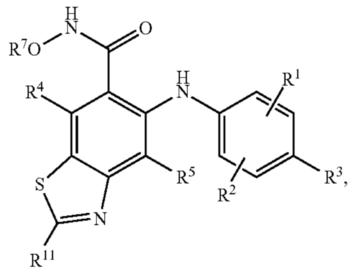

(J-3a)

wherein $R^1$, $R^2$, $R^3$, $R^4$, $R^5$, $R^7$ and $R^{11}$ are as defined for the formula (J), (I) or any variations thereof, provided that $R^3$ is other than halo; and each $R^{14}$ and $R^{15}$ is independently allyl, benzyl, benzyl substituted with 1 to 3 methoxy groups, $C_1$-$C_5$ alkyl or —$SiR^{16}R^{17}R^{18}$ where $R^{16}$, $R^{17}$ and $R^{18}$ are independently selected from $C_1$-$C_{10}$ alkyl and $C_6$-$C_{14}$ aryl.

In some embodiments, provided is a method of making a compound of the formula (J-3a) or a salt thereof, comprising the steps according to Scheme 3A-1:

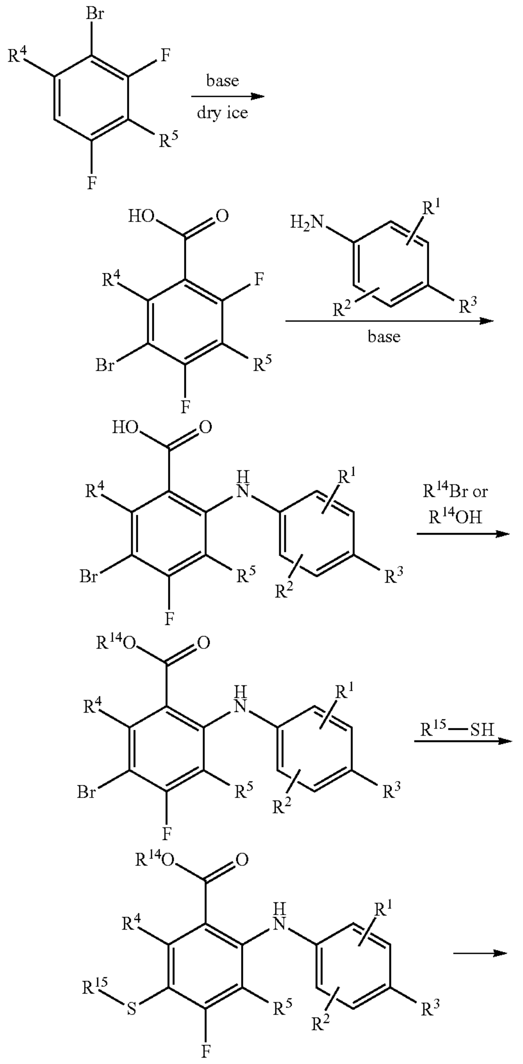

-continued

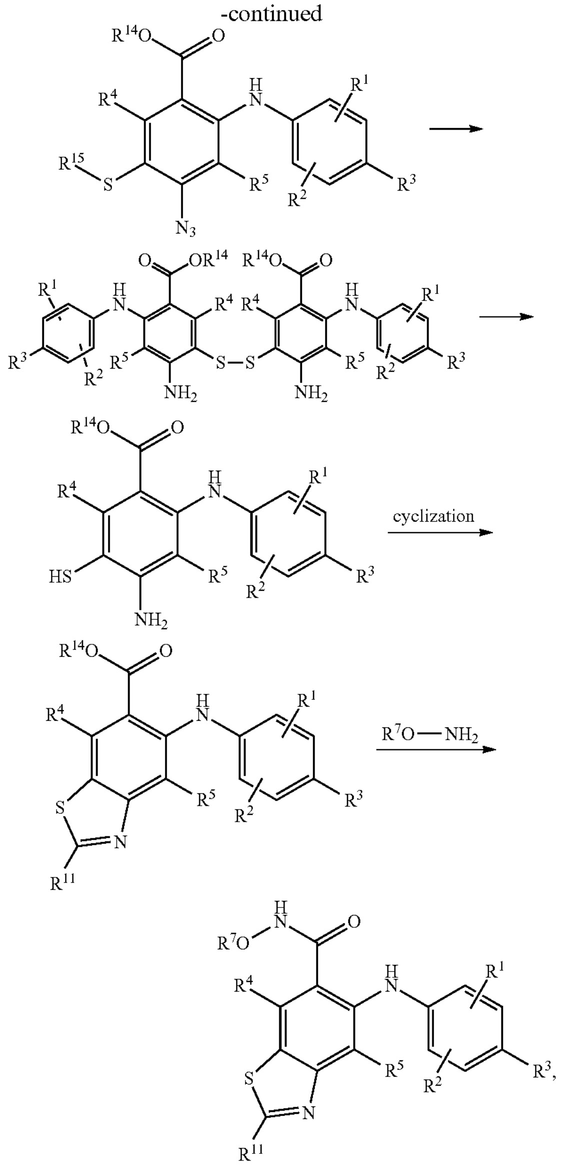

(J-3a)

wherein $R^1$, $R^2$, $R^3$, $R^4$, $R^5$, $R^7$ and $R^{11}$ are as defined for the formula (J), (I) or any variations thereof, provided that $R^3$ is other than halo; and each $R^{14}$ and $R^{15}$ is independently allyl, benzyl, benzyl substituted with 1 to 3 methoxy groups, $C_1$-$C_5$ alkyl or —$SiR^{16}R^{17}R^{18}$ where $R^{16}$, $R^{17}$ and $R^{18}$ are independently selected from $C_1$-$C_{10}$ alkyl and $C_6$-$C_{14}$ aryl.

In some embodiments, provided is a method of making a compound of the formula (J-3a) where $R^3$ is halo, or a salt thereof, comprising the steps according to Scheme 3B:

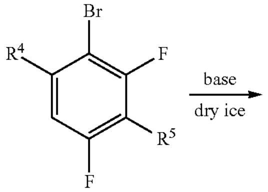

-continued

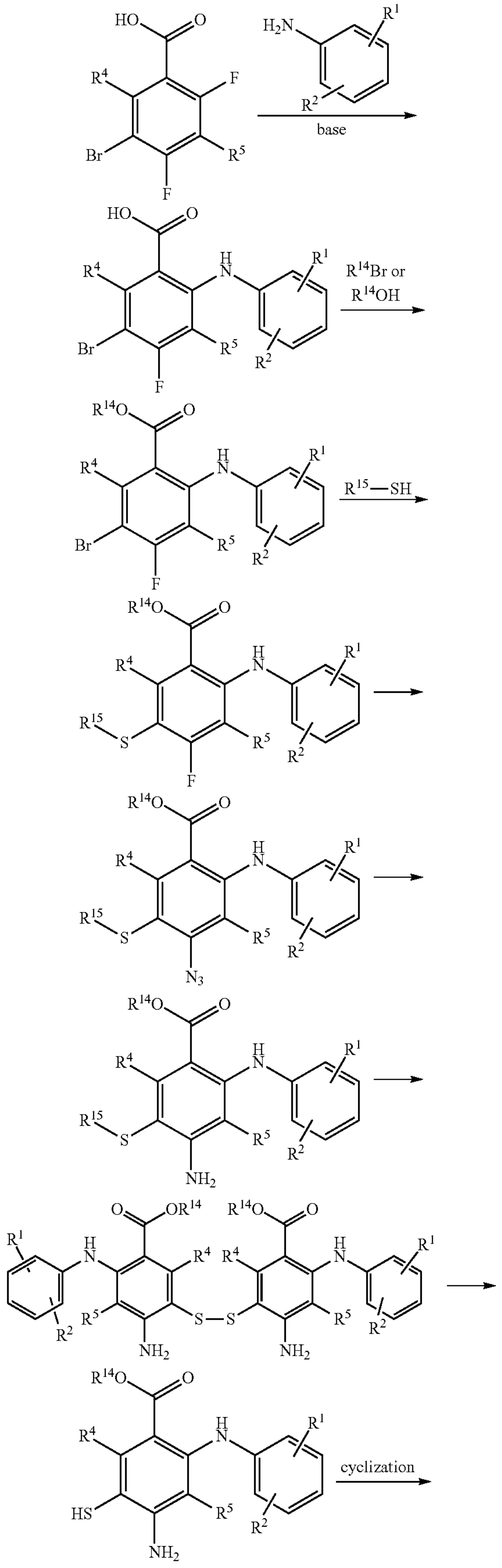

-continued

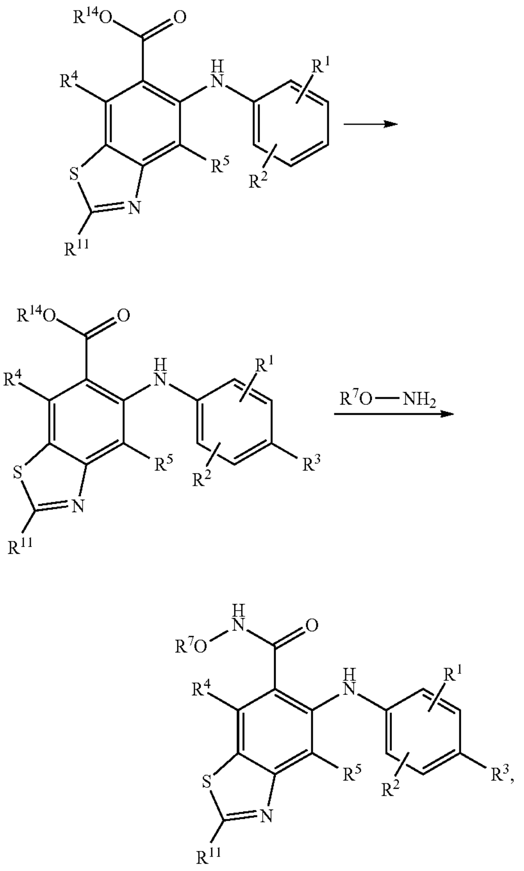

(J-3a)

wherein $R^1$, $R_2$, $R^4$, $R^5$, $R^7$ and $R^{11}$ are as defined for the formula (J), (I) or any variations thereof; and each $R^{14}$ and $R^{15}$ is independently allyl, benzyl, benzyl substituted with 1 to 3 methoxy groups, $C_1$-$C_5$ alkyl or —$SiR^{16}R^{17}R^{18}$ where $R^{16}$, $R^{17}$ and $R^{18}$ are independently selected from $C_1$-$C_{10}$ alkyl and $C_6$-$C_{14}$ aryl.

In some embodiments, provided is a method of making a compound of the formula (J-3a) where $R_3$ is halo, or a salt thereof, comprising the steps according to Scheme 3B-1:

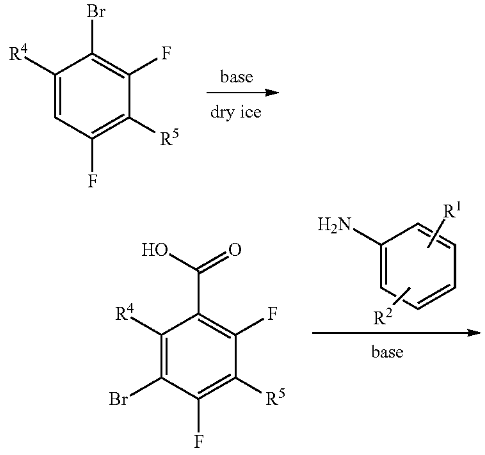

-continued

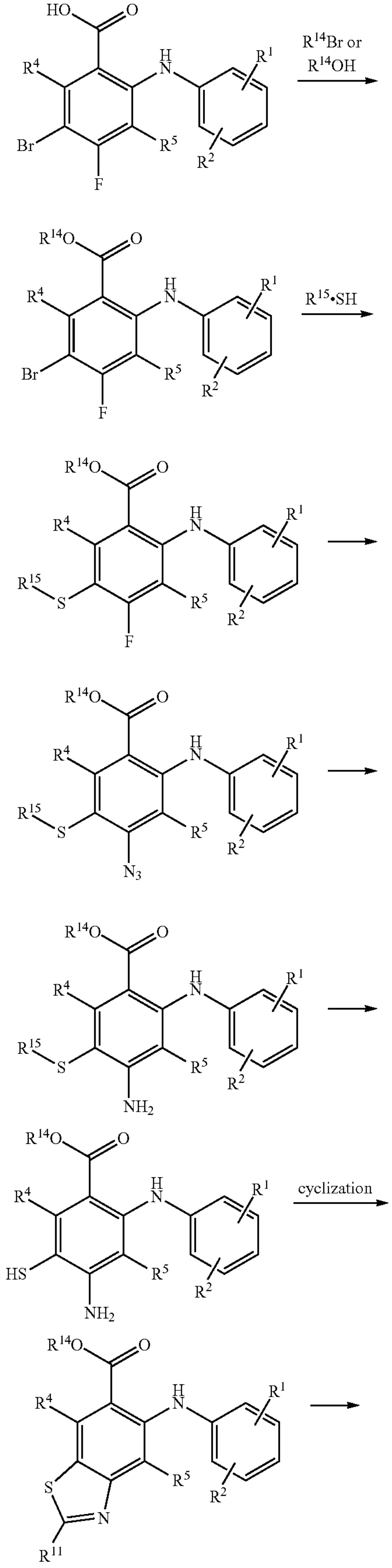

-continued

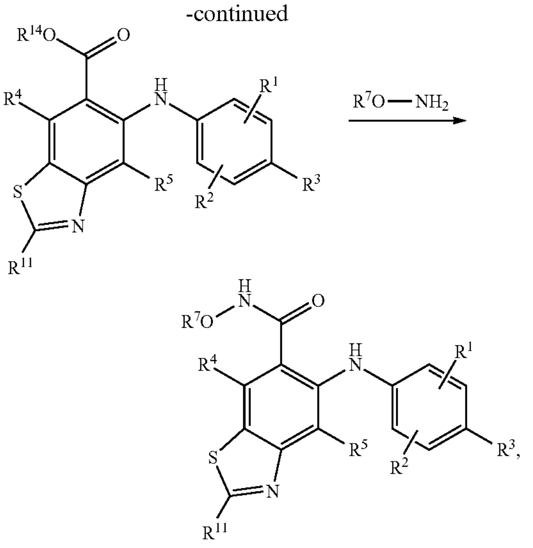

(J-3a)

wherein $R^1$, $R^2$, $R^4$, $R^5$, $R^7$ and $R^{11}$ are as defined for the formula (J), (I) or any variations thereof; and each $R^{14}$ and $R^{15}$ is independently allyl, benzyl, benzyl substituted with 1 to 3 methoxy groups, $C_1$-$C_5$ alkyl or —$SiR^{16}R^{17}R^{18}$ where $R^{16}$, $R^{17}$ and $R^{18}$ are independently selected from $C_1$-$C_{10}$ alkyl and $C_6$-$C_{14}$ aryl.

FURTHER EMBODIMENTS OF THE INVENTION

In one aspect, provided herein is a compound of formula (A-I), or a pharmaceuticals accepted salt, prodrug or solvate thereof:

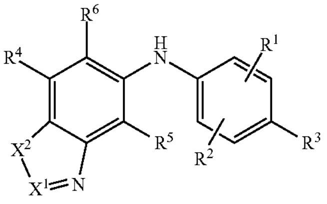

(A-I)

wherein:

each of $R^1$, $R^2$, $R^4$ and $R^5$ is independently H, halogen, nitro, azido, —$OR^7$, —$C(O)R^7$, —$C(O)OR^7$, —$NR^8C(O)OR^{10}$; —$OC(O)R^7$, —$NR^8SO_2R^{10}$, —$SO_2NR^7R^8$, —$NR^8C(O)R^7$, —$C(O)NR^7R^8$, —$NR^9C(O)NR^7R^8$, —$NR^9C(NCN)NR^7R^8$, —$NR^7R^8$, $C_1$-$C_{10}$ alkyl, $C_2$-$C_{10}$ alkenyl, $C_2$-$C_{10}$ alkynyl, $C_3$-$C_{10}$ cycloalkyl, ($C_3$-$C_{10}$ cycloalkyl)alkyl, —$S(O)_j(C_1$-$C_{10}$ alkyl), —$S(O)_j(CR^8R^9)_m$, $C_6$-$C_{14}$ aryl, $C_6$-$C_{14}$ arylalkyl, heteroaryl, heteroarylalkyl, heterocyclyl, heterocyclylalkyl, —$O(CR^8R^9)_m$-aryl, —$NR^8(CR^8R^9)_m$-aryl, —$O(CR^8R^9)_m$-heteroaryl, —$NR^8(CR^8R^9)_m$-heteroaryl, —$O(CR^8R^9)_m$-heterocyclyl, or —$NR^8(CR^8R^9)_m$-heterocyclyl;

wherein each alkyl, alkenyl, alkynyl, cycloalkyl, aryl, heteroaryl, heterocycloalkyl is optionally substituted with one or more groups independently selected from oxo-, halogen, cyano, nitro, —$CF_3$, azido, —$OR^7$, —$C(O)R^7$, —$C(O)OR^7$, —$NR^8C(O)OR^{10}$, —$OC(O)R^7$, —$NR^8SO_2R^{10}$, —$SO_2NR^7R^8$, —$NR^8C(O)R^7$, —$C(O)NR^7R^8$, —$NR^9C(O)NR^7R^8$, —$NR^9C(NCN)NR^7R^8$, —$NR^7R^8$, $C_6$-$C_{14}$ aryl, ($C_6$-$C_{14}$ aryl)$C_1$-$C_{10}$ alkyl, heteroaryl, heteroaryl($C_1$-$C_{10}$ alkyl), heterocycloalkyl, and heterocycloalkyl($C_1$-$C_{10}$ alkyl);

$R^3$ is H, halogen, cyano, nitro, azido, —$OR^7$, —$SR^7$, —$C(O)R^7$, —$C(O)OR^7$, —$NR^8C(O)OR^{10}$, —$OC(O)R^7$, —$NR^8SO_2R^{10}$, —$SO_2NR^7R^8$, —$NR^8C(O)R^7$, —$C(O)NR^7R^8$, —$NR^9C(O)NR^7R^8$, —$NR^9C(NCN)NR^7R^8$, —$NR^7R^8$, $C_1$-$C_{10}$ alkyl, $C_2$-$C_{10}$ alkenyl, $C_2$-$C_{10}$ alkynyl, $C_3$-$C_{10}$ cycloalkyl, ($C_3$-$C_{10}$ cycloalkyl)$C_1$-$C_{10}$ alkyl, —$S(O)_j(C_1$-$C_{10}$ alkyl), —$S(O)_j(CR^8R^9)_mC_6$-$C_{14}$ aryl, ($C_6$-$C_{14}$ aryl)$C_1$-$C_{10}$ alkyl, heteroaryl, (heteroaryl)$C_1$-$C_{10}$ alkyl, heterocycloalkyl, (heterocycloalkyl)$C_1$-$C_{10}$ alkyl, —$O(CR^8R^9)_m$-aryl, —$NR^8(CR^8R^9)_m$-aryl, —$O(CR^8R^9)_m$-heteroaryl, —$NR^8(CR^8R^9)_m$-heteroaryl, —$O(CR^8R^9)_m$-heterocyclyl, or —$NR^8(CR^8R^9)_m$-heterocyclyl;

wherein each alkyl, alkenyl, alkynyl, cycloalkyl, aryl, heteroaryl, heterocycloalkyl portions is optionally substituted with one or more groups independently selected from oxo-, halogen, cyano, nitro, —$CF_3$, azido, —$OR^7$, —$C(O)R^7$, —$C(O)OR^7$, —$NR^8C(O)OR^{10}$, —$OC(O)R^7$, —$NR^8SO_2R^{10}$, —$SO_2NR^7R^8$, —$NR^8C(O)R^7$, —$C(O)NR^7R^8$, —$NR^9C(O)NR^7R^8$, —$NR^9C(NCN)NR^7R^8$, —$NR^7R^8$, $C_6$-$C_{14}$ aryl, ($C_6$-$C_{14}$ aryl)$C_1$-$C_{10}$ alkyl, heteroaryl, heteroaryl($C_1$-$C_{10}$ alkyl), heterocycloalkyl, and heterocycloalkyl($C_1$-$C_{10}$ alkyl);

$R^6$ is heteroaryl, heterocycloalkyl, —$C(O)OR^7$, —$C(O)NR^7R^8$, —$C(O)NR^8OR^7$, —$C(O)R^8OR^7$, —$C(O)(C_3$-$C_{10}$ cycloalkyl), —$C(O)(C_1$-$C_{10}$ alkyl), —$C(O)(C_6$-$C_{14}$ aryl), —C(O)heteroaryl or —C(O)heterocycloalkyl; wherein each group above is optionally substituted with one or more substituents independently selected from —$NR^7R^8$, —$OR^7$, $C_1$-$C_{10}$ alkyl, $C_2$-$C_{10}$ alkenyl, $C_2$-$C_{10}$ alkynyl, wherein each group is optionally substituted with 1 or 2 substituents independently selected from —$NR^7R^8$ and —$OR^7$;

each of $R^7$, $R^8$ and $R^9$ is independently H, $C_1$-$C_{10}$ alkyl, $C_2$-$C_{10}$ alkenyl, $C_2$-$C_{10}$ alkynyl, $C_3$-$C_{10}$ cycloalkyl, ($C_3$-$C_{10}$ cycloalkyl)$C_1$-$C_{10}$ alkyl, $C_6$-$C_{14}$ aryl, ($C_6$-$C_{14}$ aryl)$C_1$-$C_{10}$ alkyl, heteroaryl, (heteroaryl)$C_1$-$C_{10}$ alkyl, heterocycloalkyl or (heterocycloalkyl)$C_1$-$C_{10}$ alkyl;

wherein each alkyl, alkenyl, alkynyl, cycloalkyl, aryl, heteroaryl, heterocycloalkyl portions is optionally substituted with one or more groups independently selected from hydroxyl, oxo-, halogen, cyano, nitro, —$CF_3$, azido, —NR'SO$_2$R'', —SO$_2$NR'R'', —C(O)R', —C(O)OR'—OC(O)R', —NR'C(O)R'''', —NR'C(O)R'', —C(O)NR'R'', —SR', —S(O)R'''', —SO$_2$R'''', —NR'R'', —NR'C(O)NR''R''', —NR'C(NCN)NR''R''', —OR', $C_6$-$C_{14}$ aryl, heteroaryl, ($C_6$-$C_{14}$ alkyl)$C_1$-$C_{10}$ alkyl, (heteroaryl)$C_1$-$C_{10}$ alkyl, heterocycloalkyl and (heterocycloalkyl)$C_1$-$C_{10}$ alkyl;

or $R^7$ and $R^8$, together with the atom to which they are attached, form, a substituted or unsubstituted 3- to 10-member ring; wherein each group is optionally substituted with one or more substituents independently selected from halogen, cyano, nitro, —$CF_3$, azido, —NR'SO$_2$R'''', —SO$_2$NR'R'', —C(O)R', —C(O)OR', —OC(O)R', —NR'C(O)R'''', —NR'C(O)R'', —C(O)NR'R'', —SR', —S(O)R'''', —SO$_2$R'''', —NR'R'', —NR'C(O)NR''R''', —NR'C(NCN)NR''R''', —OR', $C_6$-$C_{14}$ aryl, heteroaryl, ($C_6$-$C_{14}$ aryl)$C_1$-$C_{10}$ alkyl, (heteroaryl)$C_1$-$C_{10}$ alkyl, heterocycloalkyl and (heterocycloalkyl)$C_1$-$C_{10}$ alkyl;

or $R^8$ and $R^9$, together with the atom to which they are attached, form a substituted or unsubstituted 3- to 10-member ring; wherein each group is optionally substituted with one or more substituents independently selected from H, cyano, nitro, —$CF_3$, azido, —NR'$SO_2$R'''', —$SO_2$NR'R'', —C(O)R', —C(O)OR', —OC(O)R', —NR'C(O)R'''', —NR'C(O)R'', —C(O)NR'R'', —SR', —S(O)R'''', —$SO_2$R'''', —NR'R'', —NR'C(O)NR''R''', —NR'C(NCN)NR''R''', —OR', $C_6$-$C_{14}$ aryl, heteroaryl, ($C_6$-$C_{14}$ aryl)$C_1$-$C_{10}$ alkyl, (heteroaryl)$C_1$-$C_{10}$ alkyl, heterocycloalkyl and (heterocycloalkyl)$C_1$-$C_{10}$ alkyl;

$R^{10}$ is H, $C_1$-$C_{10}$ alkyl, $C_2$-$C_{10}$ alkenyl, $C_2$-$C_{10}$ alkynyl, $C_3$-$C_{10}$ cycloalkyl, ($C_3$-$C_{10}$ cycloalkyl)$C_1$-$C_{10}$ alkyl, $C_6$-$C_{14}$ aryl, ($C_6$-$C_{14}$ aryl)$C_1$-$C_{10}$ alkyl, heteroaryl, (heteroaryl)$C_1$-$C_{10}$ alkyl, heterocycloalkyl or (heterocycloalkyl)$C_1$-$C_{10}$ alkyl;

wherein each alkyl, alkenyl, alkynyl, cycloalkyl, aryl, heteroaryl, heterocycloalkyl is optionally substituted with one or more groups independently selected from oxo-, halogen, cyano, nitro, —$CF_3$, azido, —NR'$SO_2$R'''', —$SO_2$NR'R'', —C(O)R', —C(O)OR', —OC(O)R', —NR'C(O)R'''', —NR'C(O)R'', —C(O)NR'R'', —SR', —S(O)R'''', —$SO_2$R'''', —NR'R'', —NR'C(O)NR''R''', —NR'C(NCN)NR''R''', —OR', $C_6$-$C_{14}$ aryl, heteroaryl, ($C_6$-$C_{14}$ aryl)$C_1$-$C_{10}$ alkyl, (heteroaryl)$C_1$-$C_{10}$ alkyl, heterocycloalkyl and (heterocycloalkyl)$C_1$-$C_{10}$ alkyl;

R', R'' and R''' are independently H, $C_1$-$C_{10}$ alkyl, $C_2$-$C_6$ alkenyl, $C_6$-$C_{14}$ aryl, or ($C_6$-$C_{14}$ aryl)$C_1$-$C_{10}$ alkyl;

R'''' is $C_1$-$C_{10}$ alkyl, $C_2$-$C_6$ alkenyl, $C_6$-$C_{14}$ aryl or ($C_6$-$C_{14}$ aryl)$C_1$-$C_{10}$ alkyl;

or any two of R', R'', R''' and R'''', together with the atom to which they are attached, form a 4- to 10-membered heteroaryl or heterocyclic ring, wherein each heteroaryl and heterocyclic rings is optionally substituted with one or more groups independently selected from H, cyano, nitro, trifluoromethyl, difluoromethoxy, trifluoromethoxy, azido, $C_6$-$C_{14}$ aryl, heteroaryl, ($C_6$-$C_{14}$ aryl)$C_1$-$C_{10}$ alkyl, (heteroaryl)$C_1$-$C_{10}$ alkyl, heterocycloalkyl and (heterocycloalkyl)$C_1$-$C_{10}$ alkyl;

$X^1$ is $CR^{11}$ or N;

$R^{11}$ is H, $C_1$-$C_{10}$ alkyl, $C_2$-$C_{10}$ alkenyl, $C_2$-$C_{10}$ alkynyl, $C_3$-$C_{10}$ cycloalkyl, ($C_3$-$C_{10}$ cycloalkyl)$C_1$-$C_{10}$ alkyl, $C_6$-$C_{14}$ aryl, ($C_6$-$C_{14}$ aryl)$C_1$-$C_{10}$ alkyl, heteroaryl, (heteroaryl)$C_1$-$C_{10}$ alkyl, heterocycloalkyl and (heterocycloalkyl)$C_1$-$C_{10}$ alkyl, ($C_1$-$C_{10}$ alkyl)$_3$-silyl, ($C_1$-$C_{10}$ alkyl)$_2$($C_6$-$C_{14}$ aryl)silyl; wherein each alkyl, alkenyl, alkynyl, cycloalkyl, aryl, heteroaryl, heterocycloalkyl is optionally substituted with one or more groups independently selected from, oxo-, halogen, cyano, nitro, —$CF_3$, azido, —NR'$SO_2$R'''', —$SO_2$NR'R'', —C(O)R', —C(O)OR', —OC(O)R', —NR'C(O)R'''', —NR'C(O)R'', —C(O)NR'R'', —SR', —S(O)R'''', —$SO_2$R'''', —NR'R'', —NR'C(O)NR''R''', —NR'C(NCN)NR''R''', —OR', $C_6$-$C_{14}$ aryl, heteroaryl, ($C_6$-$C_{14}$ aryl)$C_1$-$C_{10}$ alkyl, (heteroaryl)$C_1$-$C_{10}$ alkyl, heterocycloalkyl and (heterocycloalkyl)$C_1$-$C_{10}$ alkyl;

$X^2$ is O, S or —C(═O);

m is 0, 1, 2, 3, 4 or 5; and j is 0, 1 or 2.

In some embodiments, the compound of the formula (A-I), where $X^1$ is —$CR^{11}$, having the formula (A-I-1), or where $X^1$ is N, having the formula (A-I-2):

(A-I-1)

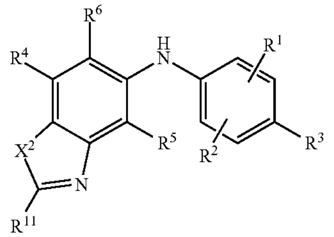

(A-I-2)

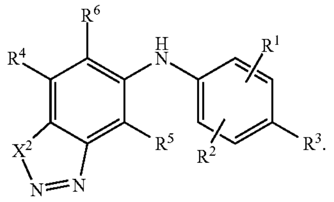

In some embodiments, the compound of the formula (A-I) where $X^1$ is —$CR^{11}$ and $X^2$ is O, S, or —C(═O) having the formula (A-I-1-a), (A-I-1-b) or (A-I-1-c) respectively:

(A-I-1-a)

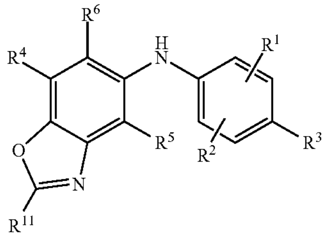

(A-I-1-b)

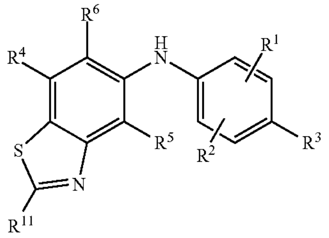

(A-I-1-c)

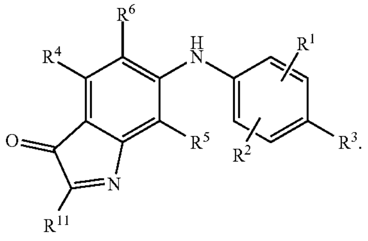

In some embodiments, the compound of the formula (A-I) where $X^1$ is N and $X^2$ is O, S, or —C(═O) having the formula (A-I-2-a), (A-I-2-b) or (A-I-2-c) respectively:

(A-I-2-a)
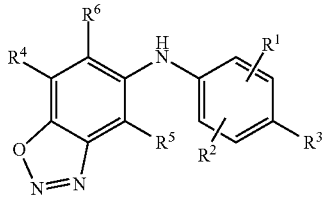
(A-I-2-b)
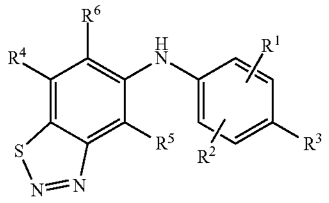
(A-I-2-c)
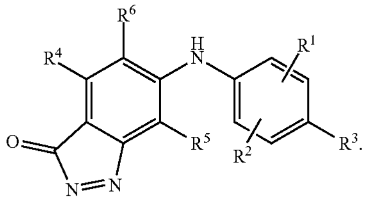
Also provided are methods of making compounds of the formula (A-I) and salts, prodrugs and solvates thereof. For example, a compound of the formula (A-I-1-a), (A-I-1-b), (A-I-2-a) or (A-I-2-b) may be prepared, according to Schemes A-1, A-2, A-3 or A-4 respectively:
Scheme A-1
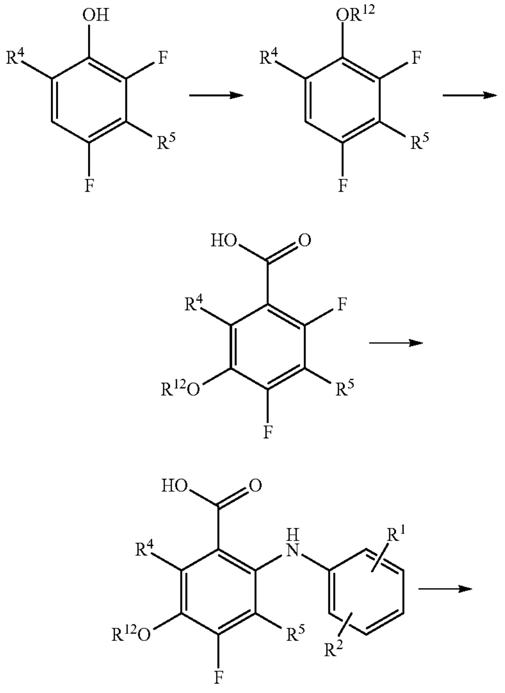
-continued
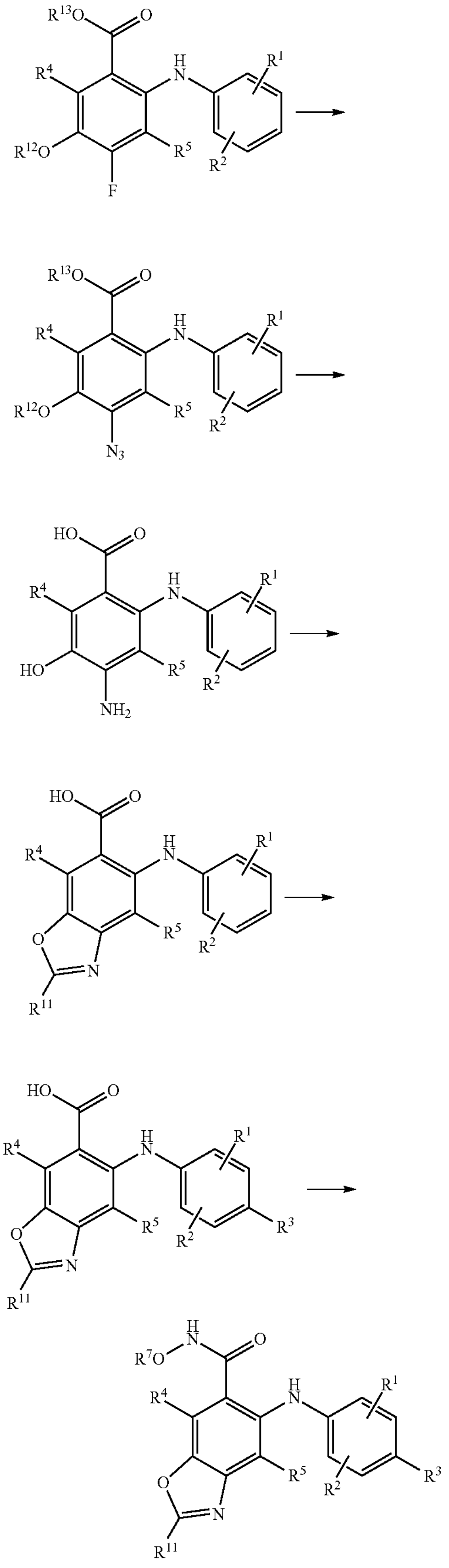

Scheme A-2
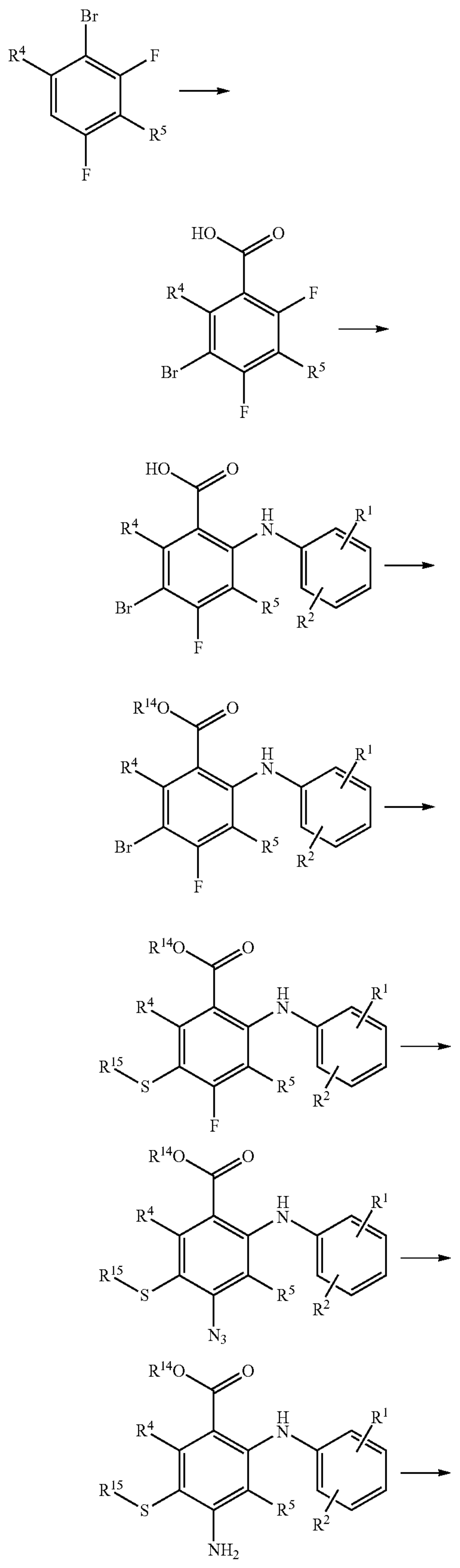
-continued
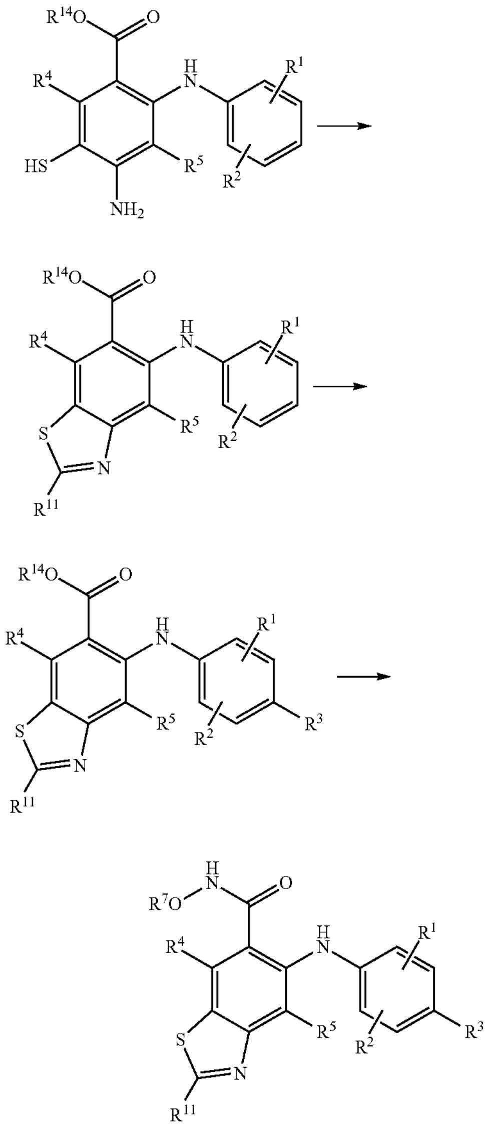
Scheme A-3
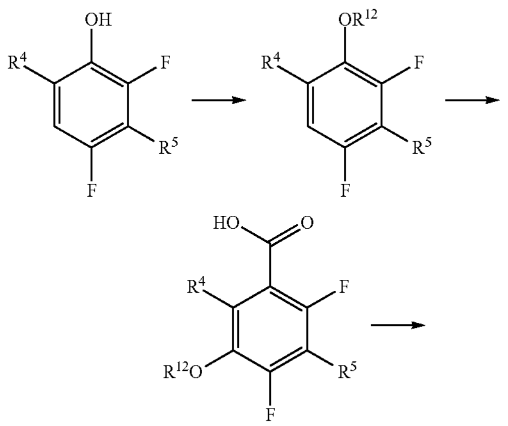

-continued
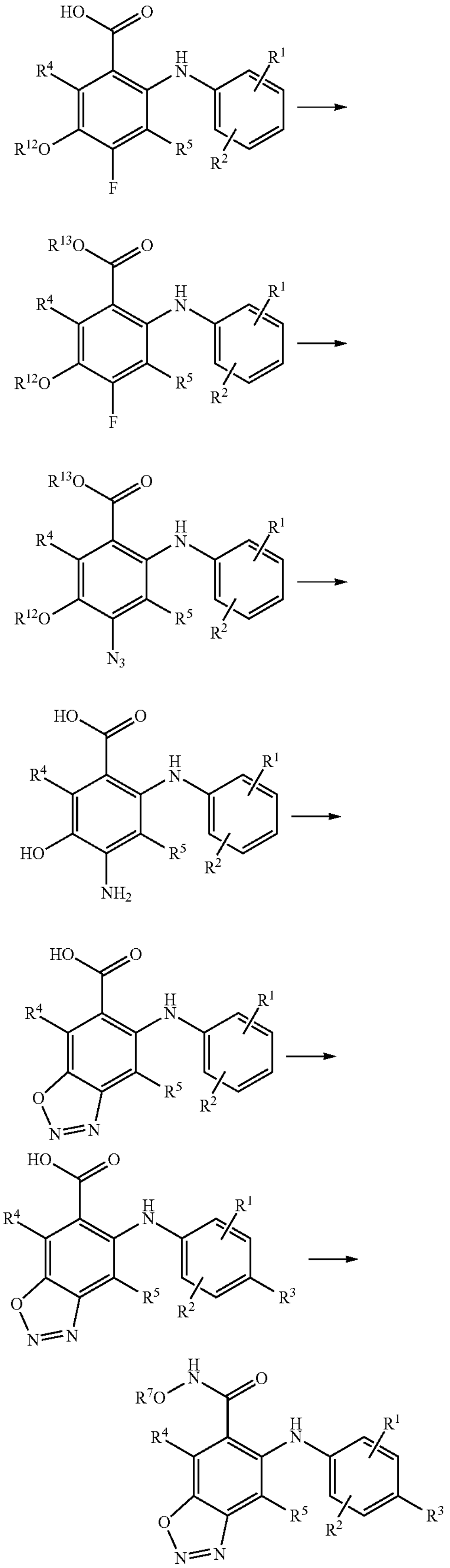
Scheme A-4
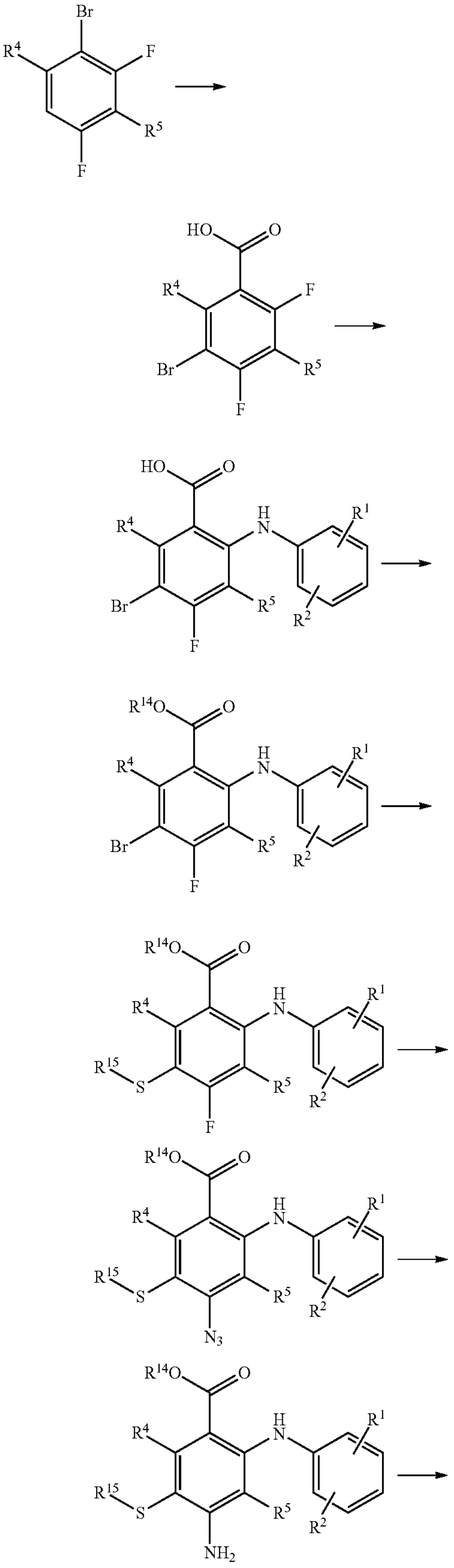

-continued

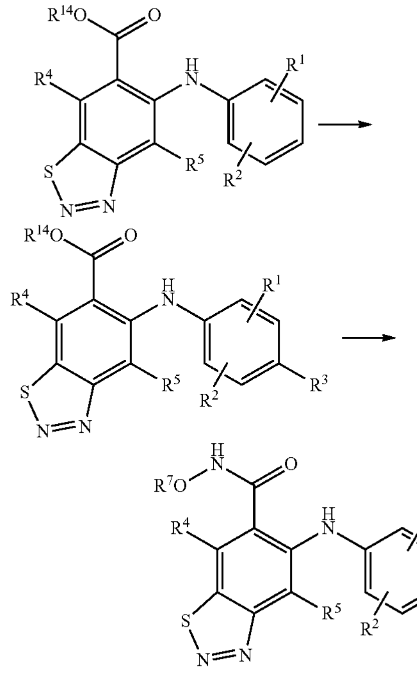

wherein $R^1$, $R^2$, $R^3$, $R^4$, $R^5$ and $R^{11}$ are as described for the formula (A-I), and $R^7$ is H, $C_1$-$C_{10}$ alkyl, $C_2$-$C_{10}$ alkenyl, $C_2$-$C_{10}$ alkynyl, $C_3$-$C_{10}$ cycloalkyl, ($C_3$-$C_{10}$ cycloalkyl)$C_1$-$C_{10}$ alkyl, $C_6$-$C_{14}$ aryl, ($C_6$-$C_{14}$ aryl)$C_1$-$C_{10}$ alkyl, heteroaryl, (heteroaryl)$C_1$-$C_{10}$ alkyl, heterocycloalkyl or (heterocycloalkyl)$C_1$-$C_{10}$ alkyl;

wherein each alkyl, alkenyl, alkynyl, cycloalkyl, and, heteroaryl, heterocycloalkyl is optionally substituted with one or more groups independently selected from oxo-, halogen, cyano, nitro, —$CF_3$, azido, —NR'$SO_2$R"", —$SO_2$NR'R", —C(O)R', —C(O)OR', —OC(O)R', —NR'C(O)R"", —NR'C(O)R", —C(O)NR'R", —SR', —S(O)R"", —$SO_2$R"", —NR'R", —NR'C(O)NR"R"', —NR'C(NCN)NR"R"', —OR', $C_6$-$C_{14}$ aryl, heteroaryl, ($C_6$-$C_{14}$ aryl)$C_1$-$C_{10}$ alkyl, (heteroaryl)$C_1$-$C_{10}$ alkyl, heterocycloalkyl and (heterocycloalkyl)$C_1$-$C_{10}$ alkyl;

R', R" and R"' are independently hydrogen, $C_1$-$C_{10}$ alkyl, $C_2$-$C_6$ alkenyl, $C_6$-$C_{14}$ aryl, or ($C_6$-$C_{14}$ aryl)$C_1$-$C_{10}$ alkyl;

R"" is $C_1$-$C_{10}$ alkyl, $C_2$-$C_6$ alkenyl, $C_6$-$C_{14}$ aryl or ($C_6$-$C_{14}$ aryl)$C_1$-$C_{10}$ alkyl;

or any two of R', R", R"' and R"", together with the atom to which they are attached, form a 4- to 10-member heteroaryl or heterocyclic ring, wherein said heteroaryl and heterocyclic rings are optionally substituted with one or more groups independently selected from, halogen, cyano, nitro, trifluoromethyl, difluoromethoxy, trifluoromethoxy, azido, $C_6$-$C_{14}$ aryl, heteroaryl, ($C_6$-$C_{14}$ aryl)$C_1$-$C_{10}$ alkyl, (heteroaryl)$C_1$-$C_{10}$ alkyl, heterocycloalkyl and (heterocycloalkyl)$C_1$-$C_{10}$ alkyl;

each of $R^{12}$, $R^{13}$, $R^{14}$ and $R^{15}$ is independently benzyl, benzyl substituted with 1 to 3 methoxy, $C_1$-$C_5$ alkyl and —$SiR^{16}R^{17}R^{18}$, wherein each of $R^{16}$, $R^{17}$ and $R^{18}$ is independently selected from $C_1$-$C_{10}$ alkyl and $C_6$-$C_{14}$ aryl.

In some preferred embodiments, the compound is of the formula (A-I), where $X^1$, $X^2$, $R^1$, $R^2$, $R^3$, $R^4$, $R^5$ and $R^6$ are as described as below with various degrees of preferences:

Preferred $X^1$ is $CR^{11}$ or N;

More preferred $X^1$ is $CR^{11}$ or N;

Especially preferred $X^1$ is $CR^{11}$ or N;

Particularly preferred $X^1$ is $CR^{11}$ or N.

Preferred $R^{11}$ is H, $C_1$-$C_6$ alkyl or ($C_3$-$C_8$ cycloalkyl)$C_1$-$C_6$ alkyl;

More preferred $R^{11}$ is H, $C_1$-$C_4$ alkyl or ($C_3$-$C_6$ cycloalkyl)$C_1$-$C_4$ alkyl;

Especially preferred $R^{11}$ is H or $C_1$-$C_4$ alkyl;

Particularly preferred $R^{11}$ is H.

Preferred $R^1$, $R^2$, $R^4$ and $R^5$ are each independently H, halogen, $C_1$-$C_{10}$ alkyl, wherein $C_1$-$C_{10}$ alkyl is optionally substituted with one or more substituents independently selected from oxo-, halogen, cyano, nitro, —$CF_3$, azido, —$OR^7$, —$C(O)R^7$, —$C(O)OR^7$, —$NR^8C(O)OR^{10}$, —$OC(O)R^7$, —$NR^8SO_2R^{10}$, —$SO_2NR^7R^8$, —$NR^8C(O)R^7$, —$C(O)NR^7R^8$, —$NR^9C(O)NR^7R^8$, —$NR^9C(NCN)NR^7R^8$, —$NR^7R^8$, $C_6$-$C_{14}$ aryl, ($C_6$-$C_{14}$ aryl)$C_1$-$C_{10}$ alkyl, heteroaryl, (heteroaryl)$C_1$-$C_{10}$ alkyl, heterocycloalkyl and (heterocycloalkyl)$C_1$-$C_{10}$ alkyl;

More preferred $R^1$ is H, halogen, $C_1$-$C_6$ alkyl, halogenated $C_1$-$C_6$ alkyl, halogenated $C_1$-$C_6$ alkoxy, or halogenated alkylsulphanyl;

Especially preferred $R^1$ is H, fluoro, chloro, bromo, $C_1$-$C_4$ alkyl, halogenated $C_1$-$C_4$ alkyl, halogenated $C_1$-$C_4$ alkoxy;

Particularly preferred $R^1$ is fluorine, chlorine, methyl, —$CF_3$, —$CF_3O$.

More preferred $R^2$ is H, halogen or $C_1$-$C_6$ alkyl;

Especially preferred $R^2$ is H, halogen or $C_1$-$C_4$ alkyl;

Particularly preferred $R^2$ is hydrogen.

More preferred $R^4$ is more preferably H;

Especially preferred $R^4$ is II;

Particularly preferred $R^4$ is H.

More preferred $R^5$ is H, halogen or $C_1$-$C_6$ alkyl;

Especially preferred $R^5$ is H, fluoro, chloro, bromo or $C_1$-$C_4$ alkyl;

Particularly preferred $R^5$ is H, fluorine, chlorine or methyl.

Preferred $R^3$ is H, halogen, $C_1$-$C_{10}$ alkoxy, $C_1$-$C_{10}$ alkyl sulphanyl, halogenated $C_1$-$C_{10}$ alkoxy, halogenated $C_1$-$C_{10}$ alkylsulphanyl or halogenated $C_1$-$C_{10}$ alkyl;

More preferred $R^3$ is fluoro, chloro, bromo, iodo, $C_1$-$C_6$ alkoxy, $C_1$-$C_6$ alkyl sulphanyl, halogenated $C_1$-$C_6$ alkoxy, halogenated $C_1$-$C_4$ alkylsulphanyl or halogenated $C_1$-$C_4$ alkyl;

Especially preferred $R^3$ is bromo, iodo, $C_1$-$C_4$ alkylsulphanyl, halogenated $C_1$-$C_4$ alkoxy, or halogenated $C_1$-$C_4$ alkyl;

Particularly preferred $R^3$ is bromo, iodo, —$SCH_3$, —$OCF_3$, —$CF_3$.

Preferred $R^6$ is —$C(O)NR^8OR^7$ or —$C(O)NR^8R^7$;

each of $R^7$, $R^8$ and $R^9$ is independently H, $C_1$-$C_{10}$ alkyl, $C_2$-$C_{10}$ alkenyl, $C_2$-$C_{10}$ alkynyl, $C_3$-$C_{10}$ cycloalkyl, ($C_3$-$C_{10}$ cycloalkyl)$C_1$-$C_{10}$ alkyl, $C_6$-$C_{14}$ aryl, ($C_6$-$C_{14}$ aryl)$C_1$-$C_{10}$ alkyl, heteroaryl, (heteroaryl)$C_1$-$C_{10}$ alkyl, heterocycloalkyl or (heterocycloalkyl)$C_1$-$C_{10}$ alkyl;

wherein each alkyl, alkenyl, alkynyl, cycloalkyl, and, heteroaryl, heterocycloalkyl is optionally substituted with one or more groups independently selected from hydroxyl, oxo-, halogen, cyano, nitro, —$CF_3$, azido, —NR'$SO_2$R"", —$SO_2$NR'R", —C(O)R', —C(O)OR', —OC(O)R', —NR'C(O)R"", —NR'C(O)R", —C(O)NR'R", —SR', —S(O)R"", —$SO_2$R"", —NR'R", —NR'C(O)NR"R"', —NR'C(NCN)NR"R"', —OR', $C_6$-$C_{14}$ aryl, heteroaryl, ($C_6$-$C_{14}$ aryl)

$C_1$-$C_{10}$ alkyl, (heteroaryl)$C_1$-$C_{10}$ alkyl, heterocycloalkyl and (heterocycloalkyl)$C_1$-$C_{10}$ alkyl;

or $R^7$ and $R^8$, together with the atom to which they are attached, form a substituted or unsubstituted 3- to 10-member ring; wherein each group is optionally substituted with one or more substituents independently selected from halogen, cyano, nitro, —$CF_3$, azido, —NR'$SO_2$R"", —$SO_2$NR'R", —C(O)R', —C(O)OR', —OC(O)R', —NR'C(O)R"", —NR'C(O)R", —C(O)NR'R", —SR', —S(O)R"", —$SO_2$R"", —NR'R", —NR'C(O)NR"R"', —NR'C(NCN)NR"R"', —OR', $C_6$-$C_{14}$ aryl, heteroaryl, ($C_6$-$C_{14}$ aryl)$C_1$-$C_{10}$ alkyl, (heteroaryl)$C_1$-$C_{10}$ alkyl, heterocycloalkyl and (heterocycloalkyl)$C_1$-$C_{10}$ alkyl;

or $R^8$ and $R^9$, together with the atom to which they are attached, form a substituted or unsubstituted 3- to 10-member ring; wherein each group is optionally substituted with one or more substituents independently selected from halogen, cyano, nitro, —$CF_3$, azido, —NR'$SO_2$R"", —$SO_2$NR'R", —C(O)R', —C(O)OR', —OC(O)R', —NR'C(O)R"", —NR'C(O)R", —C(O)NR'R", —SR', —S(O)R"", —$SO_2$R"", —NR'R", —NR'C(O)NR"R"', —NR'C(NCN)NR"R"', —OR', $C_6$-$C_{14}$ aryl, heteroaryl, ($C_6$-$C_{14}$ aryl)$C_1$-$C_{10}$ alkyl, (heteroaryl)$C_1$-$C_{10}$ alkyl, heterocycloalkyl and (heterocycloalkyl)$C_1$-$C_{10}$ alkyl;

$R^{10}$ is hydrogen, $C_1$-$C_{10}$ alkyl, $C_2$-$C_{10}$ alkenyl, $C_2$-$C_{10}$ alkynyl, $C_3$-$C_{10}$ cycloalkyl, ($C_3$-$C_{10}$ cycloalkyl)$C_1$-$C_{10}$ alkyl, $C_6$-$C_{14}$ aryl, ($C_6$-$C_{14}$ aryl)$C_1$-$C_{10}$ alkyl, heteroaryl, (heteroaryl)$C_1$-$C_{10}$ alkyl, heterocycloalkyl or (heterocycloalkyl)$C_1$-$C_{10}$ alkyl;

wherein each alkyl, alkenyl, alkynyl, cycloalkyl, aryl, heteroaryl, heterocycloalkyl is optionally substituted with one or more groups independently selected from oxo-, halogen, cyano, nitro, —$CF_3$, azido, —NR'$SO_2$R"", —$SO_2$NR'R", —C(O)R', —C(O)OR', —OC(O)R', —NR'C(O)R"", —NR'C(O)R", —C(O)NR'R", —SR', —S(O)R"", —$SO_2$R"", —NR'R", —NR'C(O)NR"R"', —NR'C(NCN)NR"R"', —OR', $C_6$-$C_{14}$ aryl, heteroaryl, ($C_6$-$C_{14}$ aryl)$C_1$-$C_{10}$ alkyl, (heteroaryl)$C_1$-$C_{10}$ alkyl, heterocycloalkyl and (heterocycloalkyl)$C_1$-$C_{10}$ alkyl;

R', R" and R"' are independently hydrogen, $C_1$-$C_{10}$ alkyl, $C_2$-$C_6$ alkenyl, $C_6$-$C_{14}$ aryl, or ($C_6$-$C_{14}$ aryl)$C_1$-$C_{10}$ alkyl;

R"" is $C_1$-$C_{10}$ alkyl, $C_2$-$C_6$ alkenyl, $C_6$-$C_{14}$ aryl or ($C_6$-$C_{14}$ aryl)$C_1$-$C_{10}$ alkyl;

or any two of R', R", R"' and R"", together with the atom to which they are attached, form a 4- to 10-member heteroaryl or heterocyclic ring, wherein each of heteroaryl and heterocyclic rings is optionally substituted with one or more groups independently selected from halogen, cyano, nitro, trifluoromethyl, difluoromethoxy, trifluoromethoxy, azido, $C_6$-$C_{14}$ aryl, heteroaryl, ($C_6$-$C_{14}$ aryl)$C_1$-$C_{10}$ alkyl, (heteroaryl)$C_1$-$C_{10}$ alkyl, heterocycloalkyl and (heterocycloalkyl)$C_1$-$C_{10}$ alkyl.

More preferred $R^6$ is —C(O)NR$^8$OR$^7$ or —C(O)NR$^8$R$^7$;

More preferred $R^7$ is $C_1$-$C_6$ alkyl substituted with 1 to 6 hydroxy groups, or ($C_3$-$C_{10}$ cycloalkyl)$C_1$-$C_{10}$ alkyl;

More preferred $R^8$ is hydrogen or $C_1$-$C_6$ alkyl.

Especially preferred $R^6$ is —C(O)NR$^8$OR$^7$ or —C(O)NR$^8$R$^7$;

Especially preferred $R^7$ is $C_1$-$C_4$ alkyl substituted with 1 to 3 hydroxy groups, or ($C_3$-$C_8$ cycloalkyl)$C_1$-$C_{10}$ alkyl;

Especially preferred $R^8$ is hydrogen or $C_1$-$C_4$ alkyl.

Particularly preferred $R^6$ is —C(O)NHOR$^7$ or —C(O)NR$^8$R$^7$;

Particularly preferred $R^7$ is ethyl, propyl or isobutyl substituted with 1 to 3 hydroxy groups, or ($C_3$-$C_6$ cycloalkyl) $C_1$-$C_4$ alkyl.

In some preferred embodiments, the compound is of the formula (A-I), where $X^1$, $X^2$, $R^1$, $R^2$, $R^3$, $R^4$, $R^5$ and $R^6$ are as defined for the preferred variations for the $X^1$, $X^2$, $R^1$, $R^2$, $R^3$, $R^4$, $R^5$ and $R^6$ groups described above.

In some more preferred embodiments, the compound is of the formula (A-I), where $X^1$, $X^2$, $R^1$, $R^2$, $R^3$, $R^4$, $R^5$ and $R^6$ are as defined for the more preferred variations for the $X^1$, $X^2$, $R^1$, $R^2$, $R^3$, $R^4$, $R^5$ and $R^6$ groups described above.

In some especially preferred embodiments, the compound is of the formula (A-I), where $X^1$, $X^2$, $R^1$, $R^2$, $R^3$, $R^4$, $R^5$ and $R^6$ are as defined for the especially preferred variations for the $X^1$, $X^2$, $R^1$, $R^2$, $R^3$, $R^4$, $R^5$ and $R^6$ groups described above.

In some particularly preferred embodiments, the compound is of the formula (A-I), where $X^1$, $X^2$, $R^1$, $R^2$, $R^3$, $R^4$, $R^5$ and $R^6$ are as defined for the particularly preferred variations for the $X^1$, $X^2$, $R^1$, $R^2$, $R^3$, $R^4$, $R^5$ and $R^6$ groups described above.

It is intended and understood that each and every variations of the $X^1$, $X^2$, $R^1$, $R^2$, $R^3$, $R^4$, $R^5$ and $R^6$ groups of the compound of the formula (A-I) may be combined, that is, the non-preferred variations and variations with different degrees of preferences as specified above for the formula (A-I) may be combined. Such combinations are applicable to the synthetic precursors and intermediates as they are applied to the final product in the synthetic methods and schemes, for example, in Schemes A-1, A-2, A-3 and A-4.

Saturated or unsaturated hydrocarbon radicals (e.g., $C_1$-$C_{10}$ alkyl, alkylene or alkenyl), as well as when they are attached a heteroatom (e.g., alkoxy) may be a linear or branched chain.

Unless otherwise specified, any groups may be optionally substituted with a single substituent or with multiple substituents, and the substituents in a multiply substituted group may be the same or different.

In some embodiments, provided is a compound of the formula (A-I-1-a-1), (A-I-1-b-1), (A-I-1-c-1), (A-I-2-a-1), (A-I-2-b-1) or (A-I-2-c-1):

(A-I-1-a-1)

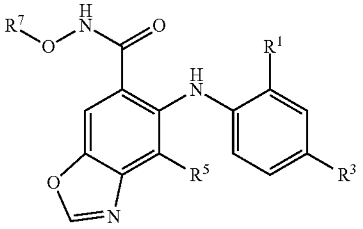

(A-I-1-b-1)

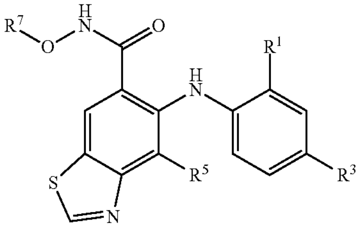

-continued (A-I-1-c-1)

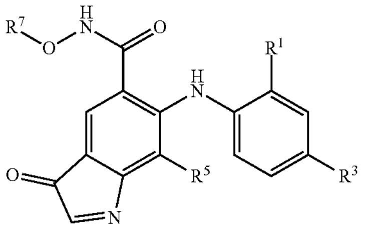

(A-I-2-a-1)

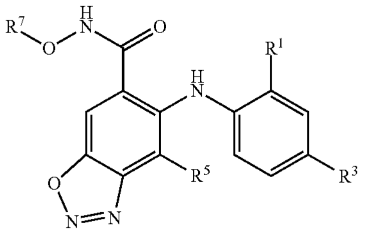

(A-I-2-b-1)

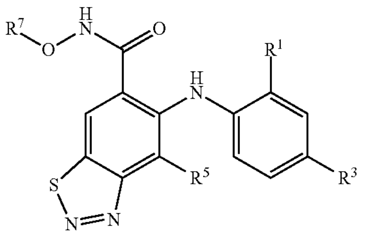

(A-I-2-c-1)

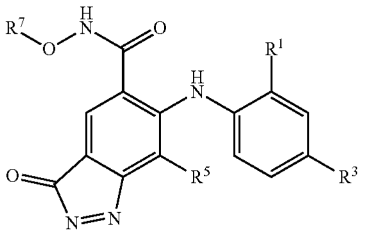

or a salt, prodrug or solvate thereof, wherein the —C(O)NHOR$^7$ moiety is selected from the group consisting of:

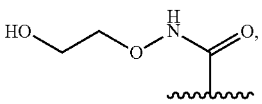

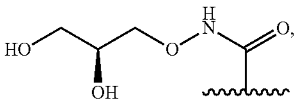

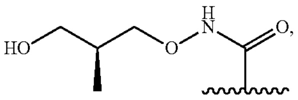

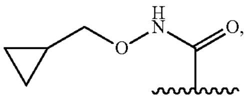

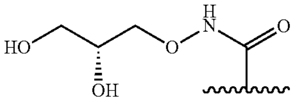

and

-continued

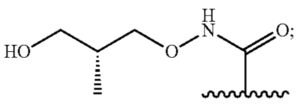

and $R^1$, $R^3$ and $R^5$ are as described in Table 4.

TABLE 4

| $R^1$ | $R^3$ | $R^5$ | $R^1$ | $R^3$ | $R^5$ | $R^1$ | $R^3$ | $R^5$ |
|---|---|---|---|---|---|---|---|---|
| F | Br | F | F | Br | Me | F | Br | H |
| F | I | F | F | I | Me | F | I | H |
| F | SMe | F | F | SMe | Me | F | SMe | H |
| F | $OCF_3$ | F | F | $OCF_3$ | Me | F | $OCF_3$ | H |
| Cl | Br | F | Cl | Br | Me | Cl | Br | H |
| Cl | I | F | Cl | I | Me | Cl | I | H |
| Cl | SMe | F | Cl | SMe | Me | Cl | SMe | H |
| Cl | $OCF_3$ | F | Cl | $OCF_3$ | Me | Cl | $OCF_3$ | H |
| Me | Br | F | Me | Br | Me | Me | Br | H |
| Me | I | F | Me | I | Me | Me | I | H |
| Me | SMe | F | Me | SMe | Me | Me | SMe | H |
| Me | $OCF_3$ | F | Me | $OCF_3$ | Me | Me | $OCF_3$ | H |

Synthesis

Compounds of the formula (A-I) or any variations thereof may be synthesized following synthetic routes illustrated in Schemes (A-1-1), (A-2-1), (A-3-1) and (A-4-1).

Scheme A-1-1

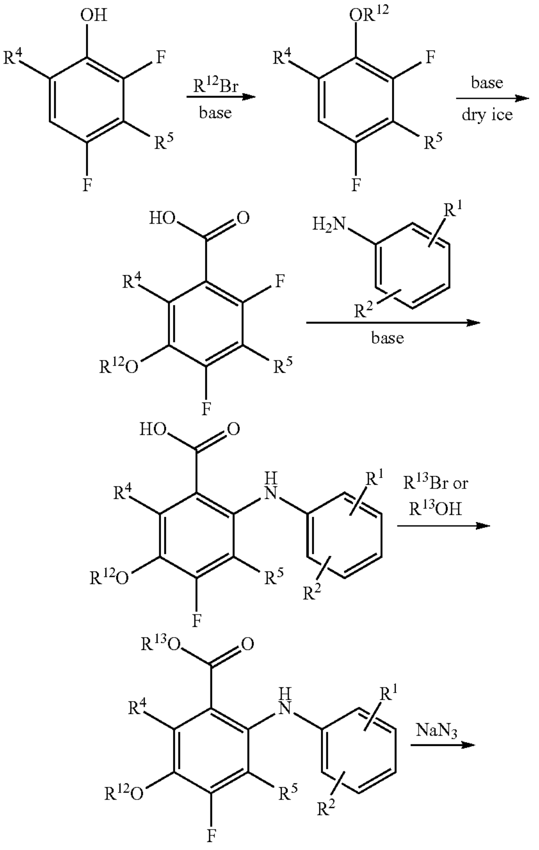

-continued
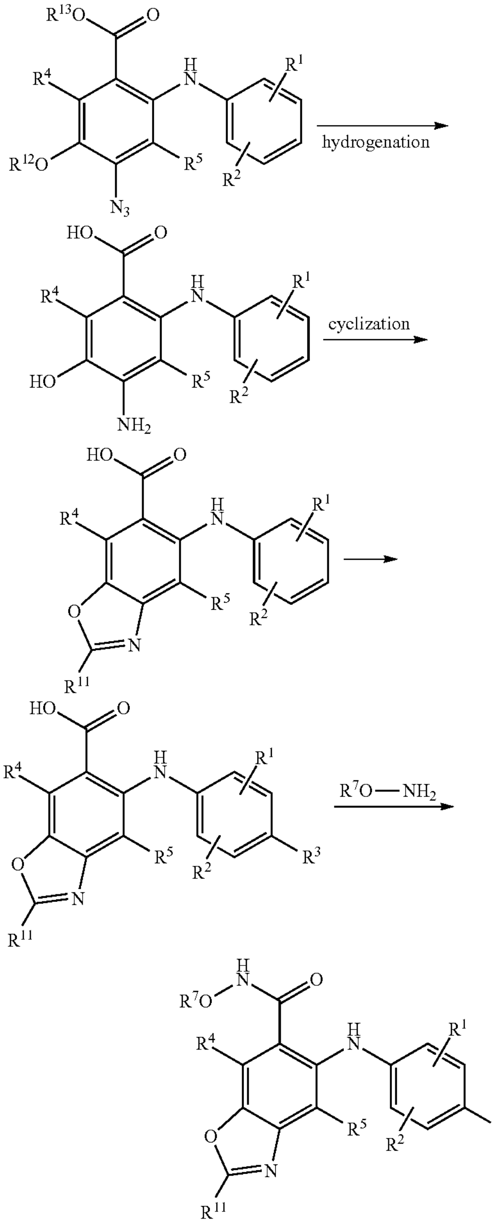
(J-3a)
The synthetic route according to Scheme A-1-1 is further illustrated by a synthetic process for 4-fluoro-5-((2-fluoro-4-iodophenyl)amino)-N-(2-hydroxyethoxy)benzo[d]oxazole-6-carboxamide as outline in Scheme A-1-1-1 and the following steps,
Scheme A-1-1-1
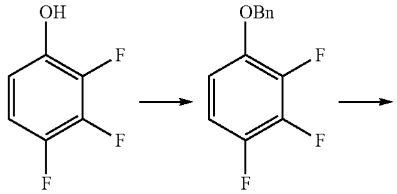
-continued
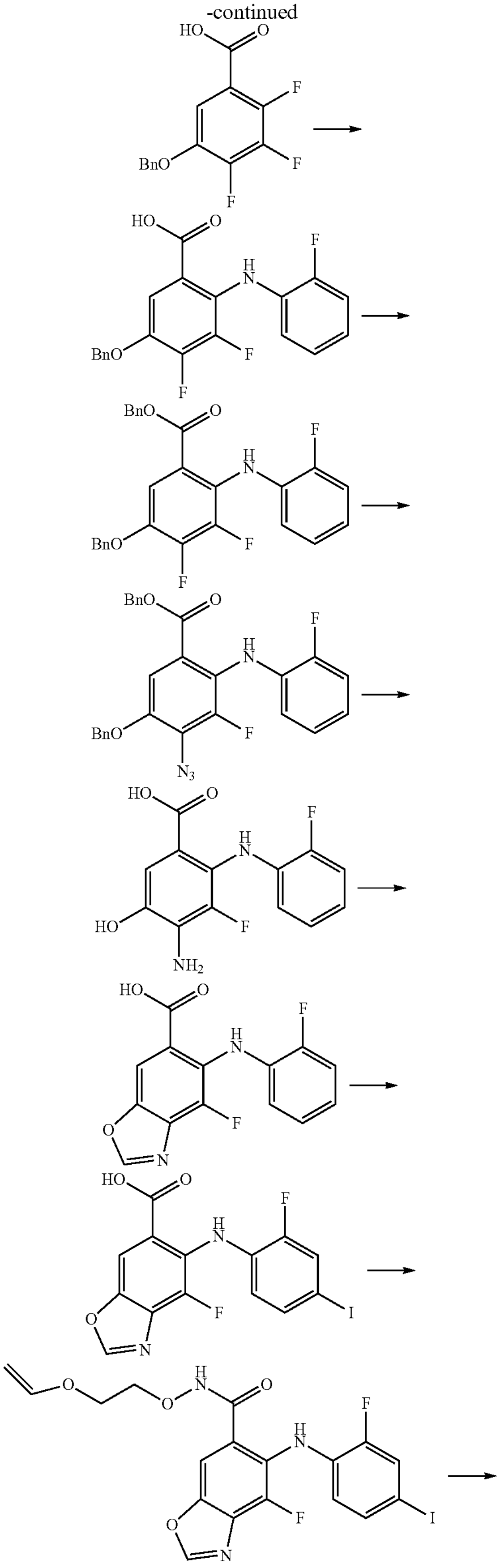

-continued

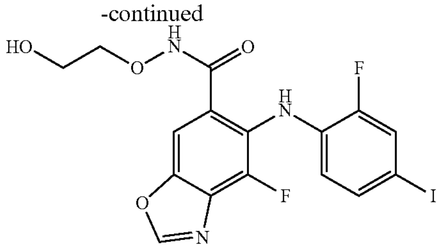

Step 1:

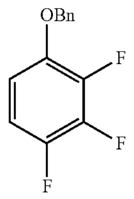 [SMILES: Fc1ccc(OCc2ccccc2)c(F)c1F]

2,3,4-Trifluorophenol was protected with hydroxy protection reagent (examples include BnBr, BnCl) at ambient temperature in the presence of base (include $Na_2CO_3$, $K_2CO_3$, $NaHCO_3$, $KHCO_3$, t-BuOK, t-BuONa) in appropriate inert solvent (include aliphatic and aromatic hydrocarbon (such as pentane, hexane, heptane, cyclohexane, petroleum ether, petrol, gasoline, benzene, toluene, xylene), aliphatic and aromatic halo-hydrocarbon (such as dichloromethane, 1,2-dichloroethane, chloroform, phenixin, chlorobenzene, o-dichlorobenzene), ether (such as diethyl ether, dibutyl ether, glycol dimethyl ether, 2-methoxyethyl ether, tetrahydrofuran, dioxane), ketone (such as acetone, methyl ethyl ketone, methyl isopropyl ketone, methyl isobutyl ketone), ester (such as ethyl acetate, methyl acetate), nitrile (such as acetonitrile, propiononitrile), amide (such as N,N-dimethylformamide, N,N-dimethylacetamide and N-methylpyrrolidin-2-one), DMSO, sulfolane, HMPA, DMPU, prefer acetone and methyl ethyl ketone). The reaction proceeds for several hours (3-12 h, prefer 5-10 h). 1-(Benzyloxy)-2,3,4-trifluorobenzene is obtained after conventional workup.

Step 2:

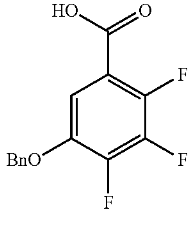 [SMILES: O=C(O)c1cc(OCc2ccccc2)c(F)c(F)c1F]

To a solution of 1-benzyloxy-2,3,4-trifluorobenzene in appropriate inert solvent (such as, but not limited to, aliphatic and aromatic hydrocarbon (such as pentane, hexane, heptane, cyclohexane, petroleum ether, petrol, gasoline, benzene, toluene, xylene), ether (such as diethyl ether, dibutyl ether, glycol dimethyl ether, 2-methoxyethyl ether, tetrahydrofuran, dioxane), sulfolane, HMPA, DMPU, prefer anhydrous THF, ethyl ether and dioxane) was added strong base (such as LDA, n-BuLi, LiHDMS) at low temperature (−50° C.−−80° C., prefer −78° C.) under nitrogen atmosphere. The stirring was maintained at this temperature for several hours (such as 0.5-12 h, prefer 0.5-2 h). The mixture was transferred to a bottle with dry ice. The mixture is stirred for some time (such as 3-12 h, prefer 5-10 h), 5-Benzoxy-2,3,4-trifluorobenzoic acid is obtained after conventional workup.

Step 3:

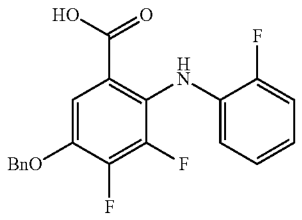 [SMILES: O=C(O)c1cc(OCc2ccccc2)c(F)c(F)c1Nc1ccccc1F]

5-Benzoxy-2,3,4-trifluorobenzoic acid can be reacted with halogenated aniline (such as o-fluoroaniline, o-chloroaniline, o-bromoaniline, o-iodoaniline) under strong basic condition (such as LDA, n-BuLi, LiHDMS) at low temperature (−50° C.−−80° C., prefer −78° C.) for some time (such as 3-12 h, prefer 5-10 h). 5-(Benzyloxy)-3,4-difluoro-2-((2-fluorophenyl)amino)benzoic acid is obtained after conventional workup.

Step 4:

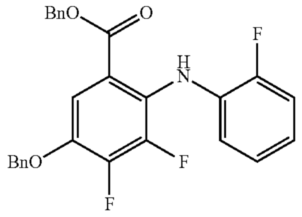 [SMILES: O=C(OCc1ccccc1)c1cc(OCc2ccccc2)c(F)c(F)c1Nc1ccccc1F]

5-(Benzyloxy)-3,4-difluoro-2-((2-fluorophenyl)amino)benzoic acid can be protected by acid or hydroxyl protection reagent (such as BnBr, BnCl) at ambient temperature in the presence of base (includes $Na_2CO_3$, $K_2CO_3$, $NaHCO_3$, $KHCO_3$, t-BuOK, t-BuONa) in appropriate inert solvent (include aliphatic and aromatic hydrocarbon (such as pentane, hexane, heptane, cyclohexane, petroleum ether, petrol, gasoline, benzene, toluene, xylene), aliphatic and aromatic halo-hydrocarbon (such as dichloromethane, 1,2-dichloroethane, chloroform, phenixin, chlorobenzene, o-dichlorobenzene), ether (such as diethyl ether, dibutyl ether, glycol dimethyl ether, 2-methoxyethyl ether, tetrahydrofuran, dioxane), ketone (such as acetone, methyl ethyl ketone, methyl isopropyl ketone, methyl isobutyl ketone), ester (such as ethyl acetate, methyl acetate), nitrile (such as acetonitrile, propiononitrile), amide (such as N,N-dimethylformamide, N,N-dimethylacetamide and N-methylpyrrolidin-2-one), DMSO, sulfolane, HMPA, DMPU, prefer acetone and methyl ethyl ketone). The reaction proceeds for several hours (3-12 h, prefer 5-10 h). Benzyl 5-(benzyloxy)-3,4-difluoro-2-((2-fluorophenyl)amino)benzoate is obtained after conventional workup.

Step 5:

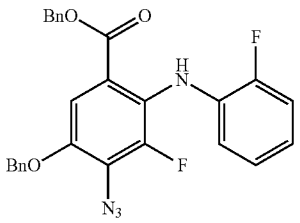 [SMILES: [N-]=[N+]=Nc1c(OCc2ccccc2)cc(C(=O)OCc2ccccc2)c(Nc2ccccc2F)c1F]

Benzyl 5-(benzyloxy)-3,4-difluoro-2-((2-fluorophenyl)amino)benzoate can be reacted with azide (such as $NaN_3$, $KN_3$) in appropriate solvent (include aliphatic and aromatic hydrocarbon (such as pentane, hexane, heptane, cyclohexane, petroleum ether, petrol, gasoline, benzene, toluene, xylene), aliphatic and aromatic halo-hydrocarbon (such as dichloromethane, 1,2-dichloroethane, chloroform, phenixin, chlorobenzene, o-dichlorobenzene), ether (such as diethyl ether, dibutyl ether, glycol dimethyl ether, 2-methoxyethyl ether, tetrahydrofuran, dioxane), ketone (such as acetone, methyl ethyl ketone, methyl isopropyl ketone, methyl isobutyl ketone), ester (such as ethyl acetate, methyl acetate), nitrile (such as acetonitrile, propiononitrile), amide (such as N,N-dimethylformamide, N,N-dimethylacetamide and A-methylpyrrolidin-2-one), DMSO, sulfolane, HMPA, DMPU, prefer N,N-dimethylformamide and N,N-dimethylacetamide) for some time (1-12 h, prefer 3-10 h). Benzyl 4-azido-5-(benzyloxy)-3-fluoro-2-((2-fluorophenyl)amino)benzoate is obtained after conventional workup.

Step 6:

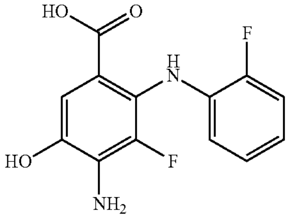 [SMILES: Nc1c(O)cc(C(=O)O)c(Nc2ccccc2F)c1F]

Benzyl 4-azido-5-(benzyloxy)-3-fluoro-2-((2-fluorophenyl)amino)benzoate can be hydrogenated catalyzed by appropriate catalyst (such as Pd/C, Pt, Ni) in the solvent (include aliphatic and aromatic hydrocarbon (such as pentane, hexane, heptane, cyclohexane, petroleum ether, petrol, gasoline, benzene, toluene, xylene), ether (such as diethyl ether, dibutyl ether, glycol dimethyl ether, 2-methoxyethyl ether, tetrahydrofuran, dioxane), ester (such as ethyl acetate, methyl acetate), amide (such as N,N-dimethylformamide, N,N-dimethylacetamide and A-methylpyrrolidin-2-one), DMSO, sulfolane, HMPA, DMPU, prefer methanol, ethanol, propan-1-ol and water) for some time (1-12 h, prefer 3-10 h). 4-Amino-3-fluoro-2-((2-fluorophenyl)amino)-5-hydroxybenzoic acid is obtained after conventional workup.

Step 7:

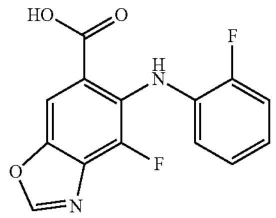 [SMILES: O=C(O)c1cc2ocnc2c(F)c1Nc1ccccc1F]

4-Amino-3-fluoro-2-((2-fluorophenyl)amino)-5-hydroxybenzoic acid can be cyclized in the presence of acid (such as/J-toluenesulfonic acid, pyridinium toluene-4-sulphonate, formic acid, acetic acid, sulfuric acid) in appropriate solvent (include aliphatic and aromatic hydrocarbon (such as pentane, hexane, heptane, cyclohexane, petroleum ether, petrol, gasoline, benzene, toluene, xylene), aliphatic and aromatic halo-hydrocarbon (such as dichloromethane, 1,2-dichloroethane, chloroform, phenixin, chlorobenzene, o-dichlorobenzene), ether (such as diethyl ether, dibutyl ether, glycol dimethyl ether, 2-methoxyethyl ether, tetrahydrofuran, dioxane), ketone (such as acetone, methyl ethyl ketone, methyl isopropyl ketone, methyl isobutyl ketone), ester (such as ethyl acetate, methyl acetate), nitrile (such as acetonitrile, propiononitrile), amide (such as N,N-dimethylformamide, N,N-dimethylacetamide and N-methylpyrrolidin-2-one), DMSO, sulfolane, HMPA, DMPU, prefer methyl acetate, ethyl acetate and trimethoxymethane) for some time (0.2-12 h, prefer 0.5-10 h). 4-Fluoro-5-((2-fluorophenyl)amino)benzo [d]oxazole-6-carboxylic acid is obtained after conventional workup.

Step 8:

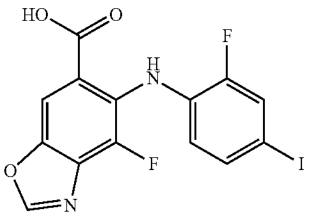 [SMILES: O=C(O)c1cc2ocnc2c(F)c1Nc1ccc(I)cc1F]

4-Fluoro-5-((2-fluorophenyl)amino)benzo[d]oxazole-6-carboxylic acid can be reacted with halogenations reagent (such as NIS) in the presence of acid (such as trifluoroacetic acid, trifluoromethanesulfonic acid, methanesulfonic acid, formic acid, acetic acid) at ambient temperature in appropriate solvent (include aliphatic and aromatic hydrocarbon (such as pentane, hexane, heptane, cyclohexane, petroleum ether, petrol, gasoline, benzene, toluene, xylene), aliphatic and aromatic halo-hydrocarbon (such as dichloromethane, 1,2-dichloroethane, chloroform, phenixin, chlorobenzene, o-dichlorobenzene), ether (such as diethyl ether, dibutyl ether, glycol dimethyl ether, 2-methoxyethyl ether, tetrahydrofuran, dioxane), ketone (such as acetone, methyl ethyl ketone, methyl isopropyl ketone, methyl isobutyl ketone), ester (such as ethyl acetate, methyl acetate), nitrile (such as acetonitrile, propiononitrile), amide (such as N,N-dimethylformamide, N,N-dimethylacetamide and A-methylpyrrolidin-2-one), DMSO, sulfolane, HMPA, DMPU, prefer N,N-dimethylformamide and N,N-dimethylacetamide) for some time (1-12 h, prefer 3-10 h). 4-Fluoro-5-((2-fluoro-4-iodophenyl)amino)benzo[d]oxazole-6-carboxylic acid is obtained after conventional workup.

Step 9:

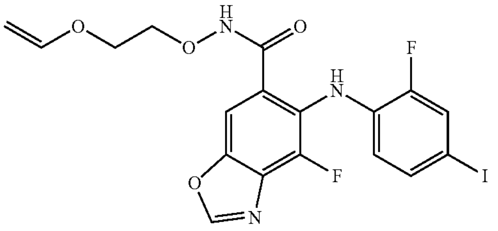 [SMILES: C=COCCONC(=O)c1cc2ocnc2c(F)c1Nc1ccc(I)cc1F]

4-Fluoro-5-((2-fluoro-4-iodophenyl)amino)benzo[d]oxazole-6-carboxyl can be reacted with O-(2-(vinyloxy)ethyl) hydroxylamine in the presence of coupling reagent (such as HOBt, EDCI, HATU, TBTU) at ambient temperature in appropriate solvent (include aliphatic and aromatic hydrocarbon (such as pentane, hexane, heptane, cyclohexane, petroleum ether, petrol, gasoline, benzene, toluene, xylene), aliphatic and aromatic halo-hydrocarbon (such as dichloromethane, 1,2-dichloroethane, chloroform, phenixin, chlorobenzene, o-dichlorobenzene), ether (such as diethyl ether, dibutyl ether, glycol dimethyl ether, 2-methoxyethyl ether, tetrahydrofuran, dioxane), ketone (such as acetone, methyl ethyl ketone, methyl isopropyl ketone, methyl isobutyl ketone), ester (such as ethyl acetate, methyl acetate), nitrile (such as acetonitrile, propiononitrile), amide (such as N,N-dimethylformamide, N,N-dimethylacetamide and N-methylpyrrolidin-2-one), DMSO, sulfolane, HMPA, DMPU, prefer dichloromethane, 1,2-dichloroethane and N,N-dimethylformamide) for some time (1-12 h, prefer 3-10 h), 4-Fluoro-5-((2-fluoro-4-iodophenyl)amino)-N-(2-(vinyloxy)ethoxy)benzo[d]oxazole-6-carboxamide is obtained after conventional workup.

Step 10:

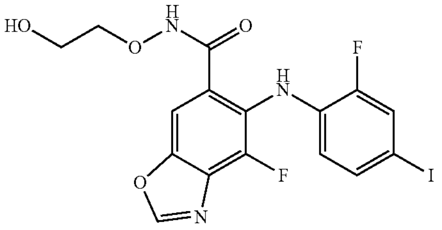

4-Fluoro-5-((2-fluoro-4-iodophenyl)amino)-N-(2-(vinyloxy)ethoxy)benzo[d]oxazole-6-carboxamide can be reacted in the presence of acid (such as hydrochloric acid, sulfuric acid, trifluoroacetic acid) in appropriate solvent (include aliphatic and aromatic hydrocarbon (such as pentane, hexane, heptane, cyclohexane, petroleum ether, petrol, gasoline, benzene, toluene, xylene), aliphatic and aromatic halo-hydrocarbon (such as dichloromethane, 1,2-dichloroethane, chloroform, phenixin, chlorobenzene, o-dichlorobenzene), ether (such as diethyl ether, dibutyl ether, glycol dimethyl ether, 2-methoxyethyl ether, tetrahydrofuran, dioxane), ketone (such as acetone, methyl ethyl ketone, methyl isopropyl ketone, methyl isobutyl ketone), ester (such as ethyl acetate, methyl acetate), nitrile (such as acetonitrile, propiononitrile), amide (such as N,N-dimethylformamide, N,N-dimethylacetamide and N-methylpyrrolidin-2-one), DMSO, sulfolane, HMPA, DMPU, prefer dichloromethane and 1,2-dichloroethane) for some time (1-12 h, prefer 3-10 h). 4-Fluoro-5-((2-fluoro-4-iodophenyl)amino)-N-(2-hydroxyethoxy)beno[d]oxazole-6-carboxamide is obtained after conventional workup.

Scheme A-2-1

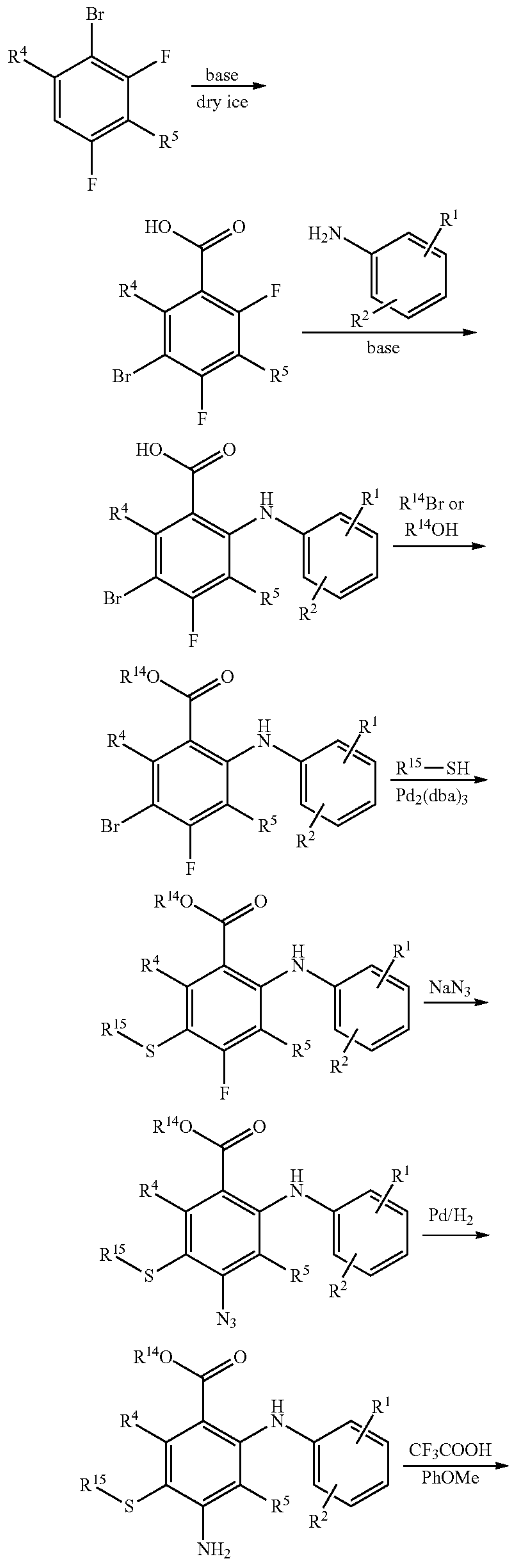

-continued
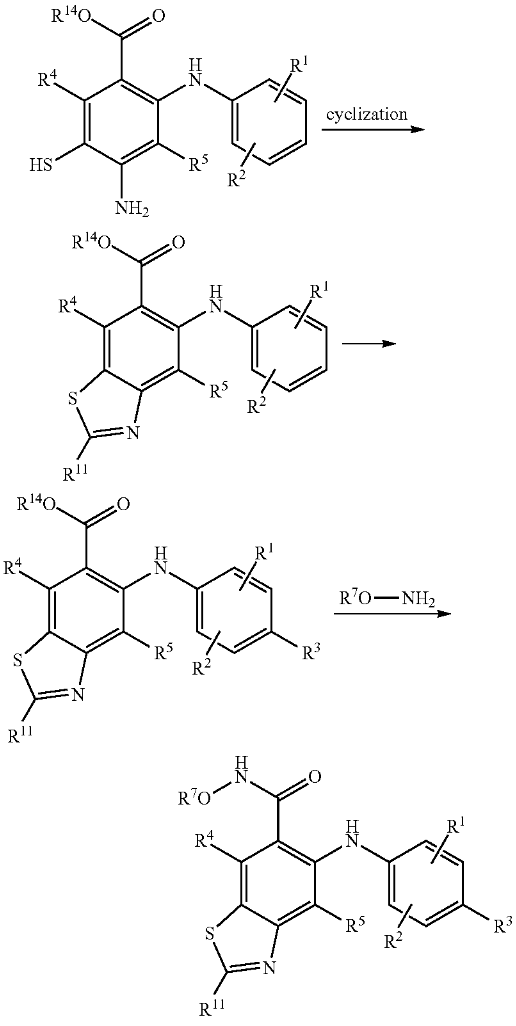
The synthetic route according to Scheme A-2-1 is further illustrated by a synthetic process for 4-fluoro-5-((2-fluoro-4-iodophenyl)amino)-N-(2-hydroxyethoxy)benzo[d]thiazole-6-carboxamide as outline in Scheme A-2-1-1 and the following steps.
Scheme A-2-1-1
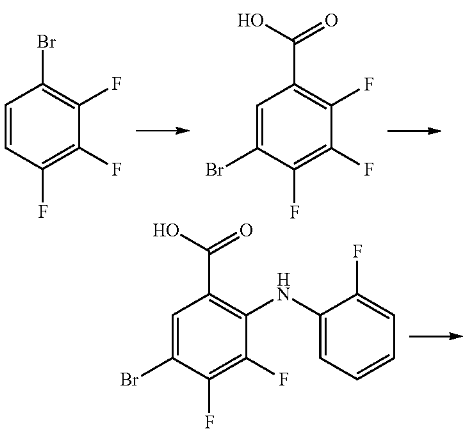
-continued
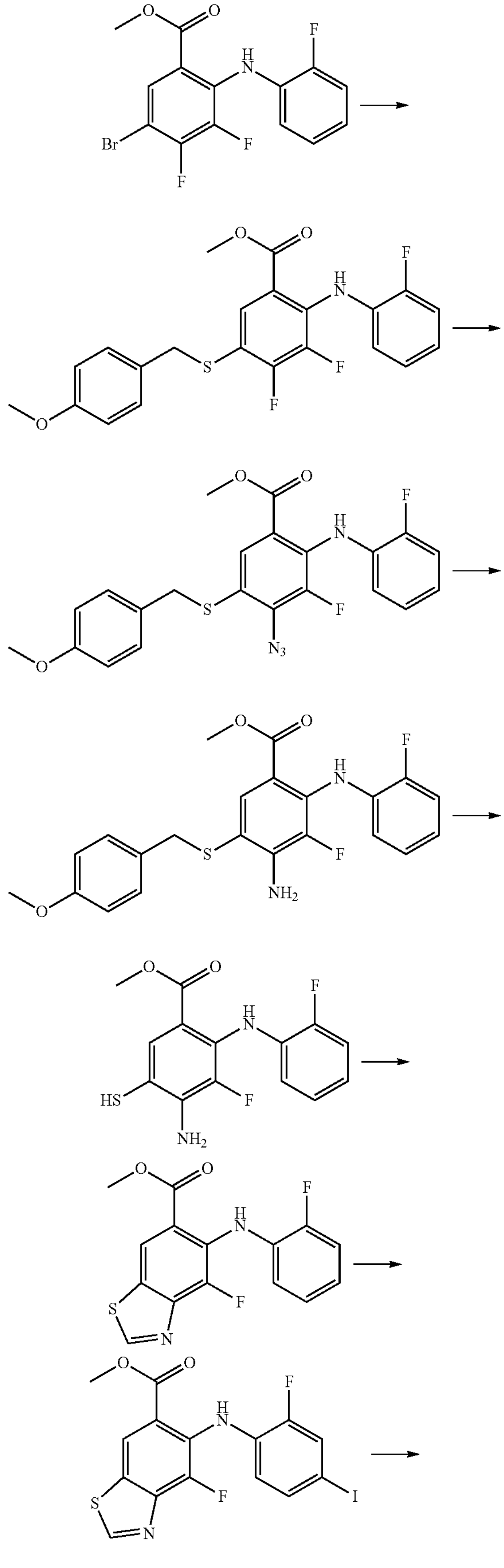

-continued

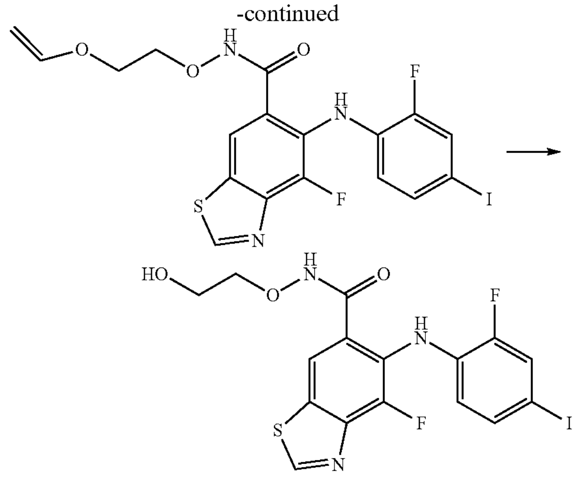

Step 1:

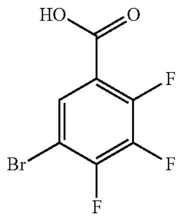 [SMILES: O=C(O)c1cc(Br)c(F)c(F)c1F]

To a solution of 2,3,4-trifluorobromobenzene in appropriate solvent (include aliphatic and aromatic hydrocarbon (such as pentane, hexane, heptane, cyclohexane, petroleum ether, petrol, gasoline, benzene, toluene, xylene), ether (such as diethyl ether, dibutyl ether, glycol dimethyl ether, 2-methoxyethyl ether, tetrahydrofuran, dioxane), sulfolane, HMPA, DMPU, prefer anhydrous THF, ethyl ether and dioxane) was added strong base (such as LDA, nBuLi, LiHDMS) at low temperature (−50° C.-−80° C., prefer −78° C.) under nitrogen atmosphere. The reaction is kept stirring for some time (0.5-12 h, prefer 0.5-2 h) and is added dry ice. After several hours (3-12 h, prefer 5-10 h), 5-bromo-2,3,4-trifluorobenzoic acid is obtained after conventional workup.

Step 2:

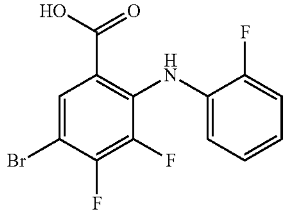 [SMILES: O=C(O)c1cc(Br)c(F)c(F)c1Nc1ccccc1F]

5-Bromo-2,3,4-trifluorobenzoic acid can be reacted with halogenated aniline (such as o-fluoroaniline, o-chloroaniline, o-bromoaniline, o-iodoaniline) in the presence of base (such as LDA, n-BuLi, LiHDMS) in appropriate solvent (include aliphatic and aromatic hydrocarbon (such as pentane, hexane, heptane, cyclohexane, petroleum ether, petrol, gasoline, benzene, toluene, xylene), ether (such as diethyl ether, dibutyl ether, glycol dimethyl ether, 2-methoxyethyl ether, tetrahydrofuran, dioxane), sulfolane, HMPA, DMPU, prefer anhydrous THF, ethyl ether and dioxane) at low temperature (−50° C.-−80° C., prefer −78° C.) for some time (such as 3-12 h, prefer 5-10 h). 5-Bromo-3,4-difluoro-2-((2-fluorophenyl)amino)benzoic acid is obtained after conventional workup.

Step 3:

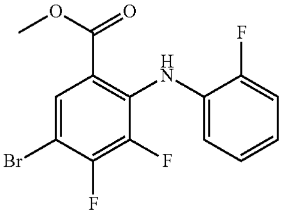 [SMILES: COC(=O)c1cc(Br)c(F)c(F)c1Nc1ccccc1F]

5-Bromo-3,4-difluoro-2-((2-fluorophenyl)amino)benzoic acid can be reacted with MeOH in the presence of $SOCl_2$ in appropriate solvent (include aliphatic and aromatic hydrocarbon (such as pentane, hexane, heptane, cyclohexane, petroleum ether, petrol, gasoline, benzene, toluene, xylene), aliphatic and aromatic halo-hydrocarbon (such as dichloromethane, 1,2-dichloroethane, chloroform, phenixin, chlorobenzene, o-dichlorobenzene), ether (such as diethyl ether, dibutyl ether, glycol dimethyl ether, 2-methoxyethyl ether, tetrahydrofuran, dioxane), ketone (such as acetone, methyl ethyl ketone, methyl isopropyl ketone, methyl isobutyl ketone), ester (such as ethyl acetate, methyl acetate), nitrile (such as acetonitrile, propiononitrile), amide (such as N,N-dimethylformamide, N,N-dimethylacetamide and N-methylpyrrolidin-2-one), DMSO, sulfolane, HMPA, DMPU, prefer methanol and ethanol). The reaction proceeds for several hours (3-12 h, prefer 5-10 h). Methyl 5-bromo-3,4-difluoro-2-((2-fluorophenyl)amino)benzoate is obtained after conventional workup.

Step 4:

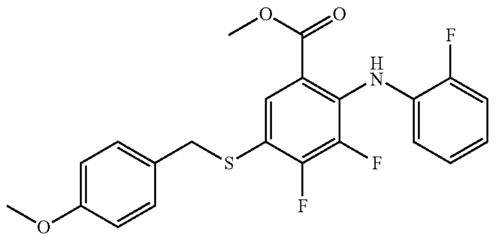 [SMILES: COC(=O)c1cc(SCc2ccc(OC)cc2)c(F)c(F)c1Nc1ccccc1F]

To a solution of methyl 5-bromo-3,4-difluoro-2-((2-fluorophenyl)amino)benzoate in appropriate solvent (include aliphatic and aromatic hydrocarbon (such as pentane, hexane, heptane, cyclohexane, petroleum ether, petrol, gasoline, benzene, toluene, xylene), ether (such as diethyl ether, dibutyl ether, glycol dimethyl ether, 2-methoxyethyl ether, tetrahydrofuran, dioxane), ester (such as ethyl acetate, methyl acetate), nitrile (such as acetonitrile, propiononitrile), amide (such as N,N-dimethylformamide, N,N-dimethylacetamide and N,N-methylpyrrolidin-2-one), DMSO, sulfolane, HMPA, DMPU, prefer dioxane) was added base (such as aliphatic and aromatic amine (such as, but not limited to, N-ethyl-N-isopropylpropan-2-amine, triethylamine, diethylamine, DBU, t-butylamine, cyclopropanamine, dibutylamine, diisopropylamine, 1,2-dimethylpropanamine), inorganic base (such as $Na_2CO_3$, $K_2CO_3$, $NaHCO_3$, $KHCO_3$, t-BuONa, t-BuOK), prefer N-ethyl-N-isopropylpropan-2-amine) at ambient temperature under nitrogen atmosphere, followed by Pd catalyst (such as tris(dibenzylideneacetone)dipalladium, bis(dibenzylideneacetone) palladium, bis(triphenylphosphine)palladium(IT) chloride, palladium diacetate, tetrakis(triphenylphosphine)palladium, bis(triphenylphosphinepalladium)acetate, prefer tris(dibenzylideneacetone) dipalladium) and phosphine ligand (such as dimethylbisdiphenylphosphinoxanthene, tri-tert-butylphosphine, tri-p-tolylphosphine, tris(4-chlorophenyl)phosphine, triisopropylphosphine, tris(2,6-dimethoxyphenyl) phosphine, 1,1'-bis(diphenylphosphino)ferrocene, prefer dimethylbisdiphenylphosphinoxanthene). The reaction is kept stirring at high temperature (80-130° C., prefer 90-110° C.) for some time (8-24 h, prefer 12-18 h). Methyl 3,4-difluoro-2-((2-fluorophenyl)amino)-5-((4-methoxybenzyl) thio)benzoate is obtained after conventional workup.

Step 5:

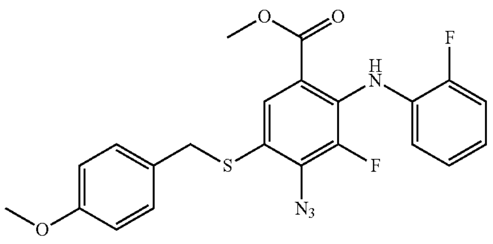 [SMILES: COC(=O)c1cc(SCc2ccc(OC)cc2)c(N=[N+]=[N-])c(F)c1Nc1ccccc1F]

Methyl 3,4-difluoro-2-((2-fluorophenyl)amino)-5-((4-methoxy benzyl)thio)benzoate can be reacted with azide (such as $NaN_3$, $KN_3$) at high temperature (60-120° C., prefer 80-100° C.) in appropriate solvent (include aliphatic and aromatic hydrocarbon (such as pentane, hexane, heptane, cyclohexane, petroleum ether, petrol, gasoline, benzene, toluene, xylene), aliphatic and aromatic halo-hydrocarbon (such as dichloromethane, 1,2-dichloroethane, chloroform, phenixin, chlorobenzene, o-dichlorobenzene), ether (such as diethyl ether, dibutyl ether, glycol dimethyl ether, 2-methoxyethyl ether, tetrahydrofuran, dioxane), ketone (such as acetone, methyl ethyl ketone, methyl isopropyl ketone, methyl isobutyl ketone), ester (such as ethyl acetate, methyl acetate), nitrile (such as acetonitrile, propiononitrile), amide (such as N,N-dimethylformamide, N,N-dimethylacetamide and N-methylpyrrolidin-2-one), DMSO, sulfolane, HMPA, DMPU, prefer N,N-dimethylformamide and N,N-dimethylacetamide) for some time (1-12 h, prefer 3-10 h). Methyl 4-azido-3-fluoro-2-((2-fluorophenyl)amino)-5-((4-methoxybenzyl)thio)benzoate is obtained after conventional workup.

Step 6:

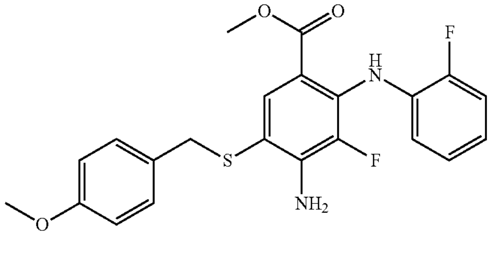 [SMILES: COC(=O)c1cc(SCc2ccc(OC)cc2)c(N)c(F)c1Nc1ccccc1F]

Methyl 4-azido-3-fluoro-2-((2-fluorophenyl)amino)-5-((4-methoxy benzyl)thio)benzoate can be hydrogenated catalyzed by appropriate catalyst (such as Pd/C, Pt, Ni) in the solvent (include aliphatic and aromatic hydrocarbon (such as pentane, hexane, heptane, cyclohexane, petroleum ether, petrol, gasoline, benzene, toluene, xylene), ether (such as diethyl ether, dibutyl ether, glycol dimethyl ether, 2-methoxyethyl ether, tetrahydrofuran, dioxane), ester (such as ethyl acetate, methyl acetate), amide (such as N,N-dimethylformamide, N,N-dimethylacetamide and N-methylpyrrolidin-2-one), DMSO, sulfolane, HMPA, DMPU, prefer methanol, ethanol, propan-1-ol and water) for some time (1-12 h, prefer 3-10 h). Methyl 4-amino-3-fluoro-2-((2-fluorophenyl)amino)-5-((4-methoxybenzyl)thio)benzoate is obtained after conventional workup.

Step 7:

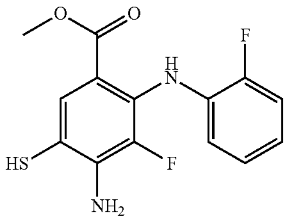 [SMILES: COC(=O)c1cc(S)c(N)c(F)c1Nc1ccccc1F]

4-Amino-3-fluoro-2-((2-fluorophenyl)amino)-5-((4-methoxybenzyl)thio)benzoate can be deprotected in the presence of acid (such as $CF_3COOH$, HCOOH, $CH_3COOH$ and n-$C_5H_{11}COOH$, prefer $CF_3COOH$) at certain temperature (20-75° C., prefer 25-75° C.) in appropriate aromatic aliphatic ether (such as anisole and phenetole, prefer anisole) for some time (1-12 h, prefer 3-10 h). Methyl 4-amino-3-fluoro-2-((2-fluorophenyl)amino)-5-mercaptobenzoate is obtained after conventional workup.

Step 8:

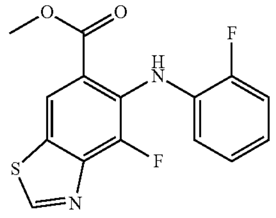 [SMILES: COC(=O)c1cc2scnc2c(F)c1Nc1ccccc1F]

Methyl 4-amino-3-fluoro-2-((2-fluorophenyl)amino)-5-mercapto benzoate can be cyclized in the presence of acid (such as p-toluenesulfonic acid, pyridinium toluene-4-sulphonate, formic acid, acetic acid, sulfuric acid) in appropriate solvent (include aliphatic and aromatic hydrocarbon (such as pentane, hexane, heptane, cyclohexane, petroleum ether, petrol, gasoline, benzene, toluene, xylene), aliphatic and aromatic halo-hydrocarbon (such as dichloromethane, 1,2-dichloroethane, chloroform, phenixin, chlorobenzene, o-dichlorobenzene), ether (such as diethyl ether, dibutyl ether, glycol dimethyl ether, 2-methoxyethyl ether, tetrahydrofuran, dioxane), ketone (such as acetone, methyl ethyl ketone, methyl isopropyl ketone, methyl isobutyl ketone), ester (such as ethyl acetate, methyl acetate), nitrile (such as acetonitrile, propiononitrile), amide (such as N,N-dimethylformamide, N,N-dimethylacetamide and N-methylpyrrolidin-2-one), DMSO, sulfolane, HMPA, DMPU, prefer methyl acetate, ethyl acetate and trimethoxymethane) for some time (0.2-12 h, prefer 0.5-10 h). Methyl 4-fluoro-5-((2-fluorophenyl)amino)benzo[d]thiazole-6-carboxylate is obtained after conventional workup.

Step 9:

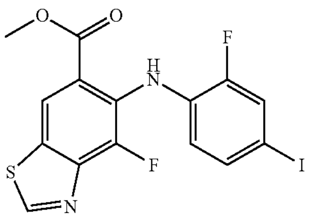 [SMILES: COC(=O)c1cc2scnc2c(F)c1Nc1ccc(I)cc1F]

Methyl 4-fluoro-5-((2-fluorophenyl)amino)benzo[d]thiazole-6-carboxylate can be reacted with halogenations reagent (such as NIS) in the presence of acid (such as trifluoroacetic acid, trifluoromethanesulfonic acid, methanesulfonic acid, formic acid, acetic acid) at ambient temperature in appropriate solvent (include aliphatic and aromatic hydrocarbon (such as pentane, hexane, heptane, cyclohexane, petroleum ether, petrol, gasoline, benzene, toluene, xylene), aliphatic and aromatic halo-hydrocarbon (such as dichloromethane, 1,2-dichloroethane, chloroform, phenixin, chlorobenzene, o-dichlorobenzene), ether (such as diethyl ether, dibutyl ether, glycol dimethyl ether, 2-methoxyethyl ether, tetrahydrofuran, dioxane), ketone (such as acetone, methyl ethyl ketone, methyl isopropyl ketone, methyl isobutyl ketone), ester (such as ethyl acetate, methyl acetate), nitrile (such as acetonitrile, propiononitrile), amide (such as N,N dimethylformamide, N,N-dimethylacetamide and A-methylpyrrolidin-2-one), DMSO, sulfolane, HMPA, DMPU, prefer N,N-dimethylformamide and N,N-dimethylacetamide) for some time (1-12 h, prefer 3-10 h). Methyl 4-fluoro-5-((2-fluoro-4-iodophenyl)amino)benzo[d]thiazole-6-carboxylate is obtained after conventional workup.

Step 10:

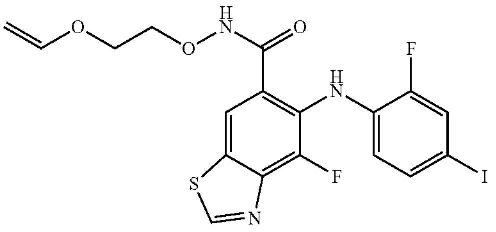 [SMILES: C=COCCONC(=O)c1cc2scnc2c(F)c1Nc1ccc(I)cc1F]

4-Fluoro-5-((2-fluoro-4-iodophenyl)amino)benzo[d]thiazole-6-carboxylic acid can be reacted with O-(2-(vinyloxy)ethyl)hydroxylamine in the presence of coupling reagent (such as HOBt, EDCI, HATU, TBTU) at ambient temperature in appropriate solvent (include aliphatic and aromatic hydrocarbon (such as pentane, hexane, heptane, cyclohexane, petroleum ether, petrol, gasoline, benzene, toluene, xylene), aliphatic and aromatic halo-hydrocarbon (such as dichloromethane, 1,2-dichloroethane, chloroform, phenixin, chlorobenzene, o-dichlorobenzene), ether (such as diethyl ether, dibutyl ether, glycol dimethyl ether, 2-methoxyethyl ether, tetrahydrofuran, dioxane), ketone (such as acetone, methyl ethyl ketone, methyl isopropyl ketone, methyl isobutyl ketone), ester (such as ethyl acetate, methyl acetate), nitrile (such as acetonitrile, propiononitrile), amide (such as N,N-dimethylformamide, N,N-dimethylacetamide and N-methylpyrrolidin-2-one), DMSO, sulfolane, HMPA, DMPU, prefer dichloromethane, 1,2-dichloroethane and N,N-dimethylformamide) for some time (1-12 h, prefer 3-10 h). 4-Fluoro-5-((2-fluoro-4-iodophenyl)amino)-N-(2-(vinyloxy)ethoxy)benzo[d]thiazole-6-carboxamide is obtained after conventional workup.

Step 11:

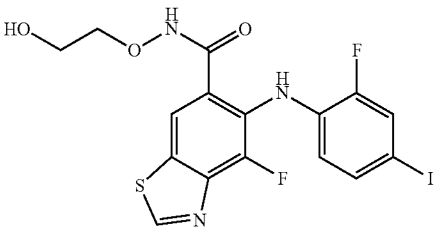

4-Fluoro-5-((2-fluoro-4-iodophenyl)amino)-N-(2-(vinyloxy)ethoxy)benzo[d]thiazole-6-carboxamide can be reacted in the presence of acid (such as HCl, $H_2SO_4$, trifluoroacetic acid) in appropriate solvent (include aliphatic and aromatic hydrocarbon (such as pentane, hexane, heptane, cyclohexane, petroleum ether, petrol, gasoline, benzene, toluene, xylene), aliphatic and aromatic halo-hydrocarbon (such as dichloromethane, 1,2-dichloroethane, chloroform, phenixin, chlorobenzene, o-dichlorobenzene), ether (such as diethyl ether, dibutyl ether, glycol dimethyl ether, 2-methoxyethyl ether, tetrahydrofuran, dioxane), ketone (such as acetone, methyl ethyl ketone, methyl isopropyl ketone, methyl isobutyl ketone), ester (such as ethyl acetate, methyl acetate), nitrile (such as acetonitrile, propiononitrile), amide (such as N,N-dimethylformamide, N,N-dimethylacetamide and N-methylpyrrolidin-2-one), DMSO, sulfolane, HMPA, DMPU, prefer dichloromethane and 1,2-dichloroethane) for some time (1-12 h, prefer 3-10 h). 4-Fluoro-5-((2-fluoro-4-iodophenyl)amino)-N-(2-hydroxy ethoxy)benzo[d]oxazole-6-carboxamide is obtained after conventional workup.

Scheme A-3-1

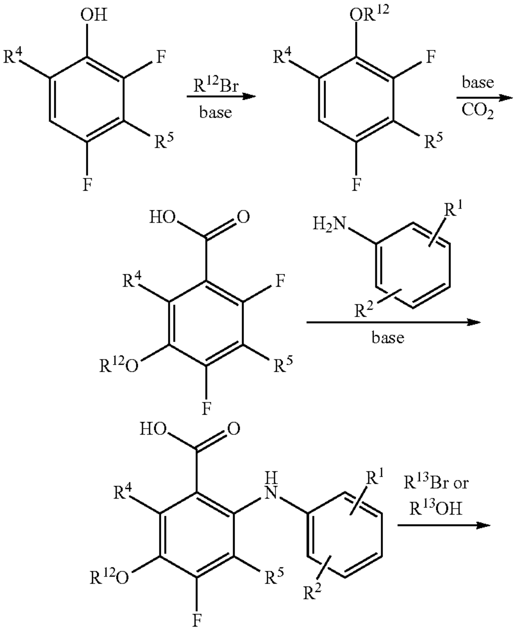

-continued
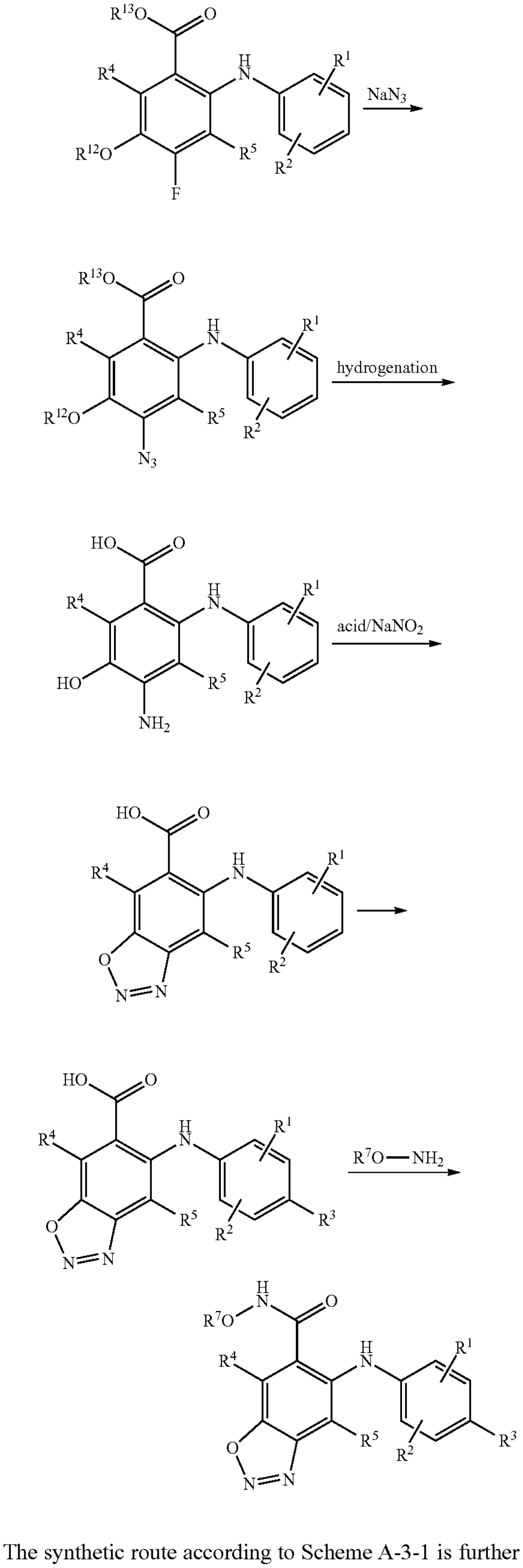
The synthetic route according to Scheme A-3-1 is further illustrated by a synthetic route for 4-fluoro-5-((2-fluoro-4-iodophenyl)amino)-N-(2-hydroxyethoxy)benzo[d][1,2,3]oxadiazole-6-carboxamide as outline in Scheme A-3-1-1.
Scheme A-3-1-1
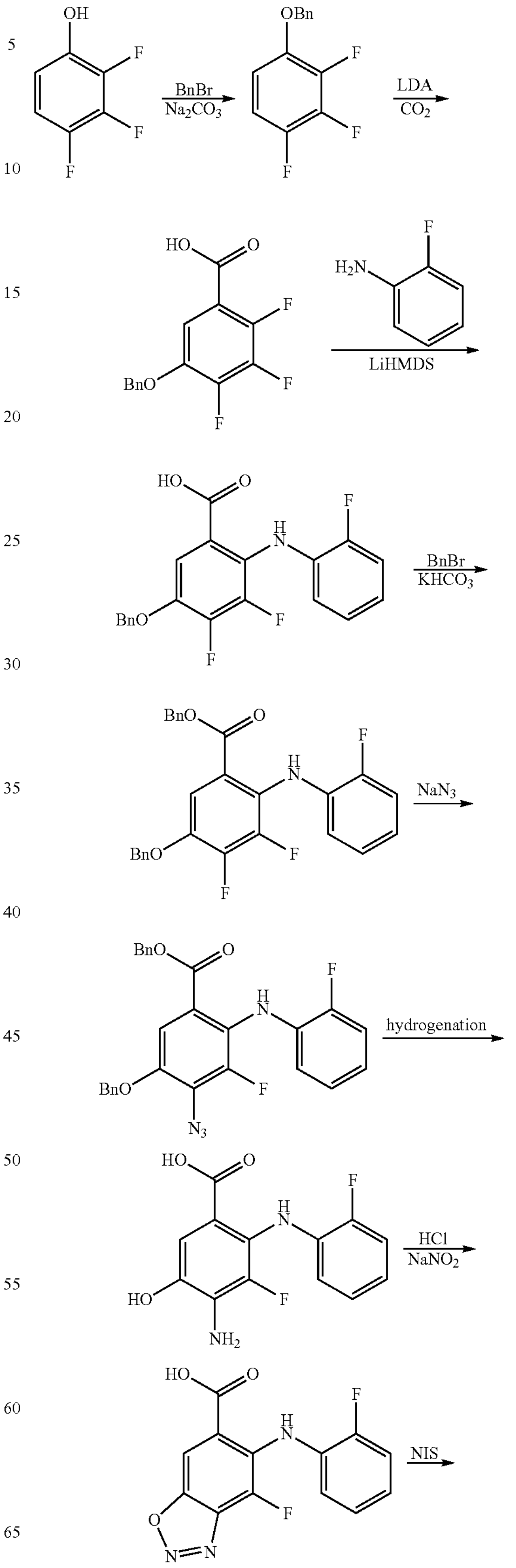

-continued
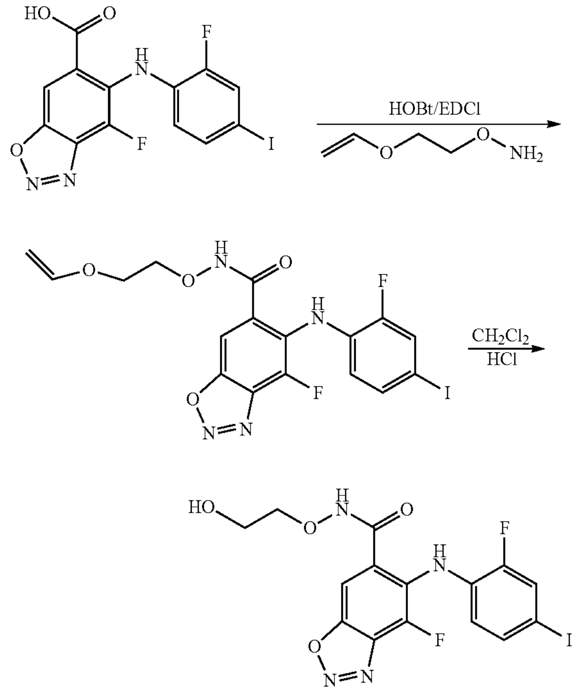
Scheme A-4-1
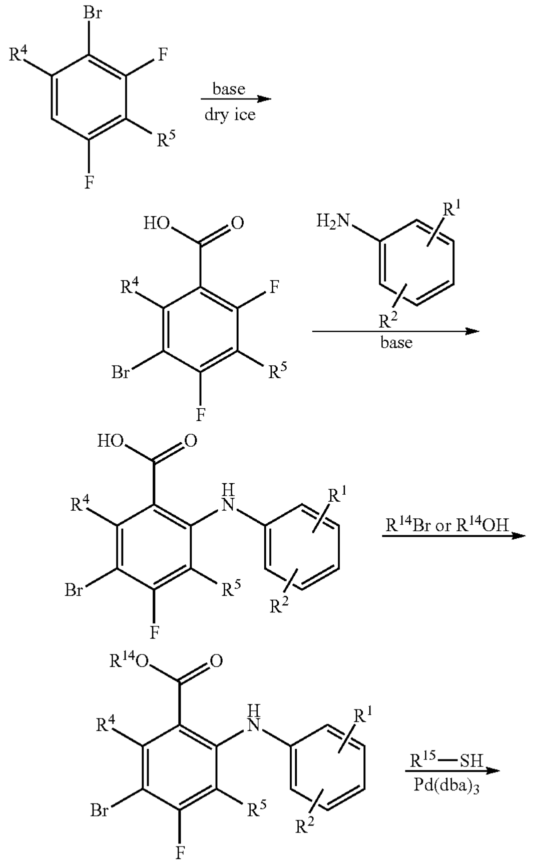
-continued
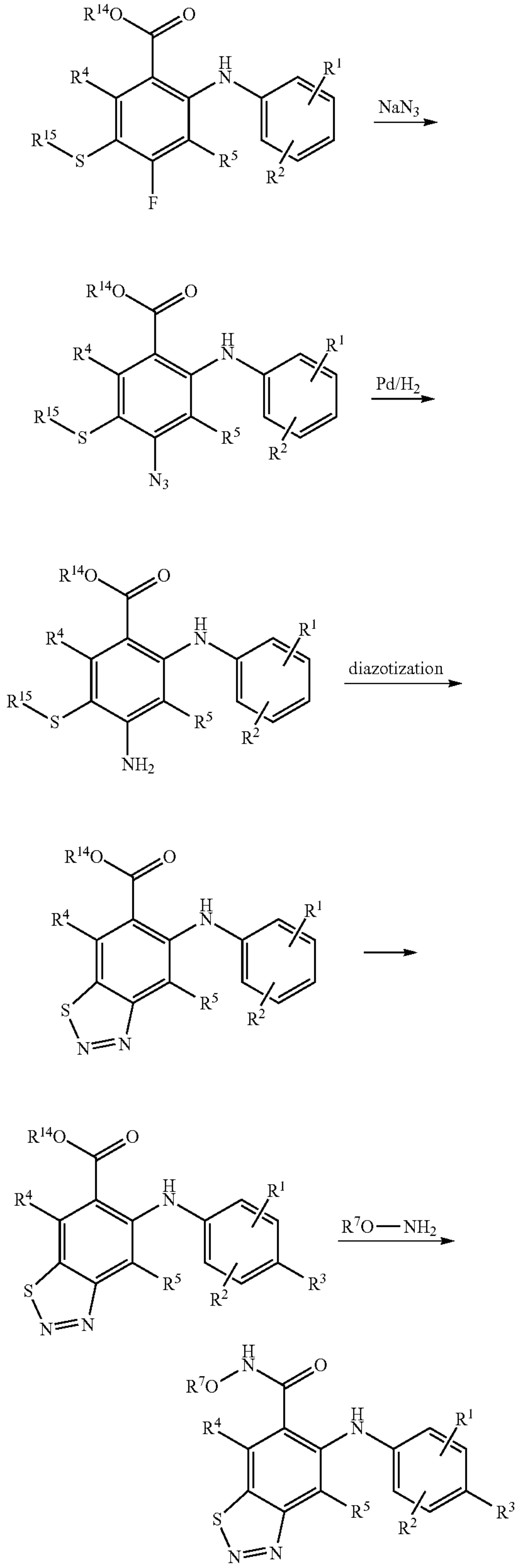
The synthetic route according to Scheme A-1-1 is further illustrated by a synthetic process for 4-fluoro-5-((2-fluoro-4-iodophenyl)amino)-N-(2-hydroxyethoxy)benzo[d][1,2,3]thiadiazole-6-carboxamide as outline in Scheme A-4-1-1.

Scheme A-4-1-1

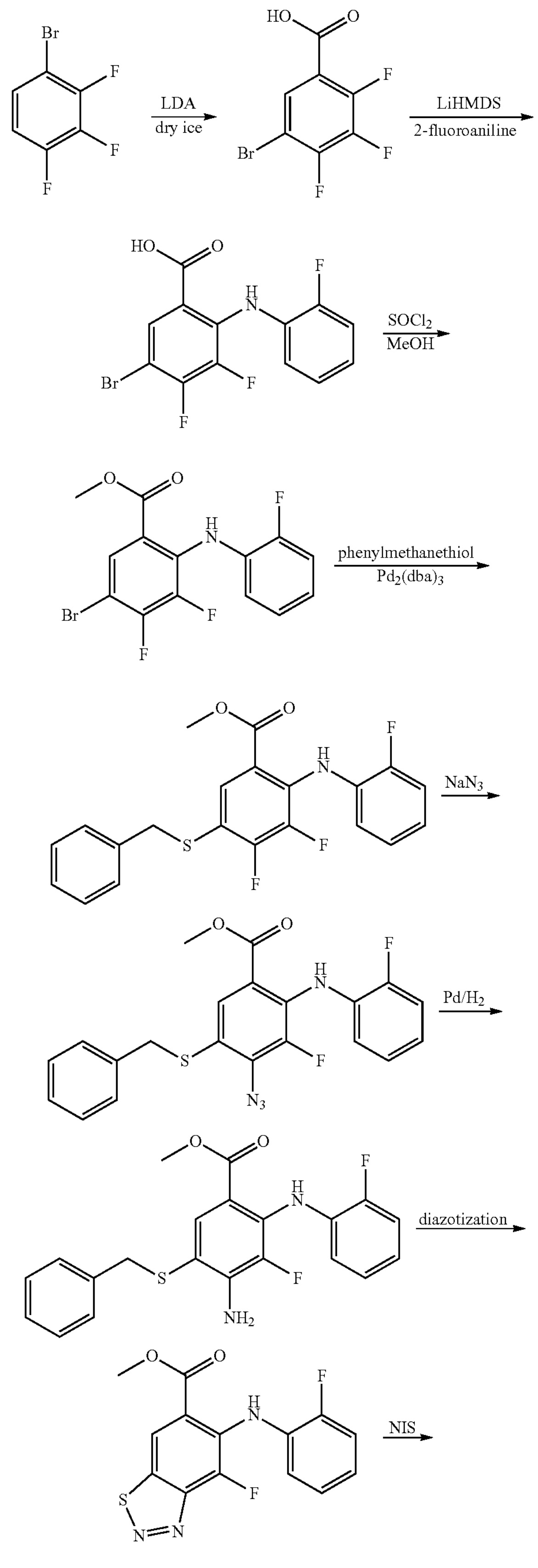

-continued

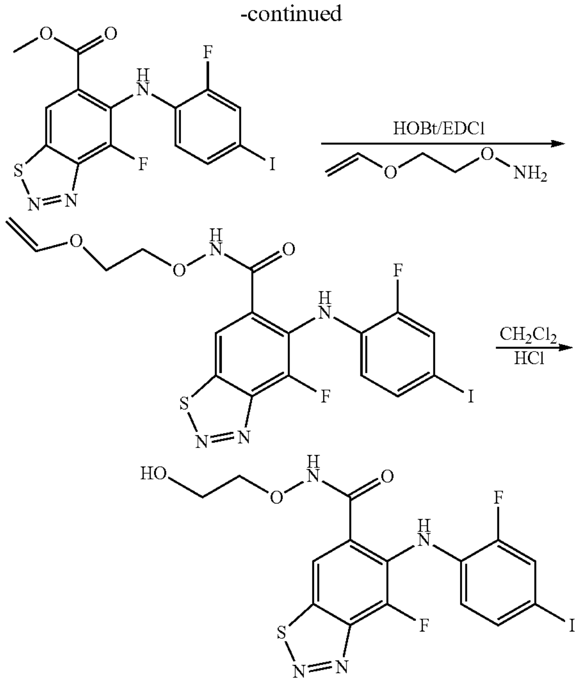

In the synthetic processes described in Schemes (A-1-1), (A-2-1), (A-3-1) and (A-4-1), $R^1$, $R^2$, $R^3$, $R^4$, $R^5$ and $R^{11}$ are as defined for the formula (A-I) or any variations thereof, such as the preferred variations, the more preferred variations, the especially preferred variations and the particularly preferred variations of $R^1$, $R^2$, $R^3$, $R^4$, $R^5$ and $R^{11}$ as describe here above, or any combinations thereof.

Preferred $R^7$ is H, $C_1$-$C_{10}$ alkyl, $C_2$-$C_{10}$ alkenyl, $C_2$-$C_{10}$ alkynyl, $C_3$-$C_{10}$ cycloalkyl, ($C_3$-$C_{10}$ cycloalkyl)$C_1$-$C_{10}$ alkyl, $C_6$-$C_{14}$ aryl, ($C_6$-$C_{14}$ aryl)$C_1$-$C_{10}$ alkyl, heteroaryl, (heteroaryl)$C_1$-$C_{10}$ alkyl, heterocycloalkyl or (heterocycloalkyl)$C_1$-$C_{10}$ alkyl;

wherein each alkyl, alkenyl, alkynyl, cycloalkyl, and, heteroaryl and heterocycloalkyl is optionally substituted with one or more groups independently selected from hydroxyl, oxo-, halogen, cyano, nitro, —$CF_3$, azido, —NR'$SO_2$R"", —$SO_2$NR'R", —C(O)R', —C(O)OR', —OC(O)R', —NR'C(O)R"", —NR'C(O)R", —C(O)NR'R", —SR', —S(O)R"", —$SO_2$R"", —NR'R", —NR'C(O)NR"R'", —NR'C(NCN)NR"R'", —OR', $C_6$-$C_{14}$ aryl, heteroaryl, ($C_6$-$C_{14}$ aryl)$C_1$-$C_{10}$ alkyl, (heteroaryl)$C_1$-$C_{10}$ alkyl, heterocycloalkyl and (heterocycloalkyl)$C_1$-$C_{10}$ alkyl;

R', R" and R'" are independently H, $C_1$-$C_{10}$ alkyl, $C_2$-$C_6$ alkenyl, $C_6$-$C_{14}$ aryl, or ($C_6$-$C_{14}$ aryl)$C_1$-$C_{10}$ alkyl;

R"" is $C_1$-$C_{10}$ alkyl, $C_2$-$C_6$ alkenyl, $C_6$-$C_{14}$ aryl or ($C_6$-$C_{14}$ aryl) $C_1$-$C_{10}$ alkyl;

or any two of R', R", R'" and R"", together with the atom to which they are attached, form a 4- to 10-member heteroaryl or heterocyclic ring, wherein said heteroaryl and heterocyclic rings are optionally substituted with one or more groups independently selected from halogen, cyano, nitro, trifluoromethyl, difluoromethoxy, trifluoromethoxy, azido, $C_6$-$C_{14}$ aryl, heteroaryl, ($C_6$-$C_{14}$ aryl)$C_1$-$C_{10}$ alkyl, (heteroaryl)$C_1$-$C_{10}$ alkyl, heterocycloalkyl and (heterocycloalkyl)$C_1$-$C_{10}$ alkyl;

More preferred $R^7$ is $C_1$-$C_6$ alkyl optionally substituted with 1 to 6 hydroxy groups, or ($C_3$-$C_{10}$ cycloalkyl)$C_1$-$C_{10}$ alkyl;

Especially preferred $R^7$ is $C_1$-$C_4$ alkyl optionally substituted with 1 to 3 hydroxy groups, or ($C_3$-$C_8$ cycloalkyl) $C_1$-$C_6$ alkyl;

Particularly preferred $R^7$ is ethyl, propyl or isobutyl which are optionally substituted with 1 to 3 hydroxy groups, or ($C_3$-$C_6$ cycloalkyl)$C_1$-$C_4$ alkyl;

Preferred $R^{12}$, $R^{13}$, $R^{14}$ and $R^{15}$ are independently benzyl, benzyl substituted with 1 to 3 methoxy, $C_1$-$C_4$ alkyl, or —$SiR^{16}R^{17}R^{18}$, wherein $R^{16}$, $R^{17}$ and $R^{18}$ are independently selected from $C_1$-$C_{10}$ alkyl and $C_6$-$C_{14}$ aryl;

More preferred $R^{12}$, $R^{13}$, $R^{14}$ and $R^{15}$ are independently benzyl, benzyl substituted with 1 to 2 methoxy, $C_1$-$C_4$ alkyl, tert-butyldimethylsilyl, triphenylsilyl, trimethylsilyl, triethylsilyl, tripropylsilyl or triisopropylsilyl;

Especially preferred $R^{12}$, $R^{13}$, $R^{14}$ and $R^{15}$ are independently benzyl, o-methoxybenzyl, m-methoxybenzyl, p-methoxybenzyl or $C_1$-$C_2$ alkyl;

Particularly preferred $R^{12}$, $R^{13}$, $R^{14}$ and $R^{15}$ are independently benzyl, p-methoxybenzyl or methyl.

Pharmaceutical Compositions

Pharmaceutical compositions of any of the compounds detailed herein are embraced by this invention. Thus, the invention includes pharmaceutical compositions comprising a compound of the invention or a pharmaceutically acceptable salt thereof and a pharmaceutically acceptable carrier or excipient. In one aspect, the pharmaceutically acceptable salt is an acid addition salt, such as a salt formed with an inorganic or organic acid. Pharmaceutical compositions according to the invention may take a form suitable for oral, buccal, parenteral, nasal, topical or rectal administration or a form suitable for administration by inhalation.

The present invention embraces the free base of compounds detailed herein, such as a compound of the formula (I), (J), (K), (A-I) or any variations thereof, as well as the pharmaceutically acceptable salts and stereoisomers thereof. The compounds of the present invention can be protonated at the N atom(s) of an amine and/or N containing heterocycle moiety to form a salt. The term “free base” refers to the amine compounds in non-salt form. The encompassed pharmaceutically acceptable salts not only include the salts exemplified for the specific compounds described herein, but also all the typical pharmaceutically acceptable salts of the free form of compounds detailed herein, such as a compound of the formula (I), (J), (K), (A-I) or any variations thereof. The free form of the specific salt compounds described may be isolated using techniques known in the art. For example, the free form may be regenerated by treating a salt with a suitable dilute aqueous base solution such as dilute aqueous NaOH, potassium carbonate, ammonia and sodium bicarbonate. The free base forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

The invention also provides pharmaceutical compositions comprising one or more compounds detailed herein, such as a compound of the formula (I), (J), (K), (A-I) or any variations thereof, and a pharmaceutically acceptable carrier. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate, granulating and disintegrating agents, for example, microcrystalline cellulose, sodium crosscarmellose, corn starch, or alginic acid; binding agents, for example starch, gelatin, polyvinylpyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethylcellulose or hydroxypropylcellulose, or a time delay material such as ethyl cellulose, cellulose acetate butyrate may be employed.

Medical Uses

Benzoheterocyclic compounds of the invention, such as such as benzothiadiazole, benzoxazole and benzothiazole derivatives detailed herein, are inhibitors of protein kinases such as MEK. The compounds may be useful in the treatment of conditions or disorders where the MEK cascade is implicated such as cancer and inflammatory diseases.

The invention provides compounds for use in the treatment or prevention of diseases or conditions which can be ameliorated by the inhibition of MEK. Thus, the present invention provides a compound, such as a compound of the formula (I), (J), (K), (A-I) or any variations thereof, for use in the manufacture of a medicament for the treatment or prevention of diseases or conditions which can be ameliorated by the inhibition of MEK, such as cancer, acute and chronic inflammatory disease, a skin disease, diabetes, an eye disease, vasculogenesis, angiogenesis, or chronic pain.

In some embodiments, the disease or conditions treatable may include tumor (non-limiting examples include: hemangioma, glioma, melanoma, Kaposi’s sarcoma, ovarian cancer, breast cancer, lung cancer, pancreatic cancer, prostate cancer, colon cancer, colorectal cancer and gastrointestinal cancer), chronic inflammatory disease (non-limiting examples include: rheumatoid arthritis), disease related to vasculogenesis or angiogenesis of mammals, atherosclerosis, inflammatory bowel disease, dermatopathya (non-limiting examples include: psoriasis, excema and sceroderma), diabetes mellitus, diabetic retinopathy, retinopathy of prematurity, age-related macular degeneration, diseases related to chronic pain (including neuralgia and pain arising from other diseases related to MEK, non-limiting examples include: phantom limb pain, burn pain, gout, trigeminal neuralgia, acute herpetic, postherpetic pain, causalgia, diabetic neuropathy, plexus avulsion, neuroma, vasculitis, crush injury, constriction injury, tissue injury, post-surgical pain, arthritis pain and limb amputation).

Also provided is a method for the treatment or prevention of a disease or condition mediated by MEK, said method comprises administering to an individual in need thereof a therapeutically effective amount of a compound detailed herein, such as a compound of the formula (I), (I), (K), (A-I) or any variations thereof, or a composition comprising a compound detailed herein, such as a compound of the formula (I), (J), (K), (A-I) or any variations thereof. In some embodiments, the disease or condition mediated by MEK is cancer, chronic inflammatory disease, a skin disease, diabetes, an eye disease, vasculogenesis, angiogenesis or chronic pain.

In some embodiments, the invention provides a method for the treatment or prevention of cancer, comprising administration to an individual in need thereof of an effective amount of a compound detailed herein, such as a compound of the formula (I), (J), (K), (A-I) or any variations thereof, or a composition comprising a compound detailed herein, such as a compound of the formula (I), (J), (K), (A-I) or any variations thereof. In some embodiments, the cancer is a cancer detailed below. In some embodiments, the cancer is colon cancer, colorectal cancer, lung cancer (e.g., non-small cell lung cancer), pancreatic cancer, breast cancer, ovarian cancer, prostate cancer or skin cancer (e.g. melanoma).

In some embodiments, the invention provides a method for the treatment or prevention of inflammatory diseases, comprising administration to an individual in need thereof of an effective amount of a compound detailed herein, such as a compound of the formula (I), (J), (K), (A-I) or any variations thereof or a composition comprising a compound detailed herein, such as a compound of the formula (I), (J), (K), (A-I) or any variations thereof. In some embodiment, the inflammatory disease is the rheumatoid arthritis or inflammatory bowel disease.

The compounds of the invention are useful for the treatment of inflammatory diseases, including conditions resulting from organ transplant rejection; chronic inflammatory diseases of the joints, including arthritis, rheumatoid arthritis; inflammatory bowel diseases such as ileitis, ulcerative colitis, Barrett's syndrome, and Crohn's disease, inflammatory lung diseases such as asthma, adult respiratory distress syndrome, and chronic obstructive airway disease; inflammatory diseases of the eye; chronic inflammatory diseases of the gum, inflammatory diseases of the kidney; inflammatory diseases of the skin; inflammatory diseases of the central nervous system, inflammatory diseases of the heart such as cardiomyopathy, ischemic heart disease, and atherosclerosis; as well as various other diseases that can have significant inflammatory components, including preeclampsia, chronic liver failure, brain and spinal cord trauma.

The present invention also provides a compound, such as a compound of the formula (I), (J), (K), (A-I) or any variations thereof, for use in the manufacture of a medicament for treating or preventing inflammatory diseases.

In some embodiments, the invention provides a method for the treatment chronic pain, comprising administration to an individual in need thereof of an effective amount of a compound detailed herein, such as a compound of the formula (I), (J), (K), (A-I) or any variations thereof or a composition comprising a compound detailed herein, such as a compound of the formula (I), (J), (K), (A-I) or any variations thereof. In some embodiment, the chronic pain is phantom limb pain, burn pain, gout, trigeminal neuralgia, acute herpetic pain, postherpetic pain, causalgia, diabetic neuropathy, plexus avulsion, neuroma, vasculitis, crush injury, constriction injury, tissue injury, post-surgical pain, arthritis pain and limb amputation.

The compounds of this invention, such as a compound of the formula (I), (J), (K), (A-I) or any variations thereof, may be administered to mammals, preferably humans, either alone or in combination with pharmaceutically acceptable carriers, excipients, diluents, adjuvants, fillers, buffers, stabilizers, preservatives, lubricants, in a pharmaceutical composition, according to standard pharmaceutical practice.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician. Where the active compound is a salt, an ester, prodrug, or the like, the amount administered is calculated on the basis of the parent compound and so the actual weight to be used is increased proportionately. As a skilled artisan would understand, the dosage may be determined using known methods, and taking into consideration the age, body weight and health of the individual in need, the type of condition treated and presence of other drugs available. In some embodiments, the effective dose is about 0.1 to about 1000 mg/kg body weight. In some embodiment, the effective dose is about 1 to about 300 mg/kg body weight. For an average adult, a daily dose may be about 10 to 2500 mg, about 100 mg, about 200 mg, about 300 mg or about 400 mg.

The compounds of this invention may be administered to an individual by any convenient route of administration, whether systemically/peripherally or at the site of desired action, including but not limited to, oral (e.g. by ingestion), topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, (e.g. by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal); and by implant of a depot (e.g. subcutaneously or intramuscularly). The individual may be an animal or a human.

The compounds may be administered in any suitable dosage forms such as solution, emulsion, water and oil suspension, powder, paste, soluble powder, granules, suspension emulsion thickener, capsule, tablet, portion, draught, pills, suppositories, and other suitable forms.

In some embodiments, the method of treating a disease on condition mediated by MEK, such as cancer, further comprises one or more additional active agent used in combination with a compound of the invention.

EXAMPLES

Compounds detailed herein may be prepared by those of skill in the art by referral to the General Method. Particular examples of the General Method are provided in the Examples below. The following Examples are provided to illustrate but not to limit the invention.

Example 1: Preparation of 4-fluoro-5-((2-fluoro-4-iodophenyl)amino)-N-(2-hydroxyethoxy)benzo[d] oxazole-6-carboxamide (Compound 1)

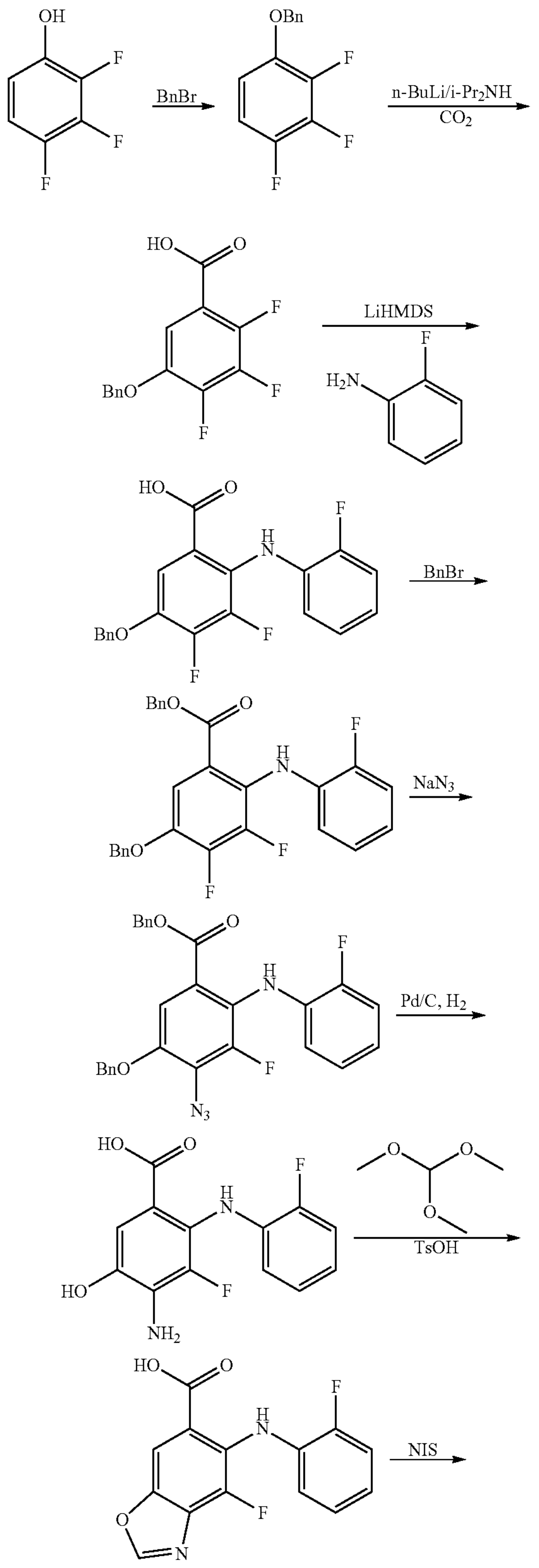

-continued

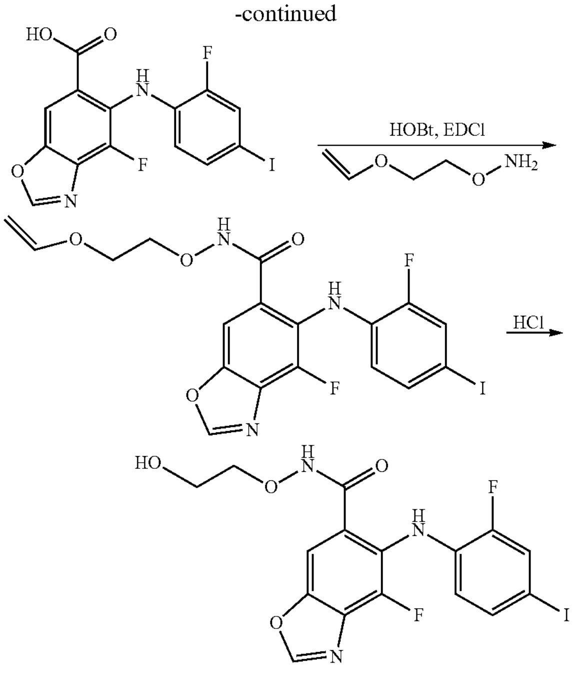

Step 1: 1-benzyloxy-2,3,4-trifluorobenzene

Sodium carbonate (19.50 g, 183.96 mmol) was dispersed into a solution of 2,3,4-trifluorophenol (13.64 g, 92.10 mmol) in acetone (300 mL). To the stirred suspension was added benzyl bromide (17.31 g, 101.21 mmol) dropwisely. The mixture was heated under reflux at 50° C. for 24 h. The acetone was removed under reduced pressure and the residue was dissolved in water (300 mL). The solution was extracted with ethyl acetate (100 mL×2). The combined organic extracts were washed with 5% sodium hydroxide (100 mL) and brine (100 mL) sequentially and dried over $Na_2SO_4$. The solvent was removed in vacuo to yield a pale yellow solid (19.89 g, 90.7% yield). $^1H$ NMR (400 MHz, $CDCl_3$): δ 7.40 (m, 5H), 6.85 (m, 1H) 6.64 (m, 1H), 5.15 (s, 2H).

Step 2: 5-benzyloxy-2,3,4-trifluorobenzoic acid

To a solution of diisopropylamine (10.14 g, 100.20 mmol) in THF (100 mL) was added n-BuLi (40.08 mL, 2.5 M in hexane, 100.20 mmol) at −78° C. under nitrogen atmosphere. The stirring was maintained at this temperature for 1 h. Then a solution of 1-benzyloxy-2,3,4-trifluorobenzene (19.89 g, 83.50 mmol) in THF (120 mL) was added. After stirring for 1 h at −78° C., the mixture was transferred to a bottle with dry ice. The mixture was stirred overnight at room temperature. The reaction was quenched with 10% aqueous HCl and pH was adjusted to 1-2. The mixture was extracted with ethyl acetate (100 mL×3). The combined organic extracts were washed with water (100 mL) and brine (100 mL) sequentially, dried over $Na_2SO_4$, filtered and concentrated under reduced pressure to afford the desired product (white solid, 19.33 g, 82% yield). $^1H$ NMR (400 MHz, $CDCl_3$): δ 7.42 (m, 6H), 5.14 (s, 2H).

Step 3: 5-benzyloxy-3,4-difluoro-2-((2-fluorophenyl)amino)benzoic acid

To a solution of 2-fluoroaniline (15.23 g, 137 mmol) and 5-benzyl-oxy-2,3,4-trifluorobenzoic acid (19.33 g, 68.50 mmol) in THF (120 mL) at −78° C. was added LiHMDS (205.5 mL, 1 M in THF, 205.50 mmol) dropwisely. The mixture was allowed to slowly warm to room temperature and stirred at this temperature overnight. The reaction was quenched with water (100 mL) and acidified to pH 2-3 with 10% HCl (aq.). The aqueous layer was extracted with ethyl acetate (100 mL×3). The combined organic extracts were washed with water (100 mL) and brine (100 mL) sequentially, dried over $Na_2SO_4$, filtered and concentrated in vacuo to afford the desired product (pale yellow solid, 19.17 g, 75% yield). $^1H$ NMR (400 MHz, DMSO-$d_6$): δ 13.76 (s, 1H), 8.58 (s, 1H), 7.61 (dd, J=8.8, 1.7 Hz, 1H), 7.44 (m, 5H), 7.20 (m, 1H), 7.05 (m, 1H), 6.90 (m, 2H), 5.26 (s, 2H).

Step 4: benzyl 5-benzyloxy-3,4-difluoro-2-((2-fluorophenyl)amino)benzoate

To a solution of 5-benzyloxy-3,4-difluoro-2-((2-fluorophenyl)amino)benzoic acid (19.17 g, 51.35 mmol) in DMF (150 mL) was added potassium bicarbonate (6.16 g, 61.62 mmol) followed by benzyl bromide (6.2 mL, 51.41 mmol). The mixture was stirred for 5 h at room temperature and water was added. The solution was extracted with ethyl acetate (100 mL×3). The combined organic extracts were washed with water (100 mL) and brine (100 mL) sequentially, dried over $Na_2SO_4$, filtered and concentrated in vacuo. After purification by column chromatography on silica gel (petroleum ether/ethyl acetate, 50:1, v/v), the corresponding product was obtained as white solid (21.42 g, 90% yield). $^1H$ NMR (400 MHz, $CDCl_3$): δ 8.51 (s, 1H), 7.51 (dd, J=8.5, 2.1 Hz, 1H), 7.41 (m, 10H), 7.09 (m, 1H) 7.03 (m 1H), 6.94 (m, 1H), 6.85 (m, 1H), 5.33 (s, 2H), 5.15 (s, 2H).

Step 5: benzyl 4-azido-5-benzyloxy-3-fluoro-2-((2-fluorophenyl)amino)benzoate

To a solution of benzyl 5-benzyloxy-3,4-difluoro-2-((2-fluoro-phenyl)amino)benzoate (21.42 g, 46.22 mmol) in DMF (150 mL) was added $NaN_3$ (3.61 g, 55.46 mmol). The mixture was stirred at 90° C. for 3 h. Then water (300 mL) was added. The solution was extracted with ethyl acetate (100 mL×3). The combined organic extracts were washed with water (100 mL) and brine (100 mL), dried over $Na_2SO_4$ and concentrated in vacuo. The residue was purified by flash column chromatography on silica gel (petroleum ether/ethyl acetate, 50:1, v/v) and gave the desired product (pale yellow solid, 14.63 g, 65% yield). $^1H$ NMR (400 MHz, $CDCl_3$): δ 8.45 (s, 1H), 7.49 (s, 1H), 7.39 (m, 10H), 7.07 (m, 1H), 7.04 (m, 1H), 6.90 (m, 1H), 6.83 (m, 1H), 5.31 (s, 2H), 5.13 (s, 2J).

Step 6: 4-amino-3-fluoro-2-((2-fluorophenyl)amino)-5-hydroxy benzoic acid

To a solution of benzyl 4-azido-5-benzyloxy-3-fluoro-2-((2-fluoro-phenyl)amino)benzoate (14.63 g, 30.07 mmol) in MeOH (200 mL) was added and 10% palladium on carbon (2.55 g) under nitrogen atmosphere. Then the nitrogen atmosphere was completely changed to hydrogen atmosphere. The mixture was stirred for 3 h at ambient temperature. After the insoluble matter was filtered off, the solvent was concentrated in vacuo to give the desired product, which was used directly in next step without further purification.

Step 7: 4-fluoro-5-((2-fluorophenyl)amino)benzo[d]oxazole-6-carboxylic acid

To a solution of 4-amino-3-fluoro-2-((2-fluorophenyl)amino)-5-hydroxy benzoic acid (7.58 g, 27.05 mmol) in trimethyl orthoformate (50 mL) was added p-TsOH (0.23 g, 1.35 mmol). The reaction mixture was stirred for 1 h and treated with water (200 mL). The precipitate was filtered off and the filter cake was washed with water to afford the desired product (7.22 g, 82.7% yield for two steps). $^1H$ NMR (400 MHz, $CDCl_3$): δ 8.28 (s, 1H), 8.27 (s, 1H), 8.24 (s, 1H), 7.14 (m, 1H), 7.05 (m, 2H), 6.86 (m, 1H).

Step 8: 4-fluoro-5-((2-fluoro-4-iodophenyl)amino)benzo[d]oxazole-6-carboxylic acid To a solution of 4-fluoro-5-((2-fluorophenyl)amino)benzo[d]oxazole-6-carboxylic acid (7.22 g, 24.88 mmol) in DMF (50 mL) was added NIS (6.08 g, 26.37 mmol) followed by trifluoroacetic acid (1.0 mL). After stirring for 5 h at ambient temperature, the reaction was quenched by saturated $NH_4Cl$ (aq.). The solution was extracted with ethyl acetate (150 mL×3). The combined organic extracts were washed with water (100 mL) and brine (100 mL) successively, dried over $Na_2SO_4$ and concentrated in vacuo. The crude product was purified by column chromatography on silica gel ($CH_2Cl_2$/MeOH, 50:1, v/v) and gave the desired product (brown solid, 6.34 g, 61.2% yield). $^1H$ NMR (400 MHz, DMSO-$d_6$): δ 8.97 (s, 1H), 8.58 (s, 1H), 8.18 (s, 1H), 7.58 (dd, J=11.0, 1.7 Hz, 1H), 7.34 (d, J=8.5 Hz, 1H), 6.55 (m, 1H).

Step 9: 4-fluoro-5-((2-fluoro-4-iodophenyl)amino)-N-(2-(vinyloxy) ethoxy)benzo[d]oxazole-6-carboxamide To a solution of 4-fluoro-5-((2-fluoro-4-iodophenyl)amino)benzo [d]oxazole-6-carboxylic acid (500 mg, 1.2 mmol) in $CH_2Cl_2$ (10 mL) was added HOBt (254 mg, 1.63 mmol) and EDCI (314 mg, 1.63 mmol). The mixture was stirred for 1 h and O-(2-(vinyloxy)ethyl) hydroxylamine (172 mg, 1.62 mmol) was added. After stirring for 4 h at ambient temperature, the reaction was treated with saturated $NH_4Cl$ (aq.). The resultant mixture was extracted with $CH_2Cl_2$ (30 mL×3). The combined organic extracts were washed with water (30 mL) and brine (30 mL), dried over $Na_2SO_4$, filtered and concentrated in vacuo. The crude product was purified by column chromatography on silica gel ($CH_2Cl_2$/MeOH, 100:1, v/v) and gave the desired product (white solid, 450 mg, 74.8% yield). $^1H$ NMR (400 MHz, DMSO-$d_6$): δ 11.82 (s, 1H), 8.96 (s, 1H), 8.01 (s, 1H), 7.88 (s, 1H), 7.53 (d, J=10.8 Hz, 1H), 7.28 (d, J=8.1 Hz, 1H), 6.50 (dd, J=13.9, 6.6 Hz, 1H), 6.40 (d, J=6.0 Hz, 1H), 4.18 (d, J=14.5 Hz, 1H), 3.99 (m, 3H), 3.83 (s, 2H).

Step 10: 4-fluoro-5-((2-fluoro-4-iodophenyl)amino)-N-(2-hydroxy ethoxy)benzo[d]oxazole-6-carboxamide To a solution of compound 4-fluoro-5-((2-fluoro-4-iodophenyl)amino)-N-(2-(vinyloxy)ethoxy)benzo[d]oxazole-6-carboxamide (450 mg, 0.9 mmol) in $CH_2Cl_2$ (10 mL) was added 1.0 N HCl (aq., 6.7 mL, 6.72 mmol). After stirring for 1 h, the reaction mixture was washed with saturated $NaHCO_3$ (aq.). The aqueous layer was washed with $CH_2Cl_2$ (10 mL×2). The combined organic layer was washed with water (10 mL) and brine (10 mL), dried over $Na_2SO_4$, filtered and concentrated in vacuo. The crude product was purified by column chromatography on silica gel ($CH_2Cl_2$/MeOH, 50:1, v/v) and gave the desired product (white solid, 380 mg, 88.9% yield). $^1H$ NMR (400 MHz, DMSO-$d_6$): δ 11.75 (s, 1H), 8.96 (s, 1H), 8.01 (s, 1H), 7.88 (s, 1H), 7.53

(d, J=9.4 Hz, 1H), 7.28 (d, J=8.7 Hz, 1H), 6.39 (m, 1H), 4.70 (s, 1H), 3.83 (s, 2H), 3.56 (s, 2H), MS APCI(+)m/z: 476.1, [M+H].

Example 1A: Preparation of 4-fluoro-5-((2-fluoro-4-iodophenyl)amino)-N-(2-hydroxyethoxy)benzo[d]oxazole-6-carboxamide (Compound 1)

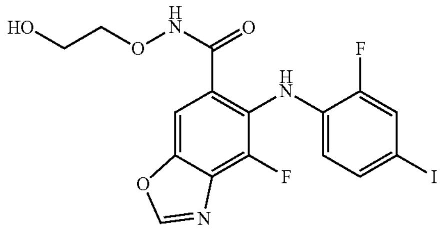

Step 1: 1-benzyloxy-2,3,4-trifluorobenzene

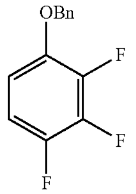 [SMILES: Fc1ccc(OCc2ccccc2)c(F)c1F]

Sodium carbonate (19.50 g, 0.184 mol) was dispersed into a solution of 2,3,4-trifluorophenol (13.64 g, 0.092 mol) in acetone (300 mL). To the stirred suspension was added the solution of benzyl bromide (17.31 g, 101.21 mmol) in acetone (100 mL) dropwisely. The mixture was heated under reflux at 50° C. for 24 h, allowed to cool to room temperature, and filtered. The filter cake was washed with acetone (50 mL×3), and acetone was removed under reduced pressure. The residue was dissolved in ethyl acetate (500 mL). The solution was washed with 5% sodium hydroxide (50 mL), water (150 mL) and brine (150 mL) sequentially and dried over $Na_2SO_4$. The solvent was removed in vacuo to yield a pale yellow solid (19.89 g, 90% yield). $^1$H NMR (400 MHz, $CDCl_3$): δ 7.40 (m, 5H), 6.85 (m, 1H), 6.64 (m, 1H), 5.15 (s, 2H).

Step 2: 5-benzyloxy-2,3,4-trifluorobenzoic acid

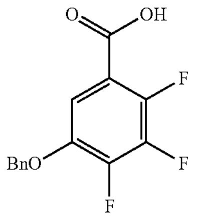 [SMILES: O=C(O)c1cc(OCc2ccccc2)c(F)c(F)c1F]

To a solution of 1-benzyloxy-2,3,4-trifluorobenzene (19.89 g, 83.6 mmol) in anhydrous THF (120 mL) was added lithium diisopropylamide (2.0 M in THF, 42.6 mL, 85.2 mmol) at −78° C. under nitrogen atmosphere. After stirring for 1 h at −78° C., the mixture was transferred to a bottle with dry ice (20.0 g, 454.5 mmol). The mixture was stirred overnight at ambient temperature. The reaction was quenched with 10% aqueous pH 1 (300 mL). The mixture was extracted with ethyl acetate (200 mL×3). The combined organic extracts were washed with 5% sodium hydroxide (300 mL). The aqueous layer was acidized to pH 1 with concentrated HCl (aq.) and extracted with ethyl acetate (200 mL×3). The combined organic layer was dried over $Na_2SO_4$, filtered and concentrated under reduced pressure to afford the desired product (white solid, 19.33 g, 82% yield), $^1$H NMR (400 MHz, $CDCl_3$): δ 14.01 (s, 1H), 7.42 (6H, m), 5.16 (2H, s).

Step 3: 5-benzyloxy-3,4-difluoro-2-((2-fluorophenyl)amino)benzoic acid

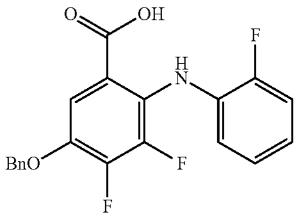 [SMILES: O=C(O)c1cc(OCc2ccccc2)c(F)c(F)c1Nc1ccccc1F]

To a solution of 2-fluoroaniline (13.21 g, 137.1 mmol) and 5-benzyl-oxy-2,3,4-trifluorobenzoic acid (19.33 g, 68.55 mmol) in THF (120 mL) at −78° C. was added LiHMDS (206.1 mL, 1 M in THF, 206.1 mmol) dropwisely. The mixture was allowed to slowly warm to room temperature and stirred at this temperature overnight. The reaction was quenched with HCl (aq., 1 N, 250 mL) and extracted with ethyl acetate (200 mL×3). The combined organic extracts were washed with water (200 mL×3) and brine (200 mL) sequentially, dried over $Na_2SO_4$, filtered and concentrated in vacuo to afford the desired product (pale yellow solid, 19.17 g, 75% yield). $^1$H NMR (400 MHz, DMSO-$d_6$): δ 13.76 (s, 1H), 8.58 (s, 1H), 7.61 (dd, J=8.8, 1.7 Hz, 1H), 7.52-7.35 (m, 5H), 7.20 (m, 1H), 7.05 (m, 1H), 6.98-6.82 (m, 2H), 5.26 (s, 2H).

Step 4: benzyl 5-benzyloxy-3,4-difluoro-2-((2-fluorophenyl)amino)benzoate

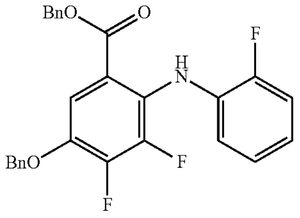 [SMILES: O=C(OCc1ccccc1)c1cc(OCc2ccccc2)c(F)c(F)c1Nc1ccccc1F]

To a solution of 5-benzyloxy-3,4-difluoro-2-((2-fluorophenyl)amino)benzoic acid (19.17 g, 51.35 mmol) in DMF (30 mL) was added potassium bicarbonate (6.16 g, 61.62 mmol) followed by benzyl bromide (6.2 mL, 51.41 mmol). The mixture was stirred for 5 h at room temperature and then water (150 mL) was added. The solution was extracted with ethyl acetate (150 mL×3). The combined organic extracts were washed with water (100 mL×3) and brine (200 mL)

sequentially, dried over $Na_2SO_4$, filtered and concentrated in vacuo to afford the corresponding product (21.42 g, 90% yield). $^1H$ NMR (400 MHz, $CDCl_3$): δ 8.51 (s, 1H), 7.51 (dd, J=8.5, 2.1 Hz, 1H), 7.46-7.36 (m, 10H), 7.12-7.06 (m, 1H), 7.03 (m, 1H), 6.94 (m, 1H), 6.85 (m, 1H), 5.33 (s, 2H), 5.15 (s, 2H).

Step 5: benzyl 4-azido-5-benzyloxy-3-fluoro-2-((2-fluorophenyl)amino)benzoate

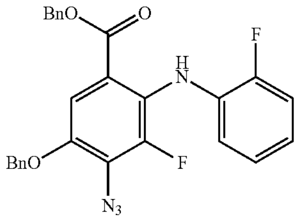 [SMILES: [N-]=[N+]=Nc1c(OCc2ccccc2)cc(C(=O)OCc2ccccc2)c(Nc2ccccc2F)c1F]

To a solution of benzyl 5-benzyloxy-3,4-difluoro-2-((2-fluoro-phenyl)amino)benzoate (21.42 g, 46.26 mmol) in DMF (35 mL) was added $NaN_3$ (3.61 g, 55.51 mmol). The mixture was stirred at 90° C. for 3 h. Then water (300 mL) was added. The solution was extracted with ethyl acetate (150 mL×3). The combined organic extracts were washed with water (100 mL×3) and brine (200 mL) sequentially, dried over $Na_2SO_4$ and concentrated in vacuo. The residue was purified by flash column chromatography on silica gel (petroleum ether/ethyl acetate, 10:1, v/v) and gave the desired product (white solid, 14.63 g, 65% yield). $^1H$ NMR (400 MHz, $CDCl_3$): δ 8.55 (s, 1H), 7.53 (dd, J=8.5, 2.1 Hz, LB), 7.50-7.33 (m, 10H), 7.09 (m, 1H), 7.05 (m, LB), 6.90 (m, 1H), 6.83 (m, 1H), 5.35 (s, 2H), 5.20 (s, 2H).

Step 6: 4-amino-3-fluoro-2-((2-fluorophenyl)amino)-5-hydroxy benzoic acid

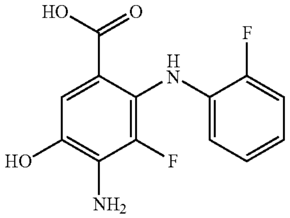 [SMILES: Nc1c(O)cc(C(=O)O)c(Nc2ccccc2F)c1F]

To a solution of benzyl 4-azido-5-benzyloxy-3-fluoro-2-((2-fluorophenyl)amino)benzoate (14.63 g, 30.07 mmol) in MeOH (200 mL) was added and 10% palladium on carbon (2.55 g) under nitrogen atmosphere. Then the nitrogen atmosphere was completely changed to hydrogen atmosphere. The mixture was stirred for 6 h at ambient temperature. After the insoluble matter was filtered off, the solvent was concentrated in vacuo to give the crude product (7.58 g, 90% yield), which was used directly in next step without further purification.

Step 7: 4-fluoro-5-((2-fluorophenyl)amino)benzo[d]oxazole-6-carboxylic acid

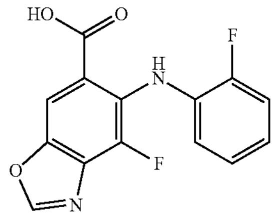 [SMILES: O=C(O)c1cc2ocnc2c(F)c1Nc1ccccc1F]

To a solution of 4-amino-3-fluoro-2-((2-fluorophenyl)amino)-5-hydroxy benzoic acid (7.58 g, 27.08 mmol) in trimethyl orthoformate (50 mL) was added p-TsOH (233 mg, 1.35 mmol). The reaction mixture was stirred for 1 h and treated with water (300 mL). The precipitate was filtered off and the filter cake was washed with water to afford the desired product (7.22 g, 92% yield). $^1H$ NMR (400 MHz, DMSO-$d_6$): δ 8.28 (s, 1H), 8.27 (s, 1H), 8.24 (s, 1H), 7.14 (m, 1H), 7.11 (m, 1H), 7.04 (m, 1H), 6.85 (m, 1H).

Step 8: 4-fluoro-5-((2-fluoro-4-iodophenyl)amino)benzo[d]oxazole-6-carboxylic acid

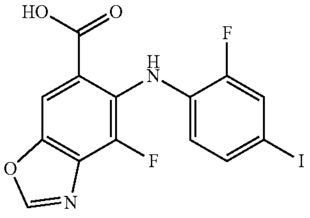 [SMILES: O=C(O)c1cc2ocnc2c(F)c1Nc1ccc(I)cc1F]

To a solution of 4-fluoro-5-((2-fluorophenyl)amino)benzo[d]oxazole-6-carboxylic acid (7.22 g, 24.90 mmol) in DMF (50 mL) was added NIS (6.08 g, 26.37 mmol) followed by trifluoroacetic acid (3 mL). After stirring for 4 h at ambient temperature, the reaction was quenched with saturated $NH_4Cl$ (aq., 100 mL). The solution was extracted with ethyl acetate (150 mL×3). The combined organic extracts were washed with water (50 mL×3) and brine (100 mL) successively, dried over $Na_2SO_4$ and concentrated in vacuo. The crude product was purified by column chromatography on silica gel (petroleum ether/ethyl acetate, 3:1, v/v) and gave the desired product (brown solid, 6.339 g, 69% yield). $^1H$ NMR (400 MHz, DMSO-$d_6$): δ 8.97 (s, 1H), 8.18 (s, 1H), 8.08 (s, 1H), 7.58 (dd, J=11.0, 1.7 Hz, 1H), 7.34 (d, J=8.5 Hz, 1H), 6.55 (m, 1H).

Step 9: 4-fluoro-5-((2-fluoro-4-iodophenyl)amino)-N-(2-(vinyloxy)ethoxy)benzo[d]oxazole-6-carboxamide

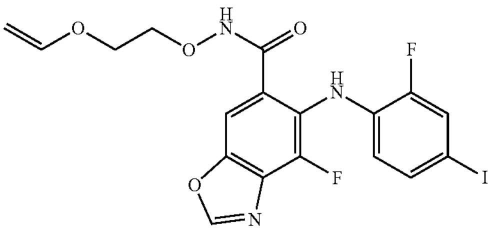 [SMILES: C=COCCONC(=O)c1cc2ocnc2c(F)c1Nc1ccc(I)cc1F]

To a solution of 4-fluoro-5-((2-fluoro-4-iodophenyl) amino)benzo [d]oxazole-6-carboxylic acid (500 mg, 1.2 mmol) in $CH_2Cl_2$ was added HOBt (254 rag, 1.63 mmol) and EDCI (314 mg, 1.63 mmol). The mixture was stirred for 1 h and O-(2-(vinyloxy)ethyl) hydroxylamine (172 mg, 1.62 mmol) was added. After stirring for 4 h at ambient temperature, the reaction was treated with saturated $NH_4Cl$ (aq., 20 mL). The resultant mixture was extracted with $CH_2Cl_2$ (30 mL×3). The combined organic extracts were washed with water (30 mL×2) and brine (30 mL) sequentially, dried over $Na_2SO_4$, filtered and concentrated in vacuo. The crude product was purified by column chromatography on silica gel ($CH_2Cl_2$/MeOH, 20:1, v/v) and gave the desired product (white solid, 598 mg, 98% yield), $^1H$ NMR (400 MHz, DMSO-$d_6$): δ 11.82 (s, 1H), 8.96 (s, 1H), 8.01 (s, 1H), 7.88 (s, 1H), 7.53 (d, J=10.8 Hz, 1H), 7.28 (d, J=8.1 Hz, 1H), 6.50 (dd, J=13.9, 6.6 Hz, 1H), 6.40 (d, J=6.0 Hz, 1H), 4.18 (d, J=14.5 Hz, 1H), 3.99 (m, 3H), 3.83 (s, 2H).

Step 10: 4-fluoro-5-((2-fluoro-4-iodophenyl)amino)-N-(2-hydroxyethoxy)benzo[d]oxazole-6-carboxamide

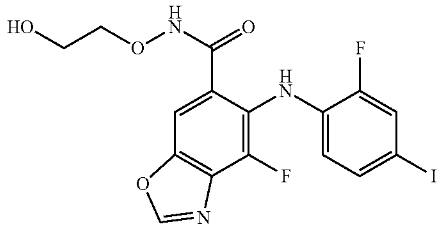 [SMILES: O=C(NOCCO)c1cc2ocnc2c(F)c1Nc1ccc(I)cc1F]

To a solution of compound 4-fluoro-5-((2-fluoro-4-iodophenyl)amino)-N-(2-(vinyloxy)ethoxy)benzo[d]oxazole-6-carboxamide (598 mg, 1.17 mmol) in $CH_2Cl_2$ (5 mL) was added 1.0 N HCl (aq., 6.7 mL, 6.72 mmol) dropwise. After stirring for 1 h, the reaction mixture was treated with saturated $NaHCO_3$ (aq.). The organic layer was washed with water (30 mL×2) and brine (30 mL), dried over $Na_2SO_4$, filtered and concentrated in vacuo. The crude product was purified by column chromatography on silica gel ($CH_2Cl_2$/MeOH, 15:1, v/v) and gave the desired product (white solid, 290 mg, 52% yield). $^1H$ NMR (400 MHz, DMSO-$d_6$): δ 11.75 (s, 1H), 8.96 (s, 1H), 8.01 (s, 1H), 7.88 (s, 1H), 7.53 (d, J=9.4 Hz, 1H), 7.28 (d, J=8.7 Hz, 1H), 6.39 (m, 1H), 4.70 (s, 1H), 3.83 (m, 2H), 3.56 (m, 2H). MS (ES+): m/z 476.34 [$MH^+$].

Example 2: Preparation of N-(2,3-dihydroxypropoxy)-4-fluoro-5-((2-fluoro-4-iodophenyl)amino)benzo[d]oxazole-6-carboxamide (Compound 2)

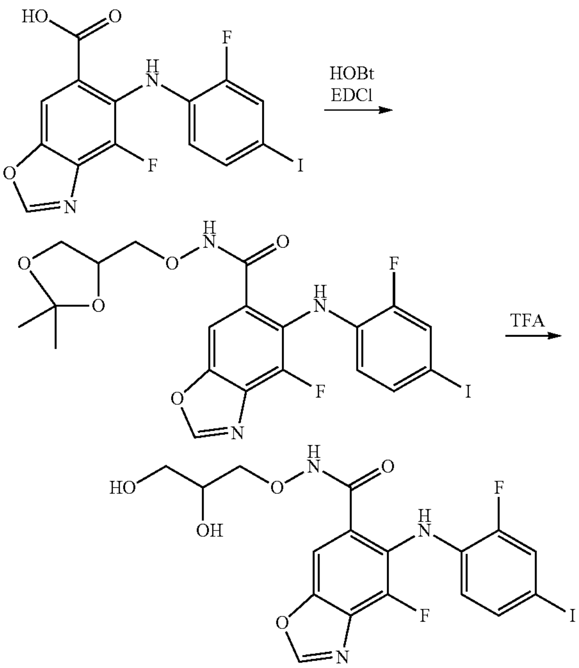

Step 1: N-((2,2-dimethyl-1,3-dioxolan-4-yl)methoxy)-4-fluoro-5-((2-fluoro-4-iodophenyl)amino)benzo[d]oxazole-6-carboxamide To a solution of 4-fluoro-5-((2-fluoro-4-iodophenyl) amino)benzo[d]oxazole-6-carboxylic acid (500 mg, 1.20 mmol) in $CH_2Cl_2$ (10 mL) was added HOBt (254 mg, 1.63 mmol) followed by EDCI (314 mg, 1.63 mmol). The mixture was stirred for 1 h and O-((2,2-dimethyl-1,3-dioxolan-4-yl)methyl)hydroxylamine (238 mg, 1.62 mmol) was added. After stirring for 4 h at ambient temperature, the reaction was treated with saturated $NH_4Cl$ (aq.). The resultant mixture was extracted with $CH_2Cl_2$ (30 mL×3). The combined organic extracts was washed by water (30 mL) and brine (30 mL) sequentially, dried over $Na_2SO_4$, filtered and concentrated in vacuo. The crude product (488 mg) was used directly in the next step without further purification.

Step 2: N-(2,3-dihydroxypropoxy)-4-fluoro-5-((2-fluoro-4-iodophenyl)amino)benzo[d]oxazole-6-carboxamide To a solution of N-((2,2-dimethyl-1,3-dioxolan-4-yl) methoxy)-4-fluoro-5-((2-fluoro-4-iodophenyl)amino)benzo [d]oxazole-6-carboxamide (488 mg, 0.89 mmol) in $CH_2Cl_2$ (10 mL) was added trifluoroacetic acid (0.2 mL, 2.69 mmol). The mixture was stirred for 1 h and washed with saturated sodium bicarbonate (aq.). The aqueous layer was extracted by $CH_2Cl_2$ (10 mL×2). The combined organic layers were washed by water (10 mL) and brine (10 mL) sequentially, dried over $Na_2SO_4$, filtered and concentrated in vacuo. The crude product was purified by column chromatography on silica gel ($CH_2Cl_2$/MeOH, 50:1, v/v) to afford the desired product (white solid, 310 mg, 48% yield for two steps). $^{1}H$ NMR (400 MHz, DMSO-$d_6$): δ 11.80 (s, 1H), 8.96 (s, 1H), 8.03 (s, 1H), 7.87 (s, 1H), 7.53 (d, 1H), 7.28 (d, 1H), 6.40 (m, 1H), 4.84 (d, 1H), 4.60 (m, 1H), 3.87 (m, 1H), 3.72 (m, 2H), 3.36 (m, 2H). MS APCI(+)m/z: 527.8, [M+Na].

Example 3: Preparation of 5-((4-bromo-2-chloro-phenyl)amino)-4-fluoro-A-(2-hydroxyethoxy)benzo[d]oxazole-6-carboxamide (Compound 3)

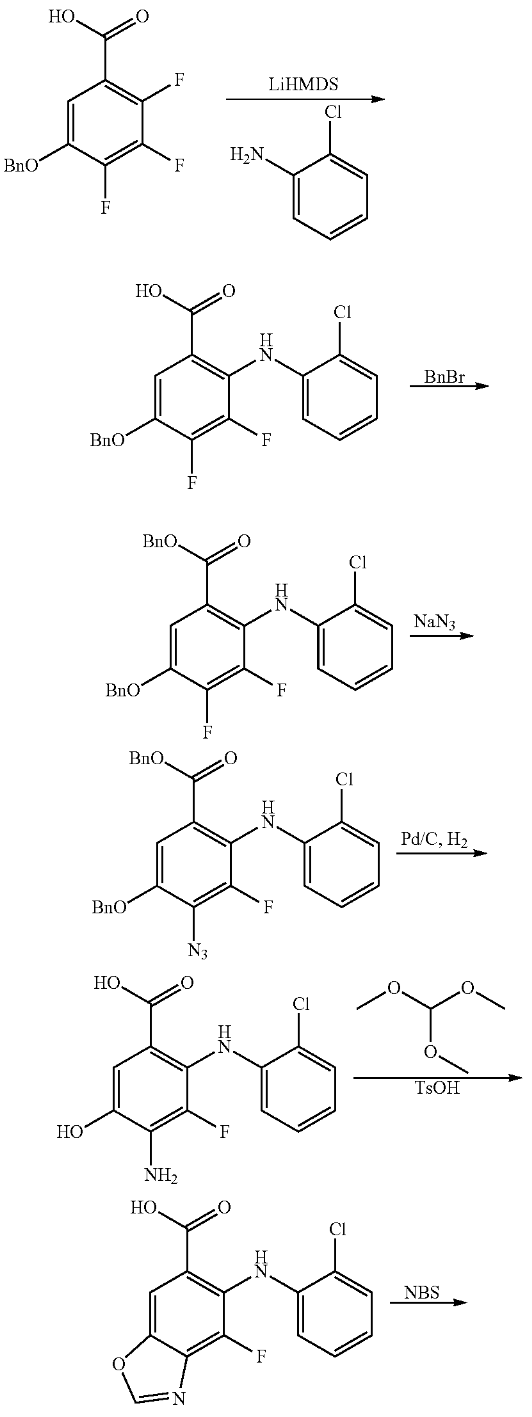

-continued

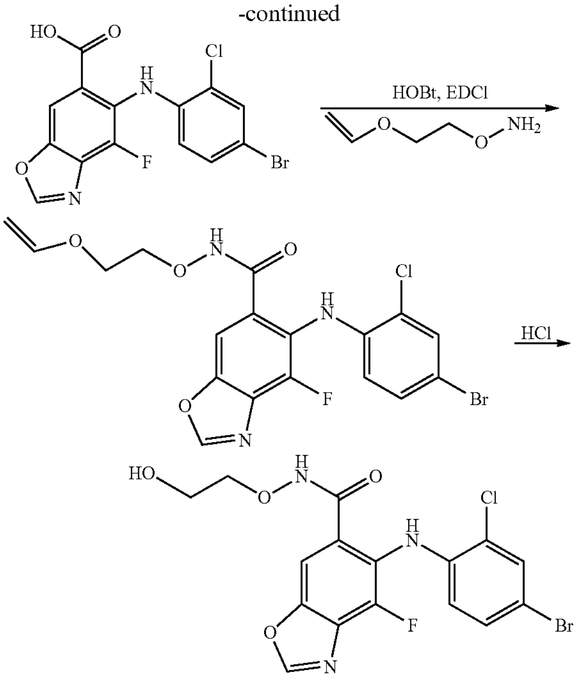

Step 1: 5-(benzyloxy)-2-((2-chlorophenyl)amino)-3,4-difluorobenzoic acid

To a solution of 2-chloroaniline (13.91 ml, 137.00 mmol) and 5-benzyloxy-2,3,4-trifluorobenzoic acid (19.33 g, 68.50 mmol) in THF (120 mL) at −78° C. was added LiHMDS (205.5 mL, 1 M in THF, 205.5 mmol) dropwisely under nitrogen atmosphere. The mixture was slowly warmed to room temperature and stirred at this temperature overnight. The reaction was quenched with water (100 mL) and acidified to pH 2-3 with 10% HCl (aq.). The mixture was extracted with ethyl acetate (100 mL×3). The combined organic extracts were washed with water (100 mL) and brine (100 mL) sequentially, dried over $Na_2SO_4$, filtered and concentrated in vacuo to afford the desired product (pale yellow solid, 23.80 g, 89.1% yield). $^{1}H$ NMR (400 MHz, DMSO-$d_6$): δ 13.80 (s, 1H), 8.66 (s, 1H), 7.64 (m, 1H), 7.34 (m, 7H), 6.92 (m, 1H), 6.78 (m, 1H), 5.26 (s, 2H).

Step 2: benzyl 5-(benzyloxy)-2-((2-chlorophenyl)amino)-3,4-difluorobenzoate

To a solution of 5-(benzyloxy)-2-((2-chlorophenyl)amino)-3,4-difluorobenzoic acid (23.80 g, 61.06 mmol) in DMF (200 mL) was added potassium bicarbonate (9.16 g, 91.6 mmol) followed by benzyl bromide (8.0 mL, 67.37 mmol). The mixture was stirred for 5 h at room temperature and water (300 mL) was added. The solution was extracted with ethyl acetate (100 mL×3). The combined organic extracts were washed with water (200 mL×3) and brine (200 mL) sequentially, dried over $Na_2SO_4$, filtered and concentrated in vacuo. After purification by column chromatography on silica gel (petroleum ether/ethyl acetate, 50:1, v/v), the corresponding product was obtained as white solid (27.82 g, 95% yield). $^{1}H$ NMR (400 MHz, $CDCl_3$): δ 8.56 (s, 1H), 7.52 (dd, J=8.5, 2.1 Hz, 1H), 7.40 (m, 11H), 7.15 (m, 1H), 6.88 (m, 1H), 6.74 (m, 1H), 5.34 (s, 2H), 5.16 (s, 2H).

Step 3: benzyl 4-azido-5-(benzyloxy)-2-((2-chlorophenyl)amino)-3-fluorobenzoate

To a solution of benzyl 5-(benzyloxy)-2-((2-chlorophenyl)amino)-3,4-difluorobenzoate (27.82 g, 57.97 mmol) in DMF (250 mL) was added $NaN_3$ (4.52 g, 69.56 mmol). The mixture was stirred at 90° C. for 3 h. Then water (400 mL) was added. The solution was extracted with ethyl acetate (150 mL×3). The combined organic extracts were washed with water (150 mL) and brine (150 mL), dried over $Na_2SO_4$, filtered and concentrated in vacuo. The residue was purified by flash column chromatography on silica gel (petroleum ether/ethyl acetate, 50:1, v/v) and gave the desired product (pale yellow solid, 22.97 g, 78.8% yield). $^1H$ NMR (400 MHz, $CDCl_3$): δ 8.41 (s, 1H), 7.40 (m, 12H), 7.13 (m, 1H), 6.87 (m, 1H), 6.69 (m, 1H), 5.34 (s, 2H), 5.17 (s, 2H).

Step 4: 4-amino-2-((2-chlorophenyl)amino)-3-fluoro-5-hydroxy benzoic acid

To a solution of compound benzyl 4-azido-5-(benzyloxy)-2-((2-chlorophenyl)amino)-3-fluorobenzoate (22.97 g, 45.67 mmol) in MeOH (500 mL) was added and 10% palladium on carbon (3.80 g) under nitrogen atmosphere. Then the nitrogen atmosphere was completely changed to hydrogen atmosphere. The mixture was stirred for 3 h at ambient temperature. After the insoluble matter was filtered off, the solvent was evaporated under reduced pressure to give the desired product, which was used directly in the next step without further purification.

Step 5: 5-((2-chlorophenyl)amino)-4-fluorobenzo[d]oxazole-6-carboxylic acid

To a solution of 4-amino-2-((2-chlorophenyl)amino)-3-fluoro-5-hydroxybenzoic acid in trimethyl orthoformate (100 mL) was added p-TsOH (0.42 g, 1.35 mmol). The reaction mixture was stirred for 1 h and treated with water (300 mL). The precipitate was filtered off and the filter cake was washed with water to afford a yellow solid (12.31 g, 87.9% yield for two steps). $^1H$ NMR (400 MHz, DMSO-$d_6$): δ 13.9 (s, 1H), 9.05 (s, 1H), 8.8 (s, 1H), 8.23 (s, 1H), 7.43 (m, 1H), 7.15 (m, 1H), 6.98 (m, 1H), 6.74 (m, 1H).

Step 6: 5-((4-bromo-2-chlorophenyl)amino)-4-fluorobenzo[d]oxazole-6-carboxylic acid To a solution of 5-((2-chlorophenyl)amino)-4-fluorobenzo[d] oxazole-6-carboxylic acid (12.31 g, 40.14 mmol) in DMF (100 mL) was added NBS (7.86 g, 44.15 mmol). After stirring for 4 h at ambient temperature, the reaction was quenched by water and the precipitate was filtered. The crude product was purified by column chromatography on silica gel ($CH_2Cl_2$/MeOH, 50:1, v/v) and gave the desired product (pale brown solid, 10.82 g, 69.9% yield). $^1H$ NMR (400 MHz, DMSO-$d_6$): δ 11.08 (s, 1H), 9.42 (s, 1H), 8.96 (s, 1H), 8.27 (s, 1H), 7.82 (d, J=12.0 Hz, 1H), 7.37 (m, 1H), 6.65 (m, 1H).

Step 7: 5-((4-bromo-2-chlorophenyl)amino)-4-fluoro-N-(2-(vinyl-oxy)ethoxy)benzo[d]oxazole-6-carboxamide To a solution of 5-((4-bromo-2-chlorophenyl)amino)-4-fluorobenzo [d]oxazole-6-carboxylic acid (463 mg, 1.20 mmol) in $CH_2Cl_2$ (10 mL) was added HOBt (254 mg, 1.63 mmol) and EDCI (314 mg, 1.63 mmol). The mixture was stirred for 1 h and O-(2-(vinyloxy)ethyl) hydroxylamine (172 mg, 1.62 mmol) was added. After stirring for 4 h at ambient temperature, the reaction was treated with saturated $NH_4Cl$ (aq.). The resultant mixture was extracted with $CH_2Cl_2$ (30 mL×3). The combined organic extracts were washed with water (30 mL) and brine (30 mL), dried over $Na_2SO_4$, filtered and concentrated in vacuo. The crude product (445 mg) was used directly in the next step without further purification.

Step 8: 5-((4-bromo-2-chlorophenyl)amino)-4-fluoro-N-(2-hydroxyethoxy)benzo[d]oxazole-6-carboxamide To a solution of 5-((4-bromo-2-chlorophenyl)amino)-4-fluoro-N-(2-(vinyloxy)ethoxy)benzo[d]oxazole-6-carboxamide (445 mg, 0.95 mmol) in $CH_2Cl_2$ (10 mL) was added 1.0 N HCl solution (6.7 mL, 6.72 mmol). After stirring for 1 h, the reaction mixture was washed with saturated $NaHCO_3$ (aq.). The aqueous layer was extracted with $CH_2Cl_2$ (10 mL×2). The combined organic layer was washed with water (10 mL) and brine (10 mL) successively, dried over $Na_2SO_4$, filtered and concentrated in vacuo. The crude product was purified by column chromatography on silica gel ($CH_2Cl_2$/MeOH, 50:1, v/v) and gave the desired product (white solid, 347 mg, 65% yield for two steps). $^1H$ NMR (400 MHz, MeOD): δ 8.65 (s, 1H), 7.8 (s, 1H), 7.54 (d, J=2.0 Hz, 1H), 7.24 (m, 1H), 6.50 (m, 1H), 3.95 (s, 2H), 3.70 (s, 2H). MS APCI(+)m/z: 445.9 [M+H], 467.8, [M+Na].

Example 4: Preparation of 5-((4-bromo-2-chlorophenyl)amino)-N-(2,3-dihydroxypropoxy)-4-fluorobenzo[d]oxazole-6-carboxamide (Compound 4)

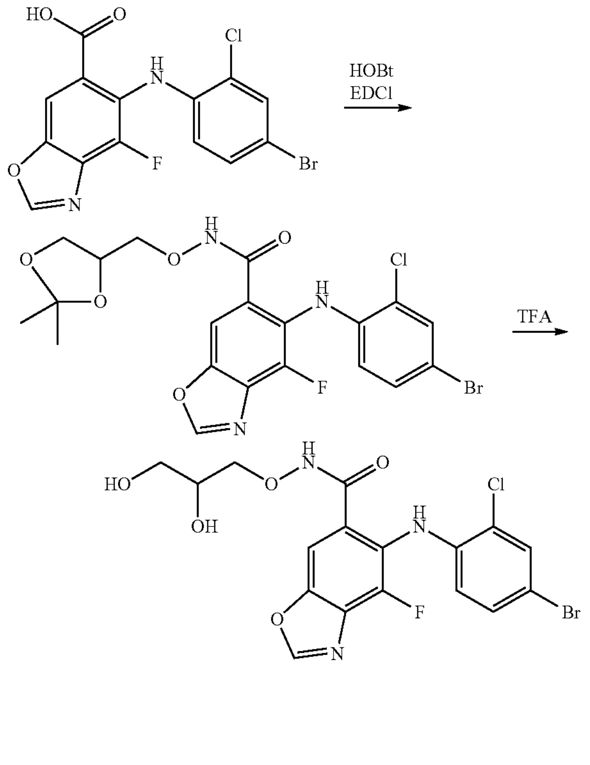

Step 1: 5-((4-bromo-2-chlorophenyl)amino)-N-((2, 2-dimethyl-1, 3-dioxolan-4-yl)methoxy)-4-fluorobenzo[d]oxazole-6-carboxamide To a solution of 5-((4-bromo-2-chlorophenyl)amino)-4-fluorobenzo[d]oxazole-6-carboxylic acid (463 mg, 1.20 mmol) in $CH_2Cl_2$ (10 mL) was added HOBt (254 mg, 1.63 mmol) followed by EDCI (314 mg, 1.63 mmol). The mixture was stirred for 1 h and O-((2,2-dimethyl-1,3-di-oxolan-4-yl)methyl)hydroxylamine (238 mg, 1.62 mmol) was added. After stirring for 4 h at ambient temperature, the reaction was treated with saturated $NH_4Cl$ (aq.). The resultant mixture was extracted with $CH_2Cl_2$ (30 mL×3). The combined organic extracts was washed by water (30 mL) and brine (30 mL) sequentially, dried over $Na_2SO_4$, filtered and concentrated in vacuo. The crude product (473 mg) was used directly in the next step without further purification.

Step 2: 5-((4-bromo-2-chlorophenyl)amino)-N-(2,3-dihydroxypropoxy)-4-fluorobenzo[d]oxazole-6-carboxamide To a solution of 5-((4-bromo-2-chlorophenyl)amino)-N-((2,2-dimethyl-1,3-dioxolan-4-yl)methoxy)-4-fluorobenzo [d]oxazole-6-carboxamide (473 mg, 0.92 mmol) in $CH_2Cl_2$ (10 mL) was added trifluoroacetic acid (0.2 mL, 2.69 mmol). The mixture was stirred for 1 h and washed with saturated sodium bicarbonate (aq.). The aqueous layer was extracted by $CH_2Cl_2$ (10 mL×2). The combined organic layers were washed by water (10 mL) and brine (10 mL) sequentially, dried over $Na_2SO_4$, filtered and concentrated in vacuo. The crude product was purified by column chromatography on silica gel ($CH_2Cl_2$/MeOH, 50:1, v/v) to afford the desired product (white solid, 255 mg, 44.7% yield for two steps). $^1H$ NMR (400 MHz, DMSO-$d_6$): δ 11.78 (s, 1H), 8.95 (s, 1H), 8.05 (s, 1H), 7.89 (s, 1H), 7.54 (d, 1H), 7.30 (d, 1H), 6.42 (m, 1H), 4.83 (d, 1H), 4.62 (m, 1H), 3.86 (m, 1H), 3.70 (m, 2H), 3.35 (m, 2H). MS APCI(+)m/z: 475.7, [M+H].

Example 5: Preparation of N-(4-fluoro-5-((2-fluoro-4-iodophenyl)amino)benzo[d]oxazol-6-yl)cyclopropanesulfonamide (Compound 5)

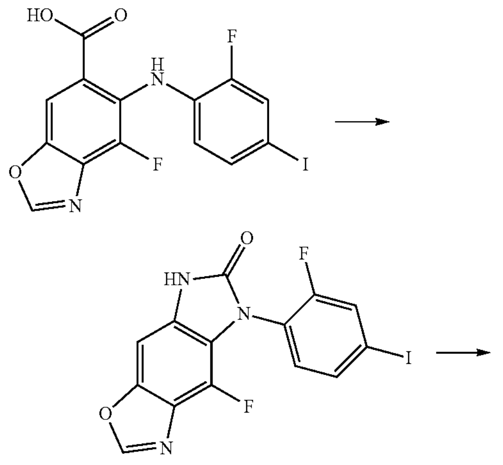

-continued

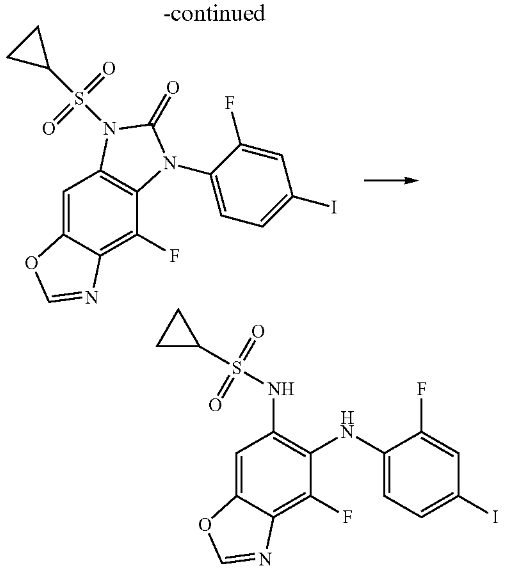

Step 1: 4-fluoro-5-(2-fluoro-4-iodophenyl)-5H-imidazo[4',5':4,5]benzo[1,2-d]oxazol-6(7H)-one To a solution of 4-fluoro-5-((2-fluoro-4-iodophenyl)amino)benzo[d]oxazole-6-carboxylic acid (70 mg, 0.17 mmol) in T-BuOH (3 mL) was added DPPA (82 mg, 0.29 mmol) followed by triethylamine (36 mg, 0.36 mmol). The mixture was heated under reflux for 3 h and allowed to slowly warm to room temperature. The solvent was removed in vacuo and the resultant crude product was purified by column chromatography on silica gel (petroleum ether/ethyl acetate, 2:1, v/v). The corresponding product was obtained (white solid, 62 mg, 89.2% yield). $^1H$ NMR (400 MHz, DMSO-$d_6$): δ 11.75 (s, 1H), 8.67 (s, 1H), 7.96 (d, 1H), 7.76 (d, 1H), 7.50 (m, 1H), 7.39 (s, 1H).

Step 2: 7-(cyclopropylsulfonyl)-4-fluoro-5-(2-fluoro-4-iodophenyl)-5H-imidazo[4',5':4,5]benzo[1,2-d]oxazol-6(7H)-one To a solution of 4-fluoro-5-(2-fluoro-4-iodophenyl)-5H-imidazo [4',5':4,5]benzo[1,2-d]oxazol-6(7H)-one (30 mg, 0.07 mmol) in $CH_2Cl_2$ (3 mL) was added triethylamine (22 mg, 0.22 mmol) at 0° C. followed by cyclopropanesulfonyl chloride (16 mg, 0.11 mmol) and DMAP (5 mg). The mixture was stirred at room temperature for 1 h and washed with saturated $NaHCO_3$ (aq.). The aqueous layer was extracted with $CH_2Cl_2$ (10 mL×2). The combined organic phase was washed with water (10 mL) and brine (10 mL) successively, dried over $Na_2SO_4$, filtered and concentrated in vacuo. The residue was purified by flash chromatography on silica gel (petroleum ether/ethyl acetate, 5:1, v/v) to give the corresponding product (40 mg, 100% yield). $^1H$ NMR (400 MHz, $CDCl_3$): δ 8.09 (s, 1H), 7.99 (s, 1H), 7.39-7.11 (d, 2H), 7.05, (m, 1H), 3.40 (m, 1H), 1.71 (m, 2H), 0.91-0.85 (m, 2H).

Step 3: N-(4-fluoro-5-((2-fluoro-4-iodophenyl)amino)benzo[d]oxazol-6-yl)cyclopropanesulfonamide To a solution of 7-(cyclopropylsulfonyl)-4-fluoro-5-(2-fluoro-4-iodo phenyl)-5H-imidazo[4',5':4,5]benzo[1,2-d]oxazol-6(7H)-one (30 mg, 0.06 mmol) in THF (3 mL) was added potassium trimethylsilanolate (12 mg, 0.09 mmol). After stirring at room temperature for 1 h, the reaction was quenched with saturated $NH_4Cl$ (aq.). The aqueous layer was extracted with ethyl acetate (5 mL×2). The combined organic phase was washed with brine (10 mL), dried over $Na_2SO_4$, filtered and concentrated in vacuo. The residual crude product was purified by flash chromatography on silica gel (petroleum ether/ethyl acetate, 5:1-3:1, v/v) to give the corresponding product as a white solid (10 mg, 35.1% yield). $^1H$ NMR (400 MHz, $CDCl_3$): δ 8.15 (s 1H), 7.88 (s, 1H) 7.46 (dd, 1H), 7.33 (s, 1H), 7.23 (dd, 1H), 6.15 (m, 1H), 5.49 (s, 1H), 2.55 (m, 1H), 1.01 (m, 2H), 0.92 (m, 2H). MS APCI(+)m/z: 492.5, [M+H].

Example 6: Preparation of 1-(2,3-dihydroxypropyl)-N-(4-fluoro-5-((2-fluoro-4-iodophenyl)amino)benzo[d]oxazol-6-yl)cyclopropane-1-sulfonamide (Compound 6)

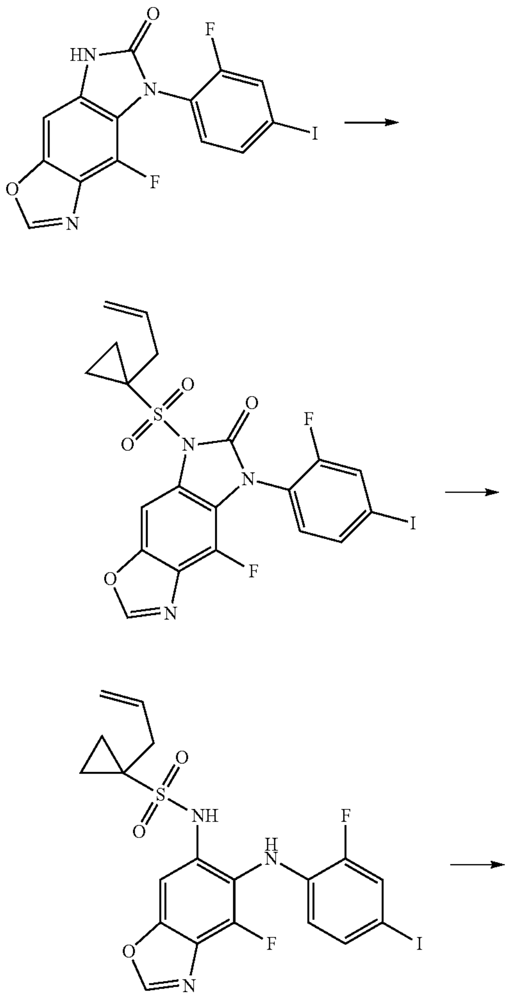

-continued

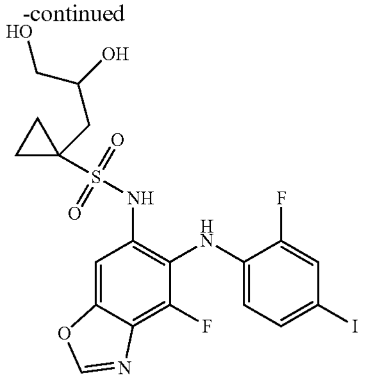

Step 1: 7-((1-allylcyclopropyl)sulfonyl)-4-fluoro-5-(2-fluoro-4-iodophenyl)-5H-imidazo[4',5': 4,5]benzo[1,2-d]oxazol-6(7H)-one To a solution of 4-fluoro-5-(2-fluoro-4-iodophenyl)-5H-imidazo [4',5':4,5]benzo[1,2-d]oxazol-6(7H)-one (100 mg, 0.24 mmol) in DCM (5 mL) was added triethylamine (74 mg, 0.73 mmol) at 0° C. followed by 1-allylcyclopropane-1-sulfonyl chloride (66 mg, 0.36 mmol) and DMAP (15 mg). After stirring at room temperature for 1 h, the mixture was washed with saturated $NaHCO_3$ (aq.). The aqueous layer was extracted with DCM (20 mL×2). The combined organic phase was washed by water (20 mL) and brine (20 mL) sequentially, dried over $Na_2SO_4$, filtered and concentrated to give a residue, which was purified by flash chromatography on silica gel (petroleum ether/ethyl acetate, 5:1, v/v) to give the corresponding product (120 mg, 89.0% yield). $^1H$ NMR (400 MHz, $CDCl_3$): δ 8.09 (s, 1H), 7.99 (s, 1H), 7.70-7.68 (d, 2H), 7.27 (m, 1H), 5.75-5.58 (m, 1H), 5.05 (m, 2H), 2.90-2.80 (m, 1H), 2.10-2.0 (m, 1H), 1.95-1.86 (m, 2H), 1.25-1.10 (m, 2H).

Step 2: 1-allyl-N-(4-fluoro-5-((2-fluoro-4-iodophenyl)amino)benzo[d]oxazol-6-yl)cyclopropane-1-sulfonamide To a solution of 7-((1-allylcyclopropyl)sulfonyl)-4-fluoro-5-(2-fluoro-4-iodophenyl)-5H-imidazo[4',5':4,5] benzo[1,2-d]oxazol-6(7H)-one (120 mg, 0.2.3 mmol) in THF (10 mL) was added potassium trimethylsilanolate (48 mg, 0.35 mmol). The reaction was stirred at room temperature for 1 h and quenched with saturated $NH_4Cl$ (aq.). The aqueous layer was extracted with EA (10 mL×2). The combined organic phase was washed with brine (10 mL), dried over $Na_2SO_4$, filtered and concentrated in vacuo. The residue was purified by flash chromatography on silica gel (petroleum ether/ethyl acetate, 5:1-3:1, v/v) to give the desired product (100 mg, 87.0% yield). $^1H$ NMR (400 MHz, $CDCl_3$): δ 8.09 (s, 1H), 7.99 (s, 1H), 7.42 (m, 1H), 7.31-7.25 (m, 1H), 6.80 (s, 1H), 6.43-6.35 (m, 1H), 6.21 (s, 1H), 5.85-5.70 (m, 1H), 5.22-5.14 (m, 2H), 2.83 (d, 2H), 1.28-1.20 (m, 2H), 0.87-0.80 (m, 2H).

Step 3: 1-(2,3-dihydroxypropyl)-N-(4-fluoro-5-((2-fluoro-4-iodophen-yl)amino)benzo[d]oxazol-6-yl) cyclopropane-1-sulfonamide To a solution of 1-allyl-N-(4-fluoro-5-((2-fluoro-4-iodophenyl)amino)benzo[d]oxazol-6-yl)cyclopropane-1-sulfonamide (100 mg, 0.38 mmol) in THF (10 mL) was added N-methylmorpholine-N-oxide (44 mg, 0.38 mmol) followed by osmium tetraoxide (10 mg, 0.04 mmol) and water (0.5 mL). The resultant was stirred at room temperature overnight. The mixture was concentrated and then diluted with ethyl acetate. The organic layer was washed with water, saturated $NaHCO_3$ (aq.) and brine sequentially, dried over $Na_2SO_4$, filtered and concentrated to give a residue, which was purified by flash chromatography on silica gel to give the product as white solid (30 mg, 28.2% yield), $^1$H NMR (400 MHz, $CDCl_3$): δ 8.09 (s, 1H), 7.99 (s, 1H), 7.46-7.36 (m, 2H) 7.30-7.20 (m, 1H), 6.82 (s, 1H), 6.45-6.32 (m, 1H), 4.40-4.26 (m, 2H), 4.20-4.10 (m, 1H), 3.75-3.60 (m, 1H), 2.86-2.79 (m, 1H), 1.30-1.25 (m, 2H), 1.15-1.20 (m, 4H), MS APCI(+)m/z: 566.3, [M+H].

Example 7: Preparation of N-(5-((4-bromo-2-chlorophenyl)amino)-4-fluorobenzo[d]oxazol-6-yl)cyclopropanesulfonamide (Compound 7)

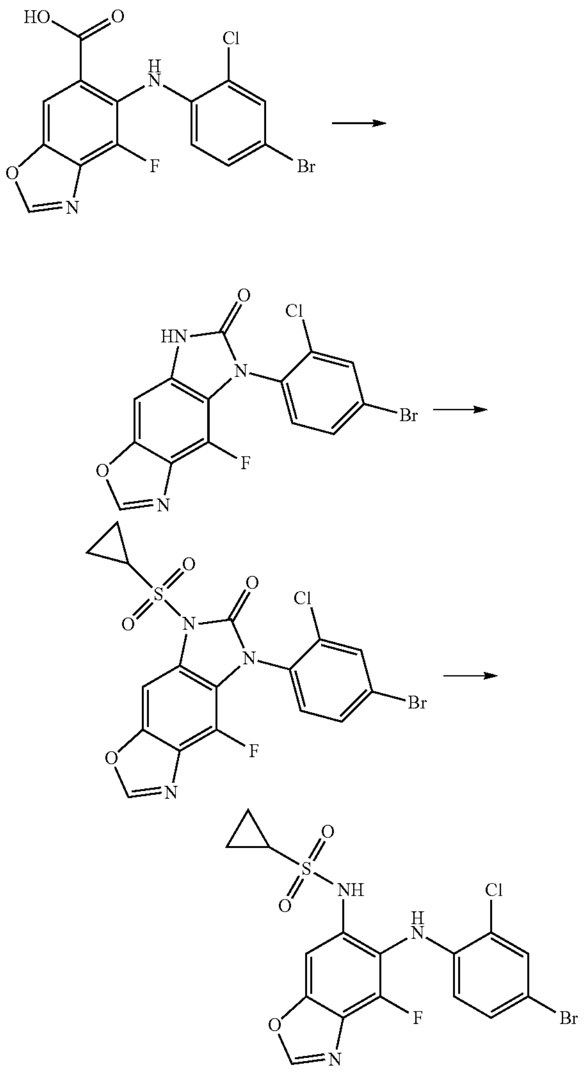

Step 1: 5-(4-bromo-2-chlorophenyl)-4-fluoro-5H-imidazo[4',5':4,5]benzo[1,2-d]oxazol-6(7H) one To a solution of 5-((4-bromo-2-chlorophenyl)amino)-4-fluorobenzo[d]oxazole-6-carboxylic acid (110 mg, 0.28 mmol) in t-BuOH (3 mL) was added DPPA (94 mg, 0.34 mmol) followed by triethylamine (58 mg, 0.57 mmol). The mixture was heated under reflux for 3 h and allowed to slowly warm to room temperature. The solvent was removed in vacuo and the resultant crude product was purified by column chromatography on silica gel (petroleum ether/ethyl acetate, 2:1, v/v). The corresponding product was obtained (white solid, 105 mg, 96.2% yield). $^1$H NMR (400 MHz, DMSO-$d_6$): δ 11.78 (s, 1H), 8.69 (s, 1H), 7.99 (d, 1H), 7.77 (d, 1H), 7.51 (m, 1H), 7.41 (s, 1H).

Step 2: 5-(4-bromo-2-chlorophenyl)-7-(cyclopropylsulfonyl)-4-fluoro-5H-imidazo[4',5':4,5]benzo[1,2-d]oxazol-6(7H)-one To a solution of 5-(4-bromo-2-chlorophenyl)-4-fluoro-5H-imidazo[4',5':4,5]benzo[1,2-d]oxazol-6(7H)-one (100 mg, 0.26 mmol) in $CH_2Cl_2$ (10 mL) was added triethylamine (80 mg, 0.78 mmol) at 0° C. followed by cyclopropanesulfonyl chloride (55 mg, 0.39 mmol) and DMAP (10 mg). The mixture was stirred at room temperature for 1 h and washed with saturated $NaHCO_3$ (aq.). The aqueous layer was extracted with $CH_2Cl_2$ (15 mL×2). The combined organic phase was washed with water (15 mL) and brine (20 mL) successively, dried over $Na_2SO_4$, filtered and concentrated in vacuo. The residue was purified by flash chromatography on silica gel (petroleum ether/ethyl acetate, 5:1, v/v) to give the corresponding product (110 mg, 86.5% yield). $^1$H NMR (400 MHz, $CDCl_3$): δ 8.09 (s, 1H), 7.99 (s, 1H), 7.71-7.69 (m, 2H), 7.32 (m, 1H), 3.35 (m, 1H), 1.69 (m, 2H), 0.88 (m, 2H).

Step 3: N-4-fluoro-5-((4-bromo-2-chlorophenyl) amino)benzo[d]oxazol-6-yl)cyclopropane sulfonamide To a solution of 5-(4-bromo-2-chlorophenyl)-7-(cyclopropylsulfonyl)-4-fluoro-5H-imidazo[4',5':4,5]benzo[1,2-d]oxazol-6(7H)-one (100 mg, 0.21 mmol) in THF (10 mL) was added potassium trimethylsilanolate (40 mg, 0.31 mmol). After stirring at room temperature for 1 h, the reaction was quenched with saturated $NH_4Cl$ (aq.). The aqueous layer was extracted with ethyl acetate (10 mL×2). The combined organic phase was washed with brine (20 mL), dried over $Na_2SO_4$, filtered and concentrated in vacuo. The residual crude product was purified by flash chromatography on silica gel (petroleum, ether/ethyl acetate, 5:1-3:1, v/v) and the product was obtained as a white solid (60 mg, 63.4% yield). $^1$H NMR (400 MHz, $CDCl_3$): δ 8.10 (s, 1H), 7.97 (s, 1H), 7.40 (m, 2H), 7.31-7.26 (m, 1H), 6.81 (s, 1H), 6.40-6.36 (m, 1H), 6.23 (s, 1H), 5.86-5.72 (m, 1H), 5.25-5.13 (m, 2H), 2.85 (d, 2H), 1.30-1.22 (m, 2H), 1.15-1.20 (m, 2H), 8.17 (s, 1H), 7.97 (s, 1H), 7.49 (dd, 1H), 7.35 (s, 1H), 7.26 (dd, 1H), 6.17 (m, 1H), 5.44 (s, 1H), 2.57 (m, 1H), 1.06-1.08 (m, 2H), 1.00-1.01 (m, 2H). MS APCI(+)m/z: 461.7, [M+H].

Example 8: Preparation of N-(5-((4-bromo-2-chlorophenyl)amino)-4-fluorobenzo[d]oxazol-6-yl)-1-(2,3-dihydroxypropyl)cyclopropane-1-sulfonamide (Compound 8)

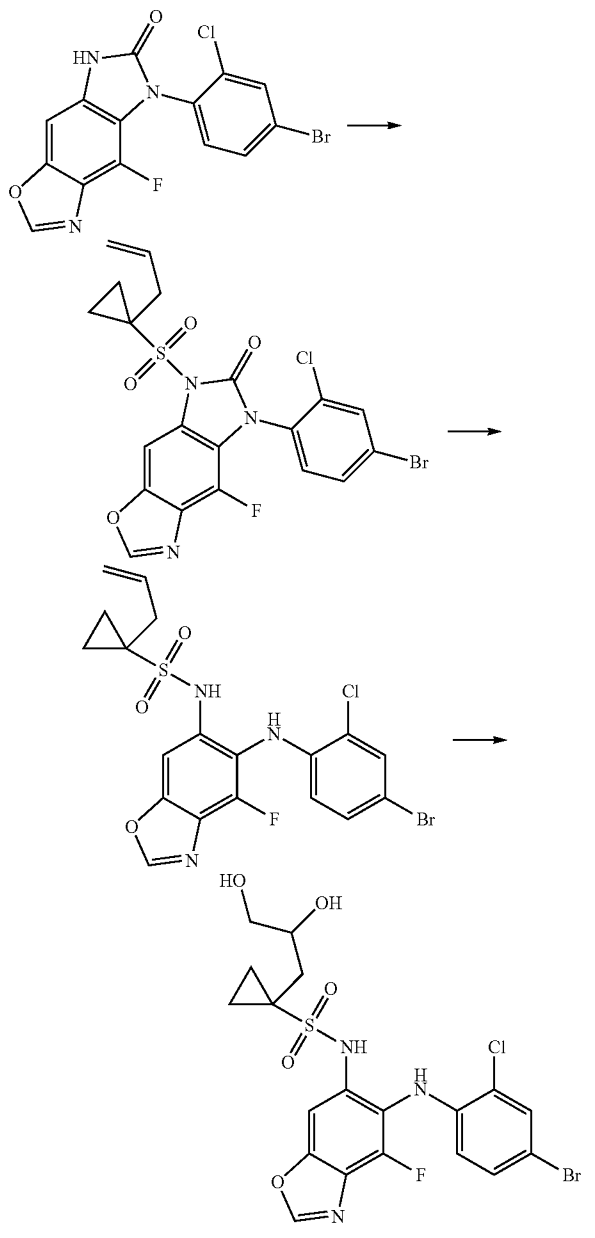

Step 1: 7-((1-allylcyclopropyl)sulfonyl)-4-fluoro-5-(4-bromo-2-chlorophenyl)-5H-imidazo[4',5':4,5]benzo[1, 2-d]oxazol-6(7H)-one To a solution of 5-(4-bromo-2-chlorophenyl)-4-fluoro-5H-imidazo[4',5':4,5]benzo[1,2-d]oxazol-6(7H)-one (100 mg, 0.26 mmol) in DCM (10 mL) was added triethylamine (80 mg, 0.78 mmol) at 0° C. followed by 1-allylcyclopropane-1-sulfonyl chloride (71 mg, 0.39 mmol) and DMAP (15 mg). After stirring at room temperature for 1 h, the reaction was treated with saturated $NaHCO_3$ (aq.). The aqueous layer was extracted with $CH_2Cl_2$ (20 mL×2). The combined organic phase was washed with water (20 mL) and brine (20 mL) sequentially, dried over $Na_2SO_4$, filtered and concentrated to give a residue, which was purified by flash chromatography on silica gel (petroleum ether/ethyl acetate, 5:1, v/v) to give the corresponding product (120 mg, 87.2% yield). $^1$H NMR (400 MHz, $CDCl_3$): δ 8.09 (s, 1H), 7.99 (s, 1H), 7.39-7.11 (d, 2H), 7.05, (m, 1H), 5.75-5.58 (m, 1H), 5.05 (m, 2H), 2.90-2.80 (m, 1H), 2.10-2.0 (m, 1H), 1.95-1.86 (m, 2H), 1.25-1.10 (m, 2H).

Step 2: 1-allyl-N-(4-fluoro-5-((4-bromo-2-chlorophenyl)amino)benzo[d]oxazol-6-yl)cyclopropane-1-sulfonamide To a solution of 7-((1-allylcyclopropyl)sulfonyl)-4-fluoro-5-(2-chloro-4-bromophenyl)-5H-imidazo[4',5':4,5]benzo[1,2-d]oxazol-6(7H)-one (120 mg, 0.23 mmol) in THF (5 mL) was added potassium trimethylsilanolate (32 mg, 0.23 mmol). The mixture was stirred at room, temperature for 1 h and treated with saturated $NH_4Cl$ (aq.). The aqueous layer was extracted with ethyl acetate (10 mL×2). The combined organic phase was washed with brine (20 mL), dried over $Na_2SO_4$, filtered and concentrated to give a residue, which was purified by flash chromatography on silica gel (petroleum ether/ethyl acetate, 5:1-3:1, v/v) to give the product as a white solid (100 mg, 87.6% yield). $^1$H NMR (400 MHz, $CDCl_3$): δ 8.09 (s, 1H), 7.99 (s, 1H), 7.42 (d, 1H), 7.31-7.25 (m, 1H), 6.80 (s, 1H), 6.43-6.35 (m, 1H), 6.21 (s, 1H), 5.85-5.70 (m, 1H), 5.22-5.14 (m, 2H), 2.83 (d, 2H), 1.28-1.20 (m, 2H), 0.87-0.80 (m, 2H).

Step 3: 1-(2,3-dihydroxypropyl)-N-(4-fluoro-5-((4-bromo-2-chloro phenyl)amino)benzo[d]oxazol-6-yl) cyclopropane-1-sulfonamide To a solution of 1-allyl-N-(4-fluoro-5-((4-bromo-2-chlorophenyl)amino)benzo[d]oxazol-6-yl)cyclopropane-1-sulfonamide (100 mg, 0.38 mmol) in THF (10 mL) was added N-methylmorpholine-N-oxide (44 mg, 0.38 mmol) followed by osmium tetraoxide (10 mg, 0.04 mmol) and water (0.5 mL). After stirring at room temperature overnight, the mixture was concentrated and then diluted with EA. The organic layer was washed with water, saturated $NaHCO_3$ (aq.) and brine sequentially, dried over $Na_2SO_4$, filtered and concentrated to give a residue, which was purified by flash chromatography to give the product as white solid (30 mg, 28.2% yield). $^1$H NMR (400 MHz, $CDCl_3$): δ 8.10 (s, 1H), 7.98 (s, 1H), 7.45-7.34 (m, 2H), 7.32-7.21 (m, 1H), 6.83 (s, 1H), 6.44-6.30 (m, 1H), 4.41-4.25 (m, 2H), 4.21-4.12 (m, 1H), 3.72-3.62 (m, 1H), 2.85-2.78 (m, 1H), 1.32-1.26 (m, 2H), 1.16-1.21 (m, 4H). MS APCI(+)m/z: 535.8, [M+H].

Example 9: Preparation of 4-fluoro-5-((2-fluoro-4-iodophenyl)amino)-N-(2-hydroxyethoxy)benzo[d]thiazole-6-carboxamide (Compound 9)

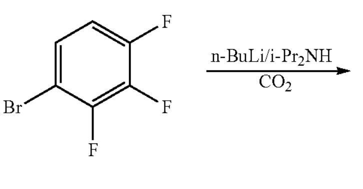

-continued

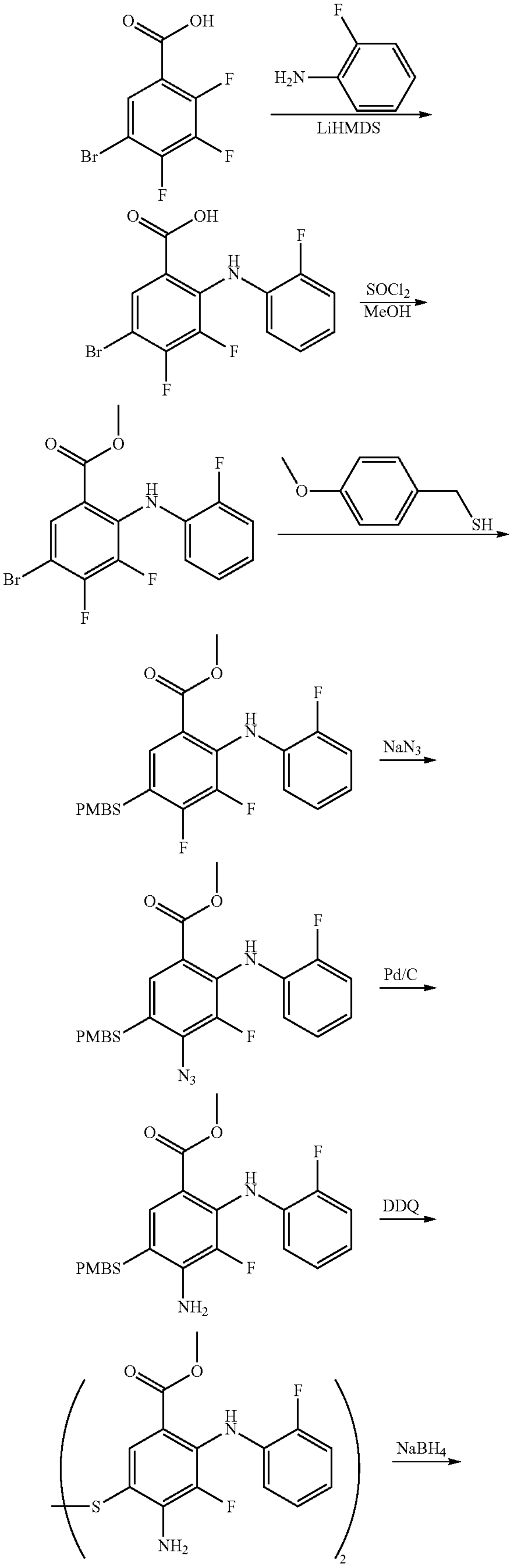

-continued

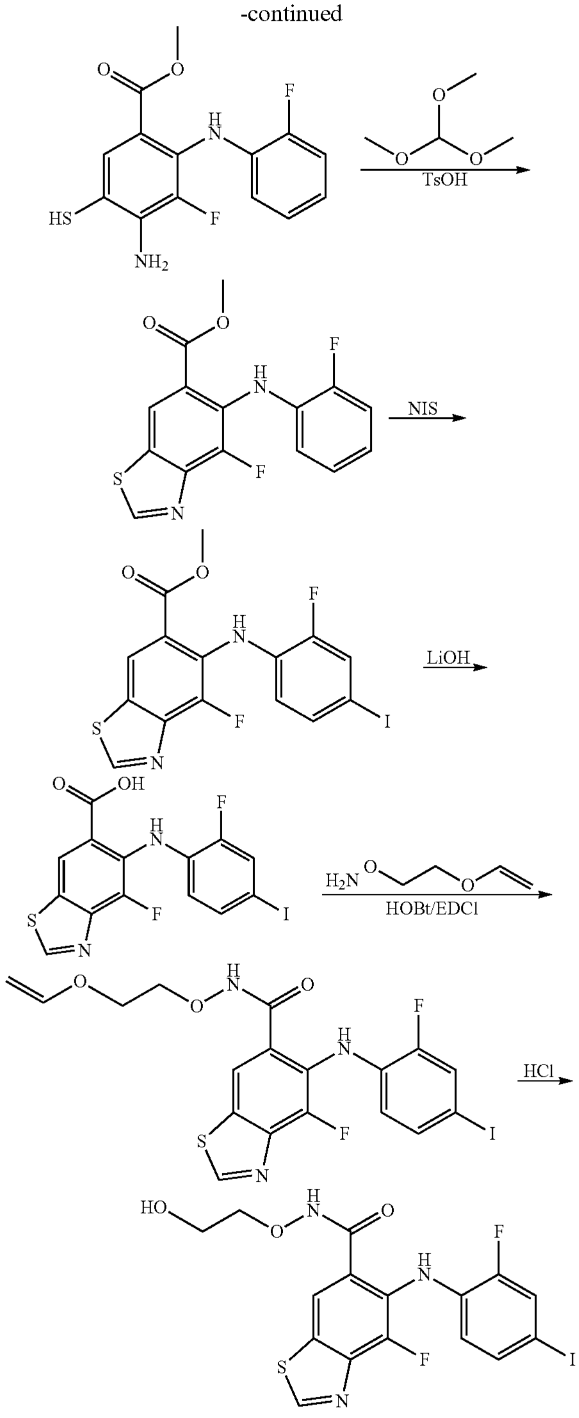

Step 1: 5-bromo-2,3,4-trifluorobenzoic acid

To a solution of diisopropylamine (10.14 g, 100.20 mmol) in THF (100 mL) was added n-BuLi (40.08 mL, 2.5 M in hexane, 100.20 mmol) at −78° C. under nitrogen atmosphere. The stirring was maintained at this temperature for 1 h. Then a solution of 1-bromo-2,3,4-trifluorobenzene (17.62 g, 83.50 mmol) in THF (120 mL) was added. After stirring for 1 h at −78° C., the mixture was transferred to a bottle with dry ice. The mixture was stirred overnight at room temperature. The reaction was quenched with 10% aqueous HCl and pH was adjusted to 1-2. The mixture was extracted with ethyl acetate (100 mL×3). The combined organic extracts were washed with water (100 mL) and brine (100 mL) sequentially, dried over $Na_2SO_4$, filtered and concentrated under reduced pressure to afford the desired product (20.12 g, 94.5% yield). $^1H$ NMR (400 MHz, DMSO-$d_6$): δ 13.95 (s, 1H), 7.97 (m, 1H).

Step 2: 5-bromo-3,4-difluoro-2-((2-fluorophenyl) amino)benzoic acid

To a solution of 2-fluoroaniline (17.54 g, 157.80 mmol) and 5-bromo-2,3,4-trifluorobenzoic acid (20.12 g, 78.90 mmol) in THF (120 mL) was added LiHMDS (236.7 mL, 1 M in THF, 236.7 mmol) dropwisely at −78° C. under nitrogen atmosphere. The mixture was allowed to slowly warm to room temperature and stirred at this temperature overnight. The reaction was quenched with water (100 mL) and acidified to pH 2-3 with 10% HCl (aq.). The mixture was extracted with ethyl acetate (100 mL×3). The combined organic extracts were washed with water (100 mL) and brine (100 mL) sequentially, dried over $Na_2SO_4$, filtered and concentrated in vacuo to afford the desired product (pale yellow solid, 24.24 g, 88.8% yield). $^1H$ NMR (400 MHz, DMSO-$d_6$): δ 9.22 (s, 1H), 8.01 (dd, J=7.4, 2.1 Hz, 1H), 7.25 (m, 1H), 7.10 (m, 3H).

Step 3: methyl 5-bromo-3,4-difluoro-2-((2-fluorophenyl)amino)benzoate

To a solution of 5-bromo-3,4-difluoro-2-((2-fluorophenyl)amino)benzoic acid (24.24 g, 70.04 mmol) in MeOH (300 mL) was added thionyl chloride (20 mL). After stirring at 85° C. overnight, most MeOH was removed in vacuo. The residue was neutralized with saturated sodium bicarbonate (aq.) and extracted with ethyl acetate (100 mL×3). The combined organic layer was washed with water (100 mL) and brine (100 mL) sequentially, dried over $Na_2SO_4$, filtered and concentrated. After purification by column chromatography on silica gel (petroleum ether/ethyl acetate, 50:1, v/v), the corresponding product was obtained as a white solid (22.33 g, 88.5% yield). $^1H$ NMR (400 MHz, $CDCl_3$): δ 9.06 (s, 1H), 8.01 (dd, J=7.1, 2.3 Hz, 1H), 7.04 (m, 4H), 3.92 (s, 3H).

Step 4: methyl 3,4-difluoro-2-((2-fluorophenyl) amino)-5-((4-methoxybenzyl)thio)benzoate To a solution of methyl 5-bromo-3,4-difluoro-2-((2-fluorophenyl)amino)benzoate (22.33 g, 62.01 mmol) in anhydrous 1,4-dioxane (200 mL) was added N,N-diisopropylethylamine (16.03 g, 124.04 mmol). Then $Pd_2(dba)_3$ (2.84 g, 3.10 mmol) followed by Xantphos (3.59 g, 6.20 mmol) and 4-methoxy-α-toluenethiol (10.27 g, 65.11 mmol) was added under nitrogen atmosphere. The mixture was stirred overnight at 100° C. under $N_2$ atmosphere and then allowed to warm to ambient temperature. The insoluble matter was filtered off and the filter cake was washed ethyl acetate. The filtrate was diluted with water (300 mL) and extracted with ethyl acetate (100 mL×3). The combined organic layers were washed with water (100 mL) and brine (100 mL) sequentially, dried over $Na_2SO_4$, filtered and concentrated. The crude product was purified by column chromatography on silica gel (petroleum ether/ethyl acetate, 50:1, v/v) to give the desired product (pale yellow solid, 24.35 g, 90.6% yield). $^1H$ NMR (400 MHz, $CDCl_3$): δ 9.12 (s, 1H), 7.78 (d, 1H), 7.25 (m, 6H), 6.85 (m, 2H), 4.03 (s, 2H), 3.90 (s, 3H), 3.80 (s, 3H).

Step 5: methyl 4-azido-5-(4-methoxybenzylthio)-3-fluoro-2-((2-fluorophenyl)amino)benzoate To a solution of methyl 5-(4-methoxybenzylthio)-3,4-difluoro-2-((2-fluorophenyl)amino)benzoate (24.35 g, 56.18 mmol) in DMF (200 mL) was added $NaN_3$ (4.38 g, 67.41 mmol) at ambient temperature. The mixture was stirred at 90° C. for 3 h. Then water (200 mL) was added. The solution was extracted with ethyl acetate (100 mL×3). The combined organic extracts were washed with water (100 mL) and brine (100 mL), dried over $Na_2SO_4$ and concentrated in vacuo. The residue was purified by flash column chromatography on silica gel (petroleum ether/ethyl acetate, 10:1, v/v) and gave the desired product (white solid, 21.04 g, 82.1% yield). $^1H$ NMR (400 MHz, $CDCl_3$): δ 8.98 (s, 1H), 7.75 (s, 1H), 7.10 (m, 6H), 6.84 (m, 2H), 4.03 (s, 2H), 3.92 (s, 3H), 3.81 (s, 3H).

Step 6: methyl 4-amino-5-(4-methoxybenzylthio)-3-fluoro-2-((2-fluorophenyl)amino)benzoate To a solution of methyl 4-azido-5-(4-methoxybenzylthio)-3-fluoro-2-((2-fluorophenyl)amino)benzoate (21.04 g, 46.09 mmol) in MeOH (500 mL) was added and 10% palladium on carbon (3.40 g) under nitrogen atmosphere. Then the nitrogen atmosphere was completely changed to hydrogen atmosphere. The mixture was stirred for 2 h at ambient temperature. After the insoluble matter was filtered off, the solvent was evaporated in vacuo to give the desired product (19.46 g, 98.1% yield). $^1H$ NMR (400 MHz, $CDCl_3$): δ 9.07 (s, 1H), 7.77 (s, 1H), 7.06 (m, 1H), 6.95 (m, 2H), 6.81 (d, J=8.3 Hz, 2H), 4.68 (s, 2H), 3.85 (s, 5H), 3.81 (s, 3H).

Step 7: dimethyl 5,5'-disulfanediylbis(4-amino-3-fluoro-2-((2-fluorophenyl)amino)benzoate)

To a solution of methyl 4-amino-5-(4-methoxybenzylthio)-3-fluoro-2-((2-fluorophenyl)amino)benzoate (19.46 g, 45.21 mmol) in $CH_2Cl_2$ (180 mL) was added DDQ (11.29 g, 49.73 mmol) followed by water (20 mL). After stirring at ambient temperature for 10 h, the reaction was quenched by saturated sodium bicarbonate (aq., 100 mL). The aqueous layer was extracted by $CH_2Cl_2$ (100 mL×3). The combined organic phase was washed with water (100 mL) and brine (100 mL) sequentially, dried over $Na_2SO_4$, filtered and concentrated. The crude product was purified by column chromatography on silica gel (petroleum ether/ethyl acetate, 5:1, v/v) to give the desired product (pale yellow solid, 9.81 g, 35.1% yield). $^1H$ NMR (400 MHz, $CDCl_3$): δ 9.34 (s, 2H), 7.46 (s, 2H), 7.06 (m, 8H), 4.89 (br, 4H), 3.75 (s, 6H).

Step 8: methyl 4-amino-3-fluoro-2-((2-fluorophenyl)amino)-5-mercaptobenzoate

To a solution of dimethyl 5,5'-disulfanediylbis(4-amino-3-fluoro-2-((2-fluorophenyl)amino)benzoate) (9.81 g, 15.86 mmol) in THF/MeOH (100 mL, 10:1, v/v) was added $NaBH_4$ (3.00 g, 79.29 mmol) portion-wise in 1 h. After stirring at ambient temperature for 1 h, the reaction was quenched with 10% HCl (aq.) and pH was adjusted to 1-2. The aqueous layer was extracted with $CH_2Cl_2$ (50 mL×3). The combined organic phase was washed with water (50 mL) and brine (50 mL) sequentially, dried over $Na_2SO_4$, filtered and concentrated in vacuo. The crude product was used directly in the next step without further purification.

Step 9: methyl 4-fluoro-5-((2-fluorophenyl)amino) benzo[d]thiazole-6-carboxylate To a solution of methyl 4-amino-3-fluoro-2-((2-fluorophenyl)amino)-5-mercaptobenzoate in trim ethyl orthoformate (50 mL) was added p-TsOH (0.61 g, 3.17 mmol). The reaction mixture was stirred for 1 h and treated with water (100 mL). The precipitate was filtered off and the filter cake was washed with water to afford the desired product (pale yellow solid, 8.64 g, 85.1% yield for two steps), $^1$H NMR (400 MHz, $CDCl_3$): δ 9.13 (s, 1H), 8.68 (s, 1H), 8.46 (s, 1H), 7.10 (m, 1H), 7.01 (m, 1H), 6.92 (s, 2H), 3.97 (s, 3H).

Step 10: methyl 4-fluoro-5-((2-fluoro-4-iodophenyl) amino)benzo[d]thiazole-6-carboxylate To a solution of methyl 4-fluoro-5-((2-fluorophenyl) amino)benzo[d]thiazole-6-carboxylate (8.64 g, 26.97 mmol) in DMF (100 mL) was added NIS (6.68 g, 29.67 mmol) followed by trifluoroacetic acid (0.5 mL). After stirring for 5 h at ambient temperature, the reaction was treated by water (150 mL). The precipitate was filtered off and the filter cake was washed with water. The desired product was obtained as a yellow solid (10.34 g, 86.0% yield). $^1$H NMR (400 MHz, $CDCl_3$): δ 9.14 (s, 1H), 8.66 (s, 1H), 8.46 (s, 1H), 7.42 (d, J=10.4 Hz, 1H), 7.31 (d, J=8.8 Hz, 1H), 6.63 (dd, J=15.0, 8.7 Hz, 1H), 3.97 (s, 3H).

Step 11: 4-fluoro-5-((2-fluoro-4-iodophenyl)amino) benzo[d]thiazole-6-carboxylic acid To a solution of methyl 4-fluoro-5-((2-fluoro-4-iodophenyl)amino)benzo[d]thiazole-6-carboxylate (10.34 g, 23.17 mmol) in THF and MeOH (20 mL, 4:1, v/v) was added 5.0 M LiOH (aq., 2 mL, 10 mmol). After stirring at ambient temperature for 2 h, the reaction was treated with 1.0 M HCl (aq.) till the solution was acidic. The aqueous layer was extracted with ethyl acetate (50 mL×3). The combined organic phase was washed with water (100 mL) and brine (100 mL) sequentially, dried over $Na_2SO_4$, filtered and concentrated to give the desired product (9.51 g, 95.0% yield). $^1$H NMR (400 MHz, DMSO-$d_6$): δ 11.10 (s, 1H), 9.18 (s, 1H), 8.68 (s, 1H), 8.45 (s, 1H), 7.41 (m, 1H), 7.30 (m, 1H), 6.65 (m, 1H).

Step 12: 4-fluoro-5-((2-fluoro-4-iodophenyl)amino)-N-(2-(vinyloxy)ethoxy)benzo[d]thiazole-6-carboxamide To a solution of 4-fluoro-5-((2-fluoro-4-iodophenyl) amino)benzo[d]thiazole-6-carboxylic acid (519 mg, 1.20 mmol) in $CH_2Cl_2$ (10 mL) was added HOBt (254 mg, 1.63 mmol) and EDCI (314 mg, 1.63 mmol). The mixture was stirred for 1 h and O-(2-(vinyloxy)ethyl)hydroxyl-amine (172 mg, 1.62 mmol) was added. After stirring for 4 h at ambient temperature, the reaction was treated with saturated $NH_4Cl$ (aq.). The resultant mixture was extracted with $CH_2Cl_2$ (30 mL×3). The combined organic extracts were washed with water (30 mL) and brine (30 mL), dried over $Na_2SO_4$ filtered, and concentrated in vacuo. The crude product (492 mg) was used directly in the next step without further purification.

Step 13: 4-fluoro-5-((2-fluoro-4-iodophenyl)amino)-N-(2-hydroxyethoxy)benzo[d]thiazole-6-carboxamide To a solution of 4-fluoro-5-((2-fluoro-4-iodophenyl) amino)-N-(2-(vinyloxy)ethoxy)benzo[d]thiazole-6-carboxamide (492 mg, 1.00 mmol) in $CH_2Cl_2$ (10 mL) was added 1.0 HCl (aq., 5 mL, 5 mmol). After stirring for 1 h, the reaction mixture was neutralized with saturated $NaHCO_3$ (aq.). The aqueous layer was washed with $CH_2Cl_2$ (30 mL). The combined organic layer was washed with water (30 mL×2) and brine (30 mL), dried over $Na_2SO_4$, filtered and concentrated in vacuo. The crude product was purified by column chromatography on silica gel ($CH_2Cl_2$, 50:1, v/v) and gave the desired product as a white solid (446 mg, 75.9% yield for the two steps). $^1$H NMR (400 MHz, DMSO-$d_6$): δ 11.80 (s, 1H), 9.55 (s, 1H), 8.22 (s, 1H), 8.12 (s, 1H), 7.55 (d, J=11.0 Hz, 1H), 7.31 (d, J=8.5 Hz, 1H), 6.48 (d, J=9.2 Hz, 1H), 4.72 (s, 1H), 3.84 (m, 2H), 3.57 (m, 2H). MS APCI(+)m/z: 491.8, [M+H].

Example 9A: Preparation of 4-fluoro-5-((2-fluoro-4-iodophenyl)amino)-N-(2-hydroxyethoxy)benzo[d]thiazole-6-carboxamide (Compound 9)

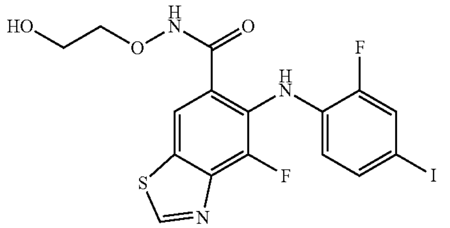

Step 1: 5-bromo-2,3,4-trifluorobenzoic acid

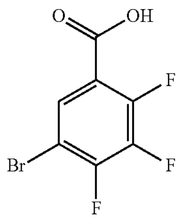

To a solution of 1-bromo-2,3,4-trifluorobenzene (13.64 g, 64.6 mmol) in THF (120 mL) was added lithium diisopropylamide (2.0 M in THF, 33.9 mL, 67.8 mmol) at −78° C. under nitrogen atmosphere. After stirring for 1 h at −78° C., the mixture was transferred to a bottle with dry ice. The mixture was stirred overnight at room temperature. The reaction was quenched with 10% aqueous HCl (300 mL) and extracted with ethyl acetate (200 mL×3). The combined organic extracts were washed with 5% sodium hydroxide (300 mL). The aqueous layer was acidized to pH 1 and extracted with ethyl acetate (200 mL×3). The combined organic extract was dried over $Na_2SO_4$, filtered and concentrated under reduced pressure to afford the desired product (white solid, 13.51 g, 82% yield). $^1$H NMR (400 MHz, $CDCl_3$): δ 13.94 (s, 1H), 7.95 (m, 1H).

Step 2: 5-bromo-3,4-difluoro-2-((2-fluorophenyl)amino)benzoic acid

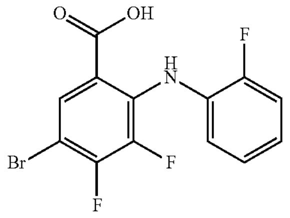 [SMILES: O=C(O)c1cc(Br)c(F)c(F)c1Nc1ccccc1F]

To a solution of 2-fluoroaniline (10.2 mL, 105.8 mmol) and 5-bromo-2,3,4-trifluorobenzoic acid (13.51 g, 52.9 mmol) in THF (120 mL) was added LiHMDS (158.7 mL, 1 M in THF, 158.7 mmol) dropwisely at −78° C. under nitrogen atmosphere. The mixture was allowed to slowly warm to room temperature and stirred at this temperature overnight. The reaction was quenched with 10% HCl (aq., 100 mL) and extracted with ethyl acetate (200 mL×3). The combined organic extracts were washed with water (200 mL×3) and brine (200 mL) sequentially, dried over $Na_2SO_4$, filtered and concentrated in vacuo to afford the desired product (pale yellow solid, 13.73 g, 75% yield). $^1H$ NMR (400 MHz, DMSO-$d_6$): δ 9.21 (s, 1H), 8.01 (d, 1H), 7.26 (m, 1H), 7.01-7.16 (m, 3H).

Step 3: methyl 5-bromo-3,4-difluoro-2-((2-fluorophenyl)amino)benzoate

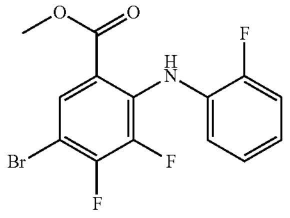 [SMILES: COC(=O)c1cc(Br)c(F)c(F)c1Nc1ccccc1F]

To a solution of 5-bromo-3,4-difluoro-2-((2-fluorophenyl)amino)benzoic acid (13.73 g, 39.6 mmol) in MeOH (300 mL) was added $SOCl_2$ (60 mL). After stirring at 85° C. overnight, most MeOH was removed in vacuo. The residue was neutralized with saturated sodium bicarbonate (aq.) and extracted with ethyl acetate (300 mL×3). The combined organic extract was washed with water (200 mL×3) and brine (200 mL) sequentially, dried over $Na_2SO_4$, filtered and concentrated in vacuo to afford the corresponding product (gray solid, 12.58 g, 90% yield). $^1H$ NMR (400 MHz, $CDCl_3$): δ 9.09 (s, 1H), 8.05 (d, 1H), 7.00-7.14 (m, 4H), 3.94 (s, 3H).

Step 4: methyl 3,4-difluoro-2-((2-fluorophenyl)amino)-5-((4-methoxybenzyl)thio)benzoate

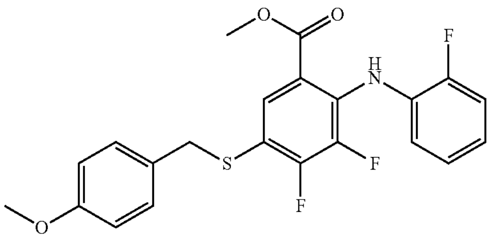 [SMILES: COC(=O)c1cc(SCc2ccc(OC)cc2)c(F)c(F)c1Nc1ccccc1F]

To a solution of methyl 5-bromo-3,4-difluoro-2-((2-fluorophenyl)amino)benzoate (12.85 g, 35.6 mmol) in anhydrous 1,4-dioxane (30 mL) was added N,N-diisopropylethylamine (9.21 g, 71.2 mmol). Then $Pd_2(dba)_3$ (1.63 g, 1.78 mmol) followed by Xantphos (2.06 g, 3.56 mmol) and 4-methoxy-α-toluenethiol (5.48 g, 35.6 mmol) was added under nitrogen atmosphere. The mixture was stirred overnight at 100° C. under $N_2$ atmosphere and then allowed to cool to ambient temperature. The reaction was quenched with water (150 mL) and extracted with ethyl acetate (200 mL×3). The combined organic extract was washed with water (200 mL×3) and brine (200 mL) sequentially, dried over $Na_2SO_4$, filtered and concentrated. The crude product was purified by column chromatography on silica gel (petroleum ether/ethyl acetate, 50:1, v/v) to give the desired product (pale yellow solid, 12.64 g, 82% yield). $^1H$ NMR (400 MHz, $CDCl_3$): δ 9.12 (s, 1H), 7.78 (d, 1H), 7.06-7.44 (m, 6H), 6.82-6.88 (m, 2H), 4.03 (s, 2H), 3.90 (s, 3H), 3.80 (s, 3H).

Step 5: methyl 4-azido-5-(4-methoxybenzylthio)-3-fluoro-2-((2-fluorophenyl)amino)benzoate

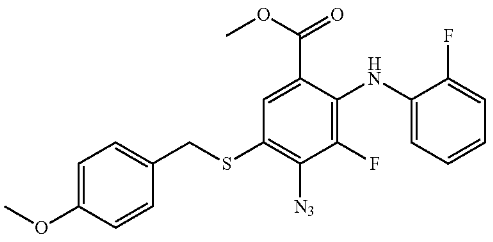 [SMILES: COC(=O)c1cc(SCc2ccc(OC)cc2)c(N=[N+]=[N-])c(F)c1Nc1ccccc1F]

To a solution of methyl 5-(4-methoxybenzylthio)-3,4-difluoro-2-((2-fluorophenyl)amino)benzoate (12.64 g, 29.2 mmol) in DMF (30 mL) was added $NaN_3$ (2.28 g, 35.0 mmol) at ambient temperature. The mixture was stirred at 90° C. for 3 h. Then water (150 mL) was added. The solution was extracted with ethyl acetate (100 mL×3). The combined organic extracts were washed with water (100 mL×3) and brine (100 mL), dried over $Na_2SO_4$ and concentrated in vacuo. The residue was purified by flash column chromatography on silica gel (petroleum ether/ethyl acetate, 10:1, v/v) and gave the desired product (white solid, 10.38 g, 78% yield). $^1H$ NMR (400 MHz, $CDCl_3$): δ 8.98 (s, 1H), 7.75 (s, 1H), 7.02-7.28 (m, 6H), 6.83-6.85 (m, 2H), 4.03 (s, 2H), 3.92 (s, 3H), 3.81 (s, 3H).

Step 6: methyl 4-amino-5-(4-methoxybenzylthio-3-fluoro-2-((2-fluorophenyl)amino)benzoate

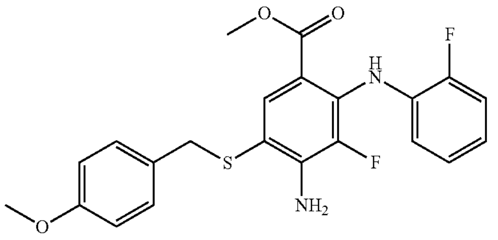 [SMILES: COC(=O)c1cc(SCc2ccc(OC)cc2)c(N)c(F)c1Nc1ccccc1F]

To a solution of methyl 4-azido-5-(4-methoxybenzylthio)-3-fluoro-2-((2-fluorophenyl)amino)benzoate (10.38 g, 22.7 mmol) in MeOH (100 mL) was added and 10% palladium on carbon (1.55 g) under nitrogen atmosphere. Then the nitrogen atmosphere was completely changed to hydrogen atmosphere. The mixture was stirred at ambient temperature for 6 h. After the insoluble matter was filtered off, the solvent was evaporated in vacuo to give the desired product (9.79 g, 100% yield). $^1$H NMR (400 MHz, $CDCl_3$): δ 9.08 (s, 1H), 7.78 (s, 1H), 6.93-7.28 (m, 8H), 4.65 (s, 2H), 4.00 (s, 2H), 3.89 (s, 3H), 3.75 (s, 3H).

Step 7: methyl 4-amino-3-fluoro-2-((2-fluorophenyl)amino)-5-mercaptobenzoate

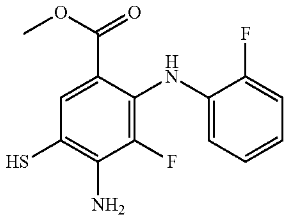 [SMILES: COC(=O)c1cc(S)c(N)c(F)c1Nc1ccccc1F]

To a solution of methyl 4-amino-3-fluoro-2-((2-fluorophenyl)amino)-5-((4-methoxybenzyl)thio)benzoate (9.79 g, 22.7 mmol) in anisole (12 mL) was added $CF_3COOH$ (20 mL). After stirring at ambient temperature for 23 h, the solvent was removed in vacuo. To the residue was added water (30 mL). The mixture was neutralized with 25% aqueous ammonia, and extracted with ethyl acetate (100 mL×3). The combined organic layer was washed with water (100 mL×3) and brine (100 mL) sequentially, dried over $Na_2SO_4$, filtered and concentrated to give the desired product (white solid, 5.28 g, 75% yield). The product was used directly in the next step without further purification.

Step 8: methyl 4-fluoro-5-((2-fluorophenyl)amino)benzo[d]thiazole-6-carboxylate

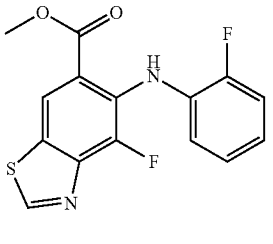 [SMILES: COC(=O)c1cc2scnc2c(F)c1Nc1ccccc1F]

To a solution of methyl 4-amino-3-fluoro-2-((2-fluorophenyl)amino)-5-mercaptobenzoate (2.07 g, 6.67 mmol) in trimethyl orthoformate (20 mL) was added p-TsOH (166 mg, 0.65 mmol). The reaction mixture was stirred for 1 h and treated with water (100 mL). The precipitate was filtered off and the filter cake was washed with water to afford the desired product (white solid, 1.963 g, 92% yield for two steps). $^1$H NMR (400 MHz, DMSO-$d_6$): δ 9.01 (s, 1H), 8.08 (s, 1H), 7.90 (s, 1H), 7.15-6.78 (m, 4H), 3.91 (s, 3H).

Step 9: methyl 4-fluoro-5-((2-fluoro-4-iodophenyl)amino)benzo[d]thiazole-6-carboxylate

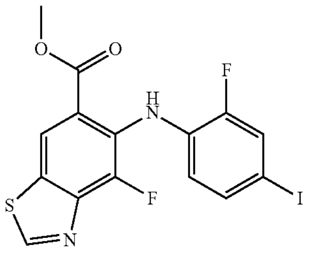 [SMILES: COC(=O)c1cc2scnc2c(F)c1Nc1ccc(I)cc1F]

To a solution of methyl 4-fluoro-5-((2-fluorophenyl)amino)benzo[d]thiazole-6-carboxylate (1.963 g, 6.14 mmol) in DMF (10 mL) was added NIS (1.5 g, 6.5 mmol) followed by trifluoroacetic acid (0.5 mL). After stirring for 4 h at ambient temperature, the reaction was treated by saturated $NH_4Cl$ (aq.). The aqueous layer was extracted with ethyl acetate (150 mL×3). The combined organic layer was washed with water (100 mL×3) and brine (100 mL) sequentially, dried over $Na_2SO_4$, filtered and concentrated in vacuo. After purification by flash column chromatography on silica gel (petroleum ether/ethyl acetate, 10:1, v/v), the desired product was obtained as white solid (1.889 g, 69% yield). $^1$H NMR (400 MHz, DMSO-$d_6$): δ 9.03 (s, 1H), 8.10 (s, 1H), 7.93 (s, 1H), 7.18-6.72 (m, 3H), 3.91 (s, 3H).

Step 10: 4-fluoro-5-((2-fluoro-4-iodophenyl)amino)-N-(2-(vinyloxy)ethoxy)benzo[d]thiazole-6-carboxamide

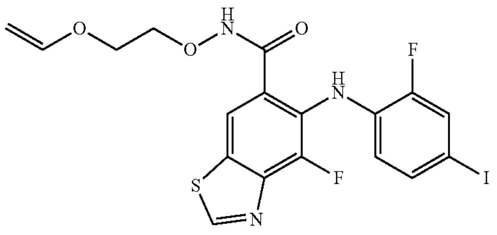 [SMILES: C=COCCONC(=O)c1cc2scnc2c(F)c1Nc1ccc(I)cc1F]

To a solution of O-(2-(vinyloxy)ethyl)hydroxyl-amine (172 mg, 1.62 mmol) in THF (6 mL) was added LiHMDS (2.5 mL, 1 M in THF, 2.5 mmol) at −78° C. After stirring at this temperature for 10 min, a solution of methyl 4-fluoro-5-((2-fluoro-4-iodophenyl)amino)benzo[d]thiazole-6-carboxylate (360 mg, 0.81 mmol) in THF was syringed dropwisely. Then the mixture was allowed to warm to ambient temperature, quenched with saturated $NH_4Cl$ (aq., 20 mL) and extracted with ethyl acetate (15 mL×3). The combined organic extract was washed with water (10 mL×3) and brine (10 mL), dried over $Na_2SO_4$, filtered and concentrated in vacuo. After purification by flash chromatography (petroleum ether/ethyl acetate, 10:1, v/v), the desired product was obtained (410 mg, 98% yield). $^1H$ NMR (400 MHz, DMSO-$d_6$): δ 11.85 (s, 1H), 8.98 (s, 1H), 8.04 (s, 1H), 7.89 (s, 1H), 7.55 (d, J=10.8 Hz, 1H), 7.31 (d, J=8.1 Hz, 1H), 6.53 (dd, J=13.9, 6.6 Hz, 1H), 6.42 (d, J=6.0 Hz, 1H), 4.21 (d, J=14.5 Hz, 1H), 4.01 (m, 3H), 3.83 (m, 2H).

Step 11: 4-fluoro-5-((2-fluoro-4-iodophenyl)amino)-N-(2-hydroxyethoxy)benzo[d]thiazole-6-carboxamide

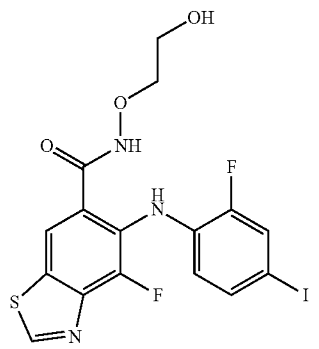 [SMILES: O=C(NOCCO)c1cc2scnc2c(F)c1Nc1ccc(I)cc1F]

To a solution of 4-fluoro-5-((2-fluoro-4-iodophenyl)amino)-N-(2-(vinyloxy)ethoxy)benzo[d]thiazole-6-carboxamide (410 mg, 0.8 mmol) in $CH_2Cl_2$ (5 mL) was added 1.0 N HCl (aq., 5 mL, 5 mmol) dropwise. After stirring for 1 h, the reaction mixture was neutralized with saturated $NaHCO_3$ (aq.). The organic layer was separated, washed with water (30 mL×2) and brine (30 mL) sequentially, dried over $Na_2SO_4$, filtered and concentrated in vacuo. The crude product was purified by column chromatography on silica gel ($CH_2Cl_2$/MeOH, 15:1, v/v) and the desired product was obtained as a white solid (290 mg, 52% yield). $^1H$ NMR (400 MHz, DMSO-$d_6$): δ 11.83 (s, 1H), 8.92 (s, 1H), 8.03 (s, 1H), 7.90 (s, 1H), 7.56 (d, J=9.4 Hz, 1H), 7.30 (d, J=8.7 Hz, 1H), 6.41 (m, 1H), 4.72 (m, 1H), 3.85 (m, 2H), 3.59 (m, 2H). MS (ES+): m/z 492.35 [$MH^+$].

Example 10: Preparation of N-(2,3-dihydroxypropoxy)-4-fluoro-5-((2-fluoro-4-iodophenyl)amino)benzo[d]thiazole-6-carboxamide (Compound 10)

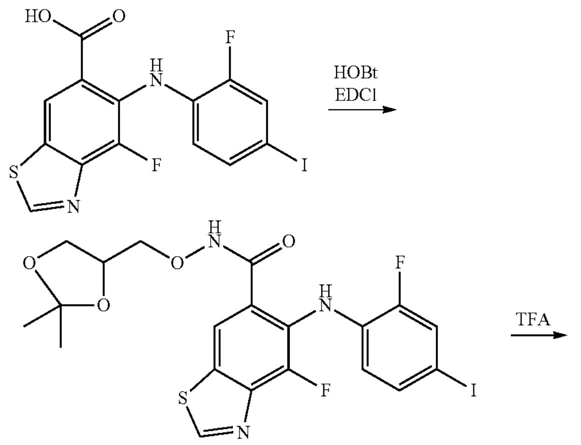

-continued

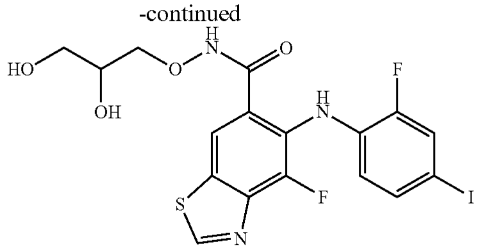

Step 1: N-((2,2-dimethyl-1,3-dioxolan-4-yl)methoxy)-4-fluoro-5-((2-fluoro-4-iodophenyl)amino)benzo[d]thiazole-6-carboxamide To a solution of 4-fluoro-5-((2-fluoro-4-iodophenyl)amino)benzo[d]thiazole-6-carboxylic acid (519 mg, 1.20 mmol) in $CH_2Cl_2$ (10 mL) was added HOBt (254 mg, 1.63 mmol) followed by EDCI (314 mg, 1.63 mmol). The mixture was stirred for 1 h and O-((2,2-dimethyl-1,3-dioxolan-4-yl)methyl)hydroxylamine (238 mg, 1.62 mmol) was added. After stirring for 4 h at ambient temperature, the reaction was treated with saturated $NH_4Cl$ (aq.). The resultant mixture was extracted with $CH_2Cl_2$ (30 mL×3). The combined organic extracts was washed by water (30 mL) and brine (30 mL) sequentially, dried over $Na_2SO_4$, filtered and concentrated in vacuo. The crude product (475 mg) was used directly in the next step without further purification.

Step 2: N-(2,3-dihydroxypropoxy)-4-fluoro-5-((2-fluoro-4-iodophenyl)amino)benzo[d]thiazole-6-carboxamide To a solution of N-((2,2-dimethyl-1,3-dioxolan-4-yl)methoxy)-4-fluoro-5-((2-fluoro-4-iodophenyl)amino)benzo[d]thiazole-6-carboxamide (475 mg, 0.85 mmol) in $CH_2Cl_2$ (10 mL) was added trifluoroacetic acid (0.2 mL, 2.69 mmol). The mixture was stirred for 1 h and neutralized with saturated sodium bicarbonate (aq.). The aqueous layer was extracted by $CH_2Cl_2$ (10 mL×2). The combined organic layers were washed by water (10 mL) and brine (10 mL) sequentially, dried over $Na_2SO_4$, filtered and concentrated in vacuo. The crude product was purified by column chromatography on silica gel ($CH_2Cl_2$/MeOH, 20:1, v/v) to afford the desired product (white solid, 310 mg, 45.4% yield for two steps). $^1H$ NMR (400 MHz, DMSO-$d_6$): δ 11.82 (s, 1H), 9.56 (s, 1H), 8.23 (s, 1H), 8.15 (s, 1H), 7.57 (d, 1H), 7.32 (d, 1H), 6.47 (m, 1H), 4.85 (d, 1H), 4.62 (m, 1H), 3.86 (m, 1H), 3.71 (m, 2H), 3.35 (m, 2H). MS APCI(+)m/z: 522.5 [M+H].

Example 11: Preparation of 5-((4-bromo-2-chlorophenyl)amino)-4-fluoro-N-(2-hydroxyethoxy)benzo[d]thiazole-6-carboxamide (Compound 11)

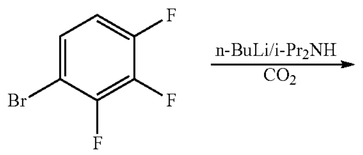

-continued

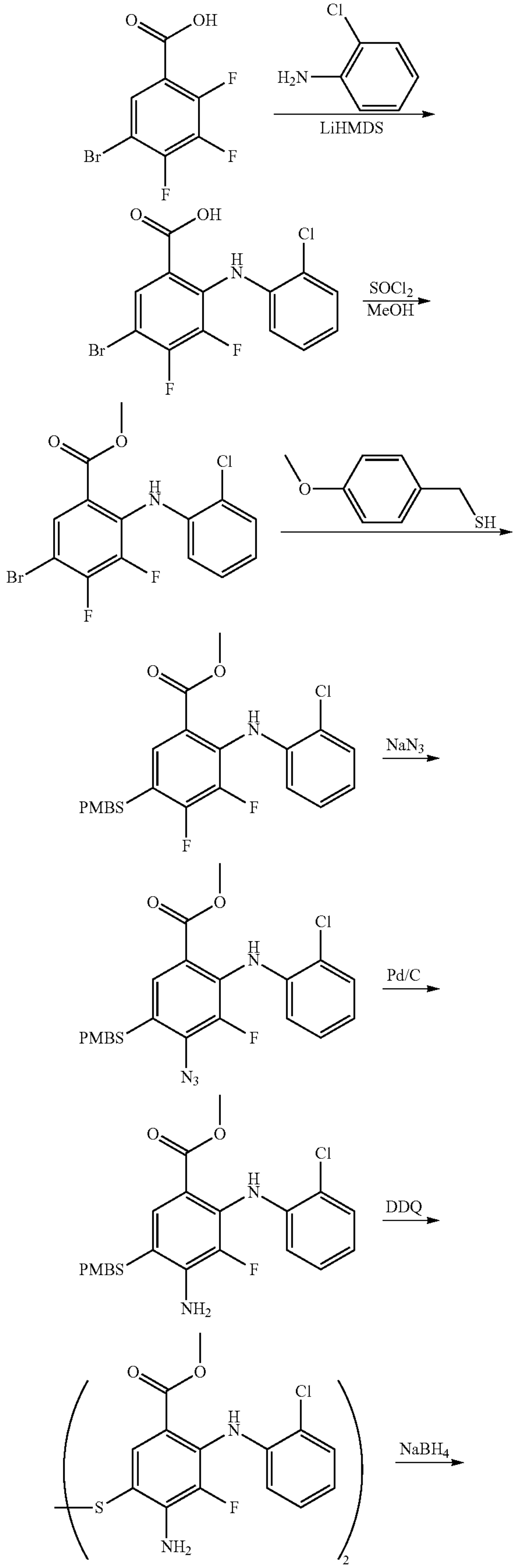

-continued

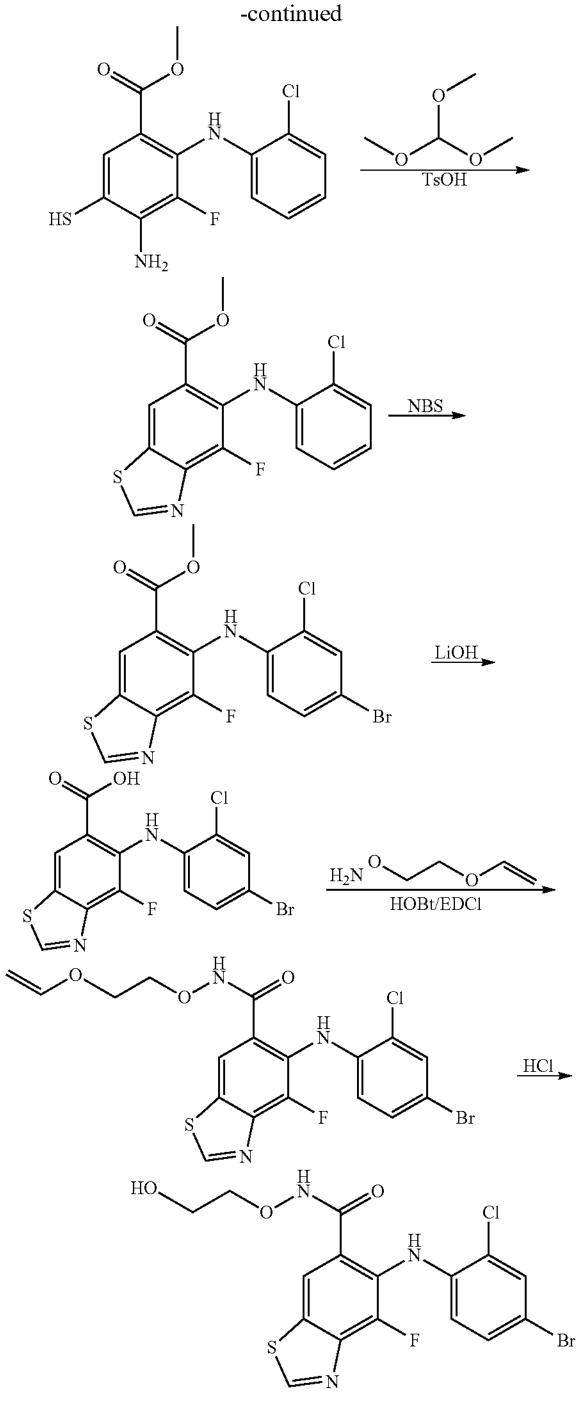

Step 1: 5-bromo-2,3,4-trifluorobenzoic acid

To a solution of diisopropylamine (10.14 g, 100.20 mmol) in THF (100 mL) was added n-BuLi (40.08 mL, 2.5 M in hexane, 100.20 mmol) at −78° C. under nitrogen atmosphere. The stirring was maintained at this temperature for 1 h. Then a solution of 1-bromo-2,3,4-trifluorobenzene (17.62 g, 83.50 mmol) in THF (120 mL) was added. After stirring for 1 h at −78° C., the mixture was transferred to a bottle with dry ice. The mixture was stirred overnight at room temperature. The reaction was quenched with 10% aqueous HCl and pH was adjusted to 1-2. The mixture was extracted with ethyl acetate (100 mL×3). The combined organic extracts were washed with water (100 mL) and brine (100 mL) sequentially, dried over $Na_2SO_4$, filtered and concentrated under reduced pressure to afford the desired product (20.12 g, 94.5% yield). $^1$H NMR (400 MHz, DMSO-$d_6$): δ 13.95 (s, 1H), 7.97 (m, 1H).

Step 2: 5-bromo-3,4-difluoro-2-((2-chlorophenyl) amino)benzoic acid

To a solution of 2-chloroaniline (20.13 g, 157.80 mmol) and 5-bromo-2,3,4-trifluorobenzoic acid (20.12 g, 78.90 mmol) in THF (120 mL) was added LiHMDS (236.7 mL, 1 M in THF, 236.7 mmol) dropwisely at −78° C. under nitrogen atmosphere. The mixture was allowed to slowly warm to room temperature and stirred at this temperature overnight. The reaction was quenched with water (100 mL) and acidified to pH 2-3 with 10% HCl (aq.). The mixture was extracted with ethyl acetate (100 mL×3). The combined organic extracts were washed with water (100 mL) and brine (100 mL) sequentially, dried over $Na_2SO_4$, filtered and concentrated in vacuo to afford the desired product (pale yellow solid, 25.63 g, 89.6% yield). $^1$H NMR (400 MHz, DMSO-$d_6$): δ 14.10 (s, 1H), 9.30 (s, 1H), 8.03 (m, 1H), 7.47 (m, 1H), 7.23 (m, 1H), 7.04 (m, 2H).

Step 3: methyl 5-bromo-3,4-difluoro-2-((2-chiorophenyl)amino)benzoate

To a solution of 5-bromo-3,4-difluoro-2-((2-chlorophenyl)amino)benzoic acid (25.63 g, 70.69 mmol) in MeOH (300 mL) was added thionyl chloride (20 mL). The resulting solution was stirred at 85° C. overnight. Most MeOH was removed in vacuo. The residue was neutralized with saturated sodium bicarbonate (aq.) and extracted with ethyl acetate (100 mL×3). The combined organic layer was washed with water (100 mL) and brine (100 mL) sequentially, dried over $Na_2SO_4$, filtered and concentrated. After purification by column chromatography on silica gel (petroleum ether/ethyl acetate, 50:1, v/v), the corresponding product was obtained as a white solid (22.84 g, 85.8% yield). $^1$H NMR (400 MHz, $CDCl_3$): δ 9.15 (s, 1H), 8.06 (m, 1H), 7.41 (m, 1H), 7.24 (m, 1H), 7.00 (m, 1H), 6.91 (m, 1H), 3.95 (s, 3H).

Step 4: methyl 3,4-difluoro-2-((chlorophenyl) amino)-5-((4-methoxybenzyl)thio)benzoate To a solution of methyl 5-bromo-3,4-difluoro-2-((2-chlorophenyl)amino)benzoate (22.84 g, 60.65 mmol) in anhydrous 1,4-dioxane (200 mL) was added N,N-diisopropylethylamine (15.68 g, 121.30 mmol). Then $Pd_2(dba)_3$ (2.78 g, 3.03 mmol) followed by Xantphos (3.51 g, 6.06 mmol) and 4-methoxy-α-toluenethiol (10.27 g, 66.72 mmol) was added under nitrogen atmosphere. The mixture was stirred overnight at 100° C. under $N_2$ atmosphere and then allowed to warm to ambient temperature. The insoluble matter was filtered off and the filter cake was washed ethyl acetate. The filtrate was diluted with water (300 mL) and extracted with ethyl acetate (100 mL×3). The combined organic layers were washed with water (100 mL) and brine (100 mL) sequentially, dried over $Na_2SO_4$, filtered and concentrated. The crude product was purified by column chromatography on silica gel (petroleum ether/ethyl acetate, 50:1, v/v) to give the desired product (pale yellow solid, 24.18 g, 88.6% yield). $^1$H NMR (400 MHz, $CDCl_3$): δ 9.14 (s, 1H), 7.77 (dd, 1H), 7.41 (dd, 1H), 7.24 (m, 3H), 7.19 (m, 1H), 7.01 (m, 1H), 6.88 (m, 2H), 4.02 (s, 2H), 3.92 (s, 3H), 3.81 (s, 3H).

Step 5: methyl 4-azido-5-(4-methoxybenzylthio)-3-fluoro-2-((2-chlorophenyl)amino)benzoate To a solution of methyl 5-(4-methoxybenzylthio)-3,4-difluoro-2-((2-chlorophenyl)amino)benzoate (24.18 g, 53.75 mmol) in DMF (200 mL) was added $NaN_3$ (4.19 g, 64.49 mmol) at ambient temperature. The mixture was stirred at 90° C. for 3 h. Then water (200 mL) was added. The solution was extracted with ethyl acetate (0.100 mL×3). The combined organic extracts were washed with water (100 mL) and brine (100 mL), dried over $Na_2SO_4$, filtered and concentrated in vacuo. The residue was purified by flash column chromatography on silica gel (petroleum ether/ethyl acetate, 10:1, v/v) and gave the desired product (pale yellow solid, 21.63 g, 85.1% yield). NMR (400 MHz, $CDCl_3$): δ 9.01 (s, 1H), 7.80 (s, 1H), 7.33 (m, 4H), 7.15 (m, 1H), 6.90 (m, 1H), 6.85 (m, 2H), 4.05 (s, 2H), 3.92 (s, 3H), 3.81 (s, 3H).

Step 6: methyl 4-amino-5-(4-methoxybenzylthio)-3-fluoro-2-((2-chlorophenyl)amino)benzoate To a solution of methyl 4-azido-5-(4-methoxybenzylthio)-3-fluoro-2-((2-chlorophenyl)amino)-benzoate (21.63 g, 4.5.74 mmol) in MeOH (500 mL) was added and 10% palladium on carbon (3.40 g) under nitrogen atmosphere. Then the nitrogen atmosphere was completely changed to hydrogen atmosphere. The mixture was stirred for 2 h at ambient temperature. After the insoluble matter was filtered off, the solvent, was evaporated in vacuo to give the desired product (19.93 g, 97.5% yield). $^1$H NMR (400 MHz, $CDCl_3$): δ 8.99 (s, 1H), 7.82 (s, 1H), 7.21 (m, 1H), 7.17 (m, 3H), 6.87 (m, 3H), 6.69 (m, 1H), 4.63 (s, 2H), 3.85 (s, 5H), 3.81 (s, 3H).

Step 7: dimethyl 5,5'-disulfanediylbis(4-amino-3-fluoro-2-((2-chlorophenyl)amino)benzoate)

To a solution of methyl 4-amino-5-(4-methoxybenzylthio)-3-fluoro-2-((2-chlorophenyl)amino)benzoate (19.93 g, 44.6 mmol) in $CH_2Cl_2$ (180 mL) was added DDQ (11.25 g, 53.73 mmol) followed by water (20 mL). After stirring at ambient temperature for 10 h, the reaction was quenched by saturated sodium bicarbonate (aq., 100 mL). The aqueous layer was extracted by $CH_2Cl_2$ (100 mL×3). The combined organic phase was washed with water (100 mL) and brine (100 mL) sequentially, dried over $Na_2SO_4$, filtered and concentrated. The crude product was purified by column chromatography on silica gel (petroleum ether/ethyl acetate, 5:1, v/v) to give the desired product (pale yellow solid, 9.39 g, 32.3% yield), $^1$H NMR (400 MHz, $CDCl_3$): δ 9.33 (s, 2H), 7.46 (s, 2H), 7.40 (m, 2H), 7.15 (m, 2H), 6.92 (m, 2H), 6.76 (m, 2H), 4.86 (br, 4H), 3.80 (s, 6H).

Step 8: methyl, 4-amino-3-fluoro-2-((2-chlorophenyl)amino)-5-mercaptobenzoate

To a solution of dimethyl 5,5'-disulfanediylbis(4-amino-3-fluoro-2-((2-chlorophenyl)amino)benzoate) (9.39 g, 14.41 mmol) in THF/MeOH (100 mL, 10:1, v/v) was added $NaBH_4$ (2.73 g, 72.05 mmol) portion-wise in 1 h. After stirring at ambient temperature for 1 h, the reaction was quenched with 10% HCl (aq.) and pH was adjusted to 1-2. The aqueous layer was extracted with $CH_2Cl_2$ (50 mL×3).

The combined organic phase was washed with water (50 mL) and brine (50 mL) sequentially, dried over $Na_2SO_4$, filtered and concentrated in vacuo. The crude product was used directly in the next step without further purification.

Step 9: methyl 4-fluoro-5-((2-chlorophenyl)amino) benzo[d]thiazole-6-carboxylate To a solution of methyl 4-amino-3-fluoro-2-((2-chlorophenyl)amino)-5-mercaptobenzoate in trimethyl orthoformate (50 mL) was added p-TsOH (0.58 g, 3.05 mmol). The reaction mixture was stirred for 1 h and treated with water (100 mL). The precipitate was filtered off and the filter cake was washed with water to afford the desired product (pale yellow solid, 8.50 g, 87.6% yield for two steps), $^1H$ NMR (400 MHz, $CDCl_3$): δ 9.13 (s, 1H), 8.70 (s, 1H), 8.50 (s, 1H), 7.41 (m, 1H), 7.15 (m, 1H), 6.89 (m, 1H), 6.73 (m, 1H), 3.93 (s, 3H).

Step 10: methyl, 4-fluoro-5-((4-bromo-2-chlorophenyl)amino)benzo[d]thiazole-6-carboxylate To a solution of methyl 4-fluoro-5-((2-chlorophenyl) amino)benzo[d]thiazole-6-carboxylate (8.50 g, 25.24 mmol) in DMF (100 mL) was added NBS (4.92 g, 27.76 mmol). After stirring for 5 h at ambient temperature, the reaction was treated by water (150 mL). The precipitate was filtered off and the filter cake was washed with water. The desired product was obtained as a pale brown solid (8.74 g, 83.3% yield). $^1H$ NMR (400 MHz, $CDCl_3$): δ 9.17 (s, 1H), 8.70 (s, 1H), 8.48 (s, 1H), 7.65 (m, 1H), 7.30 (m, 1H), 6.63 (m, 1H), 3.98 (s, 3H).

Step 11: 4-fluoro-5-((4-bromo-2-chlorophenyl) amino)benzo[d]thiazole-6-carboxylic acid To a solution of methyl 4-fluoro-5-((4-bromo-2-chlorophenyl)amino)benzo[d]thiazole-6-carboxylate (8.74 g, 21.02 mmol) in THF and MeOH (20 mL, 4:1, v/v) was added 5.0 M LiOH (aq., 9.5 mL). After stirring at ambient temperature for 2 h, the reaction was treated with 10% HCl (aq.) till the solution was acidic. The aqueous layer was extracted with ethyl acetate (50 mL×3). The combined organic phase was washed with water (100 mL) and brine (100 mL) sequentially, dried over $Na_2SO_4$, filtered and concentrated to give the desired product (8.08 g, 95.7% yield). $^1H$ NMR (400 MHz, DMSO-$d_6$): δ 11.09 (s, 1H), 9.18 (s, 1H), 8.71 (s, 1H), 8.47 (s, 1H), 7.44 (m, 1H), 7.31 (m, 1H), 6.65 (m, 1H).

Step 12: 4-fluoro-5-((4-bromo-2-chlorophenyl) amino)-N-(2-(vinyloxy)ethoxy)benzo[d]thiazole-6-carboxamide To a solution of 4-fluoro-5-((4-bromo-2-chlorophenyl) amino)benzo[d]thiazole-6-carboxylic acid (482 mg, 1.20 mmol) in $CH_2Cl_2$ (10 mL) was added HOBt (254 mg, 1.63 mmol) and EDCI (314 mg, 1.63 mmol). The mixture was stirred for 1 h and O-(2-(vinyloxy)ethyl)hydroxyl-amine (172 mg, 1.62 mmol) was added. After stirring for 4 h at ambient temperature, the reaction was treated with saturated $NH_4Cl$ (aq.). The resultant mixture was extracted with $CH_2Cl_2$ (30 mL×3). The combined organic extracts were washed with water (30 mL) and brine (30 mL), dried over $Na_2SO_4$ filtered, and concentrated in vacuo. The crude product (503 mg) was used directly in the next step without further purification.

Step 13: 4-fluoro-5-((4-bromo-2-chlorophenyl) amino)-N-(2-hydroxyethoxy)benzo[d]thiazole-6-carboxamide To a solution of 4-fluoro-5-((4-bromo-2-chlorophenyl) amino)-N-(2-(vinyloxy)ethoxy)benzo[d]thiazole-6-carboxamide (503 mg, 1.03 mmol) in $CH_2Cl_2$ (10 mL) was added 1.0 N HCl (aq., 5 mL, 5 mmol). After stirring for 1 h, the reaction mixture was neutralized with saturated $NaHCO_3$ (aq.). The aqueous layer was washed with $CH_2Cl_2$ (30 mL). The combined organic layer was washed with water (30 mL×2) and brine (30 mL), dried over $Na_2SO_4$, filtered and concentrated in vacuo. The crude product was purified by column chromatography on silica gel ($CH_2Cl_2$/MeOH, 50:1, v/v) and gave the desired product as a white solid (420 mg, 75.9% yield for the two steps). $^1H$ NMR (400 MHz, DMSO-$d_6$): δ 11.75 (s, 1H), 9.53 (s, 1H), 8.23 (s, 1H), 8.14 (s, 1H), 7.56 (d, m, 1H), 7.33 (m, 1H), 6.50 (m, 1H), 4.75 (m, 1H), 3.83 (m, 2H), 3.58 (m, 2H) MS: m/z 461.9, [M+H].

Example 12: Preparation of N-(2,3-dihydroxypropoxy)-4-fluoro-5-((4-bromo-2-chlorophenyl) amino)benzo[d]thiazole-6-carboxamide (Compound 12)

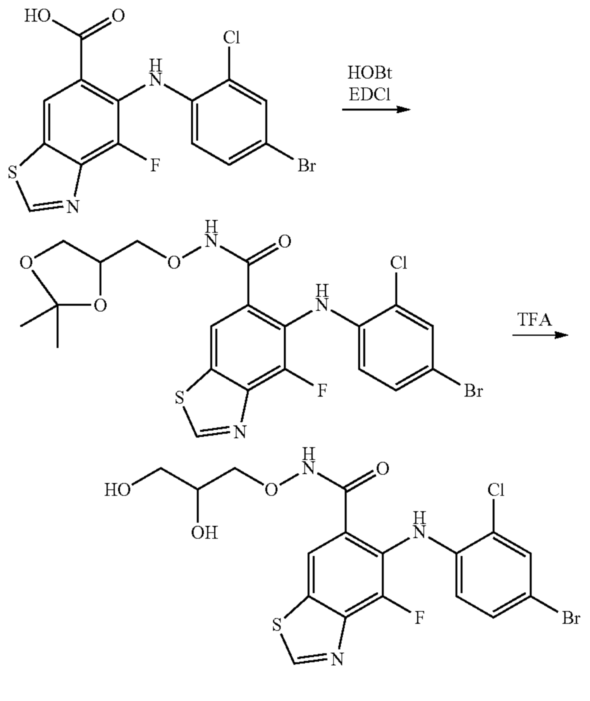

Step 1: N-((2,2-dimethyl-1,3-dioxolan-4-yl) methoxy)-4-fluoro-5-((2-chloro-4-bromophenyl) amino)benzo[d]thiazole-6-carboxamide To a solution of 4-fluoro-5-((4-bromo-2-chlorophenyl) amino)benzo[d]thiazole-6-carboxylic acid (482 mg, 1.20 mmol) in $CH_2Cl_2$ (10 mL) was added HOBt (254 mg, 1.63 mmol) followed by EDCI (314 mg, 1.63 mmol). The mixture was stirred for 1 h and O-((2,2-dimethyl-1,3-dioxolan-4-yl)methyl)hydroxylamine (238 mg, 1.62 mmol) was added. After stirring for 4 h at ambient temperature, the reaction was treated with saturated $NH_4Cl$ (aq.). The resultant mixture was extracted with $CH_2Cl_2$ (30 mL×3). The combined organic extracts was washed by water (30 mL) and brine (30 mL) sequentially, dried over $Na_2SO_4$, filtered and concentrated in vacuo. The crude product (490 mg) was used directly in the next step without further purification.

Step 2: N-(2,3-dihydroxypropoxy)-4-fluoro-5-((4-bromo-2-chlorophenyl)amino)benzo[d]thiazole-6-carboxamide To a solution of N-((2,2-dimethyl-1,3-dioxolan-4-yl)methoxy)-4-fluoro-5-((4-bromo-2-chlorophenyl)amino)benzo[d]thiazole-6-carboxamide (490 mg, 0.92 mmol) in $CH_2Cl_2$ (10 mL) was added trifluoroacetic acid (0.2 mL, 2.69 mmol). The mixture was stirred for 1 h and neutralized with saturated sodium bicarbonate (aq.). The aqueous layer was extracted by $CH_2Cl_2$ (10 mL×2). The combined organic layers were washed by water (10 mL) and brine (10 mL) sequentially, dried over $Na_2SO_4$, filtered and concentrated in vacuo. The crude product was purified by column chromatography on silica gel ($CH_2Cl_2$/MeOH, 50:1, v/v) to afford the desired product (white solid, 345 mg, 58.6% yield for two steps). $^1H$ NMR (400 MHz, DMSO-$d_6$): δ 11.80 (s, 1H), 9.54 (s, 1H), 8.24 (s, 1H), 8.18 (s, 1H), 7.60 (d, 1H), 7.34 (d, 1H), 6.46 (m, 1H), 4.84 (d, 1H), 4.60 (m, 1H), 3.88 (m, 1H), 3.74 (m, 2H), 3.36 (m, 2H). MS APCI(+)m/z: 491.9 [M+H].

Example 13: Preparation of N-(4-fluoro-5-((2-fluoro-4-iodophenyl)amino)benzo[d]thiazol-6-yl)cyclopropanesulfonamide (Compound 13)

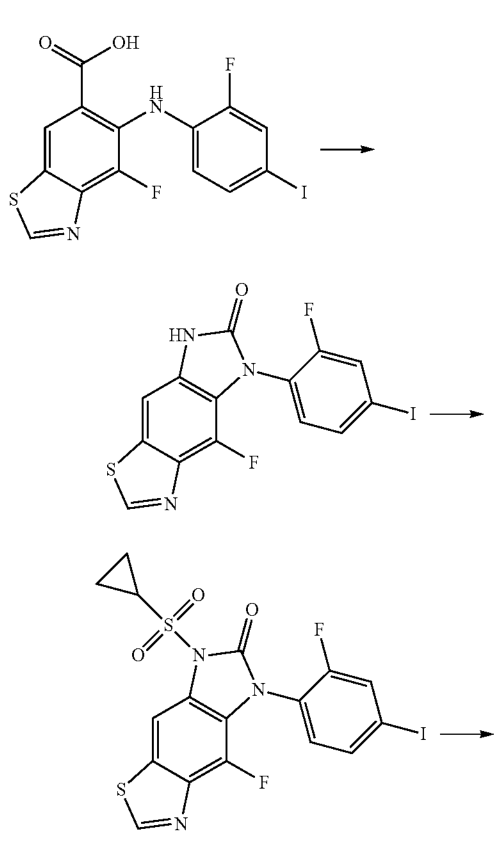

-continued

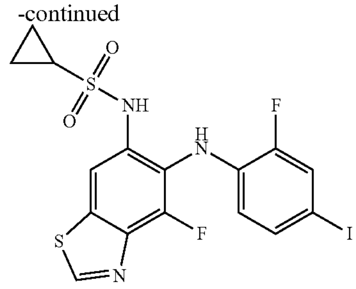

Step 1: 4-fluoro-5-(2-fluoro-4-iodophenyl)-5H-imidazo[4',5':4,5]benzo[1,2-d]thiazol-6(7H)-one To a solution of 4-fluoro-5-((2-fluoro-4-iodophenyl)amino)benzo[d]thiazole-6-carboxylic acid (75 mg, 0.17 mmol) in t-BuOH (3 mL) was added DPPA (82 mg, 0.29 mmol) followed by triethylamine (36 mg, 0.36 mmol). The mixture was heated under reflux for 3 h and allowed to slowly warm to room temperature. The solvent was removed in vacuo and the resultant crude product was purified by column chromatography on silica gel (petroleum ether/ethyl acetate, 2:1, v/v). The corresponding product was obtained (70 mg, 94.0% yield). $^1H$ NMR (400 MHz, DMSO-$d_6$): δ 11.78 (s, 1H), 8.66 (s, 1H), 7.95 (d, 1H), 7.74 (d, 1H), 7.47 (t, 1H), 7.33 (s, 1H).

Step 2: 7-(cyclopropylsulfonyl)-4-fluoro-5-(2-fluoro-4-iodophenyl)-5H-imidazo[4',5':4,5]benzo[1,2-d]thiazol-6(7H)-one To a solution of 4-fluoro-5-(2-fluoro-4-iodophenyl)-5H-imidazo[4',5':4,5]benzo[1,2-d]thiazol-6(7H)-one (70 mg, 0.16 mmol) in $CH_2Cl_2$ (5 mL) was added triethylamine (48 mg, 0.49 mmol) at 0° C. followed by cyclopropanesulfonyl chloride (35 mg, 0.25 mmol) and DMAP (10 mg). The mixture was stirred at room temperature for 1 h and washed with saturated $NaHCO_3$ (aq.). The aqueous layer was extracted with $CH_2Cl_2$ (10 mL×2). The combined organic phase was washed with water (10 mL) and brine (10 mL) successively, dried over $Na_2SO_4$, filtered and concentrated in vacuo. The residue was purified by flash chromatography on silica gel (petroleum ether/ethyl acetate, 5:1, v/v) to give the corresponding product (80 mg, 92% yield). $^1H$ NMR (400 MHz, $CDCl_3$): δ 8.68 (s, 1H), 7.98 (s, 1H), 7.91 (d, 1H), 7.76 (d, 1H), 7.45 (t, 1H), 3.35 (m, 1H), 1.69 (m, 2H), 0.91 (m, 2H).

Step 3: N-(4-fluoro-5-((2-fluoro-4-iodophenyl)amino)benzo[d]thiazol-6-yl)cyclopropanesulfonamide To a solution of 7-(cyclopropylsulfonyl)-4-fluoro-5-(2-fluoro-4-iodophenyl)-5H-imidazo[4',5':4,5]benzo[1,2-d]thiazol-6(7H)-one (50 mg, 0.09 mmol) in THF (5 mL) was added potassium trimethylsilanolate (19 mg, 0.14 mmol). After stirring at room temperature for 1 h, the reaction was quenched with saturated $NH_4Cl$ (aq., 5 mL). The aqueous layer was extracted with ethyl acetate (10 mL×2). The combined organic phase was washed with brine (10 mL), dried over $Na_2SO_4$, filtered and concentrated in vacuo. The residual crude product was purified by flash chromatography on silica gel (petroleum, ether/ethyl acetate, 5:1-3:1, v/v) to give the corresponding product as a white solid (30 mg, 63.1% yield). $^1H$ NMR (400 MHz, $CDCl_3$): δ 8.65 (s, 1H), 8.02 (s, 1H), 7.91 (d, 1H), 7.86 (s, 1H), 7.76 (d, 1H), 7.45 (m, 1H), 5.52 (s, 1H), 2.85 (m, 1H), 1.29 (m, 2H), 1.20 (m, 2H). MS APCI(+)m/z: 508.5 [M+H].

Example 14: Preparation of 1-(2,3-dihydroxypropyl)-N-(4-fluoro-5-((2-fluoro-4-iodophenyl)amino)benzo[d]thiazol-6-yl)cyclopropane-1-sulfonamide (Compound 14)

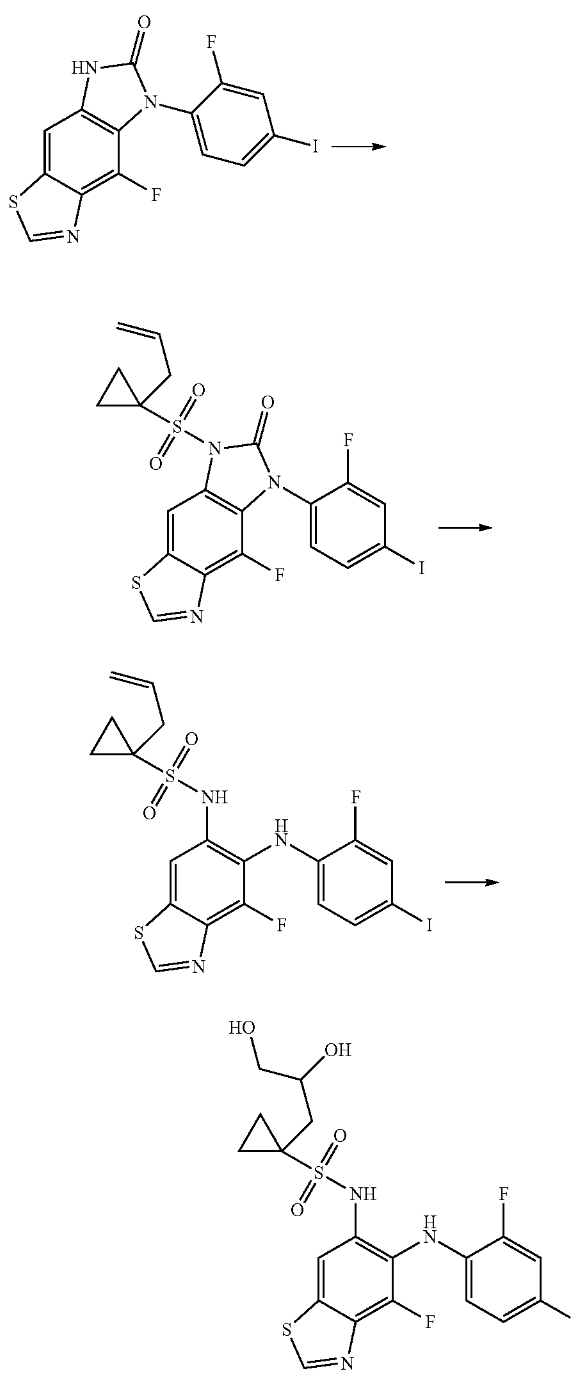

Step 1: 7-((1-allylcyclopropyl)sulfonyl)-4-fluoro-5-(2-fluoro-4-iodophenyl)-5H-imidazo[4',5':4,5]benzo[1,2-d]thiazol-6(7H)-one To a solution of 4-fluoro-5-(2-fluoro-4-iodophenyl)-5H-imidazo[4',5':4,5]benzo[1,2-d]thiazol-6(7H)-one (50 mg, 0.12 mmol) in DCM (5 mL) was added triethylamine (35 mg, 0.74 mmol) at 0° C. followed by 1-allylcyclopropane-1-sulfonyl chloride (32 mg, 0.18 mmol) and DMAP (15 mg). After stirring at room temperature for 1 h, the mixture was washed with saturated $NaHCO_3$ (aq.). The aqueous layer was extracted with DCM (20 mL×2). The combined organic phase was washed by water (20 mL) and brine (20 mL) sequentially, dried over $Na_2SO_4$, filtered and concentrated to give a residue, which was purified by flash chromatography on silica gel (petroleum ether/ethyl acetate, 5:1, v/v) to give the corresponding product (60 mg, 89.8% yield). $^1H$ NMR (400 MHz, $CDCl_3$): δ 8.67 (s, 1H), 7.97 (s, 1H), 7.92 (d, 1H), 7.78 (d, 1H), 7.46 (t, 1H), 5.76-5.60 (m, 1H), 5.06 (m, 2H), 2.91-2.81 (m, 1H), 2.11-2.01 (m, 1H), 1.95-1.86 (m, 2H), 1.25-1.10 (m, 2H).

Step 2: 1-allyl-N-(4-fluoro-5-((2-fluoro-4-iodophenyl)amino)benzo[d]thiazol-6-yl)cyclopropane-1-sulfonamide To a solution of 7-((1-allylcyclopropyl)sulfonyl)-4-fluoro-5-(2-fluoro-4-iodophenyl)-5H-imidazo[4',5':4,5]benzo[1,2-d]thiazol-6(7H)-one (60 mg, 0.11 mmol) in THF (5 mL) was added potassium trimethylsilanolate (14 mg, 0.11 mmol). The reaction was stirred at room temperature for 1 h and quenched with saturated $NH_4Cl$ (aq.). The aqueous layer was extracted with EA (10 mL×2). The combined organic phase was washed with brine (20 mL), dried over $Na_2SO_4$, filtered and concentrated in vacuo. The residue was purified by flash chromatography on silica gel (petroleum ether/ethyl acetate, 5:1-3:1, v/v) to give the desired product (50 mg, 91.3% yield). $^1H$ NMR (400 MHz, $CDCl_3$): δ 8.67 (s, 1H), 7.97 (s, 1H), 7.92 (d, 1H), 7.78 (d, 1H), 7.46 (m, 1H), 6.82 (s, 1H), 6.64 (s, 1H), 5.75-5.58 (m, 1H), 5.05 (m, 2H), 2.90-2.80 (m, 1H), 2.10-2.00 (m, 1H), 1.95-1.86 (m, 2H), 1.25-1.10 (m, 2H).

Step 3: 1-(2,3-dihydroxypropyl)-N-(4-fluoro-5-((2-fluoro-4-iodophenyl)amino)benzo[d]thiazol-6-yl)cyclopropane-1-sulfonamide To a solution of 1-allyl-N-(4-fluoro-5-((2-fluoro-4-iodophenyl)amino)benzo[d]thiazol-6-yl)cyclopropane-1-sulfonamide (50 mg, 0.09 mmol) in THF (5 mL) was added N-methylmorpholine-N-oxide (11 mg, 0.09 mmol) followed by osmium tetraoxide (3 mg, 0.01 mmol) and water (0.5 mL). The resultant was stirred at room temperature overnight. The mixture was concentrated and then diluted with ethyl acetate. The organic layer was washed with water, saturated $NaHCO_3$ (aq.) and brine sequentially, dried over $Na_2SO_4$, filtered and concentrated to give a residue, which was purified by flash chromatography on silica gel to give the product as white solid (20 mg, 37.7% yield). $^1H$ NMR (400 MHz, $CDCl_3$): δ 8.68 (s, 1H), 7.98 (s, 1H), 7.90 (d, 1H), 7.75 (d, 1H), 7.45 (m, 1H), 6.81 (s, 1H), 6.66 (s, 1H), 4.42-4.28 (m, 2H), 4.21-4.12 (m, 1H), 3.76-3.62 (m, 1H), 3.60-3.50 (m, 1H), 2.62-2.50 (m, 2H), 0.92-0.80 (m, 4H). MS APCI(+)m/z: 582.5 [M+H].

Example 15: Preparation of N-(5-((4-bromo-2-chlorophenyl)amino)-4-fluorobenzo[d]thiazol-6-yl)cyclopropanesulfonamide (Compound 15)

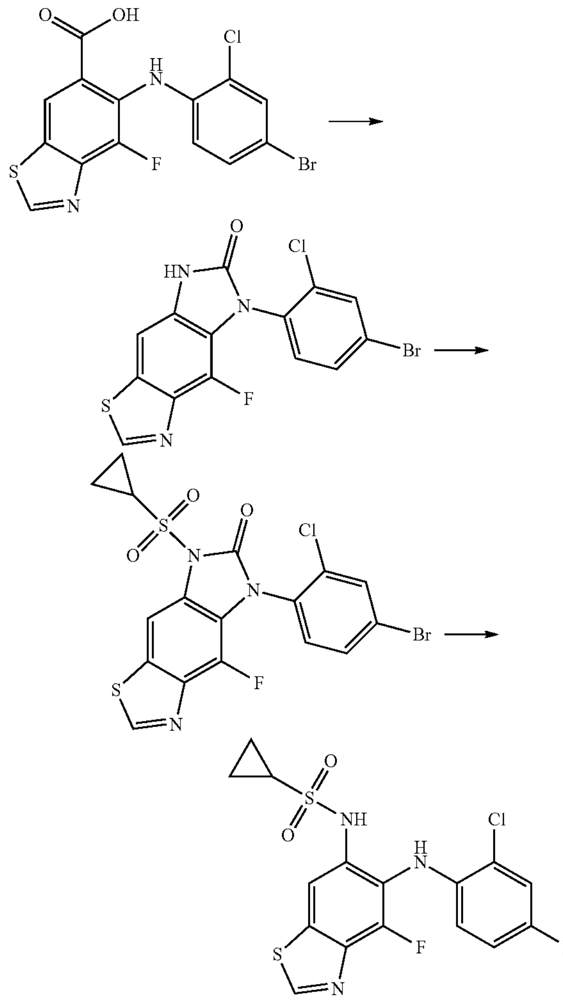

Step 1: 5-(4-bromo-2-chlorophenyl)-4-fluoro-5H-imidazo[45':4,5]benzo[1,2-d]thiazol-6(7H) one To a solution of 5-((4-bromo-2-chlorophenyl)amino)-4-fluorobenzo[d]thiazole-6-carboxylic acid (120 mg, 0.299 mmol) in t-BuOH (10 mL) was added DPPA (48 mg, 0.449 mmol) followed by triethylamine (60 mg, 0.598 mmol). The mixture was heated under reflux for 3 h and allowed to slowly warm to room temperature. The solvent was removed in vacuo and the resultant crude product was purified by column chromatography on silica gel (petroleum ether/ethyl acetate, 2:1, v/v). The corresponding product was obtained (white solid, 100 mg, 83.9% yield). $^1$H NMR (400 MHz, DMSO-$d_6$): δ 11.76 (s, 1H), 8.65 (s, 1H), 7.95 (d, 1H), 7.77 (d, 1H), 7.50 (m, 1H), 7.39 (s, 1H).

Step 2: 5-(4-bromo-2-chlorophenyl)-7-(cyclopropylsulfonyl)-4-fluoro-5H-imidazo[4',5': 4,5]benzo[1,2-d]thiazol-6(7H)-one To a solution of 5-(4-bromo-2-chlorophenyl)-4-fluoro-5H-imidazo[4',5':4,5]benzo[1,2-d]thiazol-6(7H)-one (100 mg, 0.25 mmol) in $CH_2Cl_2$ (10 mL) was added triethylamine (76 mg, 0.75 mmol) at 0° C. followed by cyclopropanesulfonyl chloride (53 mg, 0.38 mmol) and DMAP (10 mg). The mixture was stirred at room temperature for 1 h and washed with saturated $NaHCO_3$ (aq.). The aqueous layer was extracted with $CH_2Cl_2$ (15 mL×2). The combined organic phase was washed with water (15 mL) and brine (20 mL) successively, dried over $Na_2SO_4$, filtered and concentrated in vacuo. The residue was purified by flash chromatography on silica gel (petroleum ether/ethyl acetate, 5:1, v/v) to give the corresponding product (120 mg, 95.1% yield). $^1$H NMR (400 MHz, $CDCl_3$): δ 8.67 (s, 1H), 7.99 (s, 1H), 7.91 (d, 1H) 7.73 (d, 1H), 7.50 (m, 1H), 3.37 (m, 1H), 1.70 (m, 2H), 0.93 (m, 2H).

Step 3: N-(5-((4-bromo-2-chlorophenyl)amino)-4-fluorobenzo[d]thiazol-6-yl)cyclopropanesulfonamide To a solution of 5-(4-bromo-2-chlorophenyl)-7-(cyclopropylsulfonyl)-4-fluoro-5H-imidazo[4',5':4,5]benzo[1,2-d]thiazol-6(7H)one (50 mg, 0.10 mmol) in THF (5 mL) was added potassium trimethylsilanolate (13 mg, 0.10 mmol). After stirring at room temperature for 1 h, the reaction was quenched with saturated $NH_4Cl$ (aq.). The aqueous layer was extracted with ethyl acetate (10 mL×2). The combined organic phase was washed with brine (20 mL), dried over $Na_2SO_4$, filtered and concentrated in vacuo. The residual crude product was purified by flash chromatography on silica gel (petroleum ether/ethyl acetate, 5:1-3:1, v/v) and the product was obtained (30 mg, 63.3% yield). $^1$H NMR (400 MHz, $CDCl_3$): δ 8.65 (s, 1H), 8.00 (s, 1H), 7.89 (d, 1H), 7.84 (s, 1H), 7.75 (d, 1H), 7.43 (m, 1H), 5.48 (s, 1H), 2.84 (m, 1H), 1.29 (m, 2H), 1.23 (m, 2H). MS APCI(+)m/z: 477.9, [M+H].

Example 16: Preparation of N-(5-((4-bromo-2-chlorophenyl)amino)-4-fluorobenzo[d]thiazol-6-yl)-1-(2,3-dihydroxypropyl)cyclopropane-1-sulfonamide (Compound 16)

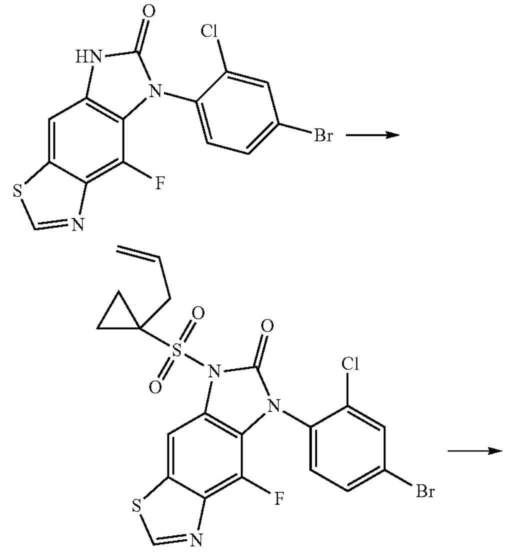

-continued

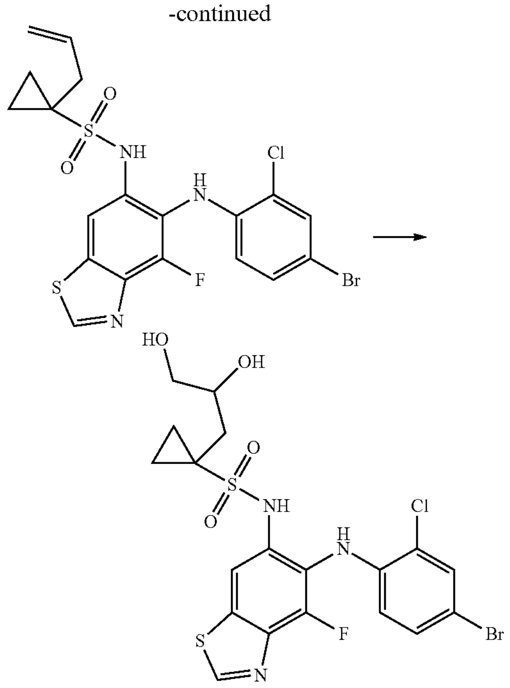

Step 1: 7-((1-allylcyclopropyl)sulfonyl)-5-(4-bromo-2-chlorophenyl)-4-fluoro-5H-imidazo[4',5':4,5]benzo[1,2-d]thiazol-6(7H)-one To a solution of 5-(4-bromo-2-chlorophenyl)-4-fluoro-5H-imidazo[4',5':4,5]benzo[1,2-d]thiazol-6(7H)-one (50 mg, 0.13 mmol) in DCM (10 mL) was added triethylamine (38 mg, 0.38 mmol) at 0° C. followed by 1-allylcyclopropane-1-sulfonyl chloride (34 mg, 0.19 mmol) and DMAP (10 mg). After stirring at room temperature for 1 h, the reaction was treated with saturated $NaHCO_3$ (aq.). The aqueous layer was extracted with $CH_2Cl_2$ (20 mL×2). The combined organic phase was washed with water (20 mL) and brine (20 mL) sequentially, dried over $Na_2SO_4$, filtered and concentrated to give a residue, which was purified by flash chromatography on silica gel (petroleum ether/ethyl acetate, 5:1, v/v) to give the corresponding product (62 mg, 91.1% yield). $^1H$ NMR (400 MHz, $CDCl_3$): δ 8.65 (s, 1H), 7.98 (s, 1H), 7.91 (d, 1H), 7.76 (d, 1H), 7.48 (t, 1H), 5.76-5.63 (m, 1H), 5.08 (m, 2H), 2.90-2.83 (m, 1H) 2.10-2.00 (m, 1H), 1.96-1.88 (m, 2H), 1.26-1.15 (m, 2H).

Step 2: 1-allyl-N-(5-((4-bromo-2-chlorophenyl)amino)-4-fluorobenzo[d]thiazol-6-yl)cyclopropane-1-sulfonamide To a solution of 7-((1-allylcyclopropyl)sulfonyl)-5-(4-bromo-2-chlorophenyl)-4-fluoro-5H-imidazo[4',5':4,5]benzo[1,2-d]thiazol-6(7H)-one (60 mg, 0.111 mmol) in THF (5 mL) was added potassium trimethylsilanolate (15 mg, 0.111 mmol). The mixture was stirred at room temperature for 1 h and treated with saturated $NH_4Cl$ (aq.). The aqueous layer was extracted with ethyl acetate (10 mL×2). The combined organic phase was washed with brine (20 mL), dried over $Na_2SO_4$, filtered and concentrated to give a residue, which was purified by flash chromatography on silica gel (petroleum ether/ethyl acetate, 5:1-3:1, v/v) to give the product as a white solid (50 mg, 87.5% yield). $^1H$ NMR (400 MHz, $CDCl_3$) δ 8.65 (s, 1H), 7.98 (s, 1H), 7.90 (d, 1H), 7.76 (d, 1H), 7.45 (m, 1H), 6.80 (s, 1H), 6.63 (s, 1H), 5.75-5.60 (m, 1H), 5.03 (m, 2H), 2.92-2.81 (m, 1H), 2.12-2.01 (m, 1H), 1.93-1.85 (m, 2H), 1.20-1.1.1 (m, 2H).

Step 3: N-(5-((4-bromo-2-chlorophenyl)amino)-4-fluorobenzo[d]thia-zol-6-yl)-1-(2,3 dihydroxypropyl)cyclopropane-1-sulfonamide To a solution of 1-allyl-N-(5-((4-bromo-2-chlorophenyl)amino)-4-fluorobenzo[d]thiazol-6-yl)cyclopropane-1-sulfonamide (50 mg, 0.10 mmol) in THF (10 mL) was added N-methylmorpholine-A-oxide (12 mg, 0.1 mmol) followed by osmium tetraoxide (5 mg, 0.02 mmol) and water (0.5 mL). After stirring at room temperature overnight, the mixture was concentrated and then diluted with EA. The organic layer was washed with water, saturated $NaHCO_3$ (aq.) and brine sequentially, dried over $Na_2SO_4$, filtered and concentrated to give a residue, which was purified by flash chromatography to give the product as white solid (25 mg, 46.9% yield). $^1H$ NMR (400 MHz, $CDCl_3$) δ 8.67 (s, 1H), 7.96 (s, 1H), 7.92 (d, 1H), 7.73 (d, 1H), 7.44 (m, 1H), 6.82 (s, 1H), 6.68 (s, 1H), 4.42-4.25 (m, 2H), 4.21-4.13 (m, 1H), 3.73-3.62 (m, 1H), 3.61-3.51 (m, 1H), 2.63-2.52 (m, 2H), 0.91-0.83 (m, 4H). MS APCI(+)m/z: 551.9, [M+H].

Example 17: Preparation of 4-fluoro-5-((2-fluoro-4-iodophenyl)amino)-N-(2-hydroxyethoxy)benzo[d][1,2,3]thiadiazole-6-carboxamide (Compound 17)

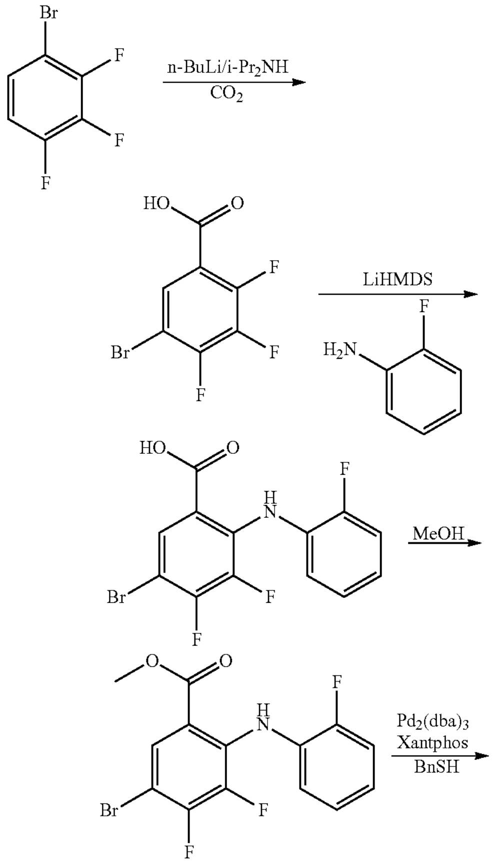

-continued

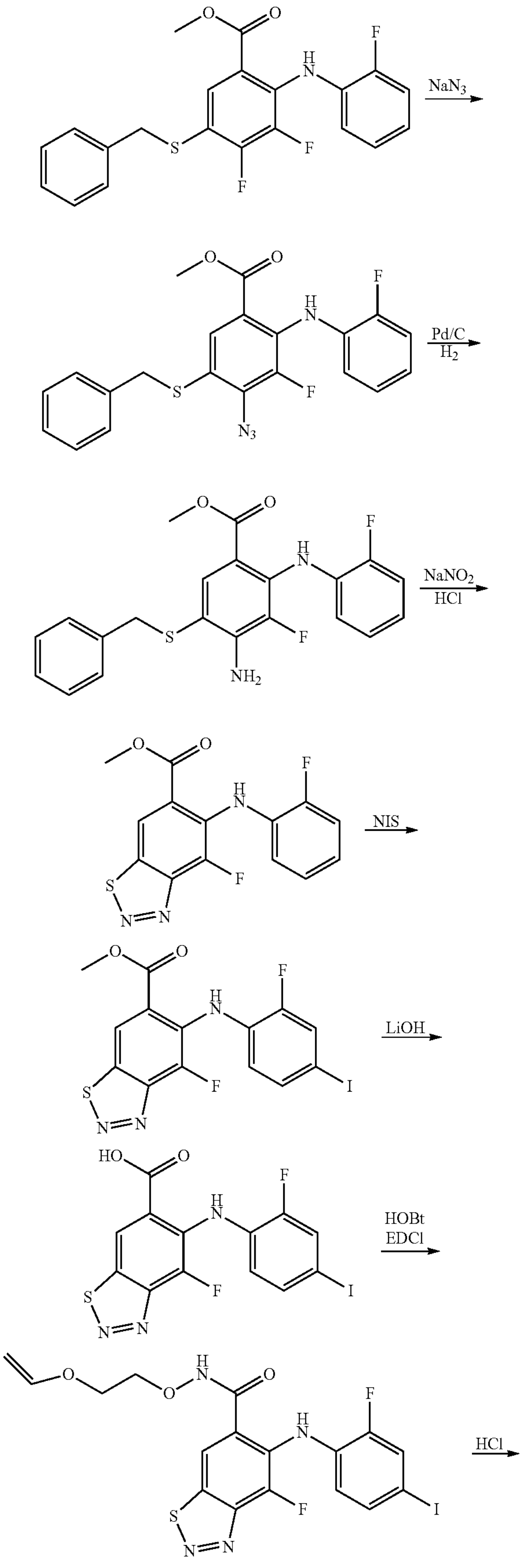

-continued

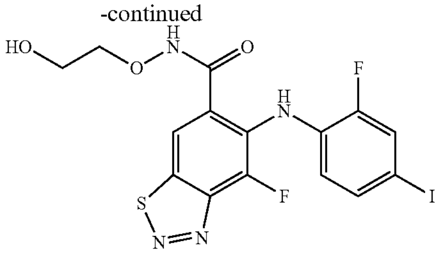

Step 1: 5-bromo-2,3,4-trifluorobenzoic acid

To a solution of diisopropylamine (10.14 g, 100.20 mmol) in THF (100 mL) was added n-BuLi (40.08 mL, 2.5 M in hexane, 100.20 mmol) at −78° C. under nitrogen atmosphere. The stirring was maintained at this temperature for 1 h. Then a solution of l-bromo-2,3,4-trifluorobenzene (17.62 g, 83.50 mmol) in THF (120 mL) was added. After stirring for 1 h at −78° C., the mixture was transferred to a bottle with dry ice. The mixture was stirred overnight at room temperature. The reaction was quenched with 10% aqueous HCl and pH was adjusted to 1-2. The mixture was extracted with ethyl acetate (100 mL×3). The combined organic extracts were washed with water (100 mL) and brine (100 mL) sequentially, dried over $Na_2SO_4$, filtered and concentrated under reduced pressure to afford the desired product (20.12 g, 94.5% yield). $^1H$ NMR (400 MHz, DMSO-$d_6$): δ 13.95 (s, 1H), 7.97 (m, 1H).

Step 2: 5-bromo-3,4-difluoro-2-((2-fluorophenyl) amino)benzoic acid

To a solution of 2-fluoroaniline (17.54 g, 157.80 mmol) and 5-bromo-2,3,4-trifluorobenzoic acid (20.12 g, 78.90 mmol) in THF (120 mL) was added LiHMDS (236.7 mL, 1 M in THF, 236.7 mmol) dropwisely at −78° C. under nitrogen atmosphere. The mixture was allowed to slowly warm to room temperature and stirred at this temperature overnight. The reaction was quenched with water (100 mL) and acidified to pH 2-3 with 10% HCl (aq.). The mixture was extracted with ethyl acetate (100 mL×3). The combined organic extracts were washed with water (100 mL) and brine (100 mL) sequentially, dried over $Na_2SO_4$, filtered and concentrated in vacuo to afford the desired product (pale yellow solid, 24.24 g, 88.8% yield). $^1H$ NMR (400 MHz, DMSO-$d_6$): δ 9.22 (s, 1H), 8.01 (dd, J=7.4, 2.1 Hz, 1H), 7.25 (m, 1H), 7.10 (m, 3H).

Step 3: methyl 5-bromo-3,4-difluoro-2-((2-fluoro-phenyl)amino)benzoate

To a solution of 5-bromo-3,4-difluoro-2-((2-fluorophenyl)amino)benzoic acid (24.24 g, 70.04 mmol) in MeOH (300 mL) was added thionyl chloride (20 mL). After stirring at 85° C. overnight, most MeOH was removed in vacuo. The residue was neutralized with saturated sodium bicarbonate (aq.) and extracted with ethyl acetate (100 mL×3). The combined organic layer was washed with water (100 mL) and brine (100 mL) sequentially, dried over $Na_2SO_4$, filtered and concentrated. After purification by column chromatography on silica gel (petroleum ether/ethyl acetate, 50:1, v/v), the corresponding product was obtained as a white solid (22.33 g, 88.5% yield). $^1H$ NMR (400 MHz, $CDCl_3$): δ 9.06 (s, 1H), 8.01 (dd, J=7.1, 2.3 Hz, 1H), 7.04 (m, 4H), 3.92 (s, 3H).

Step 4: methyl 5-(benzylthio)-3, 4-difluoro-2-((2-fluorophenyl)amino)benzoate

To a solution of methyl 5-bromo-3,4-difluoro-2-((2-fluorophenyl)amino)benzoate (22.33 g, 62.01 mmol) in anhydrous 1,4-dioxane (200 mL) was added N,N-diisopropylethylamine (16.03 g, 124.04 mmol). Then $Pd_2(dba)_3$ (2.84 g, 3.10 mmol) followed by Xantphos (3.59 g, 6.20 mmol) and BnSH (8.09 g, 65.11 mmol) was added under nitrogen atmosphere. The mixture was stirred overnight at 100° C. under $N_2$ atmosphere and then allowed to warm to ambient temperature. The insoluble matter was filtered off and the filter cake was washed ethyl acetate. The filtrate was diluted with water (300 mL) and extracted with ethyl acetate (100 mL×3). The combined organic layers were washed with water (100 mL) and brine (100 mL) sequentially, dried over $Na_2SO_4$, filtered and concentrated. The crude product was purified by column chromatography on silica gel (petroleum ether/ethyl acetate, 50:1, v/v) to give the desired product (pale yellow solid, 2.2.09 g, 88.3% yield). $^1$H NMR (400 MHz, $CDCl_3$): δ 9.04 (s, 1H), 7.68 (dd, 1H), 7.18 (m, 5H), 6.97 (m, 4H), 3.97 (s, 2H), 3.80 (s, 3H).

Step 5: methyl 4-azido-5-(benzylthio)-3-fluoro-2-((2-fluorophenyl)amino)benzoate To a solution of methyl 5-(benzylthio)-3,4-difluoro-2-((2-fluorophenyl)amino)benzoate (22.09 g, 54.76 mmol) in DMF (300 mL) was added $NaN_3$ (4.27 g, 65.71 mmol) at ambient temperature. The mixture was stirred at 90° C. for 3 h. Then water (300 mL) was added. The solution was extracted with ethyl acetate (100 mL×3). The combined organic extracts were washed with water (100 mL) and brine (100 mL), dried over $Na_2SO_4$ and concentrated in vacuo. The residue was purified by flash column chromatography on silica gel (petroleum ether/ethyl acetate, 10:1, v/v) and gave the desired product (white solid, 19.43 g, 83.2% yield). $^1$H NMR (400 MHz, $CDCl_3$): δ 8.98 (s, 1H), 7.75 (d, 1H), 7.27 (m, 5H), 7.02 (m, 4H), 4.07 (s, 2H), 3.89 (s, 3H).

Step 6: methyl 4-amino-5-(benzylthio)-3-fluoro-2-((2-fluorophenyl)amino)benzoate To a solution of methyl 4-azido-5-(benzylthio)-3-fluoro-2-((2-fluoro phenyl)amino)benzoate (19.43 g, 45.56 mmol) in MeOH (500 mL) was added and 10% palladium on carbon (3.40 g) under nitrogen atmosphere. Then the nitrogen atmosphere was completely changed to hydrogen atmosphere. The mixture was stirred for 3 h at ambient temperature. After the insoluble matter was filtered off, the solvent was evaporated in vacuo to give the desired product (18.06 g, 99.0%). $^1$H NMR (400 MHz, $CDCl_3$): δ 9.08 (s, 1H), 7.78 (s, 1H), 7.11 (m, 9H), 4.65 (s, 2H), 3.88 (s, 2H), 3.84 (s, 3H).

Step 7: methyl 4-fluoro-5-((2-fluorophenyl)amino)benzo[d][1, 2,3]thiadiazole-6-carboxylate To a solution of methyl 4-amino-5-(benzylthio)-3-fluoro-2-((2-fluorophenyl)amino)benzoate (2.07 g, 5.17 mmol) in acetic acid (60 mL) was added con. HCl (8 mL). The resultant was stirred at ambient temperature for 1 h. A solution of $NaNO_2$ (0.43 g, 6.21 mmol) in water (10 mL) was added dropwisely at 0° C. in 20 min. After stirring for 3 h, the reaction was treated with saturated $NaHCO_3$ (aq.) till the solution was neutral. The aqueous layer was extracted with ethyl acetate (30 mL×3). The combined organic phase was washed with water (30 mL) and brine (30 mL) sequentially, dried over $Na_2SO_4$, filtered and concentrated. The crude product was purified by column chromatography on silica gel (petroleum ether/ethyl acetate, 5:1, v/v) to give the corresponding product (yellow solid, 1.53 g, 92.1% yield). $^1$H NMR (400 MHz, $CDCl_3$): δ 8.74 (s, 1H), 8.57 (s, 1H), 7.08 (m, 4H), 4.03 (s, 3H).

Step 8: methyl 4-fluoro-5-((2-fluoro-4-iodophenyl)amino)benzo[d][1,2,3]thiadiazole-6-carboxylate To a solution of methyl 4-fluoro-5-((2-fluorophenyl)amino)benzo[d][1,2,3]thiadiazole-6-carboxylate (1.53 g, 4.77 mmol) in DMF (20 mL) was added NIS (1.18 g, 5.24 mmol) followed by trifluoroacetic acid (0.5 mL). After stirring for 5 h at ambient temperature, the reaction was quenched by saturated $NH_4Cl$ (aq.). The solution was extracted with ethyl acetate (30 mL×3). The combined organic extracts were washed with water (30 mL) and brine (30 mL) successively, dried over $Na_2SO_4$ and concentrated in vacuo to give the desired product (yellow solid, 1.90 g, 89.1% yield), NMR (400 MHz, $CDCl_3$): δ 8.73 (s, 1H), 8.58 (d, 1H), 7.47 (m, 1H), 7.39 (m, 1H), 6.74 (m, 1H), 4.03 (s, 3H).

Step 9: 4-fluoro-5-((2-fluoro-4-iodophenyl)amino)benzo[d][1,2,3]thiadiazole-6-carboxylic acid To a solution of methyl 4-fluoro-5-((2-fluoro-4-iodophenyl)amino)benzo[d][1,2,3]thiadiazole-6-carboxylate (1.90 g, 4.25 mmol) in THF and MeOH (20 mL, 4:1, v/v) was added 5.0 M LiOH (aq., 2 mL, 10 mmol). After stirring at ambient temperature for 2 h, the reaction was treated with 1.0 M HCl (aq.) till the solution was acidic. The aqueous layer was extracted with ethyl acetate (30 mL×3). The combined organic phase was washed with water (30 mL) and brine (30 mL) sequentially, dried over $Na_2SO_4$, filtered and concentrated to give the desired product (brown solid, 1.73 g, 94.0% yield). NMR (400 MHz, $CDCl_3$): δ 8.87 (s, 1H), 8.84 (s, 1H), 7.62 (d, 1H), 7.40 (d, 1H), 6.78 (m, 1H).

Step 10: 4-fluoro-5-((2-fluoro-4-iodophenyl)amino)-N-(2-(vinyloxy)ethoxy)benzo[d][1,2,3]thiadiazole-6-carboxamide To a solution of 4-fluoro-5-((2-fluoro-4-iodophenyl)amino)benzo[d][1,2,3]thiadiazole-6-carboxylic acid (200 mg, 0.49 mmol) in $CH_2Cl_2$ (10 mL) was added HOBt (100 mg, 0.69 mmol) and EDCI (140 mg, 0.69 mmol). The mixture was stirred for 1 h and O-(2-(vinyl-oxy)ethyl)hydroxylamine (72 mg, 0.69 mmol) was added. After stirring for 4 h at ambient temperature, the reaction was treated with saturated $NH_4Cl$ (aq.). The resultant mixture was extracted with $CH_2Cl_2$ (15 mL×3). The combined organic extracts were washed with water (10 mL) and brine (10 mL), dried over $Na_2SO_4$ filtered, and concentrated in vacuo. The crude product was purified by column chromatography on silica gel ($CH_2Cl_2$/MeOH, 50:1, v/v) and gave the desired product (yellow solid, 190 mg, 79.7% yield). $^1$H NMR (400 MHz, DMSO-$d_6$): δ 11.85 (s, 1H), 8.65 (s, 1H), 8.51 (s, 1H), 7.38 (d, 1H), 7.29 (d, 1H), 6.64 (dd, 1H), 6.42 (d, 1H), 4.21 (d, 1H), 4.01 (m, 3H), 3.83 (m, 2H).

Step 11: 4-fluoro-5-((2-fluoro-4-iodophenyl)amino)-N-(2-hydroxyethoxy)benzo[d][1,2,3]thiadiazole-6-carboxamide To a solution of 4-fluoro-5-((2-fluoro-4-iodophenyl)amino)-N-(2-(vinyloxy)ethoxy)benzo[d][1,2,3]thiadiazole- 6-carboxamide (190 mg, 0.37 mmol) in $CH_2Cl_2$ (10 mL) was added 1.0 N HCl (aq., 1.5 mL, 1.5 mmol). After stirring for 1 h, the reaction mixture was neutralized with saturated $NaHCO_3$ (aq.). The aqueous layer was washed with $CH_2C_2$ (10 mL×2). The combined organic layer was washed with water (30 mL) and brine (30 mL), dried over $Na_2SO_4$, filtered and concentrated in vacuo. The crude product was purified by column chromatography on silica gel ($CH_2Cl_2$/MeOH, 20:1, v/v) and gave the desired product as a yellow solid (154 mg, 84.6% yield). $^1H$ NMR (400 MHz, DMSO-$d_6$): δ 11.88 (s, 1H), 8.65 (s, 1H) 8.52 (s, 1H), 7.36 (d, 1H), 7.25 (d, 1H), 6.42 (d, 1H), 4.69 (m, 1H), 4.05 (m, 2H), 3.80 (m, 2H). MS APCI(+)m/z: m/z 493.2, [M+H].

Example 17A: Preparation of 4-fluoro-5-((2-fluoro-4-iodophenyl)amino)-N-(2-hydroxyethoxy)benzo[d][1,2,3]thiadiazole-6-carboxamide (Compound 17)

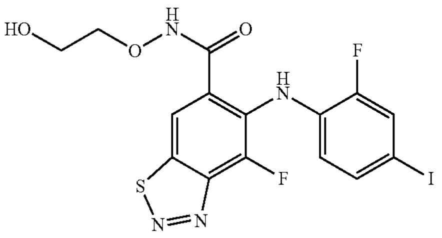 [SMILES: O=C(NOCCO)c1cc2snnc2c(F)c1Nc1ccc(I)cc1F]

Step 1: 5-bromo-2,3,4-trifluorobenzoic acid

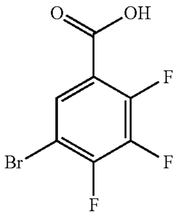 [SMILES: O=C(O)c1cc(Br)c(F)c(F)c1F]

To a solution of l-bromo-2,3,4-trifluorobenzene (13.64 g, 64.6 mmol) in THF (120 mL) was added lithium diisopropylamide (2.0 M in THF, 33.9 mL, 67.8 mmol) at −78° C. under nitrogen atmosphere. After stirring for 1 h at −78° C., the mixture was transferred to a bottle with dry ice. The mixture was stirred overnight at room temperature. The reaction was quenched with 10% aqueous HCl (300 mL) and extracted with ethyl acetate (200 mL×3). The combined organic extracts were washed with 5% sodium hydroxide (300 mL). The aqueous layer was acidized to pH 1 and extracted with ethyl acetate (200 mL×3). The combined organic extract was dried over $Na_2SO_4$, filtered and concentrated under reduced pressure to afford the desired product (white solid, 13.51 g, 82% yield). $^1H$ NMR (400 MHz, $CDCl_3$): δ 13.94 (s, 1H), 7.95 (m, 1H).

Step 2: 5-bromo-3,4-difluoro-2-((2-fluorophenyl)amino)benzoic acid

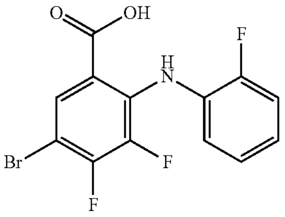 [SMILES: O=C(O)c1cc(Br)c(F)c(F)c1Nc1ccccc1F]

To a solution of 2-fluoroaniline (10.2 mL, 105.8 mmol) and 5-bromo-2,3,4-trifluorobenzoic acid (13.51 g, 52.9 mmol) in THF (120 mL) was added LiHMDS (158.7 mL, 1 M in THF, 158.7 mmol) dropwisely at −78° C. under nitrogen atmosphere. The mixture was allowed to slowly warm to room temperature and stirred at this temperature overnight. The reaction was quenched with 10% HCl (aq., 100 mL) and extracted with ethyl acetate (200 mL×3). The combined organic extracts were washed with water (200 mL×3) and brine (200 mL) sequentially, dried over $Na_2SO_4$, filtered and concentrated in vacuo to afford the desired product (pale yellow solid, 13.73 g, 75% yield). $^1H$ NMR (400 MHz, DMSO-$d_6$): δ 9.21 (s, 1H), 8.0.1 (d, 1H), 7.26 (m, 1H), 7.01-7.16 (m, 3H).

Step 3: methyl 5-bromo-3,4-difluoro-2-((2-fluorophenyl)amino)benzoate

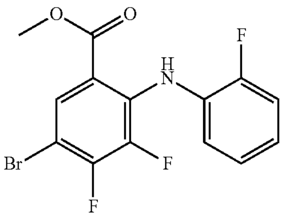 [SMILES: COC(=O)c1cc(Br)c(F)c(F)c1Nc1ccccc1F]

To a solution of 5-bromo-3,4-difluoro-2-((2-fluorophenyl)amino)benzoic acid (13.73 g, 39.6 mmol) in MeOH (300 mL) was added $SOCl_2$ (60 mL). After stirring at 85° C. overnight, most MeOH was removed in vacuo. The residue was neutralized with saturated sodium bicarbonate (aq.) and extracted with ethyl acetate (300 mL×3). The combined organic extract was washed with water (200 mL×3) and brine (200 mL) sequentially, dried over $Na_2SO_4$, filtered and concentrated in vacuo to afford the corresponding product (gray solid, 12.58 g, 90% yield). $^1H$ NMR (400 MHz, $CDCl_3$): δ 9.09 (s, 1H), 8.05 (d, 1H), 7.00-7.14 (m, 4H), 3.94 (s, 3H).

Step 4: methyl 5-(benzylthio)-3,4-difluoro-2-((2-fluorophenyl)amino)benzoate

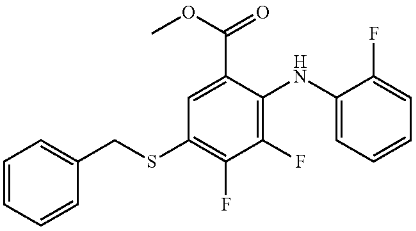 [SMILES: COC(=O)c1cc(SCc2ccccc2)c(F)c(F)c1Nc1ccccc1F]

To a solution of methyl 5-bromo-3,4-difluoro-2-((2-fluorophenyl)amino)benzoate (12.85 g, 35.80 mmol) in anhydrous 1,4-dioxane (30 mL) was added N,N-diisopropylethylamine (9.21 g, 71.60 mmol). Then $Pd_2(dba)_3$ (1.63 g, 1.78 mmol) followed by Xantphos (2.06 g, 3.56 mmol) and BnSH (4.44 g, 35.80 mmol) was added under nitrogen atmosphere. The mixture was stirred overnight at 100° C. under $N_2$ atmosphere. Then the reaction was allowed to warm to ambient temperature and quenched with water (150 mL). The aqueous layer was extracted with ethyl acetate (200 mL×3). The combined organic layers were washed with water (200 mL×3) and brine (200 mL) sequentially, dried over $Na_2SO_4$, filtered and concentrated. The crude product was purified by column chromatography on silica gel (petroleum ether/ethyl acetate, 50:1, v/v) to give the desired product (white solid, 12.64 g, 88% yield). $^1$H NMR (400 MHz, $CDCl_3$) δ 9.04 (s, 1H), 7.68 (dd, J=7.5, 2.1 Hz, 1H), 7.21-7.14 (m, 5H), 7.05-6.89 (m, 1H), 3.97 (s, 2H), 3.80 (s, 3H).

Step 5: methyl 4-azido-5-(benzylthio)-3-fluoro-2-((2-fluorophenyl)amino)benzoate

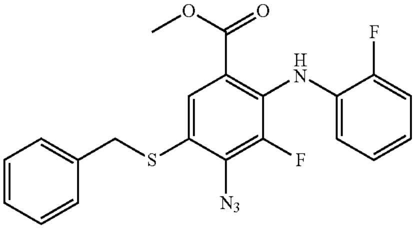 [SMILES: COC(=O)c1cc(SCc2ccccc2)c(N=[N+]=[N-])c(F)c1Nc1ccccc1F]

To a solution of methyl 5-(benzylthio)-3,4-difluoro-2-((2-fluorophenyl)amino)benzoate (12.64 g, 31.36 mmol) in DMF (30 mL) was added $NaN_3$ (2.45 g, 37.63 mmol) at ambient temperature. The mixture was stirred at 90° C. for 3 h. Then water (150 mL) was added. The solution was extracted with ethyl acetate (100 mL×3). The combined organic extracts were washed with water (100 mL×3) and brine (100 mL), dried over $Na_2SO_4$ and concentrated in vacuo. The residue was purified by flash column chromatography on silica gel (petroleum ether/ethyl acetate, 10:1, v/v) and gave the desired product (white solid, 10.38 g, 78% yield). $^1$H NMR (400 MHz. $CDCl_3$) δ 8.89 (s, 1H), 7.66 (s, 1H), 7.27-7.12 (m, 3H), 7.10-6.80 (m, 6H), 3.98 (s, 2H), 3.80 (s, 3H).

Step 6: methyl 4-amino-5-(benzylthio)-3-fluoro-2-((2-fluorophenyl)amino)benzoate

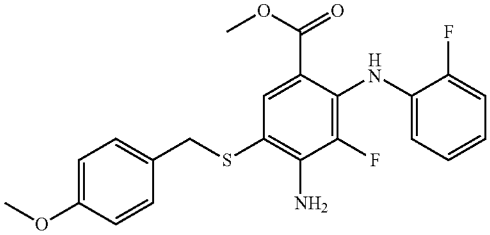 [SMILES: COC(=O)c1cc(SCc2ccc(OC)cc2)c(N)c(F)c1Nc1ccccc1F]

To a solution of methyl 4-azido-5-(benzylthio)-3-fluoro-2-((2-fluorophenyl)amino)benzoate (10.38 g, 24.36 mmol) in MeOH (100 mL) was added and 10% palladium on carbon (1.55 g) under nitrogen atmosphere. Then the nitrogen atmosphere was completely changed to hydrogen atmosphere. The mixture was stirred for 6 h at ambient temperature. After the insoluble matter was filtered off, the solvent was evaporated in vacuo to give the desired product (9.79 g, 100% yield). $^1$H NMR (400 MHz, $CDCl_3$) δ 8.98 (s, 1H), 7.69 (s, 1H), 7.19-7.17 (m, 3H) 7.15-6.83 (m, 6H), 4.54 (s, 2H) 3.79 (s, 2H), 3.75 (s, 3H).

Step 7: methyl 4-fluoro-5-((2-fluorophenyl)amino) benzo[d][1,2,3]thiadiazole-6-carboxylate

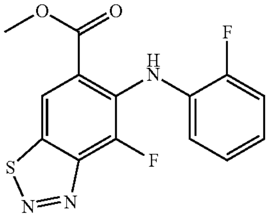 [SMILES: COC(=O)c1cc2snnc2c(F)c1Nc1ccccc1F]

To a solution of methyl 4-amino-5-(benzylthio)-3-fluoro-2-((2-fluoro-phenyl)amino)benzoate (2.07 g, 5.17 mmol) in acetic acid (60 mL) was added HCl (con., 8 mL) and water (6 mL). The resultant was stirred at ambient temperature for 1 h. A solution of $NaNO_2$ (0.43 g, 6.21 mmol) in water (10 mL) was added dropwisely at 0° C. within 20 min. After stirring for 3 h, the reaction was treated with saturated $NaHCO_3$ (aq.) till the solution was neutral. The aqueous layer was extracted with ethyl acetate (30 mL×3). The combined organic extract was washed with water (30 mL×3) and brine (30 mL) sequentially, dried over $Na_2SO_4$, filtered and concentrated. The crude product was purified by column chromatography on silica gel (petroleum ether/ethyl acetate, 5:1, v/v) to give the corresponding product (yellow solid, 1.53 g, 92.1% yield). $^1$H NMR (400 MHz, $CDCl_3$): δ 8.65 (s, 1H), 8.48 (s, 1H), 7.00-6.90 (m, 4H), 3.94 (s, 3H).

Step 8: methyl 4-fluoro-5-((2-fluoro-4-iodophenyl) amino)benzo[d][1, 2,3]thiadiazole-6-carboxylate

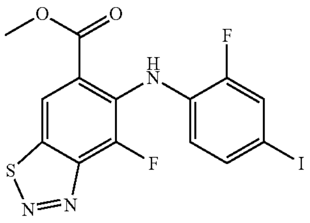 [SMILES: COC(=O)c1cc2snnc2c(F)c1Nc1ccc(I)cc1F]

To a solution of methyl 4-fluoro-5-((2-fluorophenyl) amino)benzo[d][1,2,3]thiadiazole-6-carboxylate (1.53 g, 4.77 mmol) in DMF (10 mL) was added NIS (1.18 g, 5.24 mmol) followed by trifluoroacetic acid (0.5 mL). After stirring for 4 h at ambient temperature, the reaction was quenched with saturated $NH_4Cl$ (aq.). The solution was extracted with ethyl acetate (30 mL×3). The combined organic extracts were washed with water (30 mL×3) and brine (30 mL) successively, dried over $Na_2SO_4$ and concentrated in vacuo to give the desired product (yellow solid, 1.90 g, 89% yield). $^1$H NMR (400 MHz, $CDCl_3$) δ 8.63 (s, 1H), 8.49 (s, 1H), 7.38 (d, J=10.3 Hz, 1H), 7.29 (d, J=8.6 Hz, 1H), 6.64 (dd, J=14.3, 8.3 Hz, 1H), 3.94 (s, 3H).

Step 9: 4-fluoro-5-((2-fluoro-4-iodophenyl)amino) benzo[d][1,2,3]thiadiazole-6-carboxylic acid

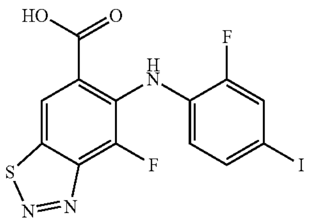 [SMILES: O=C(O)c1cc2snnc2c(F)c1Nc1ccc(I)cc1F]

To a solution of methyl 4-fluoro-5-((2-fluoro-4-iodophenyl)amino)benzo[d][1,2,3]thiadiazole-6-carboxylate (1.90 g, 4.25 mmol) in THF and MeOH (20 mL, 4:1, v/v) was added 1.0 M LiOH (aq., 10 mL, 10 mmol). After stirring at ambient temperature for 2 h, the reaction was treated with 1.0 M HCl (aq.) till the solution was acidic. The aqueous layer was extracted with ethyl acetate (30 mL×3). The combined organic phase was washed with water (30 mL×3) and brine (30 mL) sequentially, dried over $Na_2SO_4$, filtered and concentrated to give the desired product (brown solid, 1.70 g, 94.0% yield). $^1$H NMR (400 MHz, $CDCl_3$): δ 8.63 (s, 1H), 8.49 (s, 1H), 7.38 (d, J=10.3 Hz, 1H), 7.29 (d, J=8.6 Hz, 1H), 6.64 (dd, J=14.3, 8.3 Hz, 1H).

Step 10: 4-fluoro-5-((2-fluoro-4-iodophenyl)amino)-N-(2-(vinyloxy)ethoxy)benzo[d][1,2,3]thiadiazole-6-carboxamide

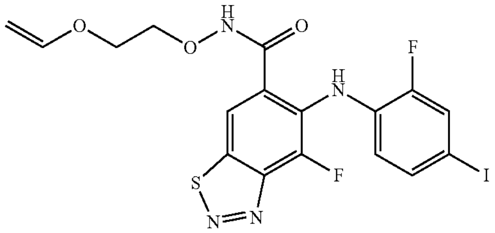 [SMILES: C=COCCONC(=O)c1cc2snnc2c(F)c1Nc1ccc(I)cc1F]

To a solution of 4-fluoro-5-((2-fluoro-4-iodophenyl) amino)benzo[d][1,2,3]thiadiazole-6-carboxylic acid (1.7 g, 5.54 mmol) in $CH_2Cl_2$ (20 mL) was added HOBt (1.21 g, 8.31 mmol) and EDCI (1.59 mg, 8.31 mmol). The mixture was stirred for 1 h and O-(2-(vinyl-oxy)ethyl)hydroxylamine (0.69 g, 6.65 mmol) was added. After stirring for 4 h at ambient temperature, the reaction was treated with saturated $NH_4Cl$ (aq., 20 mL). The resultant mixture was extracted with $CH_2Cl_2$ (15 mL×3). The combined organic extracts were washed with water (10 mL×3) and brine (10 mL), dried over $Na_2SO_4$, filtered and concentrated in vacuo. The crude product was purified by column chromatography on silica gel ($CH_2Cl_2$/MeOH, 20:1, v/v) and gave the desired product (2.44 g, 85% yield). $^1$H NMR (400 MHz, $d_6$-DMSO) δ 11.85 (s, 1H), 8.65 (s, 1H), 8.51 (s, 1H), 7.38 (d, J=10.8 Hz, 1H), 7.29 (d, J=8.1 Hz, 1H), 6.64 (dd, J=13.9, 6.6 Hz, 1H), 6.42 (d, J=6.0 Hz, 1H), 4.21 (d, J=14.5 Hz, 1H), 4.01 (m, 3H), 3.83 (m, 2H).

Step 11: 4-fluoro-5-((2-fluoro-4-iodophenyl)amino)-N-(2-hydroxyethoxy)benzo[d][1,2,3]thiadiazole-6-carboxamide

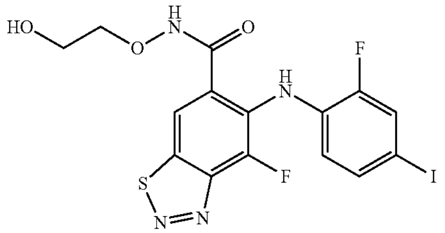 [SMILES: O=C(NOCCO)c1cc2snnc2c(F)c1Nc1ccc(I)cc1F]

To a solution of 4-fluoro-5-((2-fluoro-4-iodophenyl) amino)-N-(2-(vinyloxy)ethoxy)benzo[d][1,2,3]thiadiazole-6-carboxamide (410 mg, 0.79 mmol) in $CH_2Cl_2$ (5 mL) was added 1.0 N HCl (aq., 5 mL, 5 mmol). After stirring for 1 h, the reaction mixture was neutralized with saturated $NaHCO_3$ (aq.). The organic layer was separated, washed with water (30 mL×2) and brine (30 mL) sequentially, dried over $Na_2SO_4$, filtered and concentrated in vacuo. The crude product was purified by column chromatography on silica gel ($CH_2Cl_2$/MeOH, 20:1, v/v) and gave the desired product (343 mg, 88% yield). $^1$H NMR (400 MHz, $d_6$-DMSO) δ 11.85 (s, 1H), 8.65 (s, 1H), 8.51 (s, 1H), 7.38 (d, J=10.8 Hz, 1H), 7.29 (d, J=8.1 Hz, 1H), 6.64 (dd, J=13.9, 6.6 Hz, 1H), 4.21 (d, J=14.5 Hz, 1H), 4.01 (m, 2H), 3.83 (m, 2H). MS (ES+): m/z 493.0 [M+H].

Example 18: Preparation of N-(2,3-dihydroxypropoxy)-4-fluoro-5-((2-fluoro-4-iodophenyl)amino)benzo[d][1,2,3]thiadiazole-6-carboxamide (Compound 18)

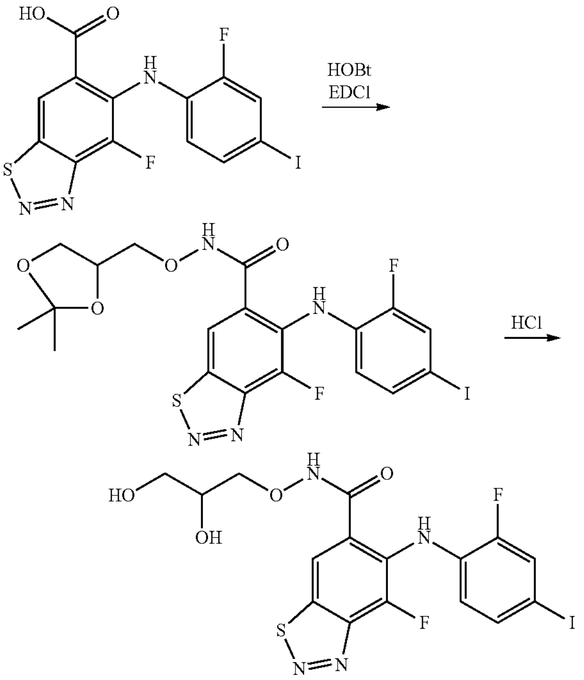

Step 1: N-((2,2-dimethyl-1,3-dioxolan-4-yl)methoxy)-4-fluoro-5-((2-fluoro-4-iodophenyl)amino)benzo[d][1,2,3]thiadiazole-6-carboxamide To a solution of 4-fluoro-5-((2-fluoro-4-iodophenyl)amino)benzo[d][1,2,3]thiadiazole-6-carboxylic acid (210 mg, 0.48 mmol) in $CH_2C_2$ (10 mL) was added HOBt (105 mg, 0.72 mmol) followed by EDCI (138 mg, 0.72 mmol). The mixture was stirred for 1 h and O-((2,2-dimethyl-1,3-dioxolan-4-yl)methyl)hydroxylamine (108 mg, 0.74 mmol) was added. After stirring for 4 h at ambient temperature, the reaction was treated with saturated $NH_4Cl$ (aq.). The resultant mixture was extracted with $CH_2Cl_2$ (15 mL×3). The combined organic extracts was washed by water (10 mL) and brine (10 mL) sequentially, dried over $Na_2SO_4$, filtered and concentrated in vacuo. The crude product (229 mg) was used directly in the next step without further purification.

Step 2: N-(2,3-dihydroxypropoxy)-4-fluoro-5-((2-fluoro-4-iodophenyl)amino)benzo[d][1,2,3]thiadiazole-6-carboxamide To a solution of N-((2,2-dimethyl-1,3-dioxolan-4-yl)methoxy)-4-fluoro-5-((2-fluoro-4-iodophenyl)amino)benzo[d][1,2,3]thiadiazole-6-carboxamide (229 mg, 0.41 mmol) in $CH_2Cl_2$ (10 mL) was added 1.0 N HCl (aq., 1.5 mL, 1.5 mmol). The mixture was stirred for 1 h and neutralized with saturated sodium bicarbonate (aq.). The aqueous layer was extracted by $CH_2Cl_2$ (10 mL×2). The combined organic layers were washed by water (30 mL×2) and brine (30 mL) sequentially, dried over $Na_2SO_4$, filtered and concentrated in vacuo. The crude product was purified by column chromatography on silica gel ($CH_2Cl_2$/MeOH, 20:1, v/v) to afford the desired product (yellow solid, 170 mg, 67.9% yield for two steps). $^1H$ NMR (400 MHz, DMSO-$d_6$): δ 11.98 (s, 1H), 8.40 (s, 1H), 8.20 (s, 1H), 7.58 (d, 1H), 7.33 (d, 1H), 6.64 (m, 1H), 4.86 (m, 1H), 4.62 (m, 1H), 3.87 (m, 1H), 3.72 (m, 2H), 3.33 (m, 2H, covered by the peak of water). MS APCI(+)m/z: 522.9 [M+H].

Example 19: Preparation of 5-((4-bromo-2-chlorophenyl)amino)-4-fluoro-N-(2-hydroxyethoxy)benzo[d][1,2,3]thiadiazole-6-carboxamide (Compound 19)

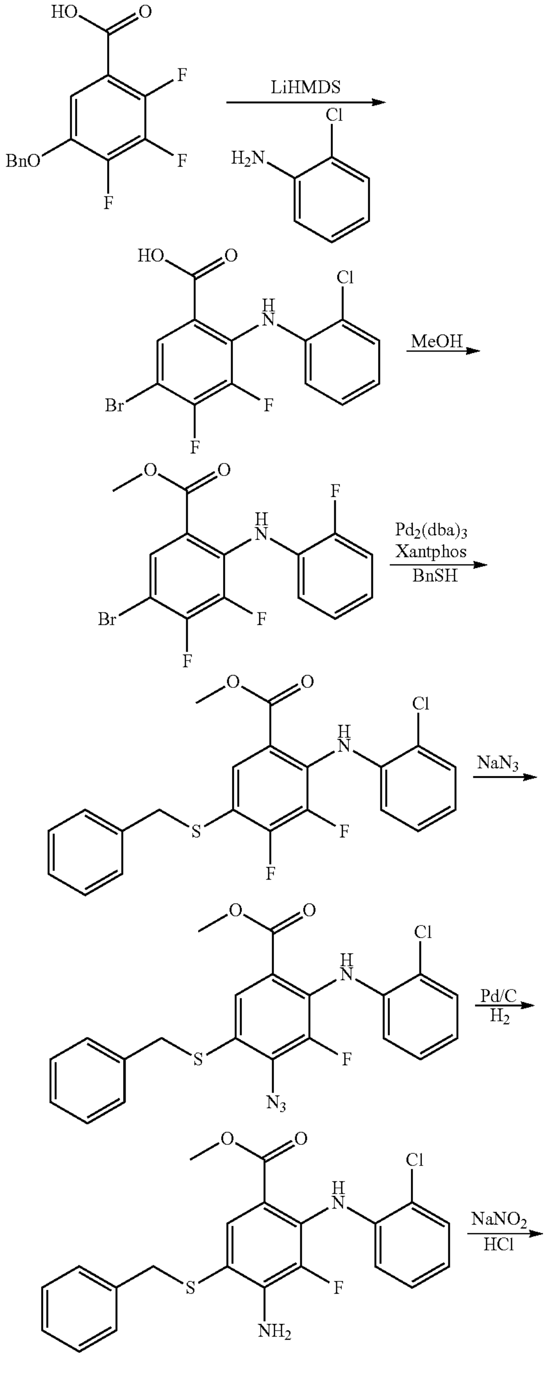

-continued

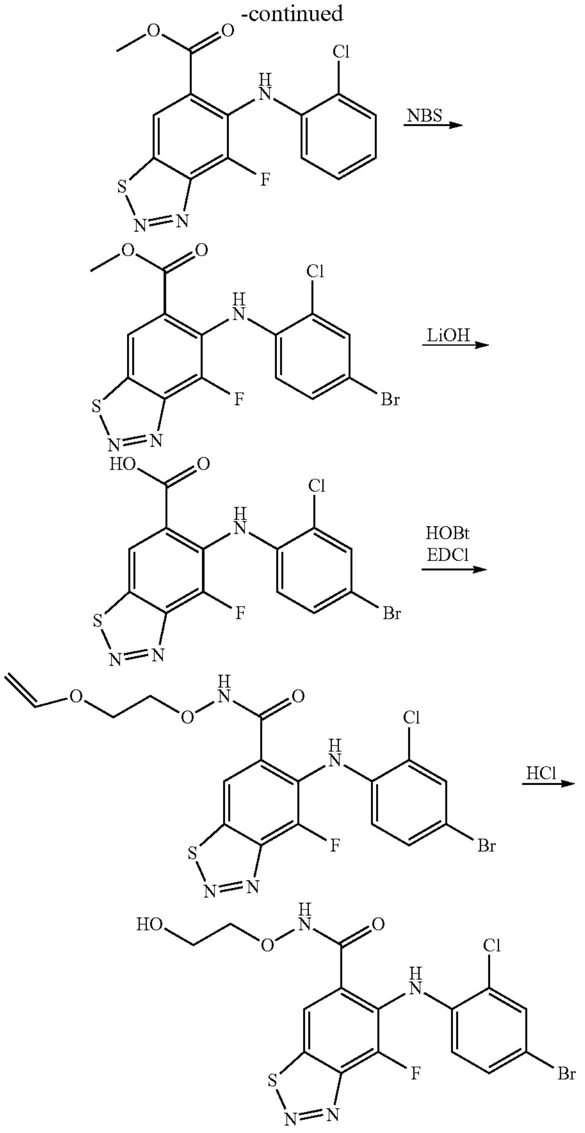

Step 1: 5-bromo-2-((2-chlorophenyl)amino)-3,4-difluorobenzoic acid

To a solution of 2-chloroaniline (12.56 g, 98.42 mmol) and 5-bromo-2,3,4 trifluorobenzoic acid (12.55 g, 49.21 mmol) in THF (120 mL) was added LiHMDS (147.6 mL, 1 M in THF, 147.6 mmol) dropwisely at −78° C. under nitrogen atmosphere. The mixture was allowed to slowly warm to room temperature and stirred at this temperature overnight. The reaction was quenched with 10% HCl (aq., 100 mL). The mixture was extracted with ethyl acetate (100 mL×3). The combined organic extracts were washed with water (100 mL) and brine (100 mL) sequentially, dried over $Na_2SO_4$, filtered and concentrated in vacuo to afford the desired product 4 (yellow solid, 13.74 g, 77% yield). $^1$H NMR (400 MHz, DMSO-$d_6$): δ 14.10 (s, 1H), 9.30 (s, 1H), 8.03 (m, 1H), 7.47 (m, 1H), 7.23 (m, 1H), 7.04 (m, 2H).

Step 2: methyl 5-bromo-3,4-difluoro-2-((2-fluorophenyl)amino)benzoate

To a solution of 5-bromo-3,4-difluoro-2-((2-chlorophenyl)amino)benzoic acid (13.74 g, 37.89 mmol) in MeOH (300 mL) was added thionyl chloride (20 mL). After stirring at 85° C. overnight, most MeOH was removed in vacuo. The residue was neutralized with saturated sodium bicarbonate (aq.) and extracted with ethyl acetate (100 mL×3). The combined organic layer was washed with water (100 mL) and brine (100 mL) sequentially, dried over $Na_2SO_4$, filtered and concentrated to give the corresponding product as a gray white solid (12.98 g, 91.1% yield). $^1$H NMR (400 MHz, $CDCl_3$): δ 9.15 (s, 1H), 8.06 (m, 1H), 7.41 (m, 1H), 7.24 (m, 1H), 7.01 (m, 1H), 6.90 (m, 1H), 3.95 (s, 3H).

Step 3: methyl 5-(benzylthio)-3,4-difluoro-2-((2-chlorophenyl)amino)benzoate

To a solution of methyl 5-bromo-3,4-difluoro-2-((2-chlorophenyl)amino)benzoate (12.98 g, 34.47 mmol) in anhydrous 1,4-dioxane (30 mL) was added N,N-diisopropylethylamine (8.86 g, 68.94 mmol). Then $Pd_2(dba)_3$ (1.63 g, 1.78 mmol) followed by Xantphos (2.06 g, 3.56 mmol) and BnSH (4.48 g, 36.19 mmol) was added under nitrogen atmosphere. The mixture was stirred overnight at 100° C. under $N_2$ atmosphere and then allowed to warm to ambient temperature. The reaction was quenched with water (150 mL) and extracted with ethyl acetate (100 mL×3). The combined organic layers were washed with waiter (100 mL) and brine (100 mL) sequentially, dried over $Na_2SO_4$, filtered and concentrated. The crude product was purified by column chromatography on silica gel (petroleum ether/ethyl acetate, 50:1, v/v) to give the desired product (white solid, 12.44 g, 86.0% yield). $^1$H NMR (400 MHz, $CDCl_3$): δ 9.19 (s, 1H), 7.79 (dd, 1H), 7.41 (dd, 1H), 7.24 (m, 5H), 7.18 (m, 1H), 7.00 (m, 1H), 6.87 (m, 1H), 4.08 (s, 2H), 3.90 (s, 3H).

Step 4: methyl 4-azido-5-(benzylthio)-3-fluoro-2-((2-chlorophenyl)amino)benzoate To a solution of methyl 5-(benzylthio)-3,4-difluoro-2-((2-chlorophenyl)amino)benzoate (12.44 g, 29.64 mmol) in DMF (100 mL) was added $NaN_3$ (2.89 g, 44.46 mmol) at ambient temperature. The mixture was stirred at 90° C. for 3 h. Then water (150 mL) was added. The solution was extracted with ethyl acetate (100 mL×3). The combined organic extracts were washed with water (100 mL) and brine (100 mL), dried over $Na_2SO_4$ and concentrated in vacuo. The residue was purified by flash column chromatography on silica gel (petroleum ether/ethyl acetate, 10:1, v/v) and gave the desired product (white solid, 9.84 g, 75.1% yield). $^1$H NMR (400 MHz, DMSO-$d_6$): δ 8.72 (s, 1H), 7.65 (s, 1H), 7.45 (m, 1H), 7.33 (m, 4H), 7.24 (m, 2H), 6.95 (m, 2H), 4.20 (s, 2H), 3.81 (s, 3H).

Step 5: methyl 4-amino-5-(benzylthio)-3-fluoro-2-((2-chlorophenyl)amino)benzoate To a solution of methyl 4-azido-5-(benzylthio)-3-fluoro-2-((2-chlorophenyl)amino)benzoate (9.84 g, 22.23 mmol) in MeOH (200 mL) was added and 10% palladium on carbon (1.55 g) under nitrogen atmosphere. Then the nitrogen atmosphere was completely changed to hydrogen atmosphere. The mixture was stirred for 2 h at ambient temperature. After the insoluble matter was filtered off, the solvent was evaporated in vacuo to give the desired product (9.26 g, 100%). $^1$H NMR (400 MHz, DMSO-$d_6$): δ 8.94 (s, 1H), 7.54 (s, 1H), 7.45 (m, 1H), 7.24 (m, 6H), 6.95 (m, 1H), 6.77 (m, 1H), 6.27 (s, 2H), 3.95 (s, 2H), 3.73 (s, 3H).

Step 6: methyl 4-fluoro-5-((2-chlorophenyl)amino) benzo[d][1,2,3]thiadiazole-6-carboxylate To a solution of methyl 4-amino-5-(benzylthio)-3-fluoro-2-((2 chlorophenyl)amino)benzoate (2.50 g, 5.99 mmol) in acetic acid (60 mL) was added con. HCl (8 mL). The resultant was stirred at ambient temperature for 1 h. A solution of $NaNO_2$ (0.45 g, 6.58 mmol) in water (10 mL) was added dropwisely at 0° C. in 20 min. After stirring for 3 h, the reaction was treated with saturated $NaHCO_3$ (aq.) till the solution was neutral. The aqueous layer was extracted with ethyl acetate (30 mL×3). The combined organic phase was washed with water (30 mL) and brine (30 mL) sequentially, dried over $Na_2SO_4$ filtered and concentrated. The crude product was purified by column chromatography on silica gel (petroleum ether/ethyl acetate, 5:1, v/v) to give the corresponding product (yellow solid, 1.82 g, 90.1% yield). $^1$H NMR (400 MHz, $CDCl_3$): δ 8.83 (s, 1H), 8.59 (d, 1H), 7.45 (m, 1H), 7.24 (m, 1H), 6.95 (m, 2H), 4.03 (s, 3H).

Step 7: methyl 4-fluoro-5-((4-bromo-2-chlorophenyl)amino)benzo[d][1,2,3]thiadiazole-6-carboxylate To a solution of methyl 4-fluoro-5-((2-chlorophenyl)amino)benzo[d][1,2,3]thiadiazole-6-carboxylate (1.82 g, 5.39 mmol) in DMF (10 mL) was added NBS (1.0 g, 5.65 mmol). After stirring for 4 h at ambient temperature, the reaction was quenched by saturated $NH_4Cl$ (aq.). The solution was extracted with ethyl acetate (30 mL×3). The combined organic extracts were washed with water (30 mL) and brine (30 mL) successively, dried over $Na_2SO_4$ and concentrated in vacuo to give the desired product (yellow solid, 2.02 g, 90.1% yield). $^1$H NMR (400 MHz, $CDCl_3$): δ 8.84 (s, 1H), 8.60 (d, 1H), 7.59 (d, 1H), 7.29 On. US) 6.77 (m, 1H), 4.04 (s, 3H).

Step 8: 4-fluoro-5-((4-bromo-2-chlorophenyl) amino)benzo[d][1,2,3]thiadiazole-6-carboxylic acid To a solution of methyl 4-fluoro-5-((4-bromo-2-chlorophenyl)amino)benzo[d][1,2,3]thiadiazole-6-carboxylate (2.02 g, 4.85 mmol) in THF and MeOH (20 mL, 4:1, v/v) was added 5.0 M LiOH (aq., 2 mL, 10 mmol). After stirring at ambient temperature for 2 h, the reaction was treated with 1.0 M HCl (1 (aq.) till the solution was acidic. The aqueous layer was extracted with ethyl acetate (30 mL×3). The combined organic phase was washed with water (30 mL) and brine (30 mL) sequentially, dried over $Na_2SO_4$, filtered and concentrated to give the desired product (brown yellow solid, 1.85 g, 95% yield). $^1$H NMR (400 MHz, $CDCl_3$): δ 13.90 (s, 1H), 8.80 (s, 1H), 8.55 (d, 1H), 7.56 (d, 1H), 7.27 (m, 1H), 6.75 (m, 1H).

Step 9: 4-fluoro-5-((4-bromo-2-chlorophenyl) amino)-N-(2-(vinyloxy)ethoxy)benzo[d][1,2,3]thiadiazole-6-carboxamide To a solution of 4-fluoro-5-((4-bromo-2-chlorophenyl) amino)benzo[d][1,2,3]thiadiazole-6-carboxylic acid (200 mg, 0.46 mmol) in $CH_2Cl_2$ (10 mL) was added HOBt (100 mg, 0.74 mmol) and EDCI (132 mg, 0.74 mmol). The mixture was stirred for 1 h and O-(2-(vinyloxy)ethyl)hydroxylamine (76 mg, 0.74 mmol) was added. After stirring for 4 h at ambient temperature, the reaction was treated with saturated $NH_4Cl$ (aq.). The resultant mixture was extracted with $CH_2Cl_2$ (15 mL×3). The combined organic extracts were washed with water (10 mL) and brine (10 mL), dried over $Na_2SO_4$ filtered, and concentrated in vacuo. The crude product (191 mg) was used directly in the next step without further purification.

Step 10: 4-fluoro-5-((4-bromo-2-chlorophenyl) amino)-N-(2-hydroxyethoxy)benzo[d][1,2,3]thiadiazole-6-carboxamide To a solution of compound 4-fluoro-5-((4-bromo-2-chlorophenyl)amino)-N-(2-(vinyloxy)ethoxy)benzo[d][1,2,3] thiadiazole-6-carboxamide (191 mg, 0.39 mmol) in $CH_2Cl_2$ (10 mL) was added 1.0 N HCl (aq., 1.5 mL, 1.5 mmol). After stirring for 1 h, the reaction mixture was neutralized with saturated $NaHCO_3$ (aq.). The aqueous layer was washed with $CH_2Cl_2$ (10 mL×2). The combined organic layer was washed with water (30 mL×2) and brine (30 mL), dried over $Na_2SO_4$, filtered and concentrated in vacuo. The crude product was purified by column chromatography on silica gel ($CH_2Cl_2$/MeOH, 20:1, v/v) and gave the desired product as a yellow solid (150 mg, 66.5% yield for two steps). $^1$H NMR (400 MHz, $CD_3OD$): δ 8.53 (s, 1H), 7.69 (s, 1H), 7.34 (d, 1H), 6.74 (m, 1H), 3.91 (m, 2H), 3.62 (m, 2H). MS APCI(+)m/z: 462.5 [M+H].

Example 20: Preparation of 5-((4-bromo-2-chlorophenyl)amino)-N-(2,3-dihydroxypropoxy)-4-fluorobenzo[d][1,2,3]thiadiazole-6-carboxamide (Compound 20)

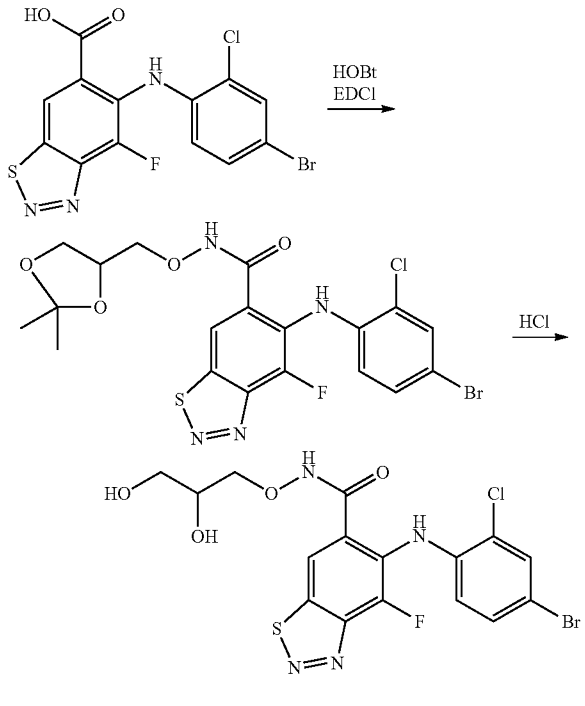

Step 1: N-((2,2-dimethyl-1,3-dioxolan-4-yl) methoxy)-4-fluoro-5-((2-chloro-4-bromophenyl) amino)benzo[d][1,2,3]thiadiazole-6-carboxamide To a solution of 4-fluoro-5-((4-bromo-2-chlorophenyl) amino)benzo[d][1,2,3]thiadiazole-6-carboxylic acid (200 mg, 0.49 mmol) in $CH_2Cl_2$ (10 mL) was added HOBt (100 mg, 0.74 mmol) followed by EDCI (140 mg, 0.74 mmol).

The mixture was stirred for 1 h and O-((2,2-dimethyl-1,3-dioxolan-4-yl)methyl)hydroxylamine (108 mg, 0.74 mmol) was added. After stirring for 4 h at ambient temperature, the reaction was treated with saturated $NH_4Cl$ (aq.). The resultant mixture was extracted with $CH_2Cl_2$ (15 mL×3). The combined organic extracts was washed by water (10 mL) and brine (10 mL) sequentially, dried over $Na_2SO_4$, filtered and concentrated in vacuo. The crude product (213 mg) was used directly in the next step without further purification.

Step 2: N-(2,3-dihydroxypropoxy)-4-fluoro-5-((4-bromo-2-chlorophenyl)amino)benzo[d][1,2,3]thiadiazole-6-carboxamide To a solution of N-((2,2-dimethyl-1,3-dioxolan-4-yl)methoxy)-4-fluoro-5-((4-bromo-2-chlorophenyl)amino)benzo[d][1,2,3]thiadiazole-6-carboxamide (60 mg, 0.11 mmol) in $CH_2Cl_2$ (10 mL) was added 1.0 N HCl (aq., 1 mL, 1.0 mmol). The mixture was stirred for 1 h and neutralized with saturated sodium bicarbonate (aq.). The aqueous layer was extracted by $CH_2Cl_2$ (10 mL×2). The combined organic layers were washed by water (10 mL) and brine (10 mL) sequentially, dried over $Na_2SO_4$, filtered and concentrated in vacuo. The crude product was purified by column chromatography on silica gel ($CH_2Cl_2$/MeOH, 20:1, v/v) to afford the desired product (yellow solid, 41 mg, 61.5% yield for two steps). $^1H$ NMR (400 MHz, $CD_3OD$): δ 11.13 (s, 1H), 8.59 (s, 1H), 7.66 (d, 1H), 7.34 (dd, 1H), 6.76 (m, 1H), 3.79 (m, 1H), 3.71 (m, 2H), 3.35 (m, 2H). MS APCI(+)m/z: m/z 492.8, [M+H].

Example 21: Preparation of N-(4-fluoro-5-((2-fluoro-4-iodophenyl)amino)benzo[d][1,2,3]thiadiazol-6-yl)cyclopropanesulfonamide (Compound 21)

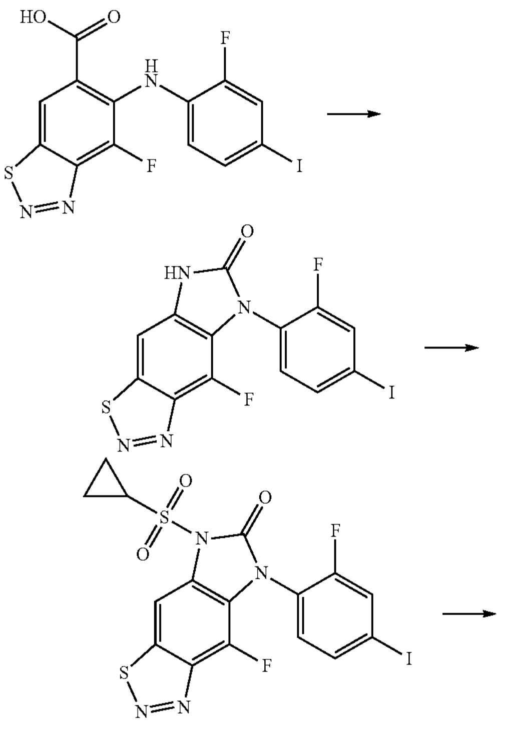

-continued

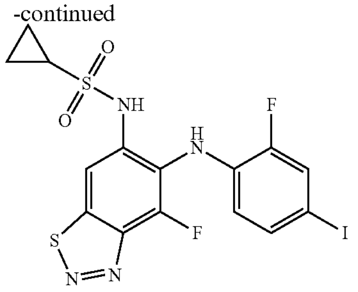

Step 1: 4-fluoro-5-(2-fluoro-4-iodophenyl)-5H-imidazo[4',5':4,5]benzo[1,2-d][1,2,3]thiadiazol-6(7H)-one To a solution of 4-fluoro-5-((2-fluoro-4-iodophenyl)amino)benzo[d][1,2,3]thiadiazole-6-carboxylic acid (120 mg, 0.30 mmol) in t-BuOH (10 mL) was added DPPA (48 mg, 0.45 mmol) followed by triethylamine (60 mg, 0.60 mmol). The mixture was heated under reflux for 3 h and allowed to slowly warm to room temperature. The solvent was removed in vacuo and the resultant crude product was purified by column chromatography on silica gel (petroleum ether/ethyl acetate, 2:1, v/v). The corresponding product was obtained (100 mg, 83.9% yield). $^1H$ NMR (400 MHz, DMSO-$d_6$): δ 12.14 (s, 1H), 8.01-7.99 (m, 1H), 7.89 (s, 1H), 7.83 (m, 1H), 7.59-7.55 (m, 1H).

Step 2: 7-(cyclopropylsulfonyl)-4-fluoro-5-(2-fluoro-4-iodophenyl)-5H-imidazo[4',5':4,5]benzo[1,2-d][1,2,3]thiadiazol-6(7H)-one To a solution of 4-fluoro-5-(2-fluoro-4-iodophenyl)-5H-imidazo[4',5':4,5]benzo[1,2-d][1,2,3]thiadiazol-6(7H)-one (60 mg, 0.14 mmol) in $CH_2Cl_2$ (3 mL) was added triethylamine (43 mg, 0.42 mmol) at 0° C. followed by cyclopropanesulfonyl chloride (31 mg, 0.21 mmol) and DMAP (5 mg). The mixture was stirred at room temperature for 1 h and washed with saturated $NaHCO_3$ (aq.). The aqueous layer was extracted with $CH_2Cl_2$ (10 mL×2). The combined organic phase was washed with water (10 mL) and brine (10 mL) successively, dried over $Na_2SO_4$, filtered and concentrated in vacuo. The residue was purified by flash chromatography on silica gel (petroleum ether/ethyl acetate, 5:1, v/v) to give the corresponding product (75 mg, 100% yield). $^1H$ NMR (400 MHz, $CDCl_3$): δ 8.34 (s, 1H), 7.75-7.73 (d, 2H), 7.34 (m, 1H), 3.34 (m, 1H), 1.68 (m, 2H), 0.85 (m, 2H).

Step 3: N-(4-fluoro-5-((2-fluoro-4-iodophenyl)amino)benzo[d][1,2,3]thiadiazol-6-yl)cyclopropanesulfonamide To a solution of 7-(cyclopropylsulfonyl)-4-fluoro-5-(2-fluoro-4-iodophenyl)-5H-imidazo[4',5':4,5]benzo[1,2-d][1,2,3]thiadiazol-6(7H)-one (70 mg, 0.13 mmol) in THF (5 mL) was added potassium trimethylsilanolate (17 mg, 0.13 mmol). After stirring at room temperature for 1 h, the reaction was quenched with saturated $NH_4Cl$ (aq.). The aqueous layer was extracted with ethyl acetate (6 mL×2). The combined organic phase was washed with brine (10 mL), dried over $Na_2SO_4$, filtered and concentrated in vacuo. The residual crude product was purified by flash chromatography on silica gel (petroleum, ether/ethyl acetate, 5:1-3:1, v/v) to give the corresponding product (40 mg, 60.1% yield). $^1H$ NMR (400 MHz, DMSO-$d_6$): δ 9.86 (s, 1H), 8.37 (s, 1H), 7.73 (s, 1H), 7.60 (dd, 1H), 7.30 (dd, 1H), 6.45 (m, 1H), 2.77 (m, 1H), 1.01-0.99 (m, 2H), 0.89-0.86 (m, 2H). MS APCI(+)m/z: 508.7, [M+H].

Example 22: Preparation of 1-(2,3-dihydroxypropyl)-N-(4-fluoro-5-((2-fluoro-4-iodophenyl)amino)benzo[d][1,2,3]thiadiazol-6-yl)cyclopropane-1-sulfonamide (Compound 22)

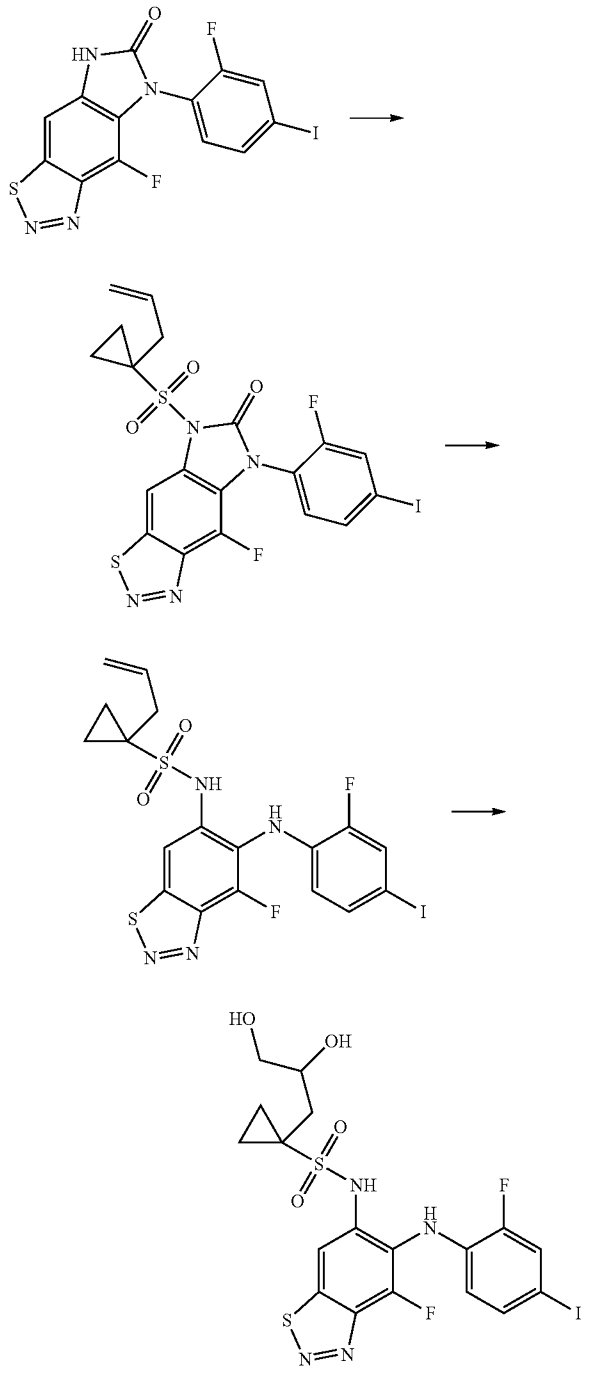

Step 1: 7-((1-allylcyclopropyl)sulfonyl)-4-fluoro-5-(2-fluoro-4-iodophenyl)-5H-imidazo[4',5': 4,5]benzo[1,2-d][1,2,3]thiadiazol-6(7H)-one To a solution of 4-fluoro-5-(2-fluoro-4-iodophenyl)-5H-imidazo[4',5':4,5]benzo[1,2-d][1,2,3]thiadiazol-6(7H)-one (50 mg, 0.12 mmol) in DCM (5 mL) was added triethylamine (24 mg, 0.23 mmol) at 0° C. followed by 1-allylcyclopropane-1-sulfonyl chloride (32 mg, 0.17 mmol) and DMAP (10 mg). After stirring at room temperature for 1 h, the mixture was washed with saturated $NaHCO_3$ (aq.). The aqueous layer was extracted with DCM (20 mL×2). The combined organic phase was washed by water (20 mL) and brine (20 mL) sequentially, dried over $Na_2SO_4$, filtered and concentrated to give a residue, which was purified by flash chromatography on silica gel (petroleum ether/ethyl acetate, 5:1, v/v) to give the corresponding product (60 mg, 89.9% yield). $^1H$ NMR (400 MHz, $CDCl_3$): δ 8.36 (s, 1H), 7.76-7.74 (m, 2H), 7.35 (m, 1H), 5.75-5.58 (m, 1H), 5.05 (m, 2H), 2.90-2.80 (m, 1H), 2.10-2.0 (m, 1H), 1.95-1.86 (m, 2H), 1.25-1.11 (m, 2H).

Step 2: 1-allyl-N-(4-fluoro-5-((2-fluoro-4-iodophenyl)amino)benzo[d][1,2,3]thiadiazol-6-yl)cyclopropane-1-sulfonamide To a solution of 7-((1-allylcyclopropyl)sulfonyl)-4-fluoro-5-(2-fluoro-4-iodophenyl)-5H-imidazo[4',5':4,5]benzo[1,2-d][1,2,3]thiadiazol-6(7H)-one (60 mg, 0.11 mmol) in THF (5 ml) was added potassium trimethylsilanolate (14 mg, 0.11 mmol). The reaction was stirred at room temperature for 1 h and quenched with saturated $NH_4Cl$ (aq.). The aqueous layer was extracted with EA (10 mL×2). The combined organic phase was washed with brine (20 mL), dried over $Na_2SO_4$, filtered and concentrated in vacuo. The residue was purified by Hash chromatography on silica gel (petroleum ether/ethyl acetate, 5:1-3:1, v/v) to give the desired product (50 mg, 87.3% yield). $^1H$ NMR (400 MHz, $CDCl_3$): δ 8.24 (s, 1H), 7.65-7.63 (m, 2H), 7.31 (m, 1H), 7.01 (s, 1H), 6.83 (s, 1H), 5.74-5.56 (m, 1H), 5.02 (m, 2H), 2.77-2.71 (m, 1H), 2.12-2.0 (m, 1H), 1.75-1.71 (m, 2H), 1.21-0.97 (m, 2H).

Step 3: 1-(2,3-dihydroxypropyl)-N-(4-fluoro-5-((2-fluoro-4-iodophenyl)amino)benzo[d][1,2,3]thiadiazol-6-yl)cyclopropane-1-sulfonamide To a solution of 1-allyl-N-(4-fluoro-5-((2-fluoro-4-iodophenyl)amino)benzo[d][1,2,3]thiadiazol-6-yl)cyclopropane-1-sulfonamide (50 mg, 0.09 mmol) in THF (5 mL) was added N-methylmorpholine-N-oxide (12 mg, 0.09 mmol) followed by osmium tetraoxide (5 mg, 0.02 mmol) and water (0.5 mL). The resultant was stirred at room temperature overnight. The mixture was concentrated and then diluted with ethyl acetate. The organic layer was washed with water, saturated $NaHCO_3$ (aq.) and brine sequentially, dried over $Na_2SO_4$, filtered and concentrated to give a residue, which was purified by flash chromatography on silica gel to give the product as white solid (30 mg, 56.5% yield). NMR (400 MHz, $CDCl_3$): δ 8.26 (s, 1H), 7.67-7.64 (d, 2H), 7.32 (m, 1H), 7.03 (s, 1H), 6.85 (s, 1H), 4.40-4.26 (m, 2H), 4.20-4.10 (m, 1H), 3.75-3.60 (m, 1H), 3.60-3.50 (m, 1H), 2.62-2.50 (m, 2H), 0.92-0.82 (m, 4H). MS APCI (+)m/z: 583.5, [M+H].

Example 23: Preparation of N-(5-((4-bromo-2-chlorophenyl)amino)-4-fluorobenzo[d][1,2,3]thiadiazol-6-yl)cyclopropanesulfonamide (Compound 23)

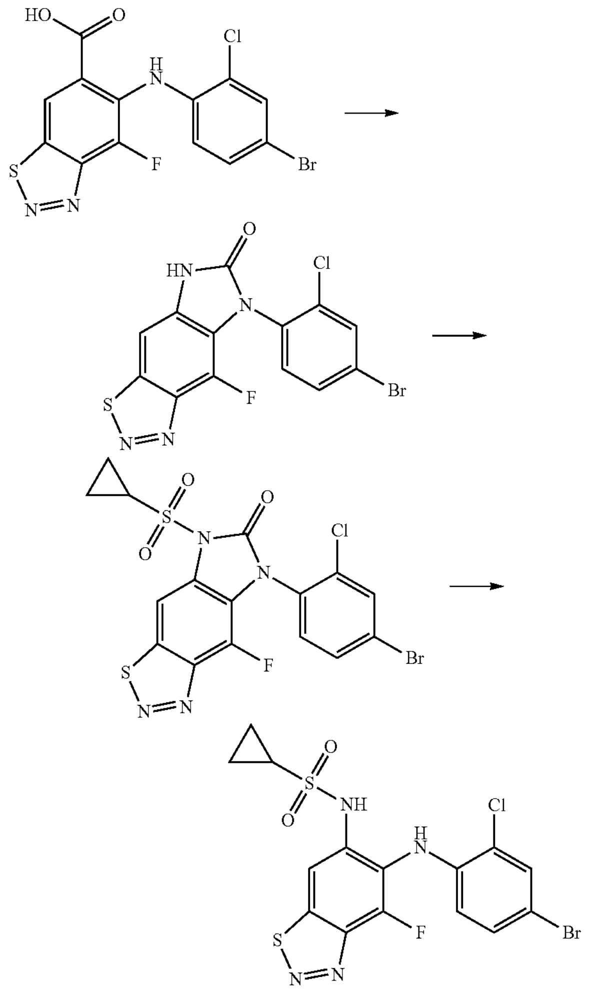

Step 1: 4-fluoro-5-(4-bromo-2-chlorophenyl)-5H-imidazo[4',5': 4,5]benzo[1, 2-d][1, 2,3]thiadiazol-6(7H)-one To a solution of 4-fluoro-5-((4-bromo-2-chlorophenyl)amino)benzo[d][1,2,3]thiadiazole-6-carboxylic acid (100 mg, 0.25 mmol) in t-BuOH (5 mL) was added DPPA (103 mg, 0.37 mmol) followed by triethylamine (76 mg, 0.75 mmol). The mixture was heated under reflux for 3 h and allowed to slowly warm to room temperature. The solvent was removed in vacuo and the resultant crude product was purified by column chromatography on silica gel (petroleum ether/ethyl acetate, 2:1, v/v). The corresponding product was obtained (90 mg, 90.7% yield). $^1$H NMR (400 MHz, DMSO-$d_6$): δ 11.75 (s, 1H), 8.67 (s, 1H), 7.96 (d, 1H), 7.76 (d, 1H), 7.50 (t, 1H).

Step 2: 7-(cyclopropylsulfonyl)-4-fluoro-5-(4-bromo-2-chlorophenyl)-5H-imidazo[4',5': 4,5]benzo[1, 2-d][1,2,3]thiadiazol-6(7H)-one To a solution of 4-fluoro-5-(4-bromo-2-chlorophenyl)-5H-imidazo[4',5':4,5]benzo[1,2-d][1,2,3]thiadiazol-6(7H)-one (50 mg, 0.13 mmol) in $CH_2Cl_2$ (5 mL) was added triethylamine (26 mg, 0.25 mmol) at 0° C. followed by cyclopropanesulfonyl chloride (26 mg, 0.19 mmol) and DMAP (10 mg). The mixture was stirred at room temperature for 1 h and washed with saturated $NaHCO_3$ (aq.). The aqueous layer was extracted with $CH_2Cl_2$ (10 mL×2). The combined organic phase was washed with water (10 mL) and brine (10 mL) successively, dried over $Na_2SO_4$, filtered and concentrated in vacuo. The residue was purified by flash chromatography on silica gel (petroleum ether/ethyl acetate, 5:1, v/v) to give the corresponding product (60 mg, 95% yield). $^1$H NMR (400 MHz, $CDCl_3$): δ 8.31 (s, 1H), 7.75-7.72 (d, 2H), 7.35 (m, 1H), 3.35 (m, 1H), 1.70 (m, 2H), 0.87 (m, 2H).

Step 3: N-(4-fluoro-5-((4-bromo-2-chlorophenyl)amino)benzo[d][1,2,3]thiadiazol-6-yl)cyclopropanesulfonamide To a solution of 7-(cyclopropylsulfonyl)-4-fluoro-5-(2-chloro-4-bromophenyl)-5H-imidazo[4',5':4,5]benzo[1,2-d][1,2,3]thiadiazol-6(7H)-one (60 mg, 0.12 mmol) in THF (5 mL) was added potassium trimethylsilanolate (16 mg, 0.12 mmol). After stirring at room temperature for 1 h, the reaction was quenched with saturated $NH_4Cl$ (aq.). The aqueous layer was extracted with ethyl acetate (10 mL×2). The combined organic phase was washed with brine (10 mL), dried over $Na_2SO_4$, filtered and concentrated in vacuo. The residual crude product was purified by flash chromatography on silica gel (petroleum ether/ethyl acetate, 5:1-3:1, v/v) to give the corresponding product (30 mg, 52.7% yield). $^1$H NMR (400 MHz, $CDCl_3$): δ 8.25 (s, 1H), 8.02-7.98 (m, 1H), 7.85 (m, 1H), 7.60-7.56 (m, 1H), 7.14 (s, 1H), 6.83 (s, 1H), 2.81-2.72 (m, 1H), 1.33 (m, 2H), 1.15 (m, 2H). MS APCI(+)m/z: 478.8, [M+H].

Example 24: Preparation of N-(5-((4-bromo-2-chlorophenyl)amino)-4-fluorobenzo[d][1,2,3]thiadiazol-6-yl)-1-(2,3-dihydroxypropyl)cyclopropane-1-sulfonamide (Compound 24)

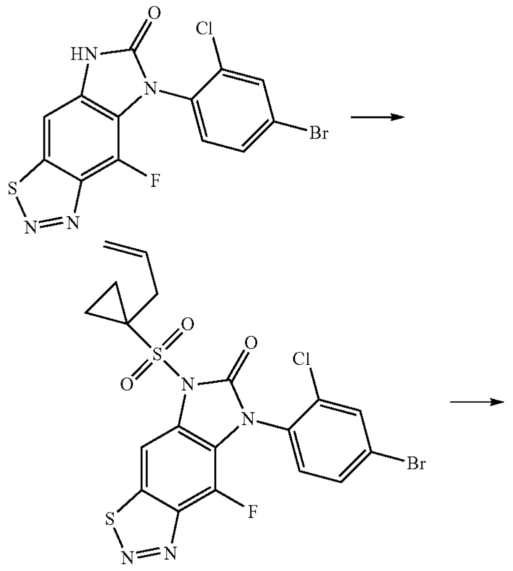

-continued

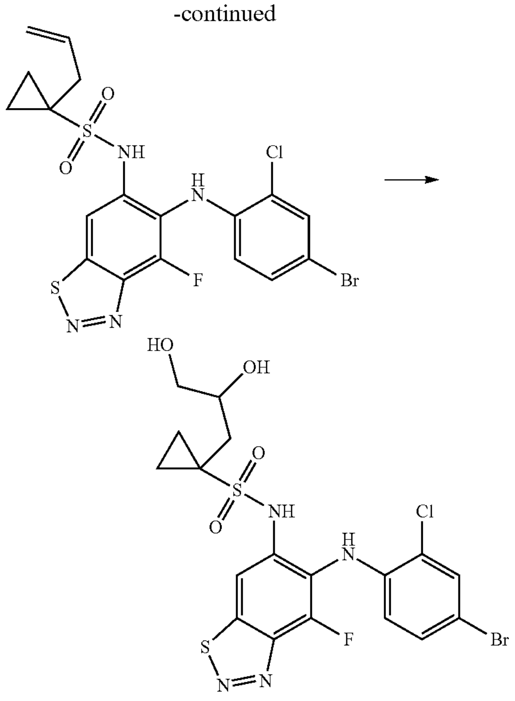

Step 1: 7-((1-allylcyclopropyl)sulfonyl)-4-fluoro-5-(4-bromo-2-chlorophenyl)-5H-imidazo[4',5':4,5]benzo[1, 2-d][1,2,3]thiadiazol-6(7H)-one To a solution of 4-fluoro-5-(4-bromo-2-chlorophenyl)-5H-imidazo[4',5':4,5]benzo[1,2-d][1,2,3]thiadiazol-6(7H)-one (40 mg, 0.10 mmol) in DCM (5 mL) was added triethylamine (21 mg, 0.20 mmol) at 0° C. followed by 1-allylcyclopropane-1-sulfonyl chloride (27 mg, 0.15 mmol) and DMAP (10 mg). After stirring at room temperature for 1 h, the mixture was washed with saturated $NaHCO_3$ (aq.). The aqueous layer was extracted with DCM (20 mL×2). The combined organic phase was washed by water (20 mL) and brine (20 mL) sequentially, dried over $Na_2SO_4$, filtered and concentrated to give a residue, which was purified by flash chromatography on silica gel (petroleum ether/ethyl acetate, 5:1, v/v) to give the corresponding product (50 mg, 87.1% yield). $^1$H NMR (400 MHz, $CDCl_3$): δ 8.37 (s, 1H), 7.78-7.76 (d, 2H), 7.33 (m, 1H), 5.76-5.58 (m, 1H), 5.08 (m, 2H), 2.93-2.86 (m, 1H), 2.13-2.0 (m, 1H), 1.97-1.87 (m, 2H), 1.28-1.16 (m, 2H).

Step 2: 1-allyl-N-(4-fluoro-5-((4-bromo-2-chlorophenyl)amino)benzo[d][1,2,3]thiadiazol)-6-yl)cyclopropane-1-sulfonamide To a solution of 7-((1-allylcyclopropyl)sulfonyl)-4-fluoro-5-(2-chloro-4-bromophenyl)-5H-imidazo[4',5':4,5]benzo[1,2-d][1,2,3]thiadiazol-6(7H)-one (50 mg, 0.09 mmol) in THF (5 mL) was added potassium trimethylsilanolate (12 mg, 0.09 mmol). The reaction was stirred at room temperature for 1 h and quenched with saturated $NH_4Cl$ (aq.). The aqueous layer was extracted with EA (10 mL×2). The combined organic phase was washed with brine (20 mL), dried over $Na_2SO_4$, filtered and concentrated in vacuo. The residue was purified by flash chromatography on silica gel (petroleum ether/ethyl acetate, 5:1-3:1, v/v) to give the desired product (45 mg, 94.5% yield). $^1$H NMR (400 MHz, $CDCl_3$): δ 8.26 (s, 1H), 7.65-7.57 (m, 2H), 7.33 (m, 1H), 7.00 (s, 1H), 6.85 (s, 1H), 5.72-5.57 (m, 1H), 5.05 (m, 2H), 2.79-2.72 (m, 1H), 2.12-2.05 (m, 1H), 1.76-1.71 (m, 2H), 1.21-0.98 (m, 2H).

Step 3: 1-(2,3-dihydroxypropyl)-N-(4-fluoro-5-((2-fluoro-4-iodophenyl)amino)benzo[d][1,2,3]thiadiazol-6-yl)cyclopropane-1-sulfonamide To a solution of 1-allyl-N-(4-fluoro-5-((4-bromo-2-chlorophenyl)amino)benzo[d][1,2,3]thiadiazol-6-yl)cyclopropane-1-sulfonamide (45 mg, 0.09 mmol) in THF (5 mL) was added N-methylmorpholine-N-oxide (10 mg, 0.09 mmol) followed by osmium tetraoxide (5 mg, 0.02 mmol) and water (0.5 mL). The resultant was stirred at room temperature overnight. The mixture was concentrated and then diluted with ethyl acetate. The organic layer was washed with water, saturated $NaHCO_3$ (aq.) and brine sequentially, dried over $Na_2SO_4$, filtered and concentrated to give a residue, which was purified by flash chromatography on silica gel to give the product as white solid (20 mg, 41.7% yield). $^1$H NMR (400 MHz, $CDCl_3$): δ 8.26 (s, 1H), 7.69-7.62 (d, 2H), 7.33 (m, 1H), 7.04 (s, 1H), 6.85 (s, 1H), 4.40-4.25 (m, 2H), 4.22-4.12 (m, 1H), 3.75-3.62 (m, 1H), 3.61-3.52 (m, 1H), 2.62-2.51 (m, 2H), 0.95-0.82 (m, 1H). MS APCI(+)m/z: 552.9, [M+H].

Examples 25-33: Preparation of Compounds 25-33

Compounds 25-33 were prepared following similar procedures used for compounds 1-8.

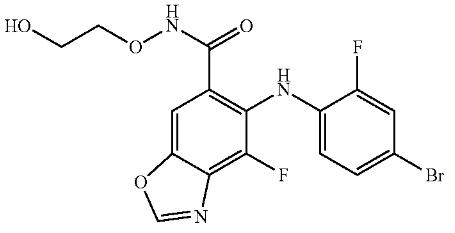

$^1$H NMR (400 MHz, DMSO) δ 11.74 (s, 1H), 8.96 (s, 1H), 8.04 (s, 1H), 7.91 (s, 1H), 7.56 (d, J=9.6 Hz, 1H), 7.32 (d, J=8.2 Hz, 1H), 6.41 (m, 1H), 4.73 (s, 1H), 3.86 (m, 2H), 3.56 (m, 2H). MS APCI(+)m/z: 429.4 [M+H].

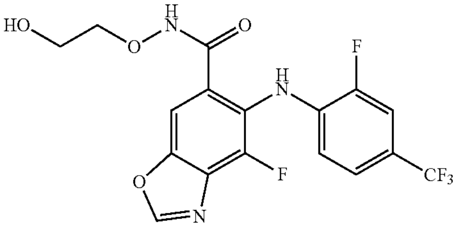 [SMILES: O=C(NOCCO)c1cc2ocnc2c(F)c1Nc1ccc(C(F)(F)F)cc1F]

$^1$H NMR (400 MHz, DMSO) δ 11.76 (s, 1H), 8.98 (s, 1H), 8.05 (s, 1H), 7.90 (s, 1H), 7.55 (d, J=9.6 Hz, 1H), 7.29 (d, J=8.8 Hz, 1H), 6.41 (m, 1H), 4.71 (s, 1H), 3.82 (m, 2H), 3.55 (in, 2H). MS APCI(+)m/z: 418.4 [M+H].

Compound 27

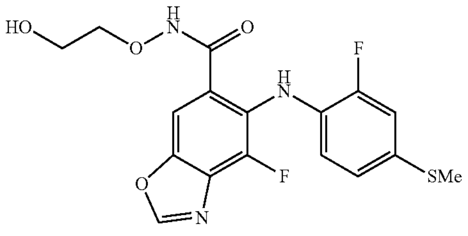

$^1$H NMR (400 MHz, DMSO) δ 11.74 (s, 1H), 8.95 (s, 1H), 8.00 (s, 1H), 7.86 (s, 1H), 7.54 (d, J=9.8 Hz, 1H), 7.27 (d, J=8.5 Hz, 1H), 6.38 (m, 1H), 4.69 (s, 1H), 3.82 (m, 2H), 3.57 (m, 2H), 2.55 (s, 3H) MS APCI(+)m/z: 396.5 [M+H].

Compound 28

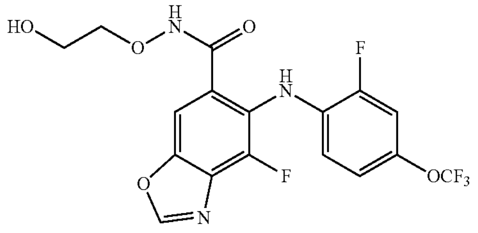

$^1$H NMR (400 MHz, DMSO) δ 11.76 (s, 1H), 8.97 (s, 1H), 8.03 (s, 1H), 7.90 (s, 1H), 7.55 (d, J=9.8 Hz, 1H), 7.30 (d, J=8.4 Hz, 1H), 6.40 (m, 1H), 4.72 (s, 1H), 3.85 (m, 2H), 3.57 (m, 2H). MS APCI(+)m/z: 434.4 [M+H].

Compound 29

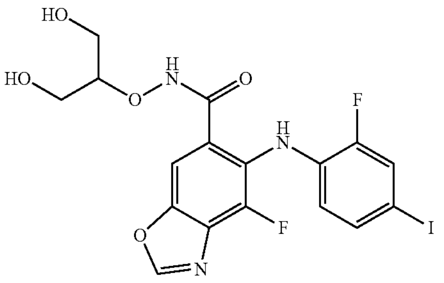

$^1$H NMR (400 MHz, DMSO) δ 11.75 (s, 1H), 8.95 (s, 1H), 8.04 (s, 1H), 7.92 (s, 1H), 7.56 (d, J=9.6 Hz, 1H), 7.31 (d, J=8.7 Hz, 1H), 6.42 (m, 1H), 4.75 (s, 2H), 3.68 (m, 4H), 3.38 (m, 1H). MS APCI(+)m/z: 506.3 [M+H].

Compound 30

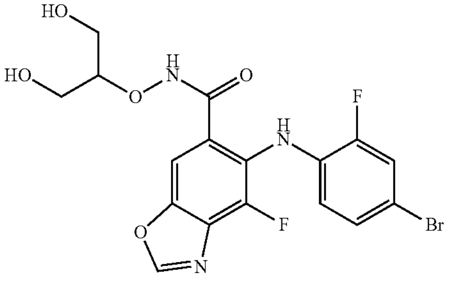

$^1$H NMR (400 MHz, DMSO) δ 11.74 (s, 1H), 8.96 (s, 1H), 8.07 (s, 1H), 7.91 (s, 1H), 7.58 (d, J=9.4 Hz, 1H), 7.33 (d, J=8.8 Hz, 1H), 6.45 (m, 1H), 4.76 (s, 2H), 3.70 (m, 4H), 3.40 (m, 1H). MS APCI(+)m/z: 459.4 [M+H].

Compound 31

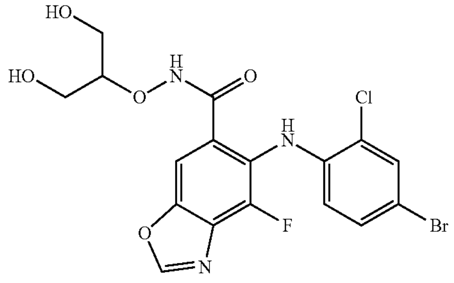

$^1$H NMR (400 MHz, DMSO) δ 11.75 (s, 1H), 8.95 (s, 1H), 8.04 (s, 1H), 7.92 (s, 1H), 7.58 (d, J=9.6 Hz, 1H), 7.35 (d, J=8.7 Hz, 1H), 6.43 (m, 1H), 4.73 (s, 2H), 3.71 (m, 4H), 3.39 (m, 1H). MS APCI(+)m/z: 475.8 [M+H].

Compound 32

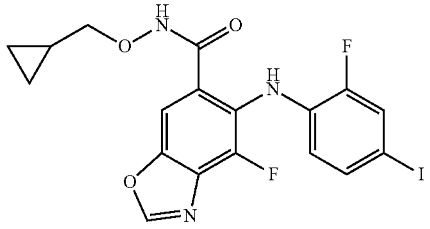

$^1$H NMR (400 MHz, DMSO) δ 11.70 (s, 1H), 8.93 (s, 1H), 8.01 (s, 1H), 7.90 (s, 1H), 7.55 (d, J=9.4 Hz, 1H), 7.32 (d, J=8.8 Hz, 1H), 6.41 (m, 1H), 3.73 (m, 2H), 0.51 (m, 1H), 0.25 (m, 4H). MS APCI(+)m/z: 486.2 [M+H].

Compound 33

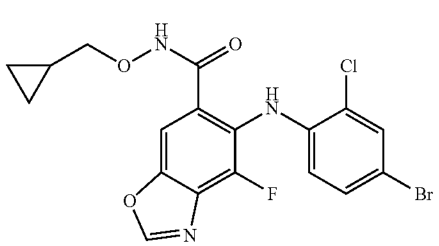

$^1$H NMR (400 MHz, DMSO) δ 11.71 (s, 1H), 8.92 (s, 1H), 8.02 (s, 1H), 7.93 (s, 1H), 7.57 (d, J=9.8 Hz, 1H), 7.33 (d, J=8.6 Hz, 1H), 6.43 (m, 1H), 3.75 (m, 2H), 0.52 (m, 1H), 0.26 (m, 4H). MS APCI(+)m/z: 455.8 [M+H].

Examples 34-42: Preparation of Compounds 43-51

Compounds 34-42 were prepared following similar procedures used for compounds 9-16.

Compound 34

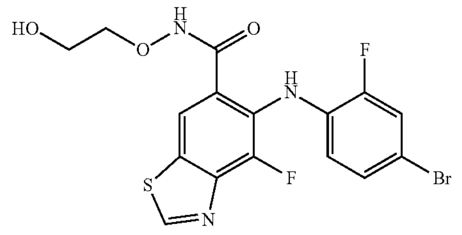

$^1$H NMR (400 MHz, DMSO) δ 11.81 (s, 1H), 9.54 (s, 1H), 8.20 (s, 1H), 8.11 (s, 1H), 7.56 (d, 1H), 7.31 (d, 1H), 6.47 (m, 1H), 4.73 (s, 1H), 3.85 (m, 2H), 3.55 (m, 2H). MS APCI(+) m/z: 445.3 [M+H].

Compound 35

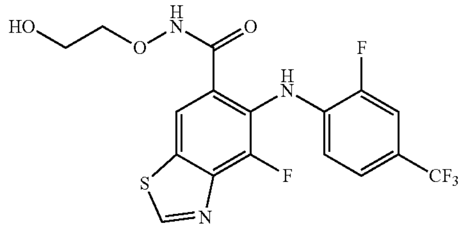

$^1$H NMR (400 MHz, DMSO) δ 11.81 (s, 1H), 9.53 (s, 1H), 8.24 (s, 1H), 8.14 (s, 1H), 7.56 (d, 1H), 7.33 (d, 1H), 6.50 (m, 1H), 4.74 (s, 1H), 3.85 (m, 2H), 3.55 (m, 2H), MS APCI(+) m/z: 434.4 [M+H].

Compound 36

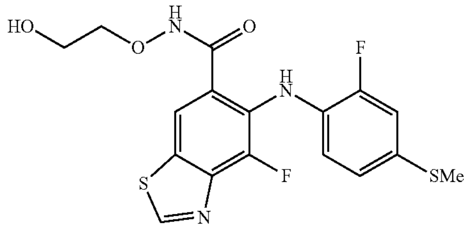

$^1$H NMR (400 MHz, DMSO) δ 11.80 (s, 1H), 9.54 (s, 1H), 8.22 (s, 1H), 8.12 (s, 1H), 7.54 (d, 1H), 7.30 (d, 1H), 6.45 (m, 1H), 4.73 (s, 1H), 3.84 (m, 2H), 3.56 (m, 2H) 2.51 (s, 3H). MS APCI(+)m/z: 412.5 [M+H].

Compound 37

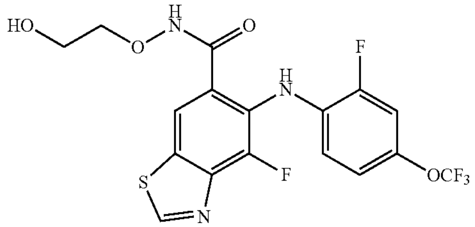

$^1$H NMR (400 MHz, DMSO) δ 11.80 (s, 1H), 9.55 (s, 1H), 8.23 (s, 1H), 8.11 (s, 1H), 7.52 (d, 1H), 7.28 (d, 1H), 6.43 (m, 1H), 4.75 (s, 1H), 3.83 (m, 2H), 3.55 (m, 2H). MS APCI(+) m/z: 450.5 [M+H].

Compound 38

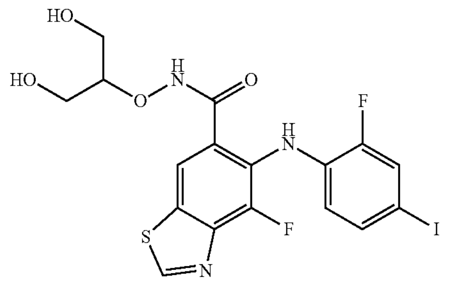

$^1$H NMR (400 MHz, DMSO) δ 11.78 (s, 1H), 9.54 (s, 1H), 8.20 (s, 1H), 8.11 (s, 1H), 7.56 (d, 1H), 7.32 (d, 1H), 6.49 (m, 1H), 4.75 (s, 2H), 3.67 (m, 4H), 3.36 (m, 1H). MS APCI(+) m/z: 522.3 [M+H].

Compound 39

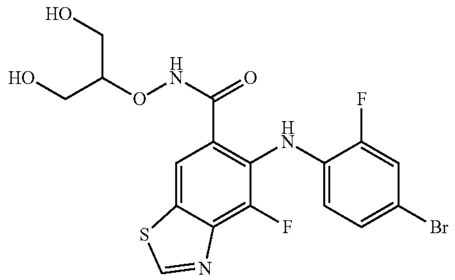

$^1$H NMR (400 MHz, DMSO) δ 11.79 (s, 1H), 9.5.5 (s, 1H), 8.21 (s, 1H), 8.12 (s, 1H), 7.57 (d, 1H), 7.31 (d, 1H), 6.50 (m, 1H), 4.74 (s, 2H), 3.68 (m, 4H), 3.35 (m, 1H). MS APCI(+) m/z: 475.3 [M+H].

Compound 40

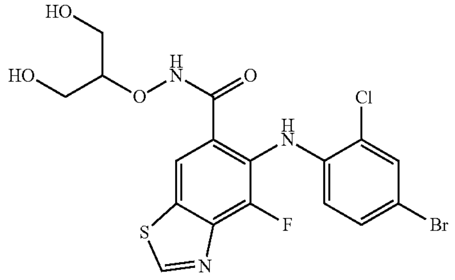

$^1$H NMR (400 MHz, DMSO) δ 11.80 (s, 1H), 9.53 (s, 1H), 8.22 (s, 1H), 8.13 (s, 1H), 7.58 (d, 1H), 7.32 (d, 1H), 6.51 (m, 1H), 4.75 (s, 2H), 3.70 (m, 4H), 3.36 (m, 1H). MS APCI(+) m/z: 491.7 [M+H].

Compound 41

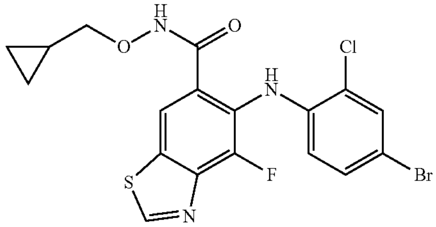

$^1H$ NMR (400 MHz, DMSO) δ 11.85 (s, 1H), 9.55 (s, 1H), 8.25 (s, 1H), 8.14 (s, 1H), 7.60 (d, 1H), 7.31 (d, 1H), 6.52 (m, 1H), 3.72 (m, 2H), 0.50 (m, 1H), 0.25 (m, 4H). MS APCI(+) m/z: 471.7 [M+H].

Compound 42

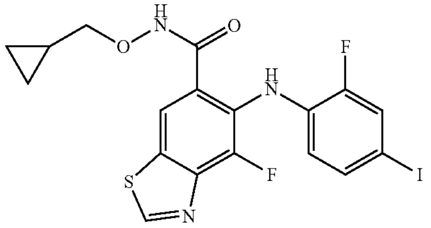

$^1H$ NMR (400 MHz, DMSO) δ 11.83 (s, 1H), 9.54 (s, 1H), 8.23 (s, 1H), 8.14 (s, 1H), 7.62 (d, 1H), 7.33 (d, 1H), 6.50 (m, 1H), 3.71 (m, 2H), 0.49 (m, 1H), 0.23 (m, 4H). MS APCI(+) m/z: 502.3 [M+H].

Examples 43-51: Preparation of Compounds 43-51

Compounds 43-51 were prepared following similar procedures used for compounds 17-24.

Compound 43

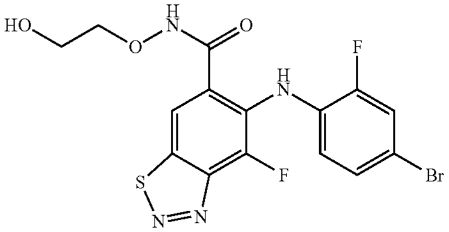

$^1H$ NMR (400 MHz, DMSO) δ 11.92 (s, 1H), 8.68 (s, 1H), 8.55 (s, 1H), 7.35 (d, 1H), 7.23 (d, 1H), 6.37 (m, 1H), 4.72 (s, 1H), 4.04 (m, 2H), 3.78 (m, 2H). MS APCI(+)m/z: 446.3 [M+H].

Compound 44

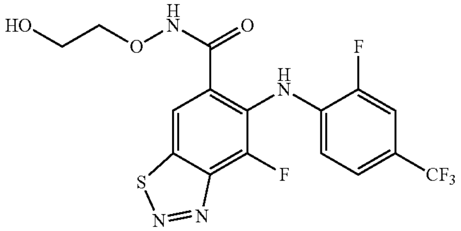

$^1H$ NMR (400 MHz, DMSO) δ 11.90 (s, 1H), 8.66 (s, 1H), 8.54 (s, 1H), 7.38 (d, 1H), 7.24 (d, 1H), 6.41 (m, 1H), 4.70 (s, 1H), 4.04 (m, 2H), 3.79 (m, 2H). MS APCI(+)m/z: 435.4 [M+H].

Compound 45

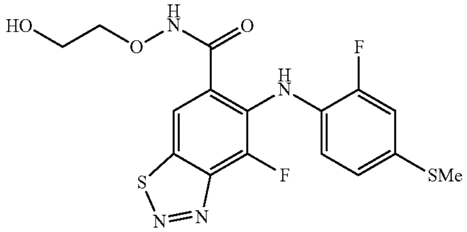

$^1H$ NMR (400 MHz, DMSO) δ 11.89 (s, 1H), 8.65 (s, 1H), 8.53 (s, 1H), 7.34 (d, 1H), 7.23 (d, 1H), 6.40 (m, 1H), 4.68 (s, 1H), 4.06 (m, 2H), 3.80 (m, 2H), 2.52 (s, 3H). MS APCI(+) m/z: 413.5 [M+H].

Compound 46

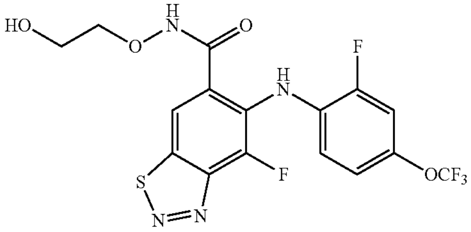

$^1H$ NMR (400 MHz, DMSO) δ 11.90 (s, 1H), 8.67 (s, 1H), 8.55 (s, 1H), 7.33 (d, 1H), 7.21 (d, 1H), 6.38 (m, 1H), 4.71 (s, 1H), 4.02 (m, 2H), 3.77 (m, 2H). MS APCI(+)m/z: 451.3 [M+H].

Compound 47

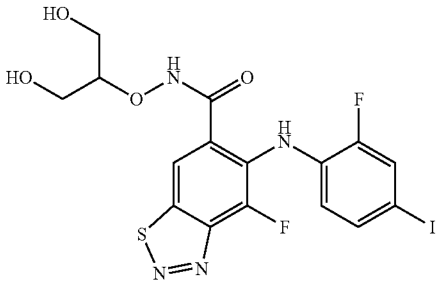

$^1H$ NMR (400 MHz, DMSO) δ 11.88 (s, 1H), 8.68 (s, 1H), 8.56 (s, 1H), 7.35 (d, 1H), 7.24 (d, 1H), 6.41 (m, 1H), 4.70 (s, 1H), 4.03 (m, 4H), 3.68 (m, 1H). MS APCI(+) m/z: 523.3 [M+H].

Compound 48

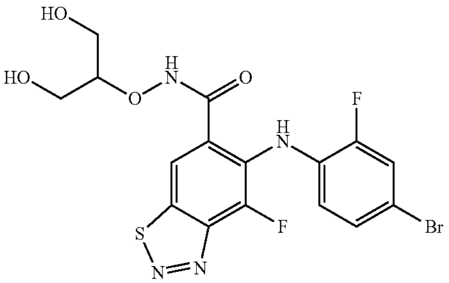

$^1H$ NMR (400 MHz, DMSO) δ 11.89 (s, 1H), 8.67 (s, 1H), 8.55 (s, 1H), 7.33 (d, 1H), 7.25 (d, 1H), 6.39 (m, 1H), 4.71 (s, 1H), 4.05 (m, 4H), 3.67 (m, 1H). MS APCI(+)m/z: 476.3 [M+H].

Compound 49

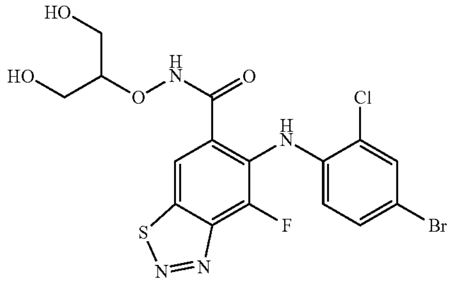

$^1H$ NMR (400 MHz, DMSO) δ 11.90 (s, 1H), 8.66 (s, 1H), 8.54 (s, 1H), 7.36 (d, 1H), 7.23 (d, 1H), 6.40 (m, 1H), 4.72 (s, 1H), 4.05 (m, 4H), 3.69 (m, 1H). MS APCI(+)m/z: 492.7 [M+H].

Compound 50

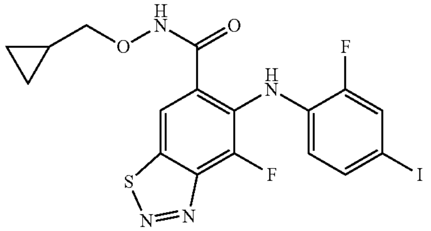

$^1H$ NMR (400 MHz, DMSO) δ 11.90 (s, 1H), 8.65 (s, 1H), 8.53 (s, 1H), 7.35 (d, 1H), 7.25 (d, 1H), 6.41 (m, 1H), 3.70 (m, 2H), 0.51 (m, 1H), 0.26 (m, 4H). MS APCI(+)m/z: 503.4 [M+H].

Compound 51

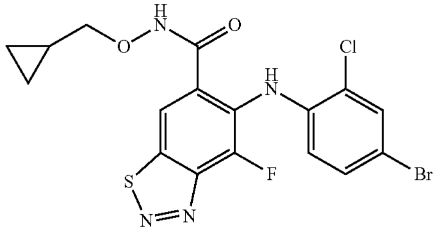

$^1H$ NMR (400 MHz, DMSO) δ 11.91 (s, 1H), 8.67 (s, 1H), 8.55 (s, 1H), 7.38 (d, 1H), 7.25 (d, 1H), 6.42 (m, 1H), 3.72 (m, 2H), 0.52 (m, 1H), 0.25 (m, 4H). MS APCI(+)m/z: 472.7 [M+H].

Example B-1: Cell Growth Inhibition Assays

Materials

CELLS: HT29, COLO205 and A375 cells were obtained from the Cell Resource Center at the Institute of Basic Medical Research, Chinese Academy of Medical Sciences.

REAGENTS: DMEM/F12 (GIBCO), 0.25% trypsin (GIBCO), MTT (5 mg/ml), DMSO, PBS

INSTRUMENT: 37° C., 5% $CO_2$ cell incubator, the TECAN infinite TM200 Series multifunctional microplate reader, clean benches, cell counting board CONSUMABLES: 96-well plates (CORING)

Methods 1 (HT29)

1. When the HT29 cells reach their exponential phase of growth, 4×103 cells/well were plated into 96-well plates, the edge of plates were filled with sterility PBS, at the same time, filled three holds only with medium as blank group.
2. The plates were cultured in a humidified 5% $CO_2$ incubator at 37° C. for 24 h, and allowed to proliferate for reaching their exponential phase of growth.
3. Samples were dissolved in DMSO (dimethyl sulfoxide), the concentration of Samples is 10 mmol/L, 1 mmol/L, 100 μmol/L, 10 μmol/L, 1 μmol/L, 0.1 μmol/L, and further diluted with cell culture medium. The final does concentration were 10 μmol/L, 1 μmol/L, 100 nmol/L, 10 nmol/L, 1 nmol/L, 0.1 nmol/L, 0 nmol/L (the control group). The final DMSO concentration used was 1% of total volume of medium in all treatments, including the control group.

Blank: medium

Control: the same dose of DMSO with experiment. Group, the DMSO was diluted with cell perfect, culture medium.

Experiment: the cells were treated with the concentration of 10 μmol/L, 1 μmol/L, 100 nmol/L, 10 nmol/L, 1 nmol/L, 0.1 nmol/L.

4. The plates were cultured in a humidified 5% $CO_2$ incubator at 37° C. for 72 h, 20 μL of 3-(4,5-dimethylthiazol-2-yl)-2,5-diphenyltetrazolium bromide (MTT) reagent (5 mg/mL) in phosphate buffered serum (PBS) was added to each well.
5. The plates were cultured in a humidified 5% $CO_2$ incubator at 37° C. for 4 h. Subsequently, the solution was aspirated and 150 μL dimethyl sulfoxide was added to release the formed formazan crystals from the living cells mitochondria into the solution.
6. After moderated shaking for 3 min, absorbance was measured at 490 nm using microplate reader.

Methods 0.2 (A375)

1. When the A375 cells reach their exponential phase of growth, 5×103 cells/well were plated into 96-well plates, the edge of plates were filled with sterility PBS, at the same time, filled three holds only with medium as blank group.
2. The plates were cultured in a humidified 5% $CO_2$ incubator at 37° C. for 24 h. Allowed to proliferate for reaching their exponential phase of growth.
3. Samples were dissolved in DMSO (Dimethyl Sulfoxide), the concentration of Samples is 10 mmol/L, 1 mmol/L, 100 μmol/L, 10 μmol/L, 1 μmol/L, 0.1 μmol/L, and further diluted with cell culture medium. The final does concentration were 10 μmol/L, 1 μmol/L, 100 nmol/L, 10 nmol/L, 1 nmol/L, 0.1 nmol/L, 0 nmol/L (the control group). The final DMSO concentration used was 1% of total volume of medium in all treatments, including the control group.

Blank: medium

Control: the same dose of DMSO with experiment group, the DMSO was diluted with cell perfect culture medium Experiment: the cells were treated with the concentration of 10 μmol/L, 1 μmol/L, 100 nmol/L, 10 nmol/L, 1 nmol/L, 0.1 nmol/L 4. The plates were cultured in a humidified 5% $CO_2$ incubator at 37° C. for 72 h, 20 μL of 3-(4,5-dimethylthiazol- 2-yl)-2,5-diphenyltetrazolium bromide (MTT) reagent (5 mg/mL) in phosphate buffered serum (PBS) was added to each well.

5. The plates were cultured in a humidified 5% $CO_2$ incubator at 37° C. for 4 h. Subsequently, the solution was aspirated and 150 uL dimethyl sulfoxide was added to release the formed formazan crystals from the living cells mitochondria into the solution.
6. After moderated shaking for 3 min, absorbance was measured at 490 nm using microplate reader.

Methods 3 (COLO205)

1. When the COLO205 cells reach their exponential phase of growth, 1×104 cells/well were plated into 96-well plates, the edge of plates were filled with sterility PBS, at the same time, filled three holds only with medium as blank group.
2. The plates were cultured in a humidified 5% $CO_2$ incubator at 37° C. for 24 h. Allowed to proliferate for reaching their exponential phase of growth.
3. Samples were dissolved in DMSO (Dimethyl Sulfoxide), the concentration of Samples is 10 mmol/L, 1 mmol/L, 100 μmol/L, 10 μmol/L, 1 μmol/L, 0.1 μmol/L, and further diluted with cell culture medium. The final does concentration were 10 μmol/L, 1 μmol/L, 100 nmol/L, 10 nmol/L, 1 nmol/L, 0.1 nmol/L, 0 nmol/L (the control group). The final DMSO concentration used was 1% of total volume of medium in all treatments, including the control group.

Blank: medium

Control: the same dose of DMSO with experiment group, the DMSO was diluted with cell perfect culture medium Experiment: the cells were treated with the concentration of 10 μmol/L, 1 μmol/L, 100 nmol/L, 10 nmol/L, 1 nmol/L, 0.1 nmol/L 4. The plates were cultured in a humidified 5% $CO_2$ incubator at 37° C. for 72 h, 20 μl of 3-(4,5-dimethylthiazol-2-yl)-2,5-diphenyltetrazolium bromide (MTT) reagent (5 mg/ml) in phosphate buffered serum (PBS) was added to each well.
5. The plates were cultured in a humidified 5% $CO_2$ incubator at 37° C. for 4 h. Subsequently, the solution was aspirated and 150 ul dimethyl sulfoxide was added to release the formed formazan crystals from the living cells mitochondria into the solution.
6. After moderated shaking for 3 min, absorbance was measured at 490 nm using microplate reader.

The cell inhibition IC50 values obtained with the HT29 and A375 cells are shown in Table 5.

TABLE 5

| Compound | $IC_{50}$ (nM) | |
|---|---|---|
| No. | HT29 | A375 |
| 1 | 2.3 | 0.85 |
| 2 | 8.1 | 4.6 |
| 3 | 51.8 | 61.3 |
| 4 | 138 | 97.5 |
| 5 | 81.6 | 125 |
| 6 | 78.3 | 103 |
| 7 | 283 | 239 |
| 8 | 1092 | 738 |
| 9 | 1.0 | 0.79 |
| 10 | 18.5 | 11.2 |
| 11 | 51.2 | 61.4 |
| 12 | 738 | 174 |
| 13 | 98.3 | 207 |
| 14 | 201 | 119 |
| 15 | 184 | 99.8 |

TABLE 5-continued

| Compound | $IC_{50}$ (nM) | |
|---|---|---|
| No. | HT29 | A375 |
| 16 | 1306 | 151 |
| 17 | 1.0 | 0.24 |
| 18 | 66.4 | 16.8 |
| 19 | 65.7 | 49.4 |
| 20 | 687 | 97.3 |
| 21 | 1078 | 1770 |
| 22 | 2620 | 1160 |
| 23 | 3640 | 562 |
| 24 | 4370 | 992 |

Example B-2: In Vivo Anti-Tumor Efficacy in HT29 Tumor Xenograft Model

Female BALB/c nude mice of 5-6 week old were used for all the in vivo efficacy studies. Mice were injected with HT29 human colon cancer cells at $5\times10^6$ cells per 100 μL, SFM into right flank. Tumor volumes were monitored by caliper measurement using the formula: tumor volume ($mm^3$)=($w^2$×1)/2, where w=width and c=length in mm of the tumor. When the tumor volumes reached 150-300 $mm^3$, mice were randomized to treatment groups (5~10 mice per group) to receive compounds (20 mg/kg doses) or vehicle by oral gavage once daily for 16 days. The tumor volumes and body weight were measured every 2-3 days for data analysis. Tumor growth inhibition (TGI) and body weight changes were calculated compared to the vehicle treated groups. TGI represents the percent volume differential between the treated and control tumors at the time vehicle tumors exceeded a volume of 1,000 based on formula TGI (%)=(1−(T−To)/(C−Co))*100%.

The results for Compounds 1, 3, 9, 11, 17 and 19 are shown in FIG. 1. The results show that the human colon FIT-29 xenograft was highly sensitive to Compounds 9 and 17, which demonstrated 95.1% TGI for Compound 9 at 20 mg/kg and 88.75% TGI for 1.7 at 20 mg/kg respectively after 16 days of treatment. Compounds 1, 11 and 19 also showed significant inhibition of HT29 xenograft growth in nude mice at 20 mg/kg with TGI at 55.1%, 68.51% and 50.9% respectively. Compound 3 at 20 mg/kg showed no significant effects on HT29 cancer cell growth with TGI at 32.3% in nude mice after 16 days treatment. Reference compound AZD6244 showed inhibition of HT29 xenograft growth in nude mice at 20 mg/kg with TGI at 48.3% after 16 days treatment.

Example B-3: In Vivo Anti-Tumor Efficacy in COLO205 Tumor Xenograft Model

The animal use and care protocol was approved by Sundia Institutional Animal Care and Use Committee. Male athymic nude mice (nu/nu; 6 weeks of age) were obtained from Beijing HFK Bioscience CO., LTD. All animals were fed with commercial diet and water ad libitum for 1 week before the study.

Each mouse was inoculated s.c. in the flank with COLO 205 tumor fragment (~1 $mm^3$). When rumors reached the appropriate size for staging (170 $mm^3$ or as indicated in data graphs), mice were randomized to eight groups (n=6) that received the following treatments: (a) 20% SBE-β-CD in purity water vehicle, (b) AZD6244 at 10 mg/kg QD, (c) test compound 19 at 10 mg/kg QD, (d) test compound 1 at 10 mg/kg QD, (e) test compound 3 at 20 mg/kg QD, (f) test compound 9 at 5 mg/kg QD, (g) test compound 11 at 10 mg/kg QD, (h) test compound 17 at 5 mg/kg QD. Mice received treatments by gavage (10 mL/kg body weight) for the duration of the study. Tumors were measured twice a week using calipers and their volumes calculated using the formula (width$^2$×length)/2. In this experiment, tumors were staged on day 0, the day of first treatment. The Reference Compounds and the test compounds were formulated in 20% SBE-β-CD.

The tumor growth inhibition ratio was calculated using the formula: TGI=100×[(tumor volume$_{final}$ for the vehicle-treated group−tumor volume$_{final}$ for the compound-treated group)/tumor volume$_{final}$ for the vehicle-treated group]. Tumor growth data are expressed as mean tumor volumes±S.E. Differences were considered significant at $P<0.05$ and statistical analysis was done using Microsoft Excel.

After 18 days consecutive treatments (QD×18 days), the Reference compound 1 inhibited 72.80% ($P<0.01$) of tumor growth, compared with the vehicle control group. The test compound 1, 3, 9, 11, 17 and 19 inhibited 91.22% (P 0.01), 47.11% ($P<0.05$), 94.70% ($P<0.01$), 82.14% ($P<0.01$), 95.35% ($P<0.01$) and 86.22% (P 0.01) of tumor growth, respectively, compared with the vehicle control group.

Figure 2:
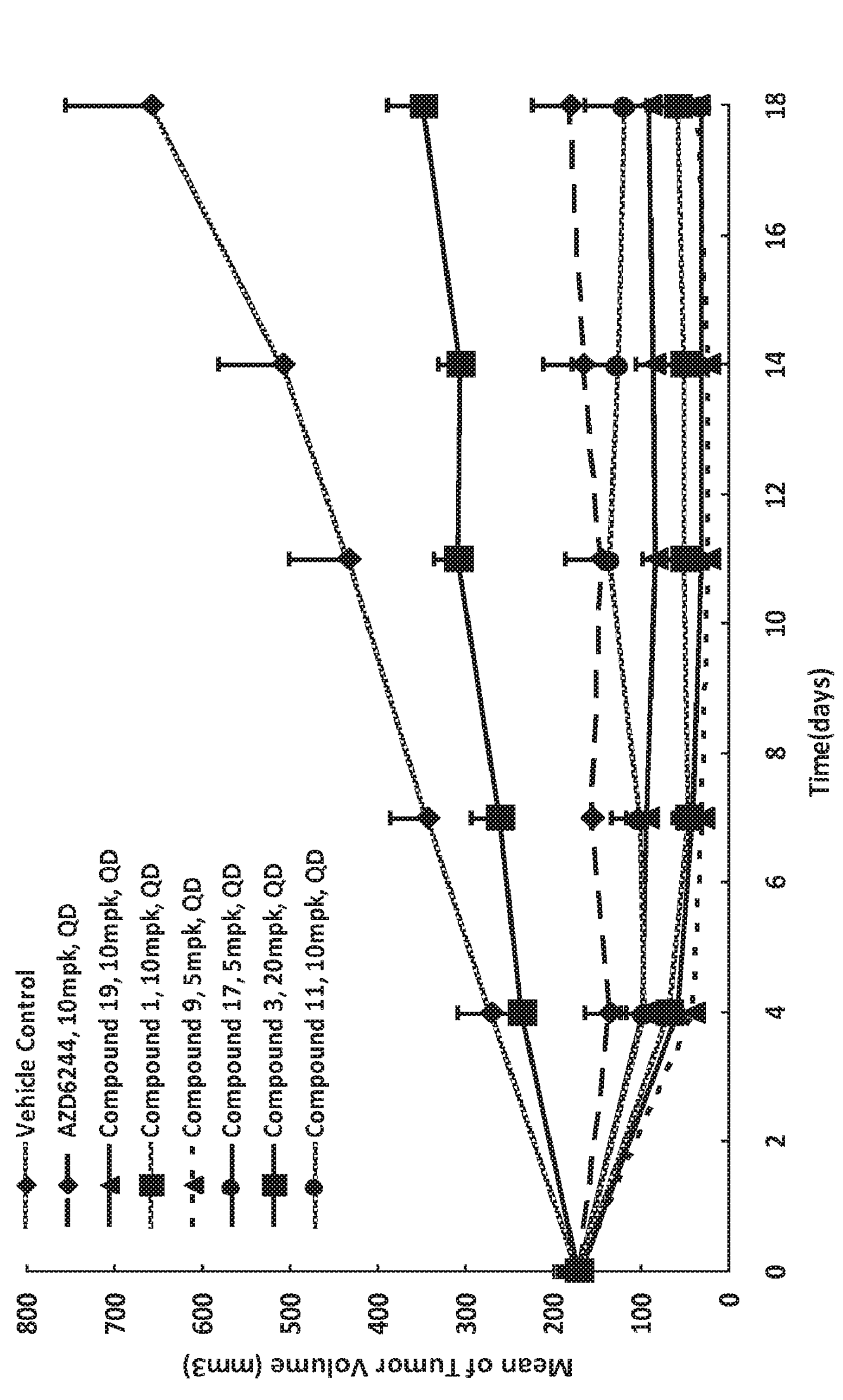
FIG. 2 shows the anti-tumor effect of Compounds 1, 3, 9, 11, 17 and 19 in a COLO-205 xenograft model.

The results for Compounds 1, 3, 9, 11, 17 and 19 are shown in FIG. 2.

Example B-4: Inhibition of Interlukin-4 (IL-4)

Method:

1. Take spleens of BALB/c gene reported mice, culture in RPMI1640 medium (HyClone).
2. Spleen will be ground into single cell suspension, add red blood cell lysis buffer (sigma) to suspension, for cracking the red blood cells.
3. The cell suspension was filtered, and suspended in 1640 medium containing 10% serum.
4. Dissolved compounds with DMSO and diluted with RPMI1640 medium containing 10% serum, diluted to a final concentration of 200 nM.
5. According with the concentration of 4×106/mL, 100 μL/well, calculate the required total number of cells, suspended in the RPMI 1640 medium containing 10% serum, in the cell suspension, added Con A (Concanavalin A, sigma) (final concentration for 2.5 ng/mL), IL-2 (interleukin-2, R&D) (final concentration of 2 ng/mL), IL-4 (interleukin-4, PeproTech) (final concentration of 20 ng/mL) into the cell suspension. After mixing, cells were added to 96 well plates, every hole is 100 μL. Joined the compound solution, 100 μL/well, the cell final concentration is 2×106/mL, the compounds final concentration is 100 nM. Each compound and control is three-hole wells, cultured at 37° C. for 48 h.
6. After 48 h, the plates removed from the incubator and each well was collected in the flow tube (BD).
7. Added cells to ice pre-cooling of PBS (phosphate buffer solution) solution to wash, and in 100 μL of PBS, join the fluorescent antibody CD4 0.5 μL, put in ice 15 min avoid light.
8. After dyeing wash antibodies with the ice pre-cooling PBS solution. And prepare for flow cytometric detection.
9. Using flow cytometry (BD FACS calibur) select the CD4+ cell populations, and detect GFP+ cells accounted for the percentage of CD4+ cells, to determine the impact of compounds on IL-4,
10. The inhibition rate of IL-4(%)=(Control %−compounds %)/control %×100%.

Control was DMSO and its concentration was same as the final concentration of test compounds. Compounds 1, 3, 9, 11, 17, 19, 25, 34 and 43 showed up to 50% IL-4 inhibition.

Example B-5: Inhibition of TNF-α Expression

Method:

1. Take spleens of BALB/c gene reported mice, cultured in RPMI1640 medium (HyClone). Spleen was ground into single cell suspension, added red blood cell lysis buffer (sigma) to suspension, for cracking the red blood cells
2. The cell suspension was filtered, and suspended in 1640 medium containing 10% serum (HyClone), the cell final concentration was 4×106/mL, added LPS to medium and final concentration was 200 ng/mL.
3. Dissolved compounds with DMSO and diluted with RPMI1640 medium containing 10% serum, diluted to a final concentration of 200 nM.
4. Cells were added to 96 well plates, every hole was 100 μL. Joined the compound solution, 100 μL/well, the cell final concentration was 2×106/mL, the compounds final concentration was 100 nM. Each compound and control is three-hole wells.
5. Cultured at 37° C. for 24 h.
6. Centrifuged at 1400 rmp, 7 min by Cell plate centrifuge (Eppendorf 5810R), drew the supernatant and placed in the new 96-well plates, placed at 4° C. to save.
7. Using ELISA (enzyme-linked immunosorbent assay) technique for the determination of the amount of TNF-α in the 24 hours.

Control was DMSO and its concentration was same as the final concentration of test compounds. Compounds 1,3,9, 11, 17, 19, 25, 34 and 43 showed up to 40% inhibition.

All references throughout, such as publications, patents, patent applications and published patent applications, are incorporated herein by reference in their entireties.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

The invention claimed is:

1. A method of killing cancerous cells or inhibiting the progress of a cancer in an individual comprising administering to an individual in need thereof a therapeutically effective amount of a compound of the formula (I):

(I)

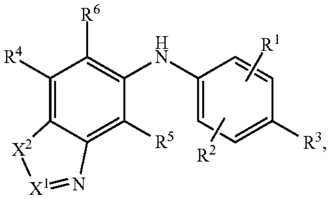

or a pharmaceutically acceptable salt, prodrug or solvate thereof, wherein:

$X^1$ is $CR^{11}$ or N;

$X^2$ is O, S or carbonyl;

$R^1$, $R^2$, $R^4$ and $R^5$ are independently hydrogen, halo, nitro, azido, hydroxy, $C_1$-$C_{10}$ alkoxy, halo-substituted $C_1$-$C_{10}$ alkoxy, acyloxy, $C_1$-$C_{10}$ alkylthio, halo-substituted $C_1$-$C_{10}$ alkylthio, amino, carboxy, $C_1$-$C_{10}$ alkyl, $C_2$-$C_{10}$ alkenyl, $C_2$-$C_{10}$ alkynyl or $C_3$-$C_{10}$ cycloalkyl;

$R^3$ is hydrogen, halo, cyano, nitro, azido, hydroxy, $C_1$-$C_{10}$ alkoxy, halo-substituted $C_1$-$C_{10}$ alkoxy, acyloxy, mercapto, $C_1$-$C_{10}$ alkylthio, halo-substituted $C_1$-$C_{10}$ alkylthio, —$SO_2R^a$, —$SO_2N(R^c)R^d$, —$N(R^c)R^d$, —C(O)$OR^b$, $C_1$-$C_{10}$ alkyl, $C_2$-$C_{10}$ alkenyl, $C_2$-$C_{10}$ alkynyl or $C_3$-$C_{10}$ cycloalkyl;

$R^a$ is $C_1$-$C_{10}$ alkyl or $C_6$-$C_{14}$ aryl;

each $R^b$, $R^c$ and $R^d$ is independently hydrogen or $C_1$-$C_{10}$ alkyl;

$R^6$ is —C(O)N($R^8$)$OR^7$ or —$NHSO_2R^{10}$;

$R^7$ is $C_1$-$C_{10}$ alkyl substituted with at least one hydroxy group;

$R^8$ is hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkyl $C_1$-$C_{10}$ alkyl or $C_1$-$C_{10}$ alkyl $C_3$-$C_{10}$ cycloalkyl;

$R^{10}$ is $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkyl $C_1$-$C_{10}$ alkyl or $C_1$-$C_{10}$ alkyl $C_3$-$C_{10}$ cycloalkyl; and $R^{11}$ is hydrogen, $C_1$-$C_{10}$ alkyl, $C_2$-$C_{10}$ alkenyl, $C_2$-$C_{10}$ alkynyl, $C_3$-$C_{10}$ cycloalkyl or $C_3$-$C_{10}$ cycloalkyl $C_1$-$C_{10}$ alkyl;

wherein each $C_1$-$C_{10}$ alkyl, $C_2$-$C_{10}$ alkenyl, $C_2$-$C_{10}$ alkynyl or $C_3$-$C_{10}$ cycloalkyl moiety may be unsubstituted or substituted with one or more groups independently selected from the group consisting of hydroxy, oxo, halo, cyano, nitro, trifluoromethyl, azido, amino, carboxy and mercapto;

wherein the individual has a cancer selected from the group consisting of a colon cancer, a colorectal cancer, a skin cancer, a lung cancer, a breast cancer, a gastrointestinal cancer and a pancreatic cancer.

2. The method of claim 1, wherein the cancer is a skin cancer.

3. The method of claim 1, wherein the cancer is a lung cancer.

4. The method of claim 1, wherein the cancer is a colon cancer or colorectal cancer.

5. The method of claim 1, wherein $X^2$ is O or S.

6. The method of claim 1, wherein $R^1$ is halo.

7. The method of claim 1, wherein $R^2$ is hydrogen.

8. The method of claim 1, wherein $R^3$ is iodo or bromo.

9. The method of claim 1, wherein $R^4$ is hydrogen.

10. The method of claim 1, wherein $R^5$ is fluoro.

11. The method of claim 1, wherein $R^6$ is —C(O)N($R^8$)$OR^7$.

12. The method of claim 11, wherein $R^8$ is hydrogen.

13. The method of claim 1, wherein the compound is of the formula (J):

(J)

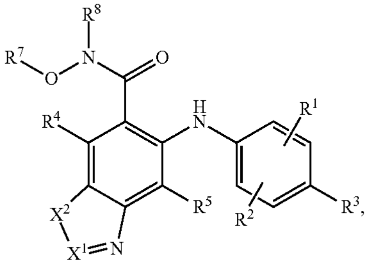

or a pharmaceutically acceptable salt thereof.

14. The method of claim 1, wherein the compound is of the formula (J-1):

(J-1)

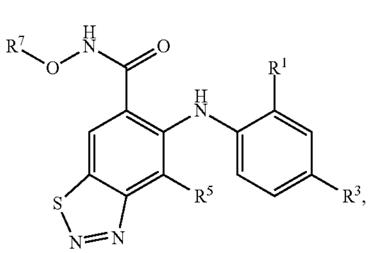

or a pharmaceutically acceptable salt thereof.

15. The method of claim 14, wherein:

$R^1$ is halo or unsubstituted or substituted $C_1$-$C_{10}$ alkyl;

$R^3$ is halo, unsubstituted or substituted $C_1$-$C_{10}$ alkyl, $C_1$-$C_{10}$ alkoxy, halo-substituted $C_1$-$C_{10}$ alkoxy, $C_1$-$C_{10}$ alkylthio, halo-substituted $C_1$-$C_{10}$ alkylthio, —$SO_2R^a$, —$SO_2N(R^c)R^d$, —$N(R^c)R^d$ or —C(O)$OR^b$; and $R^5$ is hydrogen, halo or unsubstituted or substituted $C_1$-$C_{10}$ alkyl.

16. The method of claim 13, wherein the compound is of the formula (J-2) or (J-3):

(J-2)

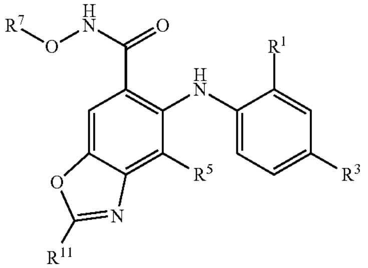

or (J-3)

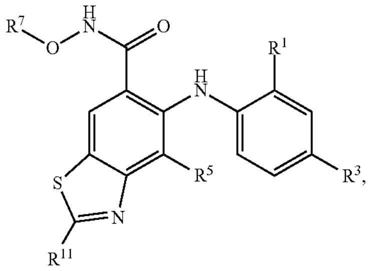

or a pharmaceutically acceptable salt thereof.

17. The method of claim 16, wherein:

$R^1$ is halo or unsubstituted or substituted $C_1$-$C_{10}$ alkyl;

$R^3$ is halo, unsubstituted or substituted $C_1$-$C_{10}$ alkyl, $C_1$-$C_{10}$ alkoxy, halo-substituted $C_1$-$C_{10}$ alkoxy, acyloxy, $C_1$-$C_{10}$ alkylthio, halo-substituted $C_1$-$C_{10}$ alkylthio, —$SO_2R^a$, —$SO_2N(R^c)R^d$, —$N(R^c)R^d$ or —C(O)$OR^b$;

$R^5$ is hydrogen, halo or unsubstituted or substituted $C_1$-$C_{10}$ alkyl; and $R^{11}$ is hydrogen.

18. The method of claim 16, wherein:

$R^1$ is fluoro or chloro;

$R^3$ is iodo or bromo;

$R^5$ is fluoro; and $R^7$ is selected from the group consisting of 2-hydroxyethyl, 3-hydroxy-2-methylpropyl, 2,3-dihydroxypropyl and 1,3-dihydroxy-2-propyl.

19. The method of claim 13, wherein the compound is of the formula (J-4):

(J-4)

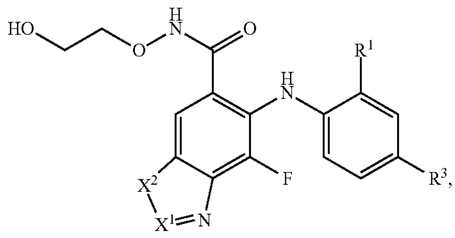

or a pharmaceutically acceptable salt thereof.

20. The method of claim 1, wherein the compound is selected from the group consisting of:

4-fluoro-5-((2-fluoro-4-iodophenyl)amino)-N-(2-hydroxyethoxy)benzo[d]oxazole-6-carboxamide;

N-(2,3-dihydroxypropoxy)-4-fluoro-5-((2-fluoro-4-iodophenyl)amino)benzo[d]oxazole-6-carboxamide;

5-((4-bromo-2-chlorophenyl)amino)-4-fluoro-N-(2-hydroxyethoxy)benzo[d]oxazole-6-carboxamide;

5-((4-bromo-2-chlorophenyl)amino)-N-(2,3-dihydroxypropoxy)-4-fluorobenzo [d]oxazole-6-carboxamide;

N-(4-fluoro-5-((2-fluoro-4-iodophenyl)amino)benzo [d]oxazol-6-yl)cyclopropanesulfonamide;

N-(4-fluoro-5-((2-fluoro-4-iodophenyl)amino)benzo[d] oxazol-6-yl)-1-(2,3-dihydroxypropyl)cyclopropane-1-sulfonamide;

N-(5-((4-bromo-2-chlorophenyl)amino)-4-fluorobenzo [d]oxazol-6-yl)cyclopropanesulfonamide;

N-(5-((4-bromo-2-chlorophenyl)amino)-4-fluorobenzo [d]oxazol-6-yl)-1-(2,3-dihydroxypropyl)cyclopropane-1-sulfonamide;

4-fluoro-5-((2-fluoro-4-bromophenyl)amino)-N-(2-hydroxyethoxy)benzo[d]oxazole-6-carboxamide;

4-fluoro-5-((2-fluoro-4-trifluoromethylphenyl)amino)-N-(2-hydroxyethoxy)benzo[d]oxazole-6-carboxamide;

4-fluoro-5-((2-fluoro-4-methylthiophenyl)amino)-N-(2-hydroxyethoxy)benzo[d]oxazole-6-carboxamide;

5-((4-trifluoromethoxy-2-chlorophenyl)amino)-4-fluoro-N-(2-hydroxyethoxy)benzo[d]oxazole-6-carboxamide;

5-((2-fluoro-4-iodophenyl)amino)-N-(1,3-dihydroxy-isopropoxy)-4-fluorobenzo[d]oxazole-6-carboxamide;

5-((4-bromo-2-fluorophenyl)amino)-N-(1,3-dihydroxy-isopropoxy)-4-fluorobenzo[d]oxazole-6-carboxamide;

5-((4-bromo-2-chlorophenyl)amino)-N-(1,3-dihydroxy-isopropoxy)-4-fluorobenzo[d]oxazole-6-carboxamide;

4-fluoro-5-((2-fluoro-4-iodophenyl)amino)-N-(2-hydroxyethoxy)benzo[d]thiazole-6-carboxamide;

N-(2,3-dihydroxypropoxy)-4-fluoro-5-((2-fluoro-4-iodophenyl)amino)benzo[d]thiazole-6-carboxamide;

5-((4-bromo-2-chlorophenyl)amino)-4-fluoro-N-(2-hydroxyethoxy)benzo[d]thiazole-6-carboxamide;

5-((4-bromo-2-chlorophenyl)amino)-N-(2,3-dihydroxypropoxy)-4-fluorobenzo [d]thiazole-6-carb oxamide;

N-(4-fluoro-5-((2-fluoro-4-iodophenyl)amino)benzo [d]thiazol-6-yl)cyclopropanesulfonamide;

1-(2,3-dihydroxypropyl)-N-(4-fluoro-5-((2-fluoro-4-iodophenyl)amino)benzo[d]thiazol-6-yl)cyclopropane-1-sulfonamide;

N-(5-((4-bromo-2-chlorophenyl)amino)-4-fluorobenzo [d]thiazol-6-yl)cyclopropanesulfonamide;

N-(5-((4-bromo-2-chlorophenyl)amino)-4-fluorobenzo [d]thiazol-6-yl)-1-(2,3-dihydroxypropyl)cyclopropane-1-sulfonamide;

4-fluoro-5-((2-fluoro-4-bromophenyl)amino)-N-(2-hydroxyethoxy)benzo[d]thiazol-6-carboxamide;

4-fluoro-5-((2-fluoro-4-trifluoromethylphenyl)amino)-N-(2-hydroxyethoxy)benzo[d]thiazol-6-carboxamide;

4-fluoro-5-((2-fluoro-4-methylthiophenyl)amino)-N-(2-hydroxyethoxy)benzo[d]thiazol-6-carboxamide;

5-((4-trifluoromethoxy-2-chlorophenyl)amino)-4-fluoro-N-(2-hydroxyethoxy)benzo[d]thiazol-6-carboxamide;

5-((2-fluoro-4-iodophenyl)amino)-N-(1,3-dihydroxy-isopropoxy)-4-fluorobenzo[d]thiazol-6-carboxamide;

5-((4-bromo-2-fluorophenyl)amino)-N-(1,3-dihydroxy-isopropoxy)-4-fluorobenzo[d]thiazol-6-carboxamide;

5-((4-bromo-2-chlorophenyl)amino)-N-(1,3-dihydroxy-isopropoxy)-4-fluorobenzo[d]thiazol-6-carboxamide;

4-fluoro-5-((2-fluoro-4-iodophenyl)amino)-N-(2-hydroxyethoxy)benzo[d][1,2,3]thiadiazole-6-carboxamide;

N-(2,3-dihydroxypropoxy)-4-fluoro-5-((2-fluoro-4-iodophenyl)amino)benzo[d][1,2,3]thiadiazole-6-carboxamide;

5-((4-bromo-2-chlorophenyl)amino)-4-fluoro-N-(2-hydroxyethoxy)benzo[d][1,2,3]thiadiazole-6-carboxamide;

5-((4-bromo-2-chlorophenyl)amino)-N-(2,3-dihydroxypropoxy)-4-fluorobenzo [d][1,2,3]thiadiazole-6-carboxamide;

N-(4-fluoro-5-((2-fluoro-4-iodophenyl)amino)benzo[d] [1,2,3]thiadiazol-6-yl)cyclopropanesulfonamide;

1-(2,3-dihydroxypropyl)-N-(4-fluoro-5-((2-fluoro-4-iodophenyl)amino)benzo [d][1,2,3]thiadiazol-6-yl)cyclopropane-1-sulfonamide;

N-(5-((4-bromo-2-chlorophenyl)amino)-4-fluorobenzo [d][1,2,3]thiadiazol-6-yl)cyclopropanesulfonamide;

N-(5-((4-bromo-2-chlorophenyl)amino)-4-fluorobenzo [d][1,2,3]thiadiazol-6-yl)-1-(2,3-dihydroxypropyl)cyclopropane-1-sulfonamide;

5-((4-bromo-2-fluorophenyl)amino)-4-fluoro-N-(2-hydroxyethoxy)benzo[d][1,2,3]thiadiazole-6-carboxamide;

4-fluoro-5-((2-fluoro-4-trifluoromethylphenyl)amino)-N-(2-hydroxyethoxy)benzo[d][1,2,3]thiadiazol-6-carboxamide;

4-fluoro-5-((2-fluoro-4-methylthiophenyl)amino)-N-(2-hydroxyethoxy)benzo[d][1,2,3]thiadiazol-6-carboxamide;

5-((4-trifluoromethoxy-2-chlorophenyl)amino)-4-fluoro-N-(2-hydroxyethoxy)benzo[d][1,2,3]thiadiazol-6-carboxamide;

5-((2-fluoro-4-iodophenyl)amino)-N-(1,3-dihydroxy-isopropoxy)-4-fluorobenzo[d][1,2,3]thiadiazol-6-carboxamide;

5-((4-bromo-2-fluorophenyl)amino)-N-(1,3-dihydroxy-isopropoxy)-4-fluorobenzo[d][1,2,3]thiadiazol-6-carboxamide; and 5-((4-bromo-2-chlorophenyl)amino)-N-(1,3-dihydroxy-isopropoxy)-4-fluorobenzo[d][1,2,3]thiadiazol-6-carboxamide;

or a pharmaceutically acceptable salt thereof.

21. The method of claim 1, wherein the compound is 4-fluoro-5-((2-fluoro-4-iodophenyl)amino)-N-(2-hydroxyethoxy)benzo[d]oxazole-6-carboxamide or a pharmaceutically acceptable salt thereof.

22. The method of claim 1, wherein the compound is 4-fluoro-5-((2-fluoro-4-bromophenyl)amino)-N-(2-hydroxyethoxy)benzo[d]oxazole-6-carboxamide or a pharmaceutically acceptable salt thereof.

23. The method of claim 1, wherein the compound is 5-((4-bromo-2-chlorophenyl)amino)-4-fluoro-N-(2-hydroxyethoxy)benzo[d]oxazole-6-carboxamide or a pharmaceutically acceptable salt thereof.

24. The method of claim 1, wherein the compound is 4-fluoro-5-((2-fluoro-4-iodophenyl)amino)-N-(2-hydroxyethoxy)benzo[d]thiazole-6-carboxamide or a pharmaceutically acceptable salt thereof.

25. The method of claim 1, wherein the compound is 4-fluoro-5-((2-fluoro-4-bromophenyl)amino)-N-(2-hydroxyethoxy)benzo[d]thiazol-6-carboxamide or a pharmaceutically acceptable salt thereof.

26. The method of claim 1, wherein the compound is 5-((4-bromo-2-chlorophenyl)amino)-4-fluoro-N-(2-hydroxyethoxy)benzo[d]thiazole-6-carboxamide or a pharmaceutically acceptable salt thereof.

27. The method of claim 1, wherein the compound is 4-fluoro-5-((2-fluoro-4-iodophenyl)amino)-N-(2-hydroxyethoxy)benzo[d][1,2,3]thiadiazole-6-carboxamide, or a pharmaceutically acceptable salt thereof.

* * * * *